(12) United States Patent
Tamura et al.

(10) Patent No.: US 8,541,408 B2
(45) Date of Patent: Sep. 24, 2013

(54) AMINODIHYDROTHIAZINE DERIVATIVES SUBSTITUTED WITH A CYCLIC GROUP

(75) Inventors: Yuusuki Tamura, Osaka (JP); Shinji Suzuki, Osaka (JP); Yukio Tada, Osaka (JP); Chiaki Fujikoshi, Osaka (JP); Sae Matsumoto, Osaka (JP); Yuuji Kooriyama, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 13/417,786

(22) Filed: Mar. 12, 2012

(65) Prior Publication Data

US 2012/0172355 A1 Jul. 5, 2012

Related U.S. Application Data

(62) Division of application No. 12/596,796, filed as application No. PCT/JP2008/057847 on Apr. 23, 2008, now Pat. No. 8,168,630.

(30) Foreign Application Priority Data

Apr. 24, 2007 (JP) ................................. 2007-114288
Nov. 8, 2007 (JP) ................................. 2007-290589

(51) Int. Cl.
- C07D 417/12 (2006.01)
- C07D 417/14 (2006.01)
- A61K 31/497 (2006.01)
- A61K 31/54 (2006.01)

(52) U.S. Cl.
USPC .......................... 514/227.2; 544/53; 544/55

(58) Field of Classification Search
USPC ................... 514/227.2; 544/53, 55
See application file for complete search history.

(56) References Cited

U.S. PATENT DOCUMENTS

| | | | |
|---|---|---|---|
| 2,899,426 A | 8/1959 | Bloom | |
| 3,115,494 A | 12/1963 | Joseph et al. | |
| 3,227,713 A | 1/1966 | Behner | |
| 3,235,551 A | 2/1966 | Werner | |
| 3,636,116 A | 1/1972 | Trepanier | |
| 3,719,674 A | 3/1973 | Trepanier | |
| 3,775,409 A | 11/1973 | Harsanyi et al. | |
| 4,311,840 A | 1/1982 | Condon | |
| 4,895,841 A | 1/1990 | Sugimoto et al. | |
| 4,906,626 A | 3/1990 | Amrein et al. | |
| 5,100,901 A | 3/1992 | Sugimoto et al. | |
| 5,236,942 A | 8/1993 | Miller | |
| 5,328,915 A | 7/1994 | Long et al. | |
| 5,880,147 A | 3/1999 | Yoshida et al. | 514/452 |
| 5,952,374 A | 9/1999 | Clarkson, Jr. et al. | |
| 6,096,753 A | 8/2000 | Spohr et al. | |
| 6,590,123 B2 | 7/2003 | Bekesi et al. | 564/161 |
| 6,713,276 B2 | 3/2004 | Cordell et al. | |
| 7,183,070 B2 | 2/2007 | Cordell et al. | |
| 7,309,706 B2 | 12/2007 | Rupp et al. | |
| 7,326,792 B2 | 2/2008 | Shum et al. | |
| 7,414,050 B2 | 8/2008 | Illig et al. | |
| 7,763,609 B2 | 7/2010 | Zhu et al. | |
| 7,902,238 B2 | 3/2011 | Galley et al. | |
| 8,173,642 B2 | 5/2012 | Kobayashi et al. | |
| 2002/0019427 A1 | 2/2002 | Carry et al. | |
| 2005/0165080 A1 | 7/2005 | Rupp et al. | |
| 2006/0173006 A1 | 8/2006 | Sun et al. | |
| 2006/0183790 A1 | 8/2006 | Cole et al. | |
| 2006/0183792 A1 | 8/2006 | Fobare et al. | |
| 2006/0183943 A1 | 8/2006 | Hu et al. | |
| 2007/0004730 A1 | 1/2007 | Zhou et al. | |
| 2007/0004786 A1 | 1/2007 | Malamas et al. | |
| 2007/0027199 A1 | 2/2007 | Malamas et al. | |
| 2007/0224656 A1 | 9/2007 | Cordell et al. | |
| 2008/0200445 A1 | 8/2008 | Zhu et al. | |

(Continued)

FOREIGN PATENT DOCUMENTS

| EP | 0 798 292 | 10/1995 |
|---|---|---|
| EP | 0 713 704 | 5/1996 |

(Continued)

OTHER PUBLICATIONS

Vippagunta et al, "Crystalline Solids" Advanced Drug Delivery Reviews, vol. 48, pp. 3-26 (2001).*

(Continued)

Primary Examiner — Kahsay T Habte
(74) Attorney, Agent, or Firm — Hamre, Schumann, Mueller & Larson, P.C.

(57) ABSTRACT

This invention provides a compound of the formula (I):

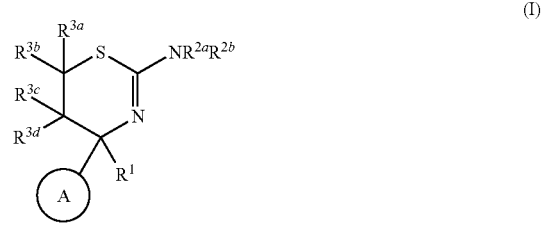

wherein the ring A is an optionally substituted carbocyclic group or an optionally substituted heterocyclic group; $R^1$ is optionally substituted lower alkyl, optionally substituted lower alkenyl, optionally substituted lower alkynyl; $R^{2a}$ and $R^{2b}$ are each independently hydrogen, optionally substituted lower alkyl or optionally substituted acyl; $R^{3a}$, $R^{3b}$, $R^{3c}$ and $R^{3d}$ are each independently hydrogen, halogen, hydroxy or optionally substituted lower alkyl etc.;

a pharmaceutically acceptable salt or solvate thereof, which is useful for treating diseases induced by production, secretion and/or deposition of amyloid β protein.

10 Claims, No Drawings

(56) References Cited

U.S. PATENT DOCUMENTS

| | | |
|---|---|---|
| 2009/0023729 A1 | 1/2009 | Nakamura et al. |
| 2009/0082560 A1 | 3/2009 | Kobayashi et al. |
| 2010/0093999 A1 | 4/2010 | Motoki et al. |
| 2010/0160290 A1 | 6/2010 | Kobayashi et al. |
| 2010/0234365 A1 | 9/2010 | Liu et al. |
| 2010/0261727 A1 | 10/2010 | Chi et al. |
| 2011/0009395 A1 | 1/2011 | Audia et al. |
| 2011/0046122 A1 | 2/2011 | Andreini et al. |
| 2011/0065695 A1 | 3/2011 | Beauchamp et al. |
| 2011/0190279 A1 | 8/2011 | Hori et al. |
| 2011/0237576 A1 | 9/2011 | Yonezawa et al. |
| 2012/0015961 A1 | 1/2012 | Tamura et al. |
| 2012/0016116 A1 | 1/2012 | Kobayashi et al. |
| 2012/0022249 A1 | 1/2012 | Kobayashi et al. |
| 2012/0238548 A1 | 9/2012 | Gabellieri et al. |
| 2012/0253035 A1 | 10/2012 | Narquizian et al. |
| 2012/0258962 A1 | 10/2012 | Hilpert et al. |
| 2012/0295900 A1 | 11/2012 | Hilpert et al. |

FOREIGN PATENT DOCUMENTS

| | | |
|---|---|---|
| EP | 0 718 294 | 6/1996 |
| EP | 0717040 | 6/1996 |
| EP | 1043312 | 10/2000 |
| EP | 1 283 039 | 2/2003 |
| EP | 1 577 294 | 9/2005 |
| EP | 1 942 105 | 7/2008 |
| EP | 1942105 | 7/2008 |
| EP | 2147914 | 1/2010 |
| EP | 2151435 | 2/2010 |
| EP | 2 233 474 | 9/2010 |
| EP | 2 305 672 | 4/2011 |
| EP | 2332943 | 6/2011 |
| EP | 2 360 155 | 8/2011 |
| EP | 2415756 | 2/2012 |
| GB | 1001093 | 8/1965 |
| GB | 140144 | 2/1980 |
| JP | 62-120374 | 6/1987 |
| JP | 8-231521 | 9/1996 |
| JP | 9-067355 | 3/1997 |
| JP | 10-505862 | 6/1998 |
| JP | 11-349572 | 12/1999 |
| JP | 2005-509651 | 4/2004 |
| JP | 2004-149429 | 5/2004 |
| JP | 2005-517634 | 6/2005 |
| JP | 2005-526005 | 9/2005 |
| JP | 2005-531520 | 10/2005 |
| JP | 2006-519758 | 8/2006 |
| JP | 2009-051828 | 3/2009 |
| JP | 2009-520685 | 5/2009 |
| WO | WO 94/12165 | 6/1994 |
| WO | WO 95/09619 | 4/1995 |
| WO | WO 96/09286 | 3/1996 |
| WO | WO 96/14842 | 5/1996 |
| WO | WO 96/18608 | 6/1996 |
| WO | WO 97/07098 | 2/1997 |
| WO | 97/14686 | 4/1997 |
| WO | 97/38977 | 10/1997 |
| WO | 99/18960 | 4/1999 |
| WO | 00/00200 | 1/2000 |
| WO | WO 01/19788 | 3/2001 |
| WO | WO 01/78709 | 10/2001 |
| WO | WO 01/87293 | 11/2001 |
| WO | 02/062766 | 8/2002 |
| WO | 02/088101 | 11/2002 |
| WO | WO 02/096897 | 12/2002 |
| WO | 2003/040096 | 5/2003 |
| WO | WO 03/039446 | 5/2003 |
| WO | WO 03/040115 | 5/2003 |
| WO | WO 03/040142 | 5/2003 |
| WO | WO 03/082191 | 10/2003 |
| WO | 2004/009549 | 1/2004 |
| WO | WO 2004/014843 | 2/2004 |
| WO | 2004/031154 | 4/2004 |
| WO | 2004/039404 | 5/2004 |
| WO | WO 2004/043916 | 5/2004 |
| WO | WO 2004/096795 | 11/2004 |
| WO | WO 2005/014555 | 2/2005 |
| WO | WO 2005/032493 | 4/2005 |
| WO | WO 2005/058311 | 6/2005 |
| WO | WO 2005/097767 | 10/2005 |
| WO | WO 2005/111031 | 11/2005 |
| WO | 2005/121100 | 12/2005 |
| WO | 2006/009655 | 1/2006 |
| WO | 2006/023750 | 3/2006 |
| WO | 2006/029850 | 3/2006 |
| WO | WO 2006/041404 | 4/2006 |
| WO | WO 2006/041405 | 4/2006 |
| WO | WO 2006/065204 | 6/2006 |
| WO | WO 2006/065277 | 6/2006 |
| WO | 2006/076284 | 7/2006 |
| WO | WO 2006/138192 | 12/2006 |
| WO | WO 2006/138217 | 12/2006 |
| WO | WO 2006/138265 | 12/2006 |
| WO | WO 2006/138304 | 12/2006 |
| WO | 2007/002220 | 1/2007 |
| WO | WO 2007/005366 | 1/2007 |
| WO | WO 2007/005404 | 1/2007 |
| WO | WO 2007/016012 | 2/2007 |
| WO | WO 2007/038271 | 4/2007 |
| WO | WO 2007/049532 | 5/2007 |
| WO | WO 2007/058580 | 5/2007 |
| WO | WO 2007/058582 | 5/2007 |
| WO | WO 2007/058583 | 5/2007 |
| WO | WO 2007/058601 | 5/2007 |
| WO | WO 2007/058602 | 5/2007 |
| WO | WO 2007049532 A1 * | 5/2007 |
| WO | WO 2007/073284 | 6/2007 |
| WO | WO 2007/078813 | 7/2007 |
| WO | 2007/092846 | 8/2007 |
| WO | 2007/092854 | 8/2007 |
| WO | WO 2007/114771 | 10/2007 |
| WO | WO 2007/120096 | 10/2007 |
| WO | WO 2007/146225 | 12/2007 |
| WO | WO 2008/011560 | 1/2008 |
| WO | 2008/022024 | 2/2008 |
| WO | 2008/073365 | 6/2008 |
| WO | WO 2008/073370 | 6/2008 |
| WO | WO 2008/103351 | 8/2008 |
| WO | WO 2008/133273 | 11/2008 |
| WO | WO 2008/133274 | 11/2008 |
| WO | WO 2009/010454 | 1/2009 |
| WO | 2009/064418 | 5/2009 |
| WO | 2009/097278 | 8/2009 |
| WO | 2009/097401 | 8/2009 |
| WO | 2009/097578 | 8/2009 |
| WO | 2009/103626 | 8/2009 |
| WO | 2009/131974 | 10/2009 |
| WO | 2009/131975 | 10/2009 |
| WO | WO 2009/134617 | 11/2009 |
| WO | WO 2009/151098 | 12/2009 |
| WO | 2010/019392 | 2/2010 |
| WO | 2010/019393 | 2/2010 |
| WO | WO 2010/013302 | 2/2010 |
| WO | WO 2010/013794 | 2/2010 |
| WO | WO 2010/047372 | 4/2010 |
| WO | 2010/056194 | 5/2010 |
| WO | 2010/056195 | 5/2010 |
| WO | 2010/056196 | 5/2010 |
| WO | WO 2010/113848 | 10/2010 |
| WO | 2010/129864 | 11/2010 |
| WO | WO 2010/128058 | 11/2010 |
| WO | WO 2011/005738 | 1/2011 |
| WO | WO 2011/009897 | 1/2011 |
| WO | WO 2011/009898 | 1/2011 |
| WO | WO 2011/009943 | 1/2011 |
| WO | WO 2011/020806 | 2/2011 |
| WO | WO 2011/029803 | 3/2011 |
| WO | WO 2011/044181 | 4/2011 |
| WO | WO 2011/044184 | 4/2011 |
| WO | WO 2011/044185 | 4/2011 |
| WO | WO 2011/044187 | 4/2011 |
| WO | 2011/060207 | 5/2011 |
| WO | WO 2011/058763 | 5/2011 |
| WO | WO 2011/069934 | 6/2011 |

| WO | WO 2011/070029 | 6/2011 |
| WO | WO 2011/070781 | 6/2011 |
| WO | WO 2011/071057 | 6/2011 |
| WO | WO 2011/071109 | 6/2011 |
| WO | WO 2011/071135 | 6/2011 |
| WO | WO 2011/077726 | 6/2011 |
| WO | WO 2011/080176 | 7/2011 |
| WO | 2011/138293 | 11/2011 |
| WO | 2011/154431 | 12/2011 |
| WO | WO 2011/154374 | 12/2011 |
| WO | 2012/006953 | 1/2012 |
| WO | WO 2012/000933 | 1/2012 |
| WO | WO 2012/019966 | 2/2012 |
| WO | 2012/038438 | 3/2012 |
| WO | 2012/057247 | 5/2012 |
| WO | 2012/057248 | 5/2012 |
| WO | 2012/085038 | 6/2012 |
| WO | 2012/093148 | 7/2012 |
| WO | 2012/098064 | 7/2012 |
| WO | 2012/098213 | 7/2012 |
| WO | 2012/098461 | 7/2012 |
| WO | 2012/104263 | 8/2012 |
| WO | 2012/107371 | 8/2012 |
| WO | 2012/110440 | 8/2012 |
| WO | 2012/110441 | 8/2012 |
| WO | 2012/110459 | 8/2012 |
| WO | 2012/117027 | 9/2012 |
| WO | 2012/120023 | 9/2012 |
| WO | 2012/126791 | 9/2012 |
| WO | 2012/136603 | 10/2012 |
| WO | 2012/139993 | 10/2012 |
| WO | 2012/147762 | 11/2012 |
| WO | 2012/147763 | 11/2012 |
| WO | 2012/156284 | 11/2012 |
| WO | 2012/162330 | 11/2012 |
| WO | 2012/162334 | 11/2012 |
| WO | 2012/163790 | 12/2012 |
| WO | 2012/168164 | 12/2012 |
| WO | 2012/168175 | 12/2012 |

OTHER PUBLICATIONS

Gavezzotti, "Are Crystal Structures Predictable?" Accounts of Chemical Research, vol. 27, pp. 309-314 (1994).*

Edwards, et al., "Application of Fragment-Based Lead Generation to the Discovery of Novel, Cyclic Amidine β-Secretase Inhibitors with Nanomolar Potency, Cellular Activity, and High Ligand Efficiency", Journal of Medicinal Chemistry, vol. 50, No. 24, 2007, pp. 5912-5925.

Kuo, et al., "A Synthesis of Estrone via Novel Intermediates. Mechanism of the Coupling Reaction of a Vinyl Carbinol with a β Diketone", The Journal of Organic Chemistry, vol. 33, No. 8, Aug. 1968, pp. 3126-3132.

Cohen, et al., "Synthesis of 2-Amino-5,6-dihydro-4,H-1,3-thiazines and Related Compounds by Acid Catalyzed Cyclizationof Allylic Isothiuronium Salts", Journal of Heterocyclic Chemistry, vol. 14, 1977, pp. 717-723.

Hünig, et al., "Azofarbstoffe Durch Oxydative Kupplung, XVIII. Synthese von-3-substituierten Thiazolon-(2)-hydrazonen and Thiazolon-(2)-benzolsulfonylhydrazonen", European Journal of Organic Chemistry, vol. 647, No. 1, May, 1961, pp. 66-76.

Schaumann, et al., "Cycloadditionsreaktionen von Heterokumulenen, XXIII. Stickstoffhaltige Fünfring-Heterocyclen aus Carbodiimiden oder Keteniminen mit 3-Dimethylamino-2H-azirinen", Liebigs Ann. Chem., 1981, pp. 290-305.

Cambie, et al., "vic-Iodothiocyanates and Iodoisothiocyanates. Part 2. New Syntheses of Thiazolidin-2-ones and 2-Amino-2-thiazolines", Journal of the Chemical Society, Perkin Transactions I, No. 3, 1979, pp. 765-770.

Fernández, et al., "Syntheses of β-iodourea derivatives of carbohydrates and glycosylamino-oxazolines", Carbohydrate Research, vol. 216, 1991, pp. 21-32.

Fernández, et al., "Syntheses and Spectral Properties of β-Iodoureas and 2-Amino-4,4-diphenyl-2-oxazolines", Journal of Heterocyclic Chemistry, vol. 28, 1991, pp. 777-780.

Liebscher, et al., "2-Arylimino-3-Thiazolines—Formation of Unusual Tautomers of 2-Arylamino-Thiazolines—a Revision", Tetrahedron Letters, vol. 26, No. 35, 1985, pp. 4179-4180.

Koriyama et al., "Reversal of diastereofacial selectivity in the nucleophilic addition reaction to chiral N-sulfinimine and application to the synthesis of indrizidine 223AB," Tetrahedron, vol. 58, 2002, pp. 9621-9628.

Fujisawa et al., "Switchover of diastereofacial selectivity in the condensation reaction of optically active N-sulfinimine with ester enolate," Tetrahedron Letters, vol. 37, No. 22, 1996, pp. 3881-3884.

Vilaivan et al., "Recent Advances in Catalytic Asymmetric Addition to Imines and Related C=N Systems," Current Organic Chemistry, vol. 9, 2005, pp. 1315-1392.

Hua et al., "N-Alkylidenesulfinamides," Sulfur Reports, vol. 21, 1999, pp. 211-239.

Savoca et al., "1,5-Diazabicyclo[4.3.0]non-5-ene[1]," Encyclopedia of Reagents for Organic Synthesis, 2006, 10 pages total.

Creeke et al., "Synthesis and elaboration of heterocycles via iodocyclisation of unsaturated thioureas," Tetrahedron Letters, 1989, vol. 30, No. 33, pp. 4435-4438.

Mellor et al.,"A general route to spirocycles by radical additions to exocyclic unsaturated sulphides and related compounds," Tetrahedron Letters, 1991, vol. 32, No. 48, pp. 7111-7114.

Murai et al., "Iodo-cyclization of N-homoallyl thioamides leading to 2,4-diaryl-5,6-dihydro-4H-1,3-thiazines," Chemistry Letters, 2004, vol. 33, No. 5, pp. 508-509.

Singh et al., "Synthesis of heterocyclic compounds via enamines. Part 8.[†]Acid-catalysed transformations in a 4,4,6-trimethyl-1,4-dihydropyrimidine-2(3H)-thione derivatives and related compounds," J. Chem. Soc., Perkin Trans. 1, 1980, pp. 1013-1018.

Kondrat'eva et al., "Noncyclic dimer of 4-methyl-2-dimethlaminoooxazole," Izvestiya Akademii Nauk SSSR, Seriya Khimicheskaya, No. 7, Jul. 1977, pp. 1680-1682 (with English translation).

Database Registry [Online], Chemical Abstracts Service, Columbus, Ohio, US; May 29, 2007, "2H-Indol-2-ome,4-(-2-amino-5,6-dihydro-4-methyl-4H-1,3-dihydro-", XP002646872, Database accession No. 935998-84-8.

Schubert et al., "Neue synthesen von 2-Amino-5,6-dihydro-4H-1,3-thiazinen," Archiv der Pharmazie, 1968, vol. 301, No. 10, pp. 750-762.

Co-pending U.S. Appl. No. 13/260,103, entitled Isothiourea Derivatives or Isourea Derivatives Having Bace1 Inhibitory Activity, filed Sep. 23, 2011.

Huang et al., "Pharmacophore model construction of β-secretase inhibitors," 2008, Acta Chimica Sinica, vol. 66, No. 16, pp. 1889-1897 (English language abstract provided).

Clark, et al., "Antitumor Imidazotetrazines. 32.[1] Synthesis of Novel Imidazotetrazinones and Related Bicyclic Heterocycles to Probe the Mode of Action of the Antitumor Drug Temozolomide", J. Med. Chem., vol. 38, 1995, pp. 1493-1504.

Congreve, et al., "Application of Fragment Screening by X-ray Crystallography to the Discovery of Aminopyridines as Inhibitors of β-Secretase", J. Med. Chem., vol. 50, 2007, pp. 1124-1132.

Huang, et al., "Progress in the Development of Nonpeptidomimetic BACE 1 Inhibitors for Alzheimer's Disease", Current Medicinal Chemistry, vol. 16, 2009, pp. 1806-1820.

Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 2003, vol. 11, pp. 4189-4206.

Siddiqui et al., "Some extensions of Von Bruan (BrCN) reaction on organic bases," Proc. Pakistan Acad. Sci., 1988, vol. 25, No. 3, pp. 231-240.

Ozawa et al., Pharmacological actions of 2-Aminoethylisothiuronium (AET) derivatives. I[1)], Yakugaku Zasshi, 1968, vol. 88, No. 2, pp. 156-162 (English language abstract provided).

Curtis et al., The byozynsethis of Phenols. Part VIII. The synthesis of (2-carboxy-3,5-dihydroxyphynyl)propan-2-one(C-acetyl-o-orsellinic acid). Journal of the Chemical Society, 1964, pp. 5382-5385.

Burton et al., "Addition reactions of quinones. Part I. The reaction of cysteine and thiourea and its derivatives with some quinones," Journal of the Chemical Society, 1952, pp. 2193-2196.

Matsui, "Yomo bochuzai no kenkyu (the 6th report) Kagaku kozo to yomo shokugai boshi koka tono kankei (III)," Journal of Synthetic Organic Chemistry, Japan, 1950, vol. 8, No. 10, pp. Ho61-Ho65 (and International Search Report issued in PCT/JP2010/055528, which corresponds to co-pending U.S. Appl. No. 13/260,103).

Desai et al., "The condensation of thiocarbamides with monochloroacetic acide and the conversion of arylformamidinethiolacetic acids into pseudothiohydantoin derivatives," Recuil des Travaux Chimiques des Pays-Bas et de la Belgique, 1935, pp. 118-121.

Cole et al., "Acylguanidines as small-molecule beta-secretase inhibitors," J. Med. Chem., 2006, pp. 6158-6161.

STN a the Web, RN 79005-45-1, 1964.

Zhu et al. "Two Novel Diasteroselective Three-Component Reactions of Alkenes or 3, 4,-Dihydro-(2H)-pyran with Urea/Thiourea-Aldehyde Mixtures: [4+2] Cycloadditional vs Biginelli-Type Reaction". *Organic Letters*, vol. 8, No. 12, pp. 2599-2602 (2006).

Co-pending U.S. Appl. No. 13/508,899, entitled Aminothiazine or Aminooxazine Derivative Having Amino Linker, filed May 9, 2012.

Co-pending U.S. Appl. No. 13/513,839, entitled Oxazine Derivatives, filed Jun. 4, 2012.

Co-pending U.S. Appl. No. 13/514,516, entitled Substituted Aminothiazine Derivative, filed Jun. 7, 2012.

Co-pending U.S. Appl. No. 13/518285, entitled 4-Amino-1,3-Thiazine or Oxazine Derivative, filed Jun. 21, 2012.

Co-pending U.S. Appl. No. 13/514,907, entitled Fused Heterocyclic Compound Having Amino Group, filed Jun. 8, 2012.

Bol'but et al., "Heterocyclizations of Functionalized Heterocumulenes with C,N- and C,O-Dinucleophiles: III.* Cyclization of N-(1-Aryl-1-chloro-2,2,2-trifluoroethyl)-N'-arylcarbodiimides with 3-Substituted 1-Phenylpyrazol-5-ones" Russian Journal of Organic Chemistry, 2003, vol. 39, No. 12, pp. 1789-1791.

Trepanier et al., "Synthesis and screening for antidepressant activity of some aminoindanooxazolines, aminoindanooxazines, and aminoacenaphthoxazolines," Journal of Medicinal Chemistry, 1970, vol. 13, No. 4, pp. 729-733.

Sayed et al., "α-Enones in heterocyclic synthesis of indazole, thiazine, chromene and quinolone derivatives with their antimicrobial activities" Journal of Chemical Research, 2009, vol. 12, pp. 726-728.

Database Caplus [Online] Chemical Abstracts Service, Columbus, Ohio, US; Xu, Yungen et al: "Preparation of benzimidazolyl and benzothiazolyl isothiourea derivatives as nitric oxide synthase inhibitors", XP002679913, retrieved from STN Database accession No. 2005:46620 *abstract* Accessed Jul. 13, 2012.

Bol'but et al., "Synthesis of 4-imino-2-trifluoromethyl-3,4-dihydro-2h-Benzo-[1,3]Thiazines" Chemistry of Heterocyclic Compounds, 2001, vol. 37, No. 4, pp. 522-523.

Vovk et al., "Intramolecular thermal cyclization of N-(1-Aryl-1-aryloxy-2,2,2-trifluoroethyl)-N'-arylcarbodiimides" Russian Journal of Organic Chemistry, 2000, vol. 36, No. 12, pp. 1739-1742.

Vovk et al., "Regioselective cyclization of 1-chloroalkylcarbodiimides with 1,1- and 1,2-bifunctional nucleophilic reagents" Russian Journal of Organic Chemistry, 1997, vol. 33, No. 1, pp. 96-102.

Potts et al., "N-Acyl-β-enamino Ketones: Versatile Heterocyclic Synthons" J. Org. Chem., 1983, 48, pp. 623-625.

Rivkin et al., "Piperazinyl pyrimidine derivatives as potent γ-secretase modulators" Bioorganic & Medicinal Chemistry Letters, 2010, 20, pp. 1269-1271.

Rivkin et al., "Purine derivatives as potent γ-secretase modulators" Bioorganic & Medicinal Chemistry Letters, 2010, 20, pp. 2279-2282.

Calabrese et al. "NO Synthase and NO-Dependent Signal Pathways in Brain Aging and Neurodegenerative Disorders: The Role of Oxidant/Antioxidant Balance". *Neurochemical Balance*, vol. 25, No. 9/10, pp. 1315-1341 (2000).

Kavya et al. "Nitric oxide synthase regulation and diversity: Implications in Parkinson's Disease". *Nitric Oxide: Biology and Chemistry*, vol. 15, No. 4, pp. 280-294 (2006).

Chiou et al. "Review: Effects of Nitric Oxide on Eye Diseases and Their Treatment". *Journal of Ocular Pharmacology and Therapeutics*, vol. 17, No. 2, pp. 189-198 (2001).

Ishii et al. "Subacute NO generation induced by Alzheimer's β-amyloid in the living brain: reversal by inhibition of the inducible NO synthase". *The Federation of American Societies for Experimental Biology Journal*, vol. 14, pp. 1485-1489 (2000).

Pak et al. "Morphine via nitric oxide modulates β-amyloid metabolism: a novel protective mechanism for Alzheimer's disease". *Medical Science Monitor*, vol. 11, No. 10, pp. BR357-BR366 (2005).

Vippagunta et al. "Crystalline Solids". Advanced Drug Delivery Reviews, vol. 48, 2001, pp. 3-26.

Gavezzotti. "Are Crystal Structures Predictable". Accounts of Chemical Research, vol. 27, 1994, pp. 309-314.

Kiselyov et al., "Design and chemical synthesis of [1,2,4]triazol[1,5-c]pyrimidin-5-yl amines, a novel class of VEGFR-2 kinase inhibitors," 2009, Tetrahedron Letters, vol. 50, pp. 3809-3812.

Mulcahy et al., "A stereoselective synthesis of (+)-Gonyautoxin 3," Journal of the American Chemical Society, 2008, vol. 130, pp. 12630-12631.

"Diphenyl Cyanocarbonimidate," e-EROS Encyclopedia of Reagents for Organic Synthesis, 2001, 2 pages total.

Shafik et al., "Synthesis of novel 2-[2-(substituted amino)phenethyl]-1H-benzimidazoles; 3,4-dihydro and 1,2,3,4-tetrahydropyrimido[1,6-a]-benzimidazoles as potential antiulcer agents," 2004, Pharmazie, vol. 59, No. 12, pp. 899-905.

Pohl et al., "Synthesis of partially saturated condensed triazoles by reaction of ω-Aminoalkyl-1,2,4-triazoles with electrophiles," Journal fuer Praktische Chemie Chemiker-Zeitung, 1992, vol. 334, pp. 630-636.

Buschauer et al., "Isohistamine und Homologe als Bausteine von H2-Antagonisten,"Arzneimittel-Forschung, 1985, vol. 35, pp. 1025-1029 (English language abstract provided).

Buschauer et al., "7,8-Dihydroimidazo[1,2-c]pyrimidin-5(6H)-one, -5(6H)-thione and -5(6H)-ylidencyanamide," Chemische Berichte, 1984, vol. 117, pp. 2597-2614.

Borchers et al., "H2-Antihystaminika, 19. Mitt.[1)] Syntheses und H2-antihistaminische Wirkung N$^{\alpha}$-substituierter Histamine," Archiv der Pharmazie (Weinheim, Germany), 1984, vol. 317, pp. 455-459.

Cheong et al., "Pharmacophore elucidation for a new series of 2-aryl-pyrazolo-triazolo-pyrimidines as potent human $A_3$ adenosine receptor antagonists," Bioorganic & Medicinal Chemistry Letters, 2011, vol. 21, pp. 2898-2905.

Xu et al., "Copper-catalyzed cascade synthesis of benzimidazoquinazoline derivatives under mild condition," Chemical Communications, 2011, vol. 47, pp. 5596-5598.

Kishore et al., "QSAR of adenosine receptor antagonists: exploring physicochemical requirements for binding of pyrazolo[4,3-e]-1,2,4-triazolo[1,5- c]pyrimidine derivatives with human adenosine $A_3$ receptor subtype," Bioorganic & Medicinal Chemistry Letters, 2011, vol. 21, No. 2, pp. 818-823.

Dolzhenko et al., "8-methyl-2-[4-(trifluoromethyl)phenyl]-8 H-pyrazolo[4,3-e][1,2,4]triazolo[1,5-c]-pyrimidin-5-amine methanol disolvate," Acta Crystallographica, Section E: Structure Reports Online, E66(7), 12 pages, Jun. 23, 2010.

Beaton et al., "3,4-dihydro-1-isoquinolinamines: a novel class of nitric oxide synthase inhibitors with a range of isoform selectivity and potency," Bioorganic & Medicinal Chemistry Letters, 2001, vol. 11, pp. 1023-1026.

Beaton et al., "The synthesis of 1-aminodihydroisoquinolines by an imine addition cyclisation reaction," 1998, Tetrahedron Letters, vol. 39, pp. 1227-1230.

Tian et al., "Radiosynthesis of 8-Fluoro-3-(4-[$^{18}$F]Fluorophenyl)-3,4-Dihydro-1-Isoquinolinamine ([$^{18}$F]FFDI), a potential PET radiotracer for the inducible nitric oxide synthase," 2008, Current Radiopharmaceuticals, vol. 1, pp. 49-53.

Weinhardt et al. "Synthesis and antidepressant profiles of phenyl-substituted 2-amino- and 2-((alkoxycarbonyl)amino)11,4,5,6-tetrahydropyrimidines," Journal of Medicinal Chemistry, vol. 28, No. 6, 1985, pp. 694-698.

Meschino et al., "2-Amino-5,6-dihydro-1,3-oxazines. The reduction of carboxylic esters with sodium borohydride," J. Org. Chem., vol. 28, 1963, pp. 3129-3134.

Poos et al., "2-amino-5-aryl-2-oxazolines. Potent new anorectic agent," J. Med. Chem., vol. 6, 1963, pp. 266-272.

Sandin et al., "A fast and parallel route to cyclic isothioureas and guanidines with use of microwave-assisted chemistry," J. Org. Chem., vol. 69, 2004, pp. 1571-1580.

Weinhardt et al., "Synthesis and central nervous system propreties of 2-[(Alkoxycarbonyl)amino]-4(5)-phenyl-2-imidazolines," Journal of Medicinal Chemistry, vol. 27, No. 5, 1984, pp. 616-627.

Woodgate et al., "A new synthesis of 2-amino-2-thiazolines," Heterocycles, vol. 7, No. 1, 1977, pp. 109-112.

Co-pending U.S. Appl. No. 13/881,112, entitled Fused Aminodihydropyrimidine Derivative, filed Apr. 23, 2013.

Co-pending U.S. Appl. No. 13/881,250, entitled Naphthyridine Derivative, filed Apr. 24, 2013.

* cited by examiner

AMINODIHYDROTHIAZINE DERIVATIVES SUBSTITUTED WITH A CYCLIC GROUP

This application is a Divisional of application Ser. No. 12/596,796, filed Dec. 3, 2009, which is a National Stage Application of PCT/JP2008/057847, filed Apr. 23, 2008, which applications are incorporated herein by reference.

TECHNICAL FIELD

This invention relates to a compound having an inhibitory activity against production of amyloid β protein and useful for treating diseases induced by production, secretion and/or deposition of amyloid β protein.

BACKGROUND ART

In the brain of Alzheimer's patient many insoluble spots (senile plaque) are found, which is formed by extraneuronal accumulation of a peptide called amyloid β protein comprised of about 40 amino acids. Neuronal death caused by the senile plaque is considered to develop Alzheimer's Disease and an enhancer of amyloid β protein decomposition or vaccine of amyloid β protein etc. are extensively studied as a remedy for Alzheimer's Disease.

Secretase is an enzyme producing amyloid β protein by intracellular cleavage of a protein called amyloid β protein precursor (APP). An enzyme playing a role for producing an N-terminal of the amyloid β protein is called BACE1 (beta-site APP-cleaving enzyme) and an inhibitor of the BACE1, which will reduce production of amyloid β protein, could be a remedy for treating Alzheimer's disease.

Patent literature 1 discloses a compound with a chemical structure similar to that of the compound of the present invention, having an inhibitory activity of NO synthetase and effective for treating dementia.

Patent literature 2-5 and non-patent literature 1-2 disclose compounds with a chemical structure similar to those of the compound of the present invention, and describe that each compound is useful as an anti-hypotensive agent, morphine-like analgesic or tranquilizer, intermediate of a therapeutic agent, NPYY5 antagonist, analgesic and the like.

Patent literatures 6-14 disclose BACE-1 inhibitors having a chemical structure different from that of the compound of the present invention. Also, patent literature 15 discloses a BACE-1 inhibitor.

Patent literature 1: WO 96/014842 Pamphlet
Patent literature 2: U.S. Pat. No. 3,235,551
Patent literature 3: U.S. Pat. No. 3,227,713
Patent literature 4: JP H09-067355
Patent literature 5: WO 2005/111031 Pamphlet
Patent literature 6: WO 02/96897 Pamphlet
Patent literature 7: WO 04/043916 Pamphlet
Patent literature 8: WO 2005/058311 Pamphlet
Patent literature 9: WO 2005/097767 Pamphlet
Patent literature 10: WO 2006/041404 Pamphlet
Patent literature 11: WO 2006/041405 Pamphlet
Patent literature 12: US 2007/0004786A
Patent literature 13: US 2007/0004730A
Patent literature 14: US 2007/27199A
Patent literature 15: WO 2007/049532 Pamphlet
Non-patent literature 1: Journal of Heterocyclic Chemistry, 14, 717-723 (1977)
Non-patent literature 2: Journal of Organic Chemistry, 33 (8), 3126-3132 (1968).

DISCLOSURE OF INVENTION

Problem to be Solved

This invention provides with a compound having an inhibitory activity against BACE-1 and useful for treating diseases induced by production, secretion and/or deposition of amyloid β protein.

Means to Solve the Problem

The present invention provides with
1) a compound of the formula (I):

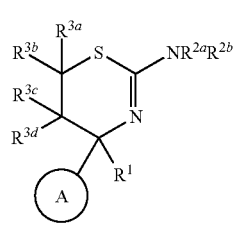

wherein the ring A is an optionally substituted carbocyclic group or an optionally substituted heterocyclic group.
$R^1$ is optionally substituted lower alkyl, optionally substituted lower alkenyl, optionally substituted lower alkynyl, an optionally substituted carbocyclic group or an optionally substituted heterocyclic group,
$R^{2a}$ and $R^{2b}$ are each independently hydrogen, optionally substituted lower alkyl or optionally substituted acyl,
$R^{3a}$, $R^{3b}$, $R^{3c}$ and $R^{3d}$ are each independently hydrogen, halogen, hydroxy, optionally substituted lower alkyl, optionally substituted lower alkenyl, optionally substituted acyl, optionally substituted lower alkoxy, optionally substituted carbocyclyl lower alkyl, optionally substituted heterocyclyl lower alkyl, optionally substituted carbocyclyl lower alkoxy, optionally substituted heterocyclyl lower alkoxy, optionally substituted aralkyl, optionally substituted heteroaralkyl, optionally substituted aralkyloxy, optionally substituted heteroaralkyloxy, optionally substituted lower alkylthio, carboxy, optionally substituted lower alkoxycarbonyl, optionally substituted amino, optionally substituted carbamoyl, an optionally substituted carbocyclic group or an optionally substituted heterocyclic group, or $R^{3a}$ and $R^{3b}$ or $R^{3c}$ and $R^{3d}$ may form a carbocyclic ring together with a linked carbon atom or may form oxo,
provided the following compounds i) and ii) are excluded;
i) a compound in which $R^{2a}$ is hydrogen, $R^{2b}$ is hydrogen, acetyl or phenyl, $R^1$ is methyl, and the ring A is phenyl or 4-methoxyphenyl;
ii) a compound in which $R^{2a}$ is hydrogen, $R^{2b}$ is hydrogen, acetyl or phenyl, $R^1$ is ethyl and the ring A is 3,4-dimethoxyphenyl,
a pharmaceutically acceptable salt or solvate thereof;
1') a compound of the formula (I):

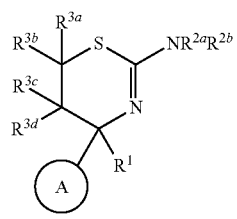

wherein the ring A is an optionally substituted carbocyclic group or an optionally substituted heterocyclic group, $R^1$ is optionally substituted lower alkyl, optionally substituted lower alkenyl, optionally substituted lower alkynyl, an optionally substituted carbocyclic group or an optionally substituted heterocyclic group, $R^{2a}$ and $R^{2b}$ are each independently hydrogen, optionally substituted lower alkyl or optionally substituted acyl, $R^{3a}$, $R^{3b}$, $R^{3c}$ and $R^{3d}$ are each independently hydrogen, halogen, hydroxy, optionally substituted lower alkyl, optionally substituted lower alkenyl, optionally substituted acyl, optionally substituted lower alkoxy, optionally substituted lower alkylthio, carboxy, optionally substituted lower alkoxycarbonyl, optionally substituted amino, optionally substituted carbamoyl, an optionally substituted carbocyclic group or an optionally substituted heterocyclic group, or $R^{3a}$ and $R^{3b}$ or $R^{3c}$ and $R^{3d}$ may form a carbocyclic ring together with a linked carbon atom, provided the following compounds i) and ii) are excluded:

i) a compound in which $R^{2a}$ is hydrogen, $R^{2b}$ is hydrogen, acetyl or phenyl, $R^1$ is methyl, and the ring A is phenyl or 4-methoxyphenyl;

ii) a compound in which $R^{2a}$ is hydrogen, $R^{2b}$ is hydrogen, acetyl or phenyl, $R^1$ is ethyl and the ring A is 3,4-dimethoxyphenyl, a pharmaceutically acceptable salt or solvate thereof;

2) the compound of 1) or 1') described above,
wherein the ring A is

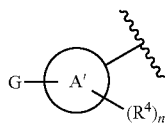

wherein the ring A' is a carbocyclic group or a heterocyclic group,
G is

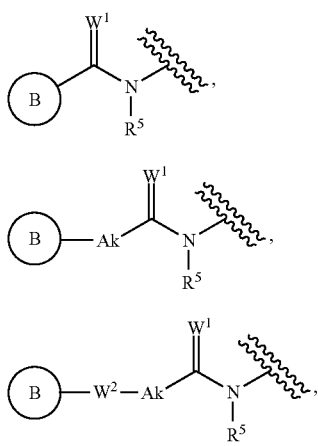

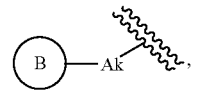 (x')

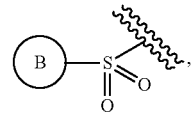 (xiii')

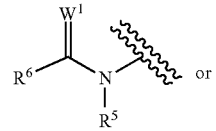 (xiv')

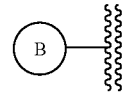 (xixi')

wherein $R^5$ is hydrogen, lower alkyl or acyl,
$R^6$ is optionally substituted lower alkyl, optionally substituted lower alkenyl or optionally substituted lower alkynyl,
$W^1$ is O or S,
$W^2$ is O, S or $NR^5$,
Ak is optionally substituted lower alkylene, optionally substituted lower alkenylene or optionally substituted lower alkynylene,
the ring B is an optionally substituted carbocyclic group or an optionally substituted heterocyclic group and each $R^5$ may be independent:

$R^4$ is halogen, hydroxyl, mercapto, halogeno lower alkyl, lower alkoxy, amino, lower alkylamino, acylamino or lower alkylthio and each $R^4$ may be independent;

A pharmaceutically acceptable salt or solvate thereof;

2') the compound of 1) or 1') described above
wherein the ring A is

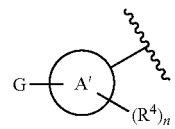

wherein the ring A' is a carbocyclic group or a heterocyclic group,
G is

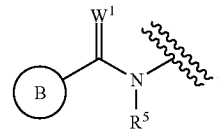 (ii')

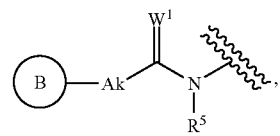 (ii")

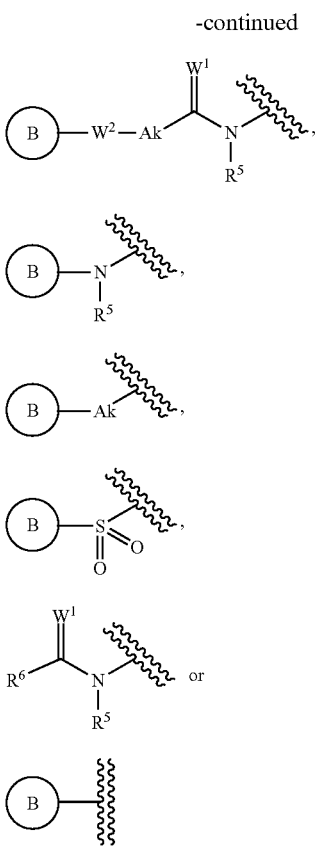

wherein R⁵ is hydrogen, lower alkyl or acyl,
R⁶ is optionally substituted lower alkyl, optionally substituted lower alkenyl or optionally substituted lower alkynyl,
W¹ is O or S,
W² is O, S or NR⁵,
Ak is optionally substituted lower alkylene, optionally substituted lower alkenylene or optionally substituted lower alkynylene,
the ring B is an optionally substituted carbocyclic group or an optionally substituted heterocyclic group and each R⁵ may be independent:
R⁴ is halogen, hydroxyl, mercapto, halogeno lower alkyl, lower alkyl, lower alkoxy, amino, lower alkylamino, acylamino or lower alkylthio and each R⁴ may be independent;
A pharmaceutically acceptable salt or solvate thereof;
3) the compound of 2) or 2') described above wherein the ring A' is phenyl or a nitrogen-containing aromatic heterocyclic group, a pharmaceutically acceptable salt or solvate thereof;
3') the compound of 2) or 2') described above wherein the ring A' is phenyl, a pharmaceutically acceptable salt or solvate thereof;
3") the compound of 2) or 2') described above wherein the ring A' is a nitrogen-containing aromatic monocyclic heterocyclic group, a pharmaceutically acceptable salt or solvate thereof;
3''') the compound of 2) or 2') described above wherein the ring A' is pyridyl, a pharmaceutically acceptable salt or solvate thereof;
4) the compound of 1)-3), 1'), 2'), 3'), 3") or 3''') described above wherein R¹ is C1-C3 alkyl, a pharmaceutically acceptable salt or solvate thereof;
4') the compound of 1)-3), 1'), 2'), 3'), 3") or 3''') described above wherein R¹ is optionally substituted lower alkynyl, a pharmaceutically acceptable salt or solvate thereof;

5) the compound of 1)-4), 1'), 2'), 3'), 3"), 3''') or 4') described above wherein R²ᵃ and R²ᵇ are both hydrogen, a pharmaceutically acceptable salt or solvate thereof;
6) the compound of 1)-5), 1'), 2'), 3'), 3"), 3''') or 4') described above wherein all of R³ᵃ, R³ᵇ, R³ᶜ and R³ᵈ are hydrogen, a pharmaceutically acceptable salt or solvate thereof;
6') the compound of 1) 5), 1'), 2'), 3'), 3"), 3''') or 4') described above wherein R³ᵃ and R³ᵇ are the same substituent selected from halogen and optionally substituted lower alkyl, a pharmaceutically acceptable salt or solvate thereof;
6") the compound of 1)-5), 1'), 2'), 3'), 3"), 3''') or 4') described above wherein R³ᶜ and R³ᵈ are the same substituent selected from halogen and optionally substituted lower alkyl, a pharmaceutically acceptable salt or solvate thereof;
6''') the compound of 1)-5), 1'), 2'), 3'), 3"), 3''') or 4') described above wherein R³ᵃ and R³ᵇ or R³ᶜ and R³ᵈ form a carbocyclic ring together with a linked carbon atom a pharmaceutically acceptable salt or solvate thereof;
7) the compound of 1)-5), 1'), 2'), 3'), 3"), 3''') 4') described above wherein R³ᶜ or R³ᵈ is optionally substituted carbocyclic ring lower alkoxy or optionally substituted heterocyclyl lower alkoxy, a pharmaceutically acceptable salt or solvate thereof;
7') the compound of 1)-5), 1'), 2'), 3'), 3"), 3''') or 4') described above wherein R³ᶜ and R³ᵈ form oxo together with a linked carbon atom, a pharmaceutically acceptable salt or solvate thereof;
8) a pharmaceutical composition comprising a compound of 1)-7), 1'), 3'), 3"), 3'''), 4') 6'), 6"), 6''') or 7') described above, a pharmaceutically acceptable salt or solvate thereof as an active ingredient; and
9) a pharmaceutical composition having a BACE 1 inhibitory activity comprising a compound of 1)-7), 1'), 2'), 3'), 3"), 3'''), 4') 6'), 6"), 6''') or 7') described above, a pharmaceutically acceptable salt or solvate thereof as an active ingredient;
The present invention also provides with
10) the pharmaceutical composition having a BACE 1 inhibitory activity of 9) described above, which is a composition having inhibitory activity of amyloid β protein production;
11) the pharmaceutical composition having a BACE 1 inhibitory activity of 9) described above, which is a medicine for treating diseases induced by production, secretion and/or deposition of amyloid β protein;
12) the pharmaceutical composition having a BACE 1 inhibitory activity of 9) described above, which is a medicine for treating Alzheimer's disease;
13) a method for treating diseases induced by production, secretion and/or deposition of amyloid β protein, characterized in administering a compound of the formula (I) described in 1) above, a pharmaceutically acceptable salt or solvate thereof;
14) use of a compound of the formula (I) described in 1) above, a pharmaceutically acceptable salt or solvate thereof described in 1) above, in manufacturing a medicine for treating diseases induced by production, secretion and/or deposition of amyloid β protein;
15) a method for treating diseases induced by BACE 1 characterized in administering a compound of the formula (I) described in 1) above, a pharmaceutically acceptable salt or solvate thereof;
16) use of a compound of the formula (I) described in 1) above, a pharmaceutically acceptable salt or solvate thereof, in manufacturing a medicine for treating diseases induced by BACE 1;

17) a method for treating Alzheimer's disease characterized in administering a compound of the formula (I) described in 1) above, a pharmaceutically acceptable salt or solvate thereof; and 18) use of a compound of the formula (I) described in 1) above, a pharmaceutically acceptable salt or solvate thereof in manufacturing a medicine for treating Alzheimer's disease.

Effect of Invention

A compound of the present invention is useful for treating diseases induced by production, secretion and/or deposition of amyloid β protein (Alzheimer's disease etc.).

BEST MODE FOR CARRYING OUT THE INVENTION

In this description, "halogen" includes fluorine, chlorine, bromine and iodine.

A moiety of halogen in "halogen lower alkyl" and "halogeno lower alkoxycarbonyl" is the same as "halogen" above.

"Lower alkyl" includes C1-C15, preferably C1-C10, more preferably C1-C6 and further more preferably C1-C3 straight or branched alkyl, and for example, methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl and n-decyl are exemplified.

A moiety of alkyl in "lower alkoxy", "halogeno lower alkyl", "hydroxyl lower alkyl", "hydroxyl lower alkoxy", "lower alkoxycarbonyl", "halogeno lower alkoxycarbonyl", "lower alkoxycarbonyl lower alkyl", "lower alkylamino", "lower alkoxy lower alkyl", "hydroxyimino lower alkyl", "lower alkoxyimino lower alkyl", "amino lower alkyl" "lower alkoxy lower alkoxy", "lower alkoxy lower alkenyl", "lower alkoxycarbonyl lower alkenyl", "lower alkoxy lower alkynyl", "lower alkoxycarbonyl lower alkynyl", "lower alkyl carbamoyl", "hydroxyl lower alkyl carbamoyl", "lower alkoxyimino", "lower alkylthio", "lower alkylsulfonyl", "lower alkylsulfonyloxy", "lower alkyl sulfamoyl", "lower alkyl sulfinyl", "carbocyclyl lower alkyl", "carbocyclyl lower alkyl", "carbocyclyl lower alkoxy", "carbocyclyl lower alkoxycarbonyl", "carbocyclyl lower alkylamino", "carbocyclyl lower alkyl carbamoyl", "cycloalkyl lower alkyl", "cycloalkyl lower alkoxy", "cycloalkyl lower alkylamino", "cycloalkyl lower alkoxycarbonyl", "cycloalkyl lower alkylcarbamoyl", "aryl lower alkyl", "aryl lower alkoxy", "aryl lower alkylamino", "aryl lower alkoxycarbonyl.", "aryl lower alkoxycarbamoyl", "heterocyclyl lower alkyl", "heterocyclyl lower alkoxy", "heterocyclyl lower alkylamino", "heterocyclyl lower alkoxycarbonyl" and "heterocyclyl lower alkylcarbamoyl" is the same as "alkyl" above.

"Optionally substituted lower alkyl" may be substituted with one or more of substituent(s) selected from a substituent group α.

Group α is a group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, imino, hydroxyimino, lower alkoxyimino, lower alkylthio, carbamoyl, lower alkylcarbamoyl, hydroxy lower alkylcarbamoyl, sulfamoyl, lower alkylsulfamoyl, lower alkylsulfonyl, cyano, nitro, a carbocyclic group and a heterocyclic group.

One or more of substituent(s) selected from the substituent group α is exemplified as a substituent of "optionally substituted lower alkoxy", "optionally substituted lower alkoxycarbonyl" and "optionally substituted lower alkylthio"

"Lower alkylidene" includes a divalent group derived from the "lower alkyl" above, and methylene, ethylidene, propylidene, isopropylidene, butylidene, pentylidene and hexylidene etc. are exemplified.

"Lower alkenyl" includes C2-C15, preferably C2-C10, more preferably C2-C6 and further more preferably C2-C4 straight or branched alkenyl having one or more double bond(s) at any position thereof. Examples of lower alkenyl include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

"Lower alkynyl" includes C2-C10, preferably C2-C8, more preferably C3-C6 straight or branched alkynyl having one or more triple bond(s) at any position thereof. Examples of lower alkynyl include ethynyl, propynyl, butynyl, pentynyl, hexynyl, heptynyl, octynyl, nonynyl, decynyl and the like. Lower alkynyl may additionally have a double bond at any position thereof.

One or more of substituent(s) selected from the substituent group α is exemplified as a substituent of "optionally substituted lower alkenyl" and "optionally substituted lower alkynyl".

A moiety of lower alkenyl in "hydroxyl lower alkenyl", "lower alkoxy lower alkenyl", "lower alkoxycarbonyl lower alkenyl", "carbocyclyl lower alkenyl", "lower alkenyloxy", "lower alkenylthio" and "lower alkenylamino" is the same as that of "lower alkenyl".

A moiety of lower alkynyl in "hydroxyl lower alkynyl", "lower alkoxy lower alkynyl", "lower alkoxycarbonyl lower alkynyl", "carbocyclyl lower alkynyl", "lower alkynyloxy", "lower alkenylamino" and "lower alkynylamino" is the same as that of "lower alkynyl" above.

One or more substituents selected from lower alkyl, acyl, hydroxyl, lower alkoxy, lower alkoxycarbonyl, a carbocyclic group and a heterocyclic group etc. is exemplified as a substituent of "optionally substituted amino" and "optionally substituted carbamoyl".

"Acyl" includes C1-C10 aliphatic acyl, carbocyclyl carbonyl and heterocyclic carbonyl, and examples of acyl include formyl, acetyl, propionyl, butyryl, isobutyryl, pivaloyl, hexanoyl, acryloyl, propioloyl, methacryloyl, crotonoyl, benzoyl, cyclohexanecarbonyl, pyridinecarbonyl, furancarbonyl, thiophenecarbonyl, benzothiazolecarbonyl, pyrazinecarbonyl, piperidinecarbonyl, thiomorpholino and the like.

A moiety of acyl in "acylamino" and "acyloxy" is the same as described above.

One or more substituents selected from the substituent group α is exemplified as a substituent in "optionally substituted acyl" and a moiety of the ring in carbocyclyl carbonyl and heterocyclylcarbonyl is optionally substituted with one or more substituent(s) selected from lower alkyl, the substituent group α and lower alkyl substituted with one or more substituent(s) selected from the substituent group α.

"A carbocyclic group" includes cycloalkyl, cycloalkenyl, aryl, and non-aromatic fused carbocyclic group etc.

"Cycloalkyl" includes C3-C10, preferably C3-C8 and more preferably C4-C8 carbocyclic group and examples of cycloalkyl include cyclopropyl, cyclobutyl, cyclopentyl cyclohexyl, cycloheptyl, cyclooctyl, cyclononyl, cyclodecyl and the like.

A moiety of cycloalkyl in "cycloalkyl lower alkyl", "cycloalkyloxy", "cycloalkyl lower alkoxy", "cycloalkylthio", "cycloalkylamino", "cycloalkyl lower alkylamino", "cycloalkylsulfamoyl", "cycloalkylsulfonyl", "cycloalkyl-carbamoyl", "cycloalkyl lower alkylcarbamoyl", "cycloalkyl lower alkoxycarbonyl" and "cycloalkylcarbonyl" is the same as "cycloalkyl" described above "Cycloalkenyl" includes the above cycloalkyl having one or more double bond(s) at any position on the ring, and examples of the cycloalkenyl include cyclopropenyl, cyclobutenyl, cyclopentenyl, cyclohexenyl, cycloheptynyl, cyclooctynyl, and cyclohexadienyl etc.

Examples of "aryl" include phenyl, naphthyl, anthryl and phenanthryl etc. and especially phenyl is preferable.

"Non-aromatic fused carbocyclic group" includes a group in which two or more cyclic groups selected front "cycloalkyl", "cycloalkenyl" and "aryl" described above fused, and examples of "Non-aromatic fused carbocyclic group" include indanyl, indenyl, tetrahydronaphthyl and fluorenyl etc.

"Forming a carbocyclic ring together with a linked carbon atom" means that two substituents jointly form "cycloalkyl" above.

A moiety of the carbocyclic ring in "carbocyclyloxy", "carbocyclyl lower alkyl", "carbocyclyl lower alkenyl", "carbocyclyl lower alkynyl", "carbocyclyl lower alkoxy", "carbocyclyl lower alkoxycarbonyl", "carbocyclylthio", "carbocyclyl amino", "carbocyclyl lower alkylamino", "carbocyclylcarbonyl", "carbocyclylsulfamoyl", "carbocyclylsulfonyl", "carbocyclylcarbamoyl", "carbocyclyl lower alkyl carbamoyl", "carbocyclyloxycarbonyl" is the same as the "carbocyclic group".

A moiety of aryl in "aryl lower alkyl", "aryloxy", "aryloxycarbonyl", "aryloxylcarbonyloxy", "aryl lower alkoxycarbonyl", "arylthio", "arylamino", "aryl lower alkoxy", "aryl lower alkylamino", "arylsulfonyl", "arylsulfonyloxy", "arylsulfinyl", "arylsulfamoyl", "arylcarbamoyl" and "aryl lower alkylcarbamoyl" is the same as the "aryl" above.

"Heterocyclic group" includes a heterocyclic group containing one or more heteroatom(s) each independently selected from O, S and N, and examples of "heterocyclic group" include 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl and thiadiazolyl etc.; a non-aromatic heterocyclic group such as dioxanyl, thin-amyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pirazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl and tetrahydropyridazinyl etc.;

a fused bicyclic heterocyclic group such as indolyl, isoindolyl, indazolyl, indolidinyl, indolinyl, isoindolinyl, quinolyl, isoquinolyl, cinnolinyl, phthaladinyl quinazolinyl, naphthilidinyl, quinoxalinyl, purinyl, pteridinyl, benzopyranyl, benzimidazolyl, benzotriazolyl, benzisoxazolyl, benzoxazolyl, benzoxadiazolyl, benzoisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyridyl, pyrazolopyridyl, thiazolopyridyl, pyrazolopyrimidinyl, pyrazolotriazinyl, pyridazolopyridyl, triazolopyridyl, imidazothiazolyl, pyrazinopyridazinyl, quinazolinyl, quinolyl, isoquinolyl, naphthilidinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxinyl, dihydrobenzooxedinyl, dihydrobenzooxepinyl and dihydrothienodioxinyl etc.; and a fused tricyclic heterocyclic group such as carbazolyl, acridinyl, xanthenyl, phenothiazinyl, phenoxathiinyl, phenoxadinyl, dibenzofuryl, imidazoquinolyl and tetrahydrocarbazolyl etc.; and preferably includes 5- or 6-membered heteroaryl and a non-aromatic heterocyclic group.

A moiety of the heterocyclic group in "heterocyclyl lower alkyl", "heterocyclyloxy", "heterocyclylthio", "heterocyclylcarbonyl", "heterocyclyl lower alkoxy", "heterocyclyl amino", "heterocyclyl carbonylamino", "heterocyclyl sulfamoyl", "heterocyclylsulfonyl", "heterocyclylcarbamoyl", "heterocyclyloxylcarbonyl", "heterocyclyl lower alkylamino", "heterocyclyl lower alkoxycarbonyl" and "heterocyclyl lower alkylcarbamoyl" is the same as the "heterocyclic group" above.

"A nitrogen-containing aromatic heterocyclic group" means a group of the "heterocyclic group" above containing at least one nitrogen atom, and examples of the "nitrogen-containing aromatic heterocyclic group" include 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl and thiadiazolyl etc.;

a fused bicyclic heterocyclo group such as indolyl, isoindolyl, indazolyl, indolidinyl, indolinyl, isoindolinyl, quinolyl, isoquinolyl, cinnolinyl, phthaladinyl, quinazolinyl, naphthilidinyl, quinoxalinyl, purinyl, pteridinyl, benzopyranyl, benzimidazolyl, benzotriazolyl, benzisoxazolyl, benzoxazolyl, benzoxadiazolyl, benzoisothiazolyl, benzothiazolyl, benzothiadiazolyl, benzotriazolyl, imidazopyridyl, pyrazolopyridine, triazolopyridyl, imidazothiazolyl, pyrazinopyridazinyl, quinazolinyl, quinolyl, isoquinolyl, naphthylidinyl, dihydrobenzofuryl, tetrahydroquinolyl, tetrahydroisoquinolyl, dihydobenzoxazine etc.; and a fused tricyclic heterocyclo group such as carbazolyl, acridinyl, xanthenyl and imidazoquinolyl etc.; and pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropiridyl, dihydrobenzimidazolyl, tetrahydropyridyl, tetrahydrothiazolyl and tetrahydroisothiazolyl etc.

"The heterocyclic group" or "nitrogen-containing aromatic heterocyclic group" above may be linked to other group at any position on the ring.

"Nitrogen-containing aromatic monocyclic heterocyclic group" means a monocyclic group in the "nitrogen-containing aromatic heterocyclic group" and examples of the "Nitrogen-containing aromatic monocyclic heterocyclic group" include 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl and thiadiazolyl etc.

"The nitrogen-containing aromatic monocyclic heterocyclic group" above may be linked to other group at any carbon atom on the ring.

Examples of a substituent in the "optionally substituted carbocyclic group" and "optionally substituted heterocyclic group" of the ring A and B include the substituent group α (preferably halogen, hydroxyl, acyl, acyloxy, carboxy, lower alkoxycarbonyl, carbamoyl, amino, cyano, lower alkylamino, lower alkylthio etc);

lower alkyl optionally substituted with one or more substituent(s) selected from the substituent group α, hydroxyimino and lower alkoxyimino, wherein examples of preferable substituents include halogen, hydroxyl, lower alkoxy, lower alkoxycarbonyl etc.;
amino lower alkyl substituted with one or more substituent(s) selected from the substituent group α, wherein examples of preferable substituents include acyl, lower alkyl and/or lower alkoxy etc.;
hydroxyimino lower alkyl, lower alkoxyimino lower alkyl;
lower alkenyl optionally substituted with one or more substituent(s) selected from the substituent group α, wherein examples of preferable substituents include lower alkoxycarbonyl, halogen and/or halogen lower alkoxycarbonyl;
lower alkynyl optionally substituted with one or more substituent(s) selected from the substituent group α, wherein examples of preferable substituents include lower alkoxycarbonyl etc;
lower alkoxy optionally substituted with one or more substituent(s) selected from the substituent group α, wherein examples of preferable substituents include halogenocarbamoyl, oxetane, lower alkylcarbamoyl, hydroxyl lower alkylcarbamoyl;
lower alkoxy lower alkoxy optionally substituted with one or more substituent(s) selected from the substituent group α;
lower alkenyloxy optionally substituted with one or more substituent(s) selected from the substituent group α wherein examples of preferable substituents include halogen, hydroxyl, amino, lower alkyl etc.;
lower alkoxy lower alkenyloxy optionally substituted with one or more substituent(s) selected from the substituent group α;
lower alkynyloxy optionally substituted with one or more substituent(s) selected from the substituent group α, wherein examples of preferable substituents include halogen, hydroxyl etc.;
lower alkoxy lower alkynyloxy optionally substituted with one or more substituent(s) selected from the substituent group α;
lower alkylthio optionally substituted with one or more substituent(s) selected from the substituent group α;
lower alkenylthio optionally substituted with one or more substituent(s) selected from the substituent group α;
lower alkynylthio optionally substituted with one or more substituent(s) selected from the substituent group α;
lower alkylamino substituted with one or more substituent(s) selected from the substituent group α;
lower alkenylamino substituted with one or more substituent(s) selected from the substituent group α;
lower alkynylamino substituted with one or more substituent(s) selected from the substituent group α;
aminooxy optionally substituted with one or more substituent(s) selected from lower alkylidene and the substituent group α;
acyl substituted with one or more substituent(s) selected from the substituent group α;
lower alkylsulfonyl optionally substituted with one or more substituent(s) selected from the substituent group α;
lower alkylsulfinyl optionally substituted with one or more substituent(s) selected from the substituent group α;
sulfamoyl;
lower alkylsulfamoyl optionally substituted with one or more substituent(s) selected from the substituent group α;
a carbocyclic group (preferably cycloalkyl, aryl etc.) optionally substituted with one or more substituent(s) selected from the substituent group α, azide, lower alkyl and halogeno lower alkyl;
a heterocyclic group optionally substituted with one or more substituent(s) selected from the substituent group α, azide, lower alkyl and halogeno lower alkyl;
carbocyclyl lower alkyl (preferably cycloalkyl lower alkyl, aryl lower alkyl etc.) optionally substituted with one or more substituent(s) selected from the substituent group α, azide, lower alkyl and halogeno lower alkyl;
heterocyclyl lower alkyl optionally substituted with one or more substituent(s) selected from the substituent group α, azide, lower alkyl and halogeno lower alkyl;
carbocyclyloxy (preferably cycloalkyloxy, aryloxy etc.) optionally substituted with one or more substituent(s) selected from the substituent group α, azide, lower alkyl and halogeno lower alkyl;
heterocyclyloxy optionally substituted with one or more substituent(s) selected from the substituent group α, azide, lower alkyl and halogeno lower alkyl;
carbocyclyl lower alkoxy (preferably cycloalkyl lower alkoxy, aryl lower alkoxy, etc.) optionally substituted with one or more substituent(s) selected from the substituent group α, azide, lower alkyl and halogeno lower alkyl;
heterocyclyl lower alkoxy (preferably cycloalkyl lower alkoxycarbonyl, aryl lower alkoxycarbonyl etc.) optionally substituted with one or more substituent(s) selected from the substituent group α, azide, lower alkyl and halogeno lower alkyl,
carbocyclyl lower alkoxycarbonyl optionally substituted with one or more substituent(s) selected from the substituent group α, azide, lower alkyl and halogen° lower alkyl;
heterocyclyl lower alkoxycarbonyl optionally substituted with one or more substituent(s) selected from the substituent group α, wide, lower alkyl and halogeno lower alkyl;
carbocyclylthio (preferably cycloalkylthio, arylthio etc.) optionally substituted with one or more substituent(s) selected from the substituent group α, azide, lower alkyl and halogen lower alkyl;
heterocyclylthio optionally substituted with one or more substituent(s) selected from the substituent group α, azide, lower alkyl and halogeno lower alkyl;
carbocyclyl amino(preferably cycloalkylamino, arylamino etc.) optionally substituted with one or more substituent(s) selected from the substituent group α, azide, lower alkyl and halogeno lower alkyl;
heterocyclyl amino optionally substituted with one or more substituent(s) selected from the substituent group α, azide, lower alkyl and halogeno lower alkyl;
carbocyclyl lower alkylamino (preferably cycloalkyl lower alkylamino, aryl lower alkylamino etc.) optionally substituted with one or more substituent(s) selected from the substituent group α, azide, lower alkyl and halogeno lower alkyl;
heterocyclyl lower allylamino optionally substituted with one or more substituent(s) selected from the substituent group α, azide, lower alkyl and halogeno lower alkyl;
lower alkylsulfamoyl optionally substituted with one or more substituent(s) selected from the substituent group α;
carbocyclylsulfamoyl (preferably cycloalkyl sulfamoyl, arylsulfamoyl etc.) optionally substituted with one or more substituent(s) selected from the substituent group α, azide, lower alkyl and halogeno lower alkyl;
heterocyclylsulfamoyl optionally substituted with one or more substituent(s) selected from the substituent group α, azide, lower alkyl and halogeno lower alkyl;
carbocyclylsulfonyl (preferably cycloalkyl sulfonyl, arylsulfonyl etc.) optionally substituted with one or more substituent(s) selected from the substituent group α, azide, lower alkyl and halogeno lower alkyl;

heterocyclylsulfonyl optionally substituted with one or more substituent(s) selected from the substituent group α, azide, lower alkyl and halogeno lower alkyl;

carbocyclylcarbamoyl (preferably cycloalkyl carbamoyl, aryl carbamoyl etc.) optionally substituted with one or more substituent(s) selected from the substituent group α, azide, lower alkyl and halogeno lower alkyl;

heterocyclyl carbamoyl optionally substituted with one or more substituent(s) selected from the substituent group α, azide, lower alkyl and halogeno lower alkyl;

carbocyclyl lower alkylcarbamoyl (preferably cycloalkyl lower alkylcarbamoyl, aryl lower alkylcarbamoyl etc.) optionally substituted with one or more substituent(s) selected from the substituent group α, azide, lower alkyl and halogeno lower alkyl;

heterocyclyl lower alkylcarbamoyl optionally substituted with one or more substituent(s) selected from the substituent group α, azide, lower alkyl and halogen lower alkyl, carbocyclyloxycarbonyl (preferably cycloalkyloxycarbonyl, aryloxycarbonyl etc.) optionally substituted with one or more substituent(s) selected from the substituent group α, azide, lower alkyl and halogen lower alkyl;

heterocyclyloxycarbonyl optionally substituted with one or more substituent(s) selected from the substituent group α, azide, lower alkyl and halogen lower alkyl;

lower alkylenedioxy optionally substituted with halogen;

oxo, azide and the like.

These may be substituted with one or more substituents selected from these groups.

Also the ring A may be substituted with one or more group(s) selected from

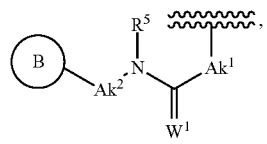

(i)

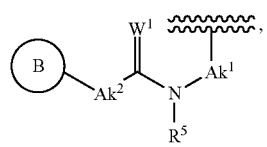

(ii)

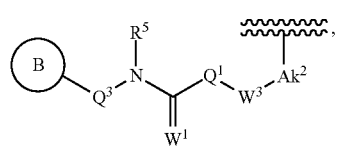

(iii)

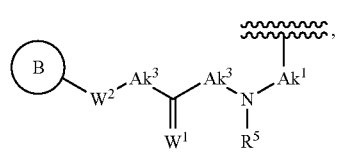

(iv)

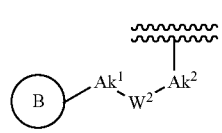

(v)

-continued

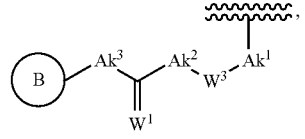

(vi)

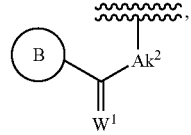

(vii)

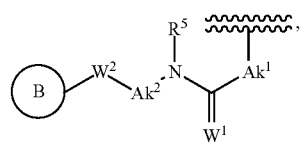

(viii)

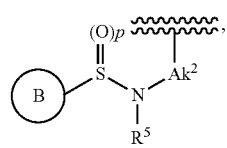

(ix)

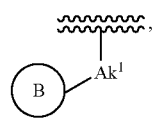

(x)

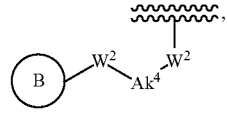

(xi)

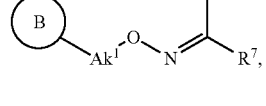

(xii)

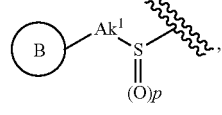

(xiii)

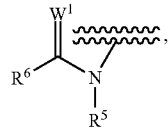

(xiv)

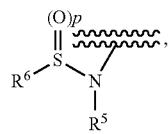

(xv)

(xvi)

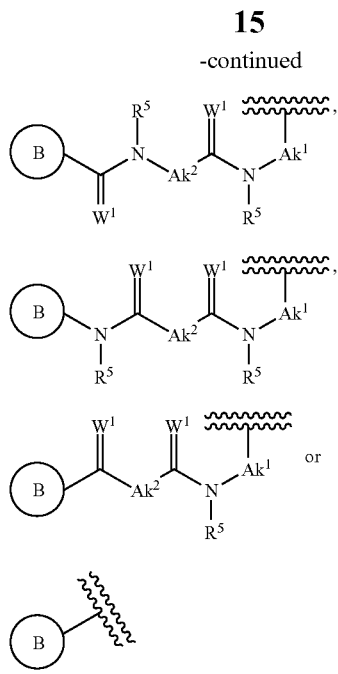

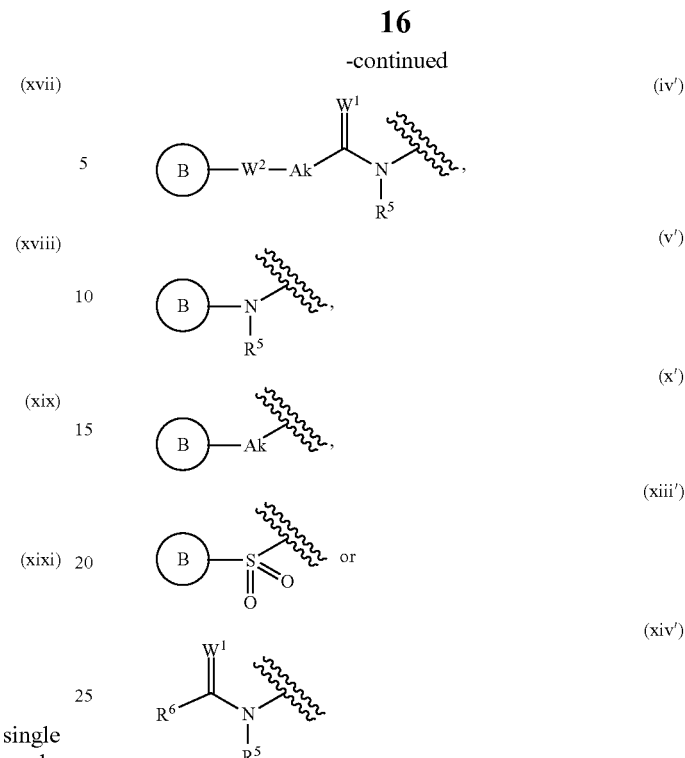

wherein $Ak^1$, $Ak^2$ and $Ak^3$ are each independently a single bond, optionally substituted lower alkylene, optionally substituted lower alkenylene or optionally substituted lower alkynylene;

$Ak^4$ is optionally substituted lower alkylene, optionally substituted lower alkenylene or optionally substituted lower alkynylene;

$W^1$ and $W^3$ are each independently O or S, $W^2$ is O, S or $NR^5$, $R^5$ and $R^6$ are each independently hydrogen, lower alkyl, hydroxy lower alkyl, lower alkoxy lower alkyl, lower alkoxycarbonyl lower alkyl, carbocyclyl lower alkyl, lower alkenyl, hydroxyl lower alkenyl, lower alkoxy lower alkenyl, lower alkoxycarbonyl lower alkenyl, carbocyclyl lower alkenyl, lower alkynyl, hydroxyl lower alkynyl, lower alkoxy lower alkynyl, lower alkoxycarbonyl lower alkynyl, carbocyclyl lower alkynyl or acyl;

$R^7$ is hydrogen or lower alkyl;

the ring B is an optionally substituted carbocyclic group or an optionally substituted heterocyclic group; and p is 1 or 2; $W^1$, $W^3$ or $W^5$ may be independent when it is pluralized. Additionally the oxygen atom of (xii) may be cis or trans to the substituent $R^7$.

Preferable examples of (i) to (xixi) above include

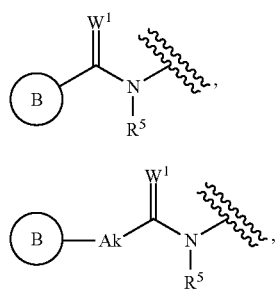

wherein Ak is optionally substituted lower alkylene, optionally substituted lower alkenylene or optionally substituted lower alkynylene, and the other symbols are the same as described above.

In other cases of "an optionally substituted carbocyclic group" and "an optionally substituted heterocyclic group", one or more substituent(s) selected from a group of lower alkyl and the substituent group a may be exemplified as a substituent of "an optionally substituted carbocyclic group" and "an optionally substituted heterocyclic group"

"Heteroaryl" includes an aromatic cyclic group among the "heterocyclic group" above.

"Lower alkylene" includes C1-C10, preferably C1-C6; more preferably C1-C3 straight or branched divalent carbon chain, and for example, methylene, dimethylene, trimethylene, tetramethylene and methyl trimethylene are exemplified.

A moiety of lower alkylene in "lower alkylenedioxy" is the same as the "lower alkylene" described above.

"Lower alkenylene" includes C2-C10, preferably C2-C6, more preferably C2-C4 straight or branched divalent carbon chain having a double bond at any arbitrary position thereof, and vinylene, propenylene, butenylene, butadienylene, methyl propenylene, pentenylene and hexenylene are exemplified.

"Lower alkynylene" includes C2-C10, preferably C2-C6, more preferably C2-C4 straight or branched divalent carbon chain having a triple bond and also a double bond at any arbitrary position thereof, and for example, ethynylene, propynylene, butynylene, pentynylene and hexynylene are exemplified.

Examples of a substituent in "optionally substituted lower alkylene", "optionally substituted lower alkenylene" and "optionally substituted lower alkynylene" include the substituent group α, and preferably halogen and hydroxyl etc. are exemplified.

Examples of a substituent in "optionally substituted carbocyclyl lower alkyl", "optionally substituted heterocyclyl lower alkyl", "optionally substituted carbocyclyl lower alkoxy", and "optionally substituted heterocyclyl lower alkoxy" include one or more substituent(s) selected from lower alkyl and the substituent group α.

In this specification, "solvate" includes a solvate with an organic solvent and a hydrate etc. and hydrate may be coordinated with optional number of water molecule.

The compound (I) includes pharmaceutical acceptable salt thereof. Examples of the pharmaceutical acceptable salt include a salt with an alkali metal such as lithium, sodium and potassium etc., an alkali earth metal such as magnesium, calcium etc., ammonium, an organic base and an amino acid; a salt with an inorganic acid such as hydrochloric acid, sulfuric acid, nitric acid, hydrobromic acid, phosphoric acid or hydroiodic acid etc., and an organic acid such as acetic acid, trifluoroacetic acid, citric acid, lactic acid, tartaric acid, oxalic acid, maleic acid, fumaric acid, mandelic acid, glutaric acid, malic acid, benzoic acid, phthalic acid, benzensulfonic acid, p-toluenesulfonic acid, methanesulfonic acid, ethanesulfonic acid, etc. Especially hydrochloric acid, phosphoric acid, tartaric acid or methane sulfuric acid is preferable. These salts can be prepared by a method usually carried out.

The compound (I) is not construed to be limited to a specific isomer but to include all possible isomers such as a keto-enol isomer, an imine-enamine isomer, a diastereoisomer, an optical isomer and a rotational isomer etc. For example, a compound (I) in which $R^{2a}$ is hydrogen includes a tautomer as follows;

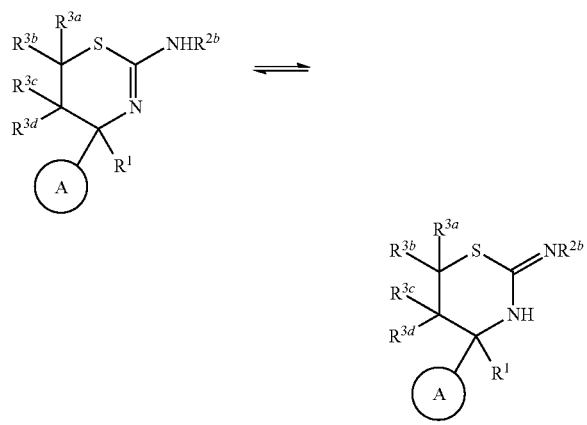

The compound (I) of the present invention can be prepared, for example, according to the non-patent literature 1 or a method described below;

Preparation of an Aminodihydrothiazine Ring (I-1) or (I-2):

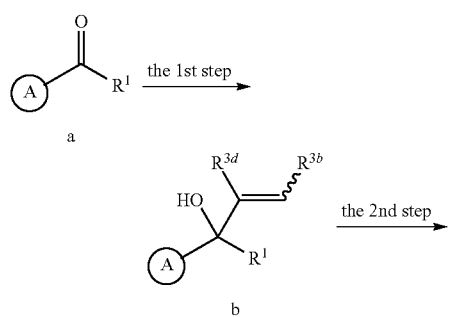

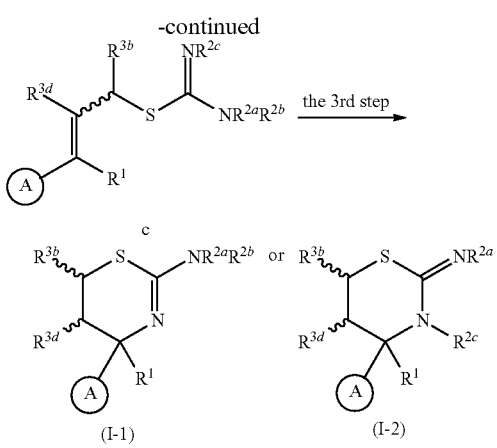

(In the scheme above, at least one of $R^{2b}$ and $R^{2c}$ is hydrogen, $R^{3b}$ and $R^{3d}$ are each independently hydrogen, halogen, hydroxyl, optionally substituted lower alkyl, optionally substituted lower alkenyl, optionally substituted acyl, optionally substituted lower alkoxy, optionally substituted lower alkylthio, carboxy, optionally substituted lower alkoxycarbonyl, optionally substituted amino, optionally substituted carbamoyl, an optionally substituted carbocyclic group, or an optionally substituted heterocyclic group, and the other symbols are the same as described above.)

The $1^{st}$ step: A Grignard reagent having a corresponding substituent of the objective compound such as vinyl magnesium chloride, vinyl magnesium bromide and propenyl magnesium bromide etc. is added to a compound a, which is commercially available or can be prepared by a known method, in a solvent such as ether, tetrahydrofuran etc. or a mixed solvent of ether-tetrahydrofuran etc., at −100° C. to 50° C., preferably −80° C. to 0° C. and the mixture is stirred for 0.2 to 24 hours, preferably 0.2 to 5 hours to give a compound b.

The $2^{nd}$ step: To a compound b in an acid such as acetic acid, trifluoroacetic acid, hydrochloric acid, sulfuric acid etc. or a mixture thereof under the presence of a solvent such as toluene etc. or without a solvent, is added a substituted thiourea having a corresponding substituent of the objective compound such as thiourea, N-methylthiourea, N,N'-dimethylthiourea etc., and the mixture is stirred at −20° C. to 100° C., preferably 0° C. to 80° C. for 0.5 hours to 120 hours, preferably 1 hour to 72 hours to give a compound c.

The $3^{rd}$ step: To a compound c in a solvent such as toluene etc. or without a solvent, is added an acid such as trifluoroacetic acid, methanesulfonic acid, trifluoromethanesulfonic acid, sulfuric acid etc. or a mixture thereof and reacted at −20° C. to 100° C., preferably 0° C. to 50° C. for 0.5 hours to 120 hours, preferably 1 hour to 72 hours to give a compound (I-2) when $R^{2b}$ is hydrogen or a compound (I-1) when $R^{2c}$ is hydrogen.

Preparation of an Aminodihydrothiazine Ring (I-3):

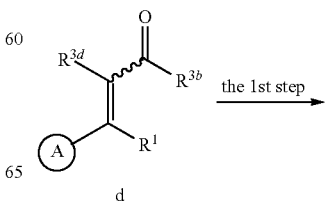

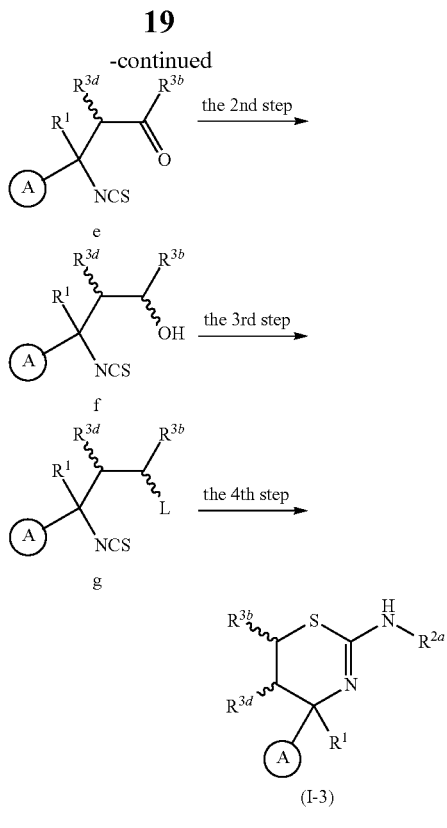

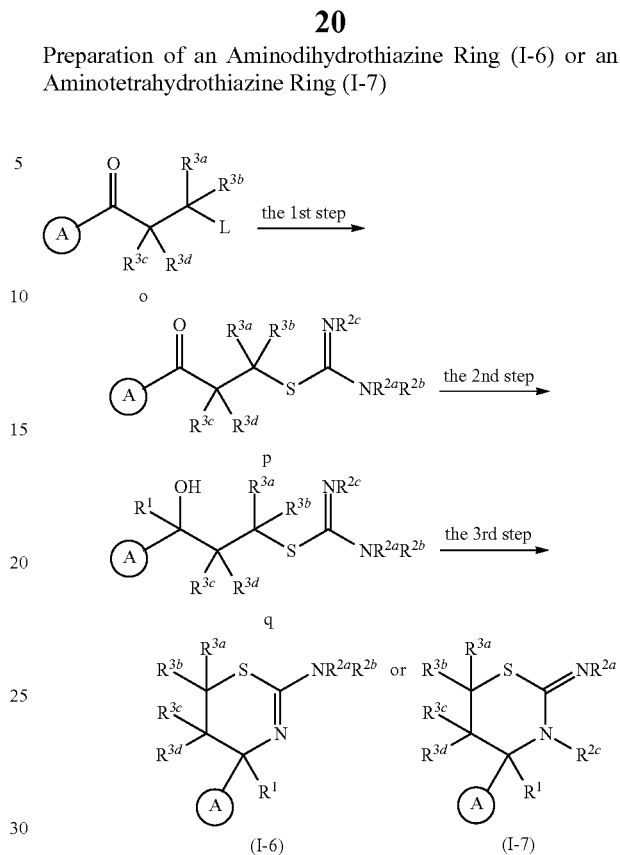

(In the scheme above, L is a leaving group such as halogen or lower alkylsulfonyl etc. and the other symbols are the same as described above.)

The 1$^{st}$ step: Thiocyanate such as sodium thiocyanate or ammonium thiocyanate etc. is reacted with a compound d, which is commercially available or can be prepared by a known method, in a solvent such as toluene, chloroform, tetrahydrofuran etc. under the presence of water and an acid such as hydrochloric acid or sulfuric acid etc. at 0° C. to 150° C., preferably at 20° C. to 100° C. for 0.5 to 24 hours, preferably 1 to 12 hours to give a compound e.

The 2$^{nd}$ step: A reducing agent such as sodium borohydride etc. is added to and reacted with a compound e in a solvent such as tetrahydrofuran, methanol, ethanol, water etc. or a mixture of ethanol-water etc. under the presence of buffering agent such as sodium dihydrogen phosphate at −80° C. to 50° C., preferably −20° C. to 20° C. for 0.1 to 24 hours, preferably 0.5 to 12 hours to give a compound f.

The 3$^{rd}$ step: A compound f is reacted with a halogenating agent such as thionyl chloride, phosphoryl chloride, carbon tetrachloride-triphenylphosphine etc. in a solvent such as toluene, dichloromethane etc. or without a solvent at −80° C. to 50° C., preferably at −20° C. to 20° C. for 0.1 to 24 hours, preferably 0.5 to 12 hours; or it is reacted with a sulfonating agent such as methanesulfonyl chloride, p-toluenesulfonyl chloride etc. in a solvent such as toluene, dichloromethane etc. under the presence of a base such as triethylamine etc. at −80° C. to 50° C., preferably at −20° C. to 20° C. for 0.1 to 24 hours, preferably 0.5 to 12 hours to give a compound g.

The 4$^{th}$ step: A compound g is reacted with ammonia or a primary amine such as methylamine etc. in a solvent such as methanol, ethanol, water etc. or a mixture of methanol-water etc. at −20° C. to 80° C., preferably at 0° C. to −40° C. for 0.5 to 48 hours, preferably 1 to 24 hours to give the compound (I-3).

Preparation of an Aminodihydrothiazine Ring (I-6) or an Aminotetrahydrothiazine Ring (I-7)

(In the scheme above, at least one of R$^{2b}$ and R$^{2c}$ is hydrogen and the other symbols are the same as described above.)

The 1$^{st}$ step: Thiourea or a substituted thiourea corresponding to the objective compound such as N-methyl thiourea, N,N-dimethylthiouers, N,N'-dimethylthiouera etc. is reacted with a compound o, which is commercially available or can be prepared by a known method, in a solvent such as ethanol, methanol, tetrahydrofuran, toluene etc. at −20° C. to 200° C., preferably at 0° C. to 150° C. for 0.5 to 200 hours, preferably 1 to 120 hours to give a compound p.

The 2$^{nd}$ step: A Grignard reagent corresponding to the objective compound such as methyl magnesium chloride, ethyl magnesium bromide and benzyl magnesium bromide etc. is added to a compound p in a solvent such as ether, tetrahydrofuran etc. or a mixed solvent thereof at −100° C. to 50° C., preferably −80° C. to 30° C. and the mixture is stirred for 0.2 to 24 hours, preferably 0.5 to 5 hours to give a compound q.

The 3$^{rd}$ step: To a compound q in a solvent such as toluene etc. or without a solvent, is added an acid such as trifluoroacetic methanesulfonic acid, trifluoromethanesulfonic acid, sulfuric acid etc. or a mixture thereof and reacted at −20° C. to 100° C., preferably 0° C. to 50° C. for 0.5 hours to 200 hours, preferably 1 hour to 150 hours to give a compound (I-6) (R$^{2c}$=H) or a compound (I-7) (R$^{2b}$=H).

Preparation of an Aminodihydrothiazine Ring (I-8)

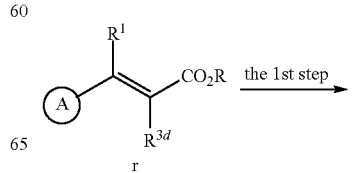

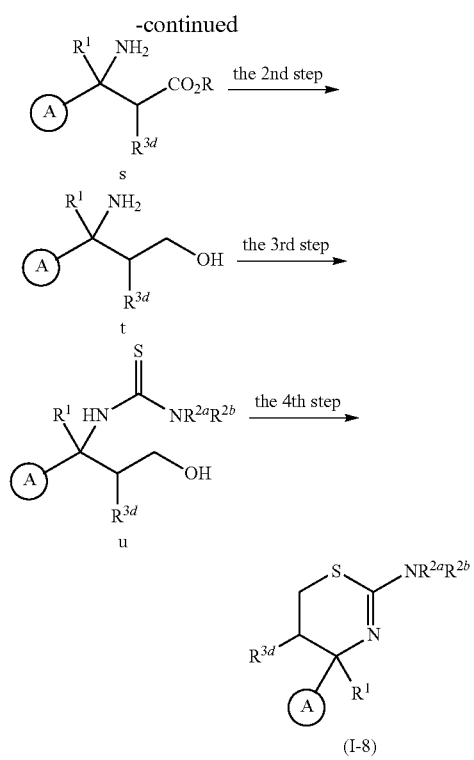

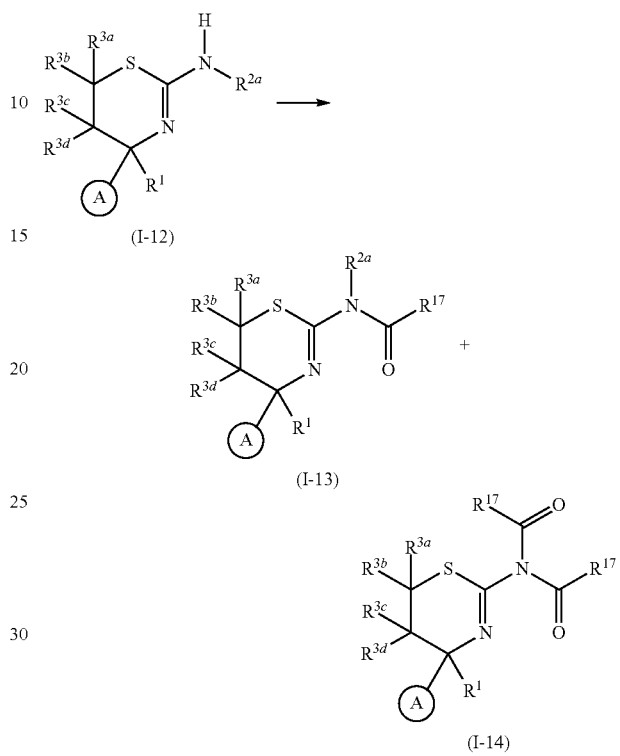

(In the scheme, each symbol is the same as described above)

The 1st step: Ammonium chloride is added to a compound r which be prepared by a known method in a solvent such as acetic acid etc. at 0° C. to 200° C., preferably 10° C. to 100° C. for 0.1 hours 100 hours, preferably 0.5 hour to 24 hours to give a compound.

The 2nd step: A reducing agent such as lithium aluminium hydride, diisobutyl aluminum hydride etc. is reacted with a compounds in a solvent such as tetrahydrofuran, diethyl ether etc. at −80° C. to 150° C., preferably 0° C. to 100° C. for 0.1 hours to 24 hours, preferably 0.5 hour to 12 hours to give a compound t.

The 3rd step: Isothiocyanate corresponding to the objective compound such as 4-methoxybenzyl isothiocyanate, t-butyl isothiocyanate etc. or carbamoyl halide corresponding to the objective compound such as N,N-dimethyl thiocarbamoyl chloride, N,N-diethyl thiocarbamoyl chloride etc. is reacted with a compound t in a solvent such as toluene, chloroform, tetrahydrofuran etc. under the presence of a base such as diisopropylethylamine, triethylamine, pyridine, sodium hydroxide etc. or without a base at 0° C. to 150° C., preferably 20° C. to 100° C. for 0.5 hours to 120 hours, preferably 1 hour to 72 hours to give a compound u.

The 4th step: A halogenating agent such as thionyl chloride, phosphoryl oxychloride, carbon tetrachloride-triphenyl phosphine etc. is reacted with a compound u in a solvent such as acetonitrile, toluene, dichloromethane etc. at −80° C. to 50° C., preferably −20° C. to 20° C. for 0.1 hours to 24 hours, preferably 0.5 hour to 12 hours, or a sulfonylating agent such as methanesulfonyl chloride, p-toluenesulfonyl chloride is reacted with a compound u in a solvent such as toluene, dichloromethane etc. under the presence of a base such as triethylamine at −80° C. to 50° C., preferably −20° C. to 20° C. for 0.1 hours to 24 hours, preferably 0.5 hour to 12 hours. The resulting halogenated compound or sulfonate ester derivative is reacted with a base such as diisopropylethylamine, potassium carbonate, sodium bicarbonate, sodium hydride, sodium hydroxide etc. at 0° C. to 150° C. preferably 20° C. to 100° C. for 0.5 hours to 120 hours, preferably 1 hour to 72 hours to give a compound (I-8).

Preparation of an Acylamino Derivative (I-13) and/or (I-14)

(In the scheme, $R^{17}$ is optionally substituted lower alkyl, an optionally substituted carbocyclic group or an optionally substituted heterocyclic group and other symbols are the same as described above)

An acylating agent corresponding to the objective compound such as benzoyl chloride, 2-furoyl chloride, acetic anhydride etc. is reacted with a compound (I-12) in which $R^{2b}$ is hydrogen under the presence of a solvent such as tetrahydrofuran, dichloromethane etc. or without a solvent and under the presence of a base such as pyridine or triethylamine etc. or without a solvent at −80° C. to 100° C., preferably −20° C. to 40° C. for 0.1 hours to 24 hours, preferably 1 hour to 12 hours, or a compound (I-12) is reacted with a carboxylic acid having a substituent corresponding to the objective compound such as amino acid or glycolic acid etc. in a solvent such as dimethylformamide, tetrahydrofuran, dichloromethane etc. under the presence of a condensation agent such as dicyclohexylcarbodiimide, carbonyldiimidazole etc. at −80° C. to 100° C., preferably −20° C. to 40° C. for 0.1 hours to 24 hours, preferably 1 hour to 12 hours to give a compound (I-13) and/or (I-14) (when $R^{2a}$ is hydrogen).

Preparation of a Carbamoyl Derivative (I-17)

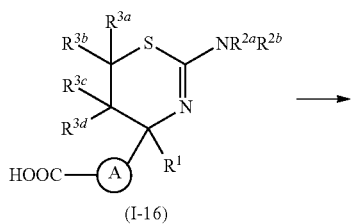

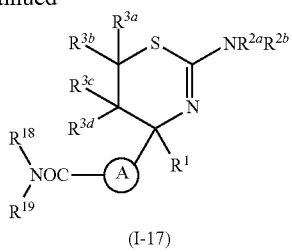

(I-17)

(In the scheme above. CONR[18]R[19] is optionally substituted carbamoyl and the other symbols are the same as described above)

A compound (I-16) having a carboxyl group as a substituent on the ring A is reacted with a primary or secondary amine having a substituent corresponding to the objective compound (e.g., aniline, 2-aminopyridine, dimethylamine etc.) in a solvent such as dimethylformamide, tetrahydrofuran, dichloromethane etc. under the presence of a condensation agent such as dicyclohexylcarbodiimide, carbonyldiimidazole, dicyclohexylcarbodiimide-N-hydroxybenzotriazole etc. at −80° C. to 100° C., preferably −20° C. to 40° C. for 0.1 hours to 24 hours, preferably 1 hour to 12 hours to give a compound (I-17).

Preparation of an Acylamino Derivative (I-19)

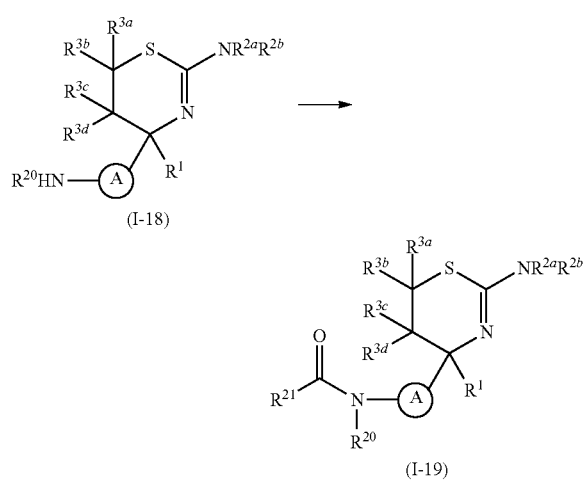

(In the scheme, NHR[20] is optionally substituted amino, NR[20]COR[21] is optionally substituted acylamino, optionally substituted ureido or carboxyamino having a substituent on the oxygen atom and the other symbols are the same as described above.)

A compound (I-18) having an optionally substituted amino group on the ring A is reacted with a reagent having a substituent corresponding to the objective compound such as acid chlorides, acid anhydrides, chlorocarbonate esters, isocyanates etc. under the presence of a solvent such as tetrahydrofuran, dichloromethane etc. or without a solvent under the presence of a base such as pyridine, triethylamine etc. or without a base at −80° C. to 100° C., preferably −20° C. to 40° C. for 0.1 hours to 24 hours, preferably 1 hour to 12 hours, or a compound (I-18) is reacted with a carboxylic acid having a substituent corresponding to the objective compound such as benzoic acid, 2-pyridinecarboxylic acid etc. in a solvent such as dimethylformamide, tetrahydrofuran, dichloromethane etc. under the presence of a condensation agent such as dicyclohexylcarbodiimide, carbonyldiimidazole, dicyclohexylcarbodiimide-N-hydroxybenzothiazole etc. at −80° C. to 100° C., preferably −20° C. to 40° C. for 0.1 hours to 24 hours, preferably 1 hour to 12 hours to give a compound (I-19).

Preparation of an Alkylamino Derivative (I-20)

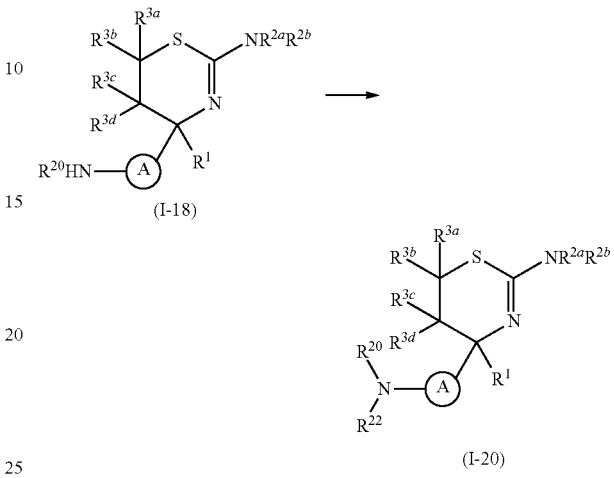

(In the scheme, NHR[20] is optionally substituted amino and R[22] is lower alkyl.)

A compound (I-18) having an amino group on the ring A is reacted with an aldehyde having a substituent corresponding to the objective compound such as benzaldehyde, pyridin-2-carboaldehyde etc. and a reducing agent such as sodium cyanoborohydride, sodium triacetoxyborohydride etc. in a solvent such as dichloromethane, tetrahydrofuran etc. under the presence of an acid such as acetic acid etc. or without an acid at −80° C. to 100° C., preferably 0° C. to 40° C. for 0.5 hours to 1.50 hours, preferably 1 hour to 24 hours to give a compound (I-20).

Preparation of a Substituted Alkoxy Derivative (I-22),

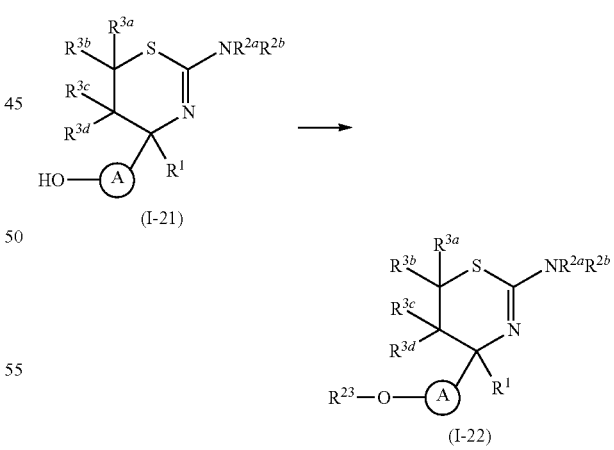

(In the scheme above, R[23] is optionally substituted lower alkyl, an optionally substituted carbocyclic group or an optionally substituted heterocyclic group and the other symbols are the same as described above.)

A compound (I-21) having a hydroxy group on the ring A is reacted with an alkylating agent having a substituent corresponding to the objective compound such as benzyl chloride, methyl iodide etc. in a solvent such as dimethylformamide, tetrahydrofuran etc. under the presence of a base such as potassium carbonate, sodium hydroxide, sodium hydride etc. at −80° C. to 100° C., preferably 0° C. to 40° C. for 0.5 hours to 150 hours, preferably 1 hour to 24 hours, or a compound (I-18) is reacted with an alcohol such as 2-aminoethanol etc. in a solvent such as dimethylformamide, tetrahydrofuran etc. under the presence of a Mitsunobu reagent such as triphenylphosphine-azodicarboxylic acid diethyl ester etc. at −80° C. to 100° C., preferably 0° C. to 40° C. for 0.5 hours to 72 hours, preferably 1 hour to 24 hours to give a compound (I-22).

Introduction of a Substituent by Palladium Coupling

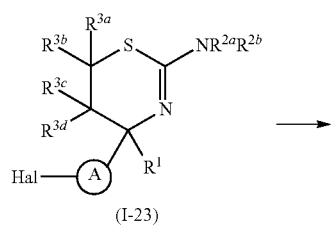

(In the scheme above, Hal is halogen, G is optionally substituted lower alkenyl, optionally substituted alkynyl, optionally substituted alkoxycarbonyl, an optionally substituted carbocyclic group or an optionally substituted heterocyclic group etc. and the other symbols are the same as described above.)

A compound (I-23) having halogen as a substituent on the ring A is reacted with a compound having a substituent corresponding to the objective compound (e.g., styrene, propargyl alcohol, aryl boronic acid, carbon monoxide etc.) in a solvent such as tetrahydrofuran, dimethylformamide, 1,2-dimethoxyethane, methanol etc. under the presence of a base such as triethylamine, sodium carbonate etc., a palladium catalyst such as palladium acetate, palladium chloride etc. and a ligand such as triphenylphosphine etc. and under irradiation of microwave or without the irradiation, at −80° C. to 150° C., preferably 0° C. to 100'C for 0.5 hours to 72 hours, preferably 1 hour to 24 hours to give a compound (I-24).

Preparation of an Oxime Derivative (I-26)

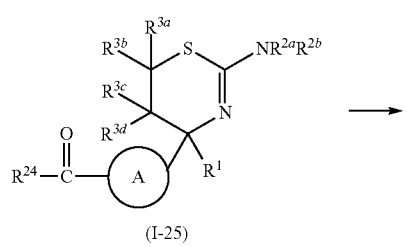

(In the scheme above, $R^{24}$ is hydrogen, optionally substituted lower alkyl etc., $R^{25}$ is hydrogen, optionally substituted lower alkyl, optionally substituted lower alkenyl, an optionally substituted carbocyclic group or an optionally substituted heterocyclic group etc., and the other symbols are the same as described above.)

A compound (I-25) having an acyl group as a substituent of the ring A is reacted with a hydroxylamine having a substituent corresponding to the objective compound such as hydroxylamine, methoxylamine, O-benzylhydroxylamine etc. or a salt thereof in a solvent such as methanol, ethanol etc. under the presence of an additive such as potassium acetate etc. or without an additive at −80° C. to 100'C, preferably 0° C. to 40° C. for 0.5 hours to 150 hours, preferably 1 hour to 72 hours to give a compound (I-26).

Coupling Reaction

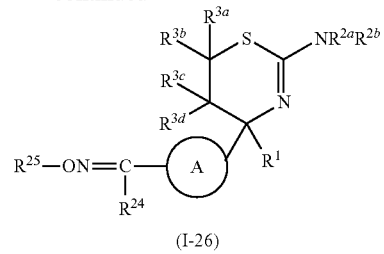

(In the scheme above, $R^{26}$ is a substituent corresponding to each objective compound)

The $1^{st}$ Step:

A compound v is reacted with a reagent having substituent corresponding to the objective compound such as acyl halide, acid anhydride, chlorocarbonate ester, isocyanate etc. (e.g., benzoyl chloride, 2-furoyl chloride, acetic anhydride, benzyl chloroformate, di-tert-butyl dicarbonate, phenyl isocyanate etc.) in a solvent such as tetrahydrofuran, dichloromethane, dimethylformamide etc. or without a solvent under the presence of a base such as pyridine, triethylamine etc. or without a base at −80° C. to 100° C., preferably −20° C. to 40° C. for 0.1 hours to 24 hours, preferably 1 hour to 12 hours, or a compound A is reacted with a carboxylic acid having a substituent corresponding to the objective compound such as benzoic acid, 2-pyridinecarboxylic acid etc. in a solvent such as dimethylformamide, tetrahydrofuran, dichloromethane, methanol etc. under the presence of a condensation agent such as dicyclohexylcarbodiimide, carbonyl diimidazole, dicyclohexylcarbodiimide-N-hydroxybenzotriazole, 4-(4,6-dimethoxy-1,3,5-triazine-2-yl)-4-methylmorpholinium chloride, 2-(7-aza-1H-benzotriazole-1-yl)-1,1,3,3-tetramethyluronium hexafluorophosphate etc. at −80° C. to 100° C., preferably −20° C. to 40° C. for 0.1 hours to 24 hours, preferably 1 hour to 12 hours to give a compound w.

When the substituent R has a functional group which disturb the said reaction, it can be carried out by protecting the functional group with a suitable protecting group and then deprotecting it at a subsequent appropriate step.

The 2$^{nd}$ Step:

A compound w is reacted in a solvent such as methanol, ethanol, ether, tetrahydrofuran, 1,4-dioxane, dichloromethane, ethyl acetate etc. containing trifluoroacetic acid etc. or in neat, or in neat trifluoroacetic acid at −30° C. to 100° C., preferably 0° C. to 90° C. for 0.5 to 12 hours to give a compound (I-27). Alternatively, the objective compound can be synthesized according to the method described in Protective Groups in Organic Synthesis, Theodora W Green (John Wiley & Sons) etc.

Preparation of an Optically Active Isomer

1) Preparation of an Optically Active Isomer ae

For example, an optically active isomer ae, one embodiment of the compounds of the present invention, can be prepared according to the following scheme:

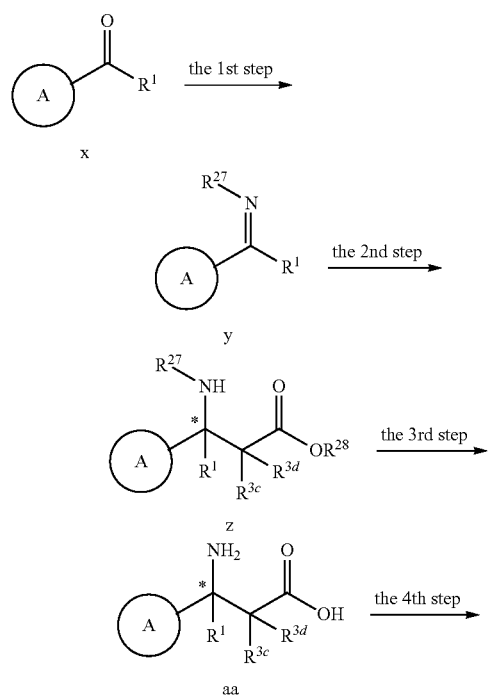

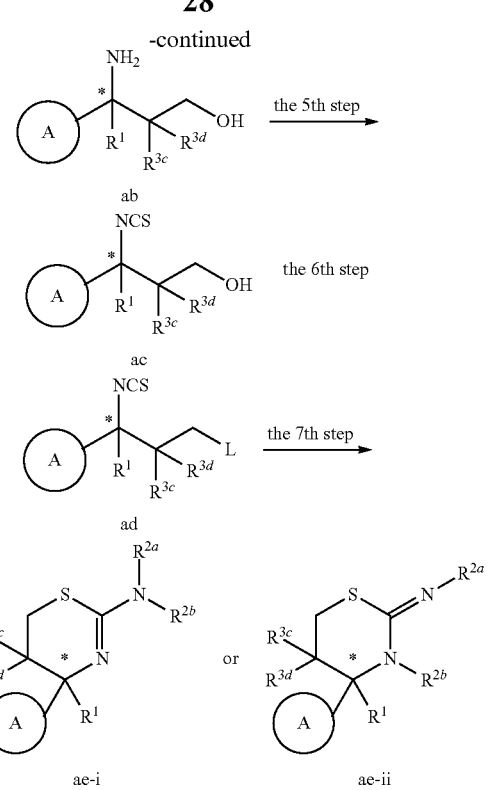

(In the scheme above, $R^1$ is optionally substituted lower alkyl, optionally substituted lower alkenyl or optionally substituted lower alkynyl, $R^{27}$ is a chiral sulfoxide having optionally substituted lower alkyl, optionally substituted lower alkenyl, an optionally substituted carbocyclic group or an optionally substituted heterocyclic group, or a chiral auxiliary group such as α-methyl benzyl etc.; $R^{3a}$, $R^{3b}$, $R^{3c}$ and $R^{3d}$ are each independently hydrogen, halogen, hydroxyl, optionally substituted lower alkyl, optionally substituted lower alkenyl, optionally substituted acyl, carboxy, optionally substituted lower alkoxycarbonyl, optionally substituted amino, optionally substituted carbamoyl, an optionally substituted carbocyclic group or an optionally substituted heterocyclic group; $R^{28}$ is optionally substituted lower alkyl or optionally substituted lower alkenyl; $R^{2a}$ and $R^{2b}$ are each independently hydrogen, optionally substituted lower alkyl or optionally substituted acyl; and the other symbols are the same as described above.)

The compounds y and z above can be prepared by a method described in (1) T. Fujisawa et al., Tetrahedron Lett., 37, 3881-3884 (1996), (2) D. Hua et al, Sulfur Reports, vol. 21, pp. 211-239 (1999)

(3) Y. Koriyama et al., Tetrahedron, 58, 9621-9628 (2002), or (4) T. Vilavan et al, Current Organic Chemistry, 9, 1315-1392 (2005).

Alternatively, these compounds can be prepared by optical resolution of each intermediate or the final product, or according to methods described below. Examples of the optical resolution method include a separation of optical isomers using an optically active column, kinetic resolution by an enzyme reaction etc., crystallization of diastereomers by salt formulation using a chiral acid or chiral base, and a preferential crystallization etc.

The 1$^{st}$ step: Compound y can be obtained by reacting Compound x, which is commercially available or can be prepared by a known method, with a chiral reagent having a substituent corresponding to the objective compound such as α-methylbenzylamine, para-toluene, tert-butylsulfine amide etc. at 60° C. to 120° C., preferably 80° C. to 100° C. in a solvent such as ether, tetrahydrofuran, toluene, benzene etc. or a mixed solvent such as ether-tetrahydrofuran etc. for 0.5 to 24 hours, preferably 0.5 to 5 hours, in the presence of molecular sieves or magnesium sulfate etc., under continuous evaporation by Dean-Stark apparatus, or according to the method described in the above literatures.

The $2^{nd}$ step: A compound z can be diastereo-selectively obtained by reacting an enolate of lithium, aluminium, zinc, titan etc. prepared form a reagent having a substituent corresponding to the objective compound such as acetate ester etc., which is commercially available or can be prepared by a known method, or ketenesilyl acetate prepared from a reagent having a substituent corresponding to the objective compound such as ethyl acetate etc. with a compound a in a solvent such as ether, tetrahydrofuran, toluene, dichloromethane etc. or a mixed solvent such as ether-tetrahydrofuran etc. under the presence of a Lewis acid such as titanium tetrachloride, ether-trifluoroborane complex etc. or without a Lewis acid at −100° C. to 50° C., preferably −80° C. to −30° C. for 0.5 to 24 hours, preferably 0.5 to 5 hours. Alternatively, the compound z can be diastereo-selectively prepared by the method described in the literature (1) or (3).

The $3^{rd}$ step: A compound z is reacted with a compound c in a solvent such as methanol, ethanol, ether, tetrahydrofuran, 1,4-dioxane, dichloromethane, ethyl acetate etc. containing hydrogen chloride, trifluoroacetic acid etc. or in neat trifluoroacetic acid at −30° C. to 100° C., preferably −10° C. to 90° C. for 0.5 to 12 hours, preferably 0.5 to 5 hours to give a compound aa.

The $4^{th}$ step: A reducing agent such as borane-tetrahydrofuran complex, borane-dimethyl sulfoxide complex, borane-triethylamine complex, borane-pyridine complex etc. or ether- or tetrahydrofuran-solution thereof is reacted with a compound aa in a solvent such as ether, tetrahydrofuran, toluene etc. or a mixed solvent such as ether-tetrahydrofuran etc. at −30° C. to 30° C., preferably −10° C. to 20° C. for 0.5 to 12 hours, preferably 0.5 to 5 hours to give a compound ab.

The $5^{th}$ step: Calcium carbonate or potassium carbonate etc. is added to a compound ab in a solvent such as dichloromethane, toluene etc. or a mixed solvent such as dichloromethane-water etc. and thiophosgene is added at −30° C. to 50° C., preferably −10° C. to 25° C. and the mixture is reacted for 0.5 to 12 hours, preferably 0.5 to 5 hours to give a compound ac.

The $6^{th}$ step: Oxalyl chloride or thionyl chloride etc. and a catalytic amount of N,N-dimethylformamide are added to a compound ac in a solvent such as dichloromethane, tetrahydrofuran, toluene etc. at −30° C. to 50° C., preferably −10° C. to 20° C. and the mixture is reacted at 0° C. to 100° C., preferably 20° C. to 90° C. for 0.5 to 12 hours, preferably 0.5 to 5 hours to give a compound ad. Alternatively, it is obtained by a method described in Comprehensive Organic Transformations, Richard C Larock (Megaw-Hill).

The $7^{th}$ step: 15% to 30% Ammonia water or a reagent having a substituent corresponding to the objective compound such as tert-butylamine etc. is added to a compound ad in a solvent such as ethyl acetate, dichloromethane, tetrahydrofuran, toluene etc. at −30° C. to 50° C., preferably −10° C. to 30° C. and the mixture is reacted at −10° C. to 30° C., preferably 0° C. to 30° C. for 0.5 to 72 hours to give a compound ae-i or a compound ae-ii.

When $R^{2a}$ and/or $R^{2b}$ is hydrogen in the resulting compound ae-i or ae-ii, a substituent of the objective compound, $R^{2a}$ and/or $R^{2b}$, may be further introduced by a conventional method if it is necessary, 1') Method for Preparing an Optically Active Isomer Method B An optically active compound ah of the present invention can be also prepared by a method below:

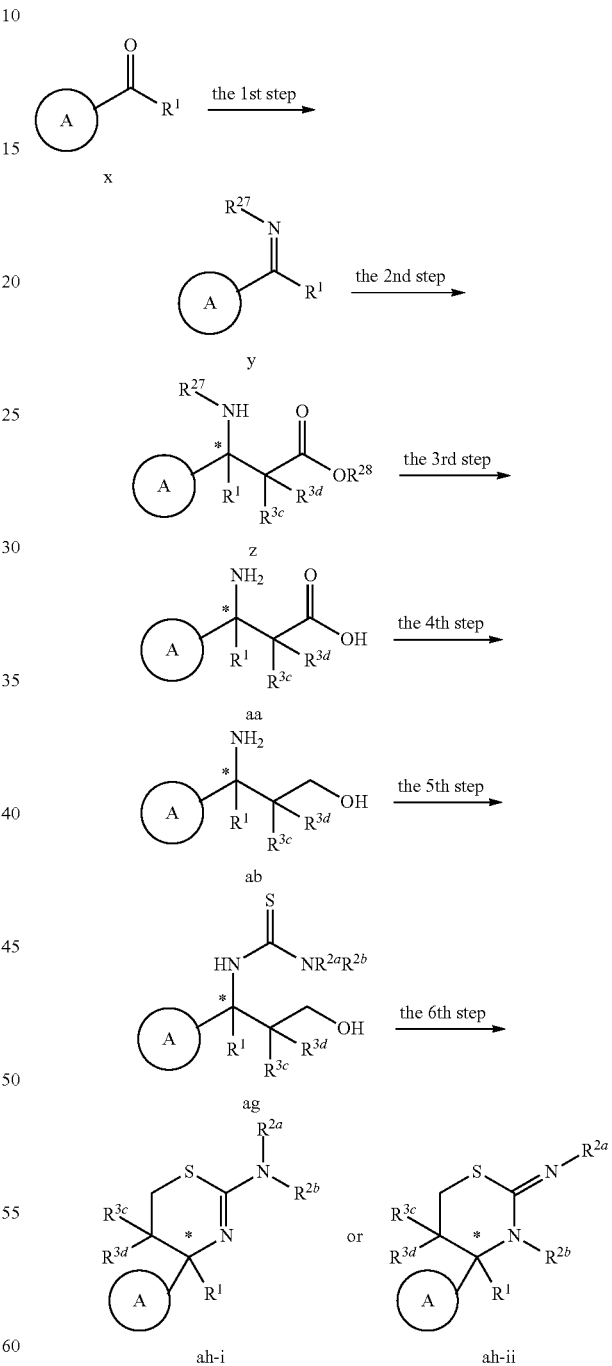

(In the scheme the symbols are the same as described above.)
The $1^{st}$ step to the $4^{th}$ step: the same as described in 1) above.
The $5^{th}$ step: isothiocyanate having a protecting group which is commercially available or can be prepared by a known method is added to a compound ab in a solvent such as dichloromethane, toluene, acetone etc. or a mixed solvent at −30° C. to 50° C., preferably −10° C. to 25° C. and the mixture is reacted for 0.5 to 12 hours, preferably 0.5 to 5 hours to give a compound ag.

The 6$^{th}$ step: Oxalyl chloride or thionyl chloride etc. and a catalytic amount of N,N-dimethylformamide are added to a compound ag in a solvent such as dichloromethane, tetrahydrofuran, toluene etc. at −30° C. to 50° C., preferably −10° C. to 25° C., or 1-chloro-N,N-2-trimethyl-1-propenenylamine is added to a compound ag, and reacted at 0° C. to 100° C., preferably 20° C. to 90'C for 0.5 to 1ot to give a compound ah-i ah-ii, 2) Introduction of $R^{3a}$ and $R^{3b}$ An optically active compound ae-iii or ae-iv of the present invention can be also prepared by introducing $R^{3a}$ and $R^{3b}$ as shown below:

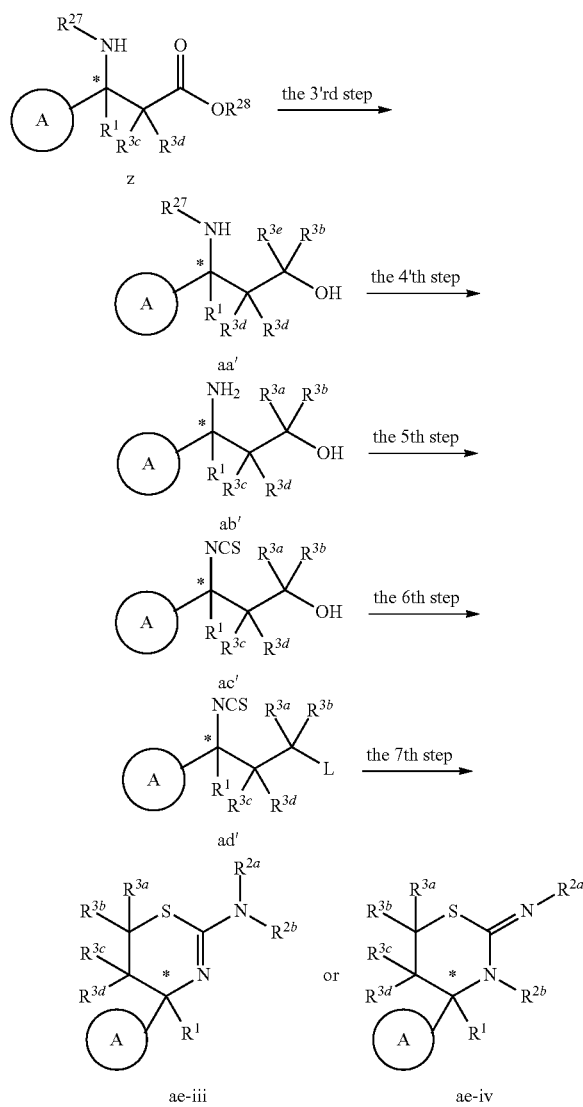

(In the scheme above, each symbol is the same as described above)

When preparing a compound ae-iii or ae-iv in which $R^{3a}$ and $R^{3b}$ are substituted on the carbon atom next to S atom, a compound z is processed through the 3$^{rd}$ and 4$^{th}$ steps in place of the 3$^{rd}$ and 4$^{th}$ steps of 1) described above, and $R^{3a}$ and $R^{3b}$ are introduced in advance.

The 3$^{rd}$ step: A Grignard reagent having a substituent corresponding to the objective compound such as methyl magnesium chloride, ethyl magnesium bromide etc: is added to a compound z in a solvent such as ether, tetrahydrofuran etc. or a mixed solvent such as ether-tetrahydrofuran etc. at −100° C. to 50° C., preferably −80° C. to 30° C., or a compound z is converted to Weinreb Amide and reacted with a Grignard reagent having a substituent corresponding to the objective compound such as $R^{3a}$MgBr, $R^{3b}$MgBr. The reaction mixture is reacted for 0.2 to 24 hours, preferably 0.2 to 5 hours to give a compound aa'.

The 4$^{th}$ step: A compound aa' is reacted in a solvent such as methanol, ethanol, ether, tetrahydrofuran, 1,4-dioxane, dichloromethane, ethyl acetate etc. containing hydrogen chloride, trifluoroacetic acid etc. or in neat, trifluoroacetic acid at −30° C. to 100° C., preferably −10° C. to 90° C. for 0.5 to 12 hours, preferably 0.5 to 5 hours to give a compound ab'.

The compound ab' is processed in the same reactions as the 5$^{th}$ to 7$^{th}$ steps of 1) above to give the objective compound ae-iii or ae-iv.

When the substituent L of a compound ad' is eliminated to give a compound ad" shown below, the objective compound ae'-iii or ae'-iv is obtained by processing the compound ad" it through the 7$^{th}$ step in place of the 7$^{th}$ step described in 1) above.

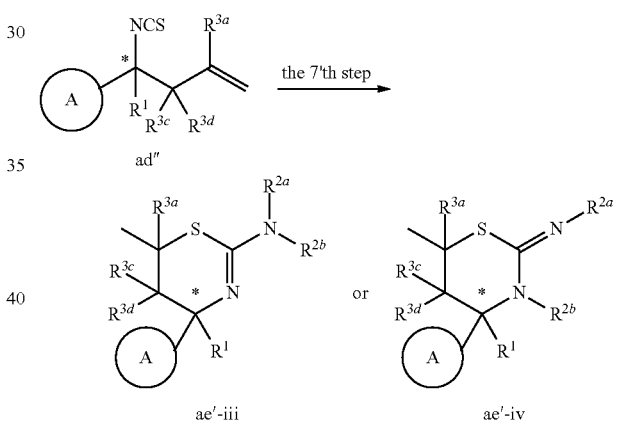

The 7$^{th}$ step: A compound ad" is dissolved in conc, sulfuric acid, trifluoroacetic acid, trifluoromethanesulfonic acid etc. and reacted at −30° C. to 100° C., preferably −10° C. to 40° C. for 0.1 to 12 hours, preferably 0.5 to 5 hours to give a compound ae'.

3) Conversion of a Substituent (1)

A preparation of a compound af-1 by conversion of the substituent is illustrated below:

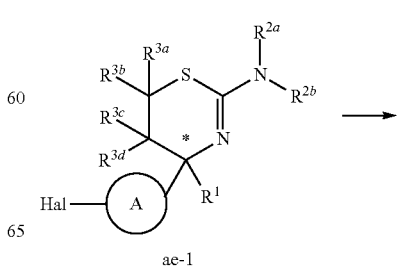

-continued

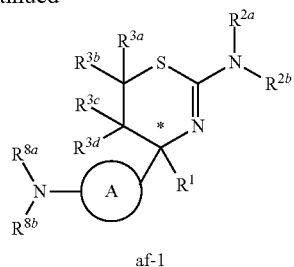

af-1

(In the scheme, $R^{8a}$ and $R^{8b}$ are an amino-protecting up, and the other symbols are the same as described above.)

Trisdibenzylideneacetonedipalladium, palladium acetate, palladium(0) prepared situ etc. and a phosphine ligand such as tri-tert-butylphosphine, dicyclohexylbiphenylphosphine etc. are added to a compound ae-1 in a solvent such as tetrahydrofuran, toluene, xylene etc. and further a reagent having a substituent corresponding to the objective compound such as lithium hexamethylenedisilazide, benzophenonimine etc. is added thereto at −10° C. to 30° C., then the reaction mixture is reacted at 30° C. to 120° C., preferably 50° C. to 100° C. for 0.5 to 48 hours, preferably 3 to 20 hours to give a compound af-1.

Any amino-protecting group which is deprotected by a method described in Protective Groups in Organic Synthesis, Theodora W Green (John Wiley & Sons) etc. can be used and examples of the protecting group include lower alkoxycarbonyl, lower alkenyloxycarbonyl, trialkylsilyl, acyl, methanesulfonyl, trifluoromethanesulfonyl and toluenesulfonyl etc.

4) Conversion of a Substituent (2)

A preparation of a compound af-2 by conversion of the substituent is illustrated below:

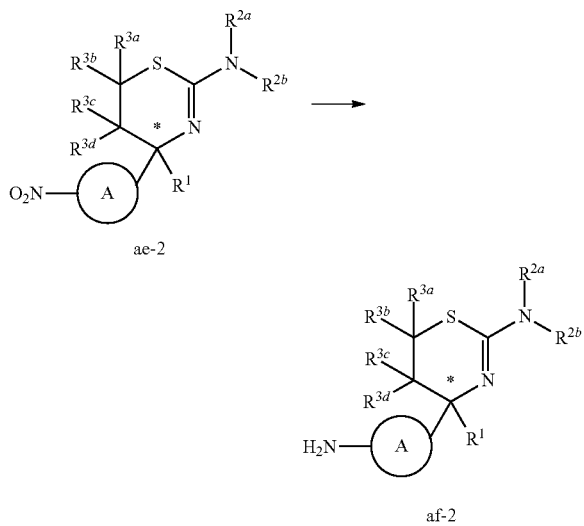

(In the scheme, each symbol is the same as described above.)

A catalyst of catalytic reduction such as 10% palladium-carbon etc. is added to a compound ae-2 in a solvent such as tetrahydrofuran, ethyl acetate, methanol etc. and it is reacted under the pressure of normal to 5 atom, preferably normal to 2 atom of hydrogen atmosphere at 30° C. to 120° C., preferably 50'C to 80° C. for 0.5 to 48 hours, preferably 6 to 20 hours to give a compound af-2. Alternatively, the compound af-2 is Obtained by a method described in Comprehensive Organic Transformations, Richard C Larock (Mcgraw-Hill).

5) Conversion of a Substituent (3)

A preparation of a compound af-3 by conversion of the substituent is illustrated below:

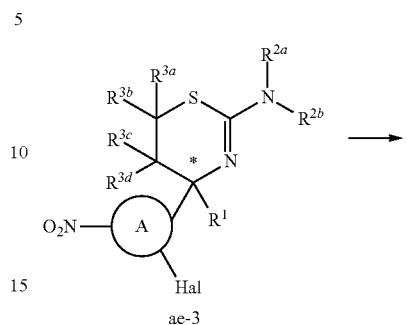

ae-3

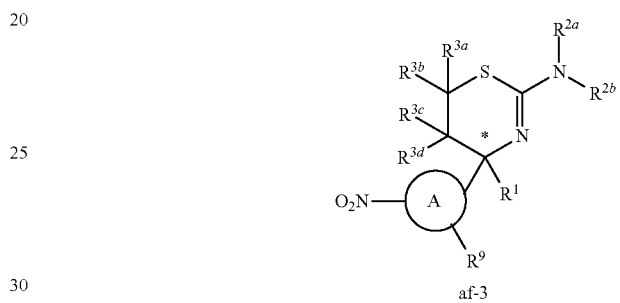

af-3

(In the scheme, $R^9$ is hydroxyl, optionally substituted lower alkyl, optionally substituted lower alkoxy, optionally substituted lower alkylthio, optionally substituted lower alkyl amino, optionally substituted aromatic carbocyclyloxy, optionally substituted heterocyclyloxy, optionally substituted aromatic carbocyclylthio, optionally substituted heterocyclylthio, optionally substituted carbocyclylamino, optionally substituted heterocyclylamino, cyano, azide, an optionally substituted carbocyclic group, an optionally substituted heterocyclic group, optionally substituted carbamoyl etc. and the other symbols are the same as described above.)

A reagent having a substituent corresponding to the objective compound such as ethanol, methanthiol, dimethylamine etc. is added to a compound ae-3 in a solvent such as tetrahydrofuran, ethanol etc. under the presence of a base such as sodium methoxide, potassium tert-butoxide, sodium hydroxide, sodium hydride etc. or without a base at −10° C. to 50° C. and it is reacted for 0.5 to 12 hours, preferably 1 to 8 hours to give a compound af-3. If necessary, a coupling reaction may be carried out in the same manner as the method for preparing a compound (I-19) described above.

In every step described above, if a starting compound has a functional group which disturb the reaction (e.g., hydroxyl, mercapto, amino, formyl, carbonyl, carboxyl etc.), it is recommended to protect the functional group and deprotect it at a subsequent appropriate step with a method described in Protective Groups in Organic Synthesis, Theodora W Green (John Wiley & Sons) etc.

Further the order of steps may be changed and each reaction intermediate may be isolated and used in the subsequent step.

Examples of a preferable compound in the present invention include the followings:
In a formula (I')

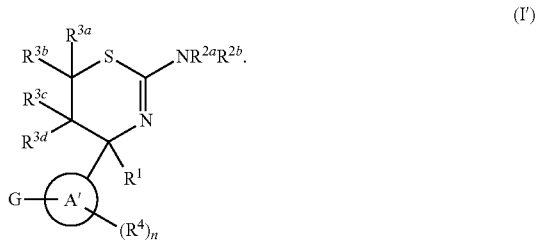

(I')

1) a compound in which the ring A' is phenyl or a nitrogen-containing aromatic heterocyclic getup (hereinafter called a compound in which the ring A' is A'1),
a compound in which the ring A' is benzene, pyridine, indole, benzisoxazole, benzopyrazole, benzofuran, benzothiophene, benzodioxole, or dihydrobenzodioxolane (hereinafter called a compound in which the ring A' is A'2),
a compound in which the ring A' is benzene (hereinafter called a compound in which the ring A' is A'3),
a compound in which the ring A' is pyridine (hereinafter called a compound in which the ring A' is A'4)
2) a compound in which $R^1$ is optionally substituted lower alkyl (hereinafter called a compound in which $R^1$ is R1-1),
a compound in which $R^1$ is methyl (hereinafter called a compound in which $R^1$ is R1-2),
3) a compound in which $R^{2a}$ and $R^{2b}$ are each independently hydrogen, lower alkyl or acyl (hereinafter called a compound in which $R^{2a}$ and $R^{2b}$ are R2-1),
a compound in which both of $R^{2a}$ and $R^{2b}$ are hydrogens (hereinafter called a compound in which $R^{2a}$ and $R^{2b}$ are R2-2),
4) a compound in which $R^{3a}$, $R^{3b}$, $R^{3c}$ and $R^{3d}$ are each independently hydrogen, halogen, hydroxyl, lower alkyl or amino (hereinafter called a compound in which $R^{3a}$, $R^{3b}$, $R^{3c}$ and $R^{3d}$ are R3-1),
a compound in which $R^{3a}$ and $R^{3b}$, or $R^{3c}$ and $R^{3d}$ taken together form cyclopropyl, cyclobutyl, cyclopentyl or cyclohexyl together (hereinafter called a compound in which $R^{3a}$, $R^{3b}$, $R^{3c}$ and $R^{3d}$ are R3-2),
a compound in which $R^{3a}$ and $R^{3b}$, or $R^{3c}$ and $R^{3d}$ are the same substituent selected from halogen and lower alkyl (hereinafter called a compound in which $R^{3a}$, $R^{3b}$, $R^{3c}$ and $R^{3d}$ are R3-3),
a compound in which all of $R^{3a}$, $R^{3b}$, $R^{3c}$ and $R^{3d}$ are hydrogens (hereinafter called a compound in which $R^{3a}$, $R^{3b}$, $R^{3c}$, and $R^{3d}$ are R3-4),
5) a compound in which n is 0 to 2, $R^4$ is each independently halogen, lower alkoxy, lower alkylamino, lower alkylthio, oxo or lower alkylenedioxy (hereinafter called a compound in which $R^4$ is R4-1),
a compound in which n is 0 to 2, $R^4$ is each independently halogen (hereinafter called a compound in which $R^4$ is R4-2),
6) a compound in which G is (ii), (iv), (v), (x), (xiii) or (xiv) above (hereinafter called a compound in which G is G1),
a compound in which G is (ii'), (ii''), (iv'), (v'), (x'), (xiii') or (xiv') above (hereinafter called a compound in which G is G2),
a compound in which G is (ii'), (ii''), (iv'), (v'), (x'), (xiii') or (xiv') above, and the ring B is optionally substituted pyridyl, optionally substituted pyrazinyl, optionally substituted thiazolyl, optionally substituted isoxazolyl, optionally substituted benzothiazolyl, optionally substituted thiazolopyridyl, optionally substituted quinolyl, optionally substituted isoquinolyl or optionally substituted naphthylidinyl, optionally substituted quinazolinyl, or optionally substituted pyridopyrimidinyl (hereinafter called a compound in which G is G3),
a compound in which G is (ii') above (hereinafter called a compound in which G is G4),
a compound in which a combination of the ring A', $R^1$, $R^{2a}$ and $R^{2b}$, $R^{3a}$, $R^{3b}$, $R^{3c}$ and $R^{3d}$, n and $R^4$, and G is as follows;
(A'1,R1-1,R2-1,R3-1,R4-1,G1), (A'1,R1-1,R2-1,R3-1,R4-1,G2), (A'1,R1-1,R2-1,R3-1,R4-1, G3), (A'1,R1-1,R2-1,R3-1,R4-1,G4), (A'1,R1-1,R2-1,R3-1,R4-2,G1), (A'1,R1-1,R2-1,R3-1,R4-2,G2), (A'1,R1-1,R2-1,R3-1,R4-2,G3), (A'1,R1-1,R2-1,R3-1,R4-2,G4), (A'1,R1-1,R2-1,R3-2,R4-1,G1), (A'1,R1-1,R2-1,R3-2,R4-1,G2), (A'1,R1-1,R2-1,R3-2,R4-1,G3), (A'1,R1-1,R2-1, R3-2,R4-1,G4), (A'1,R1-1,R2-1,R3-2,R4-2,G1), (A'1,R1-1,R2-1,R3-2,R4-2,G2), (A'1,R1-1,R2-1,R3-2,R4-2,G3), (A'1,R1-1,R2-1,R3-2,R4-2,G4), (A'1,R1-1,R2-1,R3-3,R4-1,G1), (A'1,R1-1,R2-1,R3-3,R4-1,G2), (A'1,R1-1,R2-1,R3-3,R4-1,G3),    (A'1,R1-1,R2-1,R3-3,R4-1,G4), (A'1,R1-1,R2-1,R3-3,R4-2,G1), (A'1,R1-1,R2-1,R3-3,R4-2,G2), (A'1,R1-1,R2-1,R3-3,R4-2,G3), (A'1,R1-1,R2-1,R3-3,R4-2,G4), (A'1,R1-1,R2-1,R3-4,R4-1,G1), (A'1,R1-1,R2-1,R3-4,R4-1,G2), (A'1,R1-1,R2-1,R3-4,R4-1,G3), (A'1,R1-1,R2-1,R3-4,R4-1,G4), (A'1,R1-1,R2-1,R3-4,R4-2,G1), (A'1,R1-1,R2-1,R3-4,R4-2,G2), (A'1,R1-1,R2-1,R3-4,R4-2,G3), (A'1,R1-1,R2-1,R3-4,R4-2,G4), (A'1,R1-1,R2-2,R3-1,R4-1,G1), (A'1,R1-1,R2-2,R3-1,R4-1,G2), (A'1,R1-1,R2-2,R3-1,R4-1,G3), (A'1,R1-1,R2-2,R3-1,R4-1,G4), (A'1,R1-1,R2-2,R3-1,R4-2,G1), (A'1,R1-1,R2-2,R3-1,R4-2,G2), (A'1,R1-1,R2-2,R3-1,R4-2,G3), (A'1,R1-1,R2-2,R3-1,R4-2,G4), (A'1,R1-1,R2-2,R3-2,R4-1,G1), (A'1,R1-1,R2-2,R3-2,R4-1,G2), (A'1,R1-1,R2-2,R3-2,R4-1,G3), (A'1,R1-1,R2-2,R3-2,R4-1,G4), (A'1,R1-1,R2-2,R3-2,R4-2,G1), (A'1,R1-1,R2-2,R3-2,R4-2,G2), (A'1,R1-1,R2-2,R3-2,R4-2,G3), (A'1,R1-1,R2-2,R3-2,R4-2,G4), (A'1,R1-1,R2-2,R3-3,R4-1,G1), (A'1,R1-1,R2-2,R3-3,R4-1,G2), (A'1,R1-1,R2-2,R3-3,R4-1,G3), (A'1,R1-1,R2-2,R3-3,R4-1, G4), (A'1,R1-1,R2-2,R3-3,R4-2,G1), (A'1,R1-1,R2-2,R3-3,R4-2,G2), (A'1,R1-1,R2-2,R3-3,R4-2,G3), (A'1,R1-1,R2-2,R3-3,R4-2,G4), (A'1,R1-1,R2-2,R3-4,R4-1,G1), (A'1,R1-1,R2-2,R3-4,R4-1,G2), (A'1,R1-1,R2-2,R3-4,R4-1,G3), (A'1,R1-1,R2-2,R3-4,R4-1,G4), (A'1,R1-1,R2-2,R3-4,R4-2,G1), (A'1,R1-1,R2-2,R3-4,R4-2,G2), (A'1,R1-1,R2-2,R3-4,R4-2,G3), (A'1,R1-1,R2-2,R3-4,R4-2,G4), (A'1,R1-2,R2-1,R3-1,R4-1,G1), (A'1,R1-2,R2-1,R3-1,R4-1,G2), (A'1,R1-2,R2-1,R3-1,R4-1,G3), (A'1,R1-2,R2-1,R3-1,R4-1,G4), (A'1,R1-2,R2-1,R3-1,R4-2,G1), (A'1,R1-2,R2-1,R3-1,R4-2,G2), (A'1,R1-2,R2-1,R3-1,R4-2,G3), (A'1,R1-2,R2-1,R3-1,R4-2,G4), (A'1,R1-2,R2-1,R3-2,R4-1,G1), (A'1,R1-2,R2-1,R3-2,R4-1,G2), (A'1,R1-2,R2-1,R3-2,R4-1,G3), (A'1,R1-2,R2-1,R3-2,R4-1,G4), (A'1,R1-2,R2-1,R3-2,R4-2,G1), (A'1,R1-2,R2-1,R3-2,R4-2,G2), (A'1,R1-2,R2-1,R3-2,R4-2,G3), (A'1,R1-2,R2-1,R3-2,R4-2,G4), (A'1,R1-2,R2-1,R3-3, R4-1,G1), (A'1,R1-2,R2-1,R3-3,R4-1,G2), (A'1,R1-2,R2-1,R3-3,R4-1,G3), (A'1,R1-2,R2-1,R3-3,R4-1,G4), (A'1,R1-2,R2-1,R3-3,R4-2,G1), (A'1,R1-2,R2-1,R3-3,R4-2,G2), (A'1,R1-2,R2-1,R3-3,R4-2,G3), (A'1,R1-2,R2-1,R3-3,R4-2,G4), (A'1,R1-2,R2-1,R3-4,R4-1,G1), (A'1,R1-2,R2-1,R3-4,R4-1,G2), (A'1,R1-2,R2-1,R3-4,R4-1,G3), (A'1,R1-2,R2-1,R3-4,R4-1,G4), (A'1,R1-2,R2-1,R3-4,R4-2,G1), (A'1,R1-2,R2-1,R3-4,R4-2,G2), (A'1,R1-2,R2-1,R3-4,R4-2,G3), (A'1,R1-2,R2-1,R3-4,R4-2,G4), (A'1,R1-2,R2-2,R3-1,R4-1,G1), (A'1,R1-2,R2-2,R3-1,R4-1,G2), (A'1,R1-2,R2-2,R3-1,R4-1,G3), (A'1,R1-2,R2-2,R3-1,R4-1,G4), (A'1,R1-2,R2-2,R3-1,R4-2,G1), (A'1,R1-2,R2-2,R3-1,R4-2,G2), (A'1,R1-2,R2-2,R3-1,R4-2,G3), (A'1,R1-2,R2-2,R3-1,R4-2,G4), (A'1,R1-2,R2-2,R3-2,R4-1,G1), (A'1,R1-2,R2-2,R3-2,R4-1,G2), (A'1, R1-2,R2-2,R3-2,R4-1,G3), (A'1,R1-2,R2-2,R3-2,R4-1,G4), (A'1,R1-2,R2-2,R3-2,R4-2,G1), (A'1,R1-2,R2-2,R3-2,R4-2,G2), (A'1,R1-2,R2-2,R3-2,R4-2,G3), (A'1,R1-2,R2-2,R3-2,R4-2,G4), (A'1,R1-2,R2-2,R3-3,R4-1,G1), (A'1,R1-2,R2-2,R3-3,R4-1,G2), (A'1,R1-2,R2-2,R3-3,R4-1,G3), (A'1,R1-2,R2-2,R3-3,R4-1,G4), (A'1,R1-2,R2-2,R3-3,R4-2,G1), (A'1,R1-2,R2-2,R3-3,R4-2,G2), (A'1,R1-2,R2-2,R3-3,R4-2,G3), (A'1,R1-2,R2-2,R3-3,R4-2,G4), (A'1,R1-2,R2-2,R3-4,R4-1,G1), (A'1,R1-2,R2-2,R3-4,R4-1,G2), (A'1,R1-2,R2-2,R3-4,R4-1,G3), (A'1,R1-2,R2-2,R3-4,R4-1,G4), (A'1,R1-2,R2-2,R3-4,R4-2,G1), (A'1,R1-2,R2-2,R3-4,R4-2,G2), (A'1,R1-2,R2-2,R3-4,R4-2,G3), (A'1,R1-2,R2-2,R3-4,R4-2,G4), (A'2,R1-1,R2-1,R3-1,R4-1,G1), (A'2,R1-1,R2-1,R3-1,R4-1,G2), (A'2,R1-1,R2-1,R3-1,R4-1,G3), (A'2,R1-1,R2-1,R3-1,R4-1,G4), (A'2,R1-1,R2-1,R3-1,R4-2,G1), (A'2,R1-1,R2-1,R3-1,R4-2,G2), (A'2,R1-1,R2-1,R3-1,R4-2,G3), (A'2,R1-1,R2-1,R3-1,R4-2,G4), (A'2,R1-1,R2-1,R3-2,R4-1,G1), (A'2,R1-1,R2-1,R3-2,R4-1,G2), (A'2,R1-1,R2-1,R3-2,R4-1,G3), (A'2,R1-1,R2-1,R3-2,R4-1,G4), (A'2,R1-1,R2-1,R3-2,R4-2,G1), (A'2,R1-1,R2-1,R3-2,R4-2,G2), (A'2,R1-1,R2-1,R3-2,R4-2,G3), (A'2,R1-1,R2-1,R3-2,R4-2,G4), (A'2,R1-1,R2-1,R3-3,R4-1,G1), (A'2,R1-1,R2-1,R3-3,R4-1,G2), (A'2,R1-1,R2-1,R3-3,R4-1,G3), (A'2,R1-1,R2-1,R3-3,R4-1,G4), (A'2,R1-1,R2-1,R3-3,R4-2,G1), (A'2,R1-1,R2-1,R3-3,R4-2,G2), (A'2,R1-1,R2-1,R3-3,R4-2,G3), (A'2,R1-1,R2-1,R3-3,R4-2,G4), (A'2,R1-1,R2-1,R3-4,R4-1,G1), (A'2,R1-1,R2-1,R3-4,R4-1,G2), (A'2,R1-1,R2-1,R3-4,R4-1,G3), (A'2,R1-1,R2-1,R3-4,R4-1,G4), (A'2,R1-1,R2-1,R3-4,R4-2,G1), (A'2,R1-1,R2-1,R3-4,R4-2,G2), (A'2,R1-1,R2-1,R3-4,R4-2,G3), (A'2,R1-1,R2-1,R3-4,R4-2,G4), (A'2,R1-1,R2-2,R3-1,R4-1,G1), (A'2,R1-1,R2-2,R3-1,R4-1,G2), (A'2,R1-1,R2-2,R3-1,R4-1,G3), (A'2,R1-1,R2-2,R3-1,R4-1,G4), (A'2,R1-1,R2-2,R3-1,R4-2,G1), (A'2,R1-1,R2-2,R3-1,R4-2,G2), (N'2,R1-1,R2-2,R3-1,R4-2,G3), (A'2,R1-1,R2-2,R3-1,R4-2,G4), (A'2,R1-1,R2-2,R3-2,R4-1,G1), (A'2,R1-1,R2-2,R3-2,R4-1,G2), (A'2,R1-1,R2-2,R3-2,R4-2,G3), (A'2,R1-1,R2-2,R3-2,R4-1,G4), (A'2,R1-1,R2-2,R3-2,R4-2,G1), (A'2,R1-1,R2-2,R3-2,R4-2,G2), (A'2,R1-1,R2-2,R3-2,R4-2,G3), (A'2,R1-1,R2-2,R3-2,R4-2,G4), (A'2,R1-1,R2-2,R3-3,R4-1,G1), (A'2,R1-1,R2-2,R3-3,R4-1,G2), (A'2,R1-1,R2-2,R3-3,R4-1,G3), (A'2,R1-1,R2-2,R3-3,R4-1, G4), (A'2,R1-1,R2-2,R3-3,R4-2,G1), (A'2,R1-1,R2-2,R3-3,R4-2,G2), (A'2,R1-1,R2-2,R3-3,R4-2,G3), (A'2,R1-1,R2-2,R3-3,R4-2,G4), (A'2,R1-1,R2-2,R3-4,R4-1,G1), (A'2,R1-1,R2-2,R3-4,R4-1,G2), (A'2,R1-1,R2-2,R3-4,R4-1,G3), (A'2,R1-1,R2-2,R3-4,R4-1,G4), (A'2,R1-1,R2-2,R3-4,R4-2,G1), (A'2,R1-1,R2-2,R3-4,R4-2,G2), (A'2,R1-1,R2-2,R3-4,R4-2,G3), (A'2,R1-1,R2-2,R3-4,R4-2,G4), (A'2,R1-2,R2-1,R3-1,R4-1,G1), (A'2,R1-2,R2-1,R3-1,R4-1,G2), (A'2,R1-2,R2-1,R3-1,R4-1,G3), (A'2,R1-2,R2-1,R3-1,R4-1,G4), (A'2,R1-2,R2-1,R3-1,R4-2,G1), (A'2,R1-2,R2-1,R3-1,R4-2,G2), (A'2,R1-2,R2-1,R3-1,R4-2,G3), (A'2,R1-2,R2-1,R3-1,R4-2,G4), (A'2,R1-2,R2-1,R3-2,R4-1,G1), (A'2,R1-2,R2-1,R3-2,R4-1,G2), (A'2,R1-2,R2-1,R3-2,R4-1,G3), (A'2,R1-2,R2-1,R3-2,R4-1,G4), (A'2,R1-2,R2-1,R3-2,R4-2,G1), (A'2,R1-2,R2-1,R3-2,R4-2,G2), (A'2,R1-2,R2-1,R3-2,R4-2,G3), (A'2,R1-2,R2-1,R3-2,R4-2,G4), (A'2,R1-2,R2-1,R3-3,R4-1,G1), (A'2,R1-2,R2-1,R3-3,R4-1,G2), (A'2,R1-2,R2-1,R3-3,R4-1,G3), (A'2,R1-2,R2-1,R3-3,R4-1,G4), (A'2,R1-2,R2-1,R3-3,R4-2,G1), (A'2,R1-2,R2-1,R3-3,R4-2,G2), (A'2,R1-2,R2-1,R3-3,R4-2,G3), (A'2,R1-2,R2-1,R3-3,R4-2,G4), (A'2,R1-2,R2-1,R3-4,R4-1,G1), (A'2,R1-2,R2-1,R3-4,R4-1,G2), (A'2,R1-2,R2-1,R3-4,R4-1,G3), (A'2,R1-2,R2-1,R3-4,R4-1,G4), (A'2,R1-2,R2-1,R3-4,R4-2,G1), (A'2,R1-2,R2-1,R3-4,R4-2,G2), (A'2,R1-2,R2-1,R3-4,R4-2,G3), (A'2,R1-2,R2-1,R3-4,R4-2,G4), (A'2,R1-2,R2-2,R3-1,R4-1,G1), (A'2,R1-2,R2-2,R3-1,R4-1,G2), (A'2,R1-2,R2-2,R3-1,R4-1,G3), (A'2,R1-2,R2-2,R3-1,R4-1,G4), (A'2,R1-2,R2-2,R3-1,R4-2,G1), (A'2,R1-2,R2-2,R3-1,R4-2,G2), (A'2,R1-2,R2-2,R3-1,R4-2,G3), (A'2,R1-2,R2-2,R3-1,R4-2,G4), (A'2,R1-2,R2-2,R3-2,R4-1,G1), (A'2,R1-2,R2-2,R3-2,R4-1,G2), (A'2,R1-2,R2-2,R3-2,R4-1,G3), (A'2,R1-2,R2-2,R3-2,R4-1,G4), (A'2,R1-2,R2-2,R3-2,R4-2,G1), (A'2,R1-2,R2-2,R3-2,R4-2,G2), (A'2,R1-2,R2-2,R3-2,R4-2,G3), (A'2,R1-2,R2-2,R3-2,R4-2,G4), (A'2,R1-2,R2-2,R3-3,R4-1,G1), (A'2,R1-2,R2-2,R3-3,R4-1,G2), (A'2,R1-2,R2-2,R3-3,R4-1,G3), (A'2,R1-2,R2-2,R3-3,R4-1,G4), (A'2,R1-2,R2-2,R3-3,R4-2,G1), (A'2,R1-2,R2-2,R3-3,R4-2,G2), (A°2,R1-2,R2-2,R3-3,R4-2,G3), (A'2,R1-2,R2-2,R3-3,R4-2,G4), (A'2,R1-2,R2-2,R3-4,R4-1,G1), (A'2,R1-2,R2-2,R3-4,R4-1,G2), (A'2,R1-2,R2-2,R3-4,R4-1,G3), (A'2,R1-2,R2-2,R3-4,R4-1,G4), (A'2,R1-2,R2-2,R3-4,R4-2,G1), (A'2,R1-2,R2-2,R3-4,R4-2,G2), (A'2,R1-2,R2-2,R3-4,R4-2,G3), (A'2,R1-2,R2-2,R3-4,R4-2,G4), (A'3,R1-1,R2-1,R3-1,R4-1,G1), (A'3,R1-1,R2-1,R3-1,R4-1,G2), (A'3,R1-1,R2-1,R3-1,R4-1,G3), (A'3,R1-1,R2-1,R3-1,R4-1,G4), (A'3,R1-1,R2-1,R3-1,R4-2,G1), (A'3,R1-1,R2-1,R3-1,R4-2,G2), (A'3,R1-1,R2-1,R3-1,R4-2,G3), (A'3,R1-1,R2-1,R3-1,R4-2,G4), (A'3,R1-1,R2-1,R3-2,R4-1,G1), (A'3,R1-1,R2-1,R3-2,R4-1,G2), (A'3,R1-1,R2-1,R3-2,R4-1,G3), (A'3,R1-1,R2-1,R3-2,R4-1,G4), (A'3,R1-1,R2-1,R3-2,R4-2,G1), (A'3,R1-1,R2-1,R3-2,R4-2,G2), (A'3,R1-1,R2-1,R3-2,R4-2,G3), (A'3,R1-1,R2-1,R3-2,R4-2,G4), (A'3,R1-1,R2-1,R3-3,R4-1,G1), (A'3,R1-1,R2-1,R3-3,R4-1,G2), (A'3,R1-1,R2-1,R3-3,R4-1,G3), (A'3,R1-1,R2-1,R3-3,R4-1,G4), (A'3,R1-1,R2-1,R3-3,R4-2,G1), (A'3,R1-1,R2-1,R3-3,R4-2,G2), (A'3,R1-1,R2-1,R3-3,R4-2,G3), (A'3,R1-1,R2-1,R3-3,R4-2,G4), (A'3,R1-1,R2-1,R3-4,R4-1,G1), (A'3,R1-1,R2-1,R3-4,R4-1,G2), (A'3,R1-1,R2-1,R3-4,R4-1,G3), (A'3,R1-1,R2-1,R3-4,R4-1,G4), (A'3,R1-1,R2-1,R3-4,R4-2,G1), (A'3,R1-1,R2-1,R3-4,R4-2,G2), (A'3,R1-1,R2-1,R3-4,R4-2,G3), (A'3,R1-1,R2-1,R3-4,R4-2,G4), (A'3,R1-1,R2-2,R3-1,R4-1,G1), (A'3,R1-1,R2-2,R3-1,R4-1,G2), (A'3,R1-1,R2-2,R3-1,R4-1,G3), (A'3,R1-1,R2-2,R3-1,R4-1,G4), (A'3,R1-1,R2-2-1,R4-2,G1), (A'3,R1-1,R2-2,R3-1,R4-2,G2), (A'3,R1-1,R2-2,R3-1,R4-2,G3), (A'3,R1-1,R2-2,R3-1,R4-2,G4), (A'3,R1-1,R2-2,R3-2,R4-1,G1), (A'3,R1-1,R2-2,R3-2,R4-1,G2), (A'3,R1-1,R2-2,R3-2,R4-1,G3), (A'3,R1-1,R2-2,R3-2,R4-1,G4), (A'3,R1-1,R2-2,R3-2,R4-2,G1), (A'3,R1-1,R2-2,R3-2,R4-2,G2), (A'3,R1-1,R2-2,R3-2,R4-2,G3), (A'3,R1-1,R2-2,R3-2,R4-2,G4), (A'3,R1-1,R2-2,R3-3,R4-1,G1), (A'3,R1-1,R2-2,R3-3,R4-1,G2), (A'3,R1-1,R2-2,R3-3,R4-1,G3), (A'3,R1-1,R2-2,R3-3,R4-1,G4), (A'3,R1-1,R2-2,R3-3,R4-2,G1), (A'3,R1-1,R2-2,R3-3,R4-2,G2), (A'3,R1-1,R2-2,R3-3,R4-2,G3), (A'3,R1-1,R2-2,R3-3,R4-2,G4), (A'3,R1-1,R2-2,R3-4,R4-1,G1), (A'3,R1-1,R2-2,R3-4,R4-1,G2), (A'3,R1-1,R2-2,R3-4,R4-1,G3), (A'3,R1-1,R2-2,R3-4,R4-1,G4), (A'3,R1-1,R2-2,R3-4,R4-2,G1), (A'3,R1-1,R2-2,R3-4,R4-2,G2), (A'3,R1-1,R2-2,R3-4,R4-2,G3), (A'3,R1-1,R2-2,R3-4,R4-2,G4), (A'3,R1-2,R2-1,R3-1,R4-1,G1), (A'3,R1-2,R2-1,R3-1,R4-1,G2), (A'3,R1-2,R2-1,R3-1,R4-1,G3), (A'3,R1-2,R2-1,R3-1,R4-1,G4), (A'3,R1-2,R2-1,R3-1,R4-2,G1), (A'3,R1-2,R2-1,R3-1,R4-2,G2), (A'3,R1-2,R2-1,R3-1,R4-2,G3), (A'3,R1-2,R2-1,R3-1,R4-2,G4), (A'3,R1-2,R2-1,R3-2,R4-1,G1), (A'3,R1-2,R2-1,R3-2,R4-1,G2), (A'3,R1-2,R2-1,R3-2,R4-1,G3), (A'3,R1-2,R2-1,R3-2,R4-1,G4), (A'3,R1-2,R2-1,R3-2,R4-2,G1), (A'3,R1-2,R2-1,R3-2,R4-2,G2), (A'3,R1-2,R2-1,R3-2,R4-2,G3), (A'3,R1-2,R2-1,R3-2,R4-2,G4), (A'3,R1-2,R2-1,R3-3,R4-1,G1), (A'3,R1-2,R2-1,R3-3,R4-1,G2), (A'3,R1-2,R2-1,R3-3,R4-1,G3), (A'3,R1-2,R2-1,R3-3,R4-1,G4), (A'3,R1-2,R2-1,R3-3,R4-2,G1), (A'3,R1-2,R2-1,R3-3,R4-2,G2), (A'3,R1-2,R2-1,R3-3,R4-2,G3), (A'3,R1-2,R2-1,R3-3,R4-2,G4), (A'3,R1-2,R2-1,R3-4,R4-1,G1), (A'3,R1-2,R2-1,R3-4,R4-1,G2), (A'3,R1-2,R2-1,R3-4,R4-1,G3), (A'3,R1-2,R2-1,R3-4,R4-1,G4), (A'3,R1-2,R2-1,R3-4,R4-2,G1), (A'3,R1-2,R2-1,R3-4,R4-2,G2), (A'3,R1-2,R2-1,R3-4,R4-2,G3), (A'3,R1-2, R2-1,R3-4,R4-2,G4), (A'3,R1-2,R2-2,R3-1,R4-1,G1), (A'3, R1-2,R2-2,R3-1,R4-1,G2), (A'3,R1-2,R2-2,R3-1,R4-1,G3), (A'3,R1-2,R2-2,R3-1,R4-1,G4), (A'3,R1-2,R2-2,R3-1,R4-2, G1), (A'3,R1-2,R2-2,R3-1,R4-2,G2), (A'3,R1-2,R2-2,R3-1, R4-2,G3), (A'3,R1-2,R2-2,R3-4-2,G4), (A'3,R1-2,R2-2,R3-2,R4-1,G1), (A'3,R1-2,R2-2,R3-2,R4-1,G2), (A'3,R1-2,R2-2-2,R4-1,G3), (A'3,R1-2,R1-2,R3-2,R4-1,G4), (A'3,R1-2, R2-2,R3-2,R4-2,G1), (A'3,R1-2,R2-2,R3-2,R4-2,G2), (A'3, R1-2,R2-2,R3-2,R4-2,G3), (A'3,R1-2,R2-2,R3-2,R4-2,G4), (A'3,R1-2,R2-2,R3-3,R4-1,G1), (A'3,R1-2,R2-2,R3-3,R4-1, G2), (A'3,R1-2,R2-2,R3-3,R4-1,G3), (A'3,R2,R2-2,R3-3, R4-1,G4), (A'3,R1-2,R2-2,R3-3,R4-2,G1), (A'3,R1-2,R2-2, R3-3,R4-2,G2), (A'3,R1-2,R2-2,R3-3,R4-2,G3), (A'3,R1-2, R2-2,R3-3,R4-2,G4), (A'3,R1-2,R2-2,R3-4,R4-1,G1), (A'3, R1-2,R2-2,R3-4,R4-1,G2), (A'3,R1-2,R2-2,R3-4,R4-1,G3), (A'3,R1-2,R2-2,R3-4,R4-1,G4), (A'3,R1-2,R2-2,R3-4,R4-2, G1), (A'3,R1-2,R2-2,R3-4,R4-2,G2), (A'3,R1-2,R2-2,R3-4, R4-2,G3), (A'3,R1-2,R2-2,R3-4,R4-2,G4),
(A'4,R1-1,R2-1,R3-1,R4-1,G1), (A'4,R1-1,R2-1,R3-1,R4-1, G2), (A'4,R1-1,R2-1,R3-1,R4-1,G3), (A'4,R1-1,R2-1,R3-1, R4-1,G4), (A'4,R1-1,R2-1,R3-1,R4-2,G1), (A'4,R1-1,R2-1, R3-1,R4-2,G2), (A'4,R1-1,R2-1,R3-1,R4-2,G3), (A'4,R1-1, R2-1,R3-1,R4-2,G4), (A'4,R1-1,R2-1,R3-2,R4-1,G1), (A'4, R1-1,R2-1,R3-2,R4-1,G2), (A'4,R1-1,R2-1,R3-2,R4-1,G3), (A'4,R1-1,R2-1,R3-2,R4-1,G4), (A'4,R1-1,R2-1,R3-2,R4-2, G1), (A'4,R1-1,R2-1,R3-2,R4-2,G2), (A'4,R1-1,R2-1,R3-2, R4-2,G3), (A'4,R1-1,R2-1,R3-2,R4-2,G4), (A'4,R1-1,R2-1, R3-3,R4-1,G1), (A'4,R1-1,R2-1,R3-3,R4-1,G2), (A'4,R1-1, R2-1,R3-3,R4-1,G3), (A'4,R1-1,R2-1,R3-3,R4-1,G4), (A'4, R1-1,R2-1,R3-3,R4-2,G1), (A'4,R1-1,R2-1,R3-3,R4-2,G2), (A'4,R1-1,R2-1,R3-3,R4-2,G3), (A'4,R1-1,R2-1,R3-3,R4-2, G4), (A'4,R1-1,R2-1,R3-4,R4-1,G1), (A'4,R1-1,R2-1,R3-4, R4-1,G2), (A'4,R1-1,R2-1,R3-4,R4-1,G3), (A'4,R1-1,R2-1, R3-4,R4-1,G4), (A'4,R1-1,R2-1,R3-4,R4-2,G1), (A'4,R1-1, R2-1,R3-4,R4-2,G2), (A'4,R1-1,R2-1,R3-4,R4-2,G3), (A'4, R1-1,R2-1,R3-4,R4-2,G4), (A'4,R1-1,R2-2,R3-1,R4-1,G1), (A'4,R1-1,R2-2,R3-1,R4-1,G2), (A'4,R1-1,R2-2,R3-1,R4-1, G3), (A'4,R1-1,R2-2,R3-1,R4-1,G4), (A'4,R1-1,R2-2,R3-1, R4-2,G1), (A'4,R1-1,R2-2,R3-1,R4-2,G2), (A'4,R1-1,R2-2, R3-1,R4-2,G3), (A'4,R1-1,R2-2,R3-1,R4-2,G4), (A'4,R1-1, R2-2,R3-2,R4-1,G1), (A'4,R1-1,R2-2,R3-2,R4-1,G2), (A'4, R1-1,R2-2,R3-2,R4-1,G3), (A'4,R1-1,R2-2,R3-2,R4-1,G4), (A'4,R1-1,R2-2,R3-2,R4-2,G1), (A'4,R1-1,R2-2,R3-2,R4-2, G2), (A'4,R1-1,R2-2,R3-2,R4-2,G3), (A'4,R1-1,R2-2,R3-2, R4-2,G4), (A'4,R1-1,R2-2,R3-3,R4-1,G1), (A'4,R1-1,R2-2, R3-3,R4-1,G2), (A'4,R1-1,R2-2,R3-3,R4-1,G3), (A'4,R1-1, R2-2,R3-3,R4-1,G4), (A'4,R1-1,R2-2,R3-3,R4-2,G1), (A'4, R1-1,R2-2,R3-3,R4-2,G2), (A'4,R1-2,R2-2,R3-3,R4-2,G3), (A'4,R1-1,R2-2,R3-3,R4-2,G4), (A'4,R1-2,R2-3,R4-1, G1), (A'4,R1-1,R2-2,R3-4,R4-1,G2) (A'4,R1-2,R2-3,R4-, R4-1,G3), (A'4,R1-1,R2-2,R3-4,R4-1,G4), (A'4,R1-2,R2-2, R3-4,R4-2,G1), (A'4,R1-1,R2-2,R3-4,R4-2,G2), (A'4,R1-1, R2-2,R3-4,R4-2,G3), (A'4,R1-1,R2-2,R3-4,R4-2,G4), (A'4, R1-2,R2-1,R3-1,R4-1,G1), (A'4,R1-2,R2-1,R3-1,R4-1,G2), (A'4,R1-2,R2-1,R3-1,R4-1,G3), (A'4,R1-2,R2-1,R3-1,R4-1, G4), (A'4,R1-2,R2-1,R3-1,R4-2,G1), (A'4,R1-2,R2-1,R3-1, R4-2,G2), (A'4,R1-2,R2-1,R3-1,R4-2,G3), (A'4,R1-2,R2-1, R3-1,R4-2,G4), (A'4,R1-2,R2-1,R3-2,R4-1,G1), (A'4,R1-2, R2-1,R3-2,R4-1,G2), (A'4,R1-2,R2-1,R3-2,R4-1,G3), (A'4, R1-2,R2-1,R3-2,R4-1,G4), (A'4,R1-2,R2-1,R3-2,R4-2,G1), (A'4,R1-2,R2-1,R3-2,R4-2,G2), (A'4,R1-2,R2-1,R3-2,R4-2, G3), (A'4,R1-2,R2-1,R3-2,R4-2,G4), (A'4,R1-2,R2-1,R3-3, R4-1,G1), (A'4,R1-2,R2-1,R3-3,R4-1,G2), (A'4,R1-2,R2-1, R3-3,R4-1,G3), (A'4,R1-2,R2-1,R3-3,R4-1,G4), (A'4,R1-2, R2-1,R3-3,R4-2,G1), (A'4,R1-2,R2-1,R3-3,R4-2,G2), (A'4, R1-2,R2-1,R3-3,R4-2,G3), (A'4,R1-2,R2-1,R3-3,R4-2,G4), (A'4,R1-2,R2-1,R3-4,R4-1,G1), (A'4,R1-2,R2-1,R3-4,R4-1, G2), (A'4,R1-2,R2-1,R3-4,R4-1,G3), (A'4,R1-2,R2-1,R3-4, R4-1,G4), (A'4,R1-2,R2-1,R3-4,R4-2,G1), (A'4,R1-2,R2-1, R3-4,R4-2,G2), (A'4,R1-2,R2-1,R3-4,R4-2,G3), (A'4,R1-2, R2-1,R3-4,R4-2,G4), (A'4,R1-2,R2-2,R3-1,R4-1,G1), (A'4, R1-2,R2-2,R3-1,R4-1,G2), (A'4,R1-2,R2-2,R3-1,R4-1,G3), (A'4,R1-2,R2-2,R3-1,R4-1,G4), (A'4,R1-2,R2-2,R3-1,R4-2,G 1), (A'4,R1-2,R2-2,R3-1,R4-2,G2), (A'4,R1-2,R2-2,R3-1,R4-2,G3), (A'4,R1-2,R2-2,R3-1,R4-2,G4), (A'4,R1-2,R2-2,R3-2,R4-1,G1), (A'4,R1-2,R2-2,R3-2,R4-1,G2), (A'4,R1-2,R2-2,R3-2,R4-1, G3), (A'4,R1-2,R2-2,R3-2,R4-1,G4), (A'4,R1-2,R2-2,R3-2,R4-2,G1), (A'4,R1-2,R2-2,R3-2,R4-2, G2), (A'4,R1-2,R2-2,R3-2,R4-2,G3), (A'4,R1-2,R2-2,R3-2, R4-2,G4), (A'4,R1-2,R2-2,R3-3,R4-1,G1), (A'4,R1-2,R2-2, R3-3,R4-1,G2), (A'4,R1-2,R2-2,R3-3,R4-1,G3), (A'4,R1-2, R2-2,R3-3,R4-1,G4), (A'4,R1-2,R2-2,R3-3,R4-2, G1), (A'4, R1-2,R2-2,R3-3,R4-2,G2), (A'4,R1-2,R2-2,R3-3,R4-2,G3), (A'4,R1-2,R2-2,R3-3,R4-2, G4), (A'4,R1-2,R2-2,R3-4,R4-1,G1), (A'4,R1-2,R2-2,R3-4,R4-1,G2), (A'4,R1-2,R2-2,R3-4,R4-1,G3), (A'4,R1-2,R2-2,R3-4,R4-1,G4), (A'4,R1-2,R2-2,R3-4,R4-2,G1), (A'4,R1-2,R2-2,R3-4,R4-2,G2), (A'4,R1-2,R2-2,R3-4,R4-2,G3) or (A'4,R1-2,R2-2,R3-4,R4-2,G4).

Compounds of the present invention are useful for treating diseases induced by production, secretion or deposition of amyloid β protein, and effective for the treatment and/or prophylaxis, or improvement of conditions for Alzheimer's dementia (Alzheimer's disease, senile dementia of Alzheimer type etc.), Down's disease, disturbance of memory, prion disease (Creutzfeldt-Jakob disease etc.), mild cognitive impairment (MCI), Dutch-type hereditary cerebral hemorrhage with amyloidosis, cerebral amyloid angiopathy, other degenerated dementia, vascular degenerated mixed dementia, dementia associated with Parkinson's disease, dementia associated with progressive supranuclear paralysis, dementia associated with corticobasal degeneration, diffuse Lewy Bodies Alzheimer's disease, age-related macular degeneration, Parkinson's disease, or amyloid angiopathy etc.

Since compounds of the present invention have several efficacies such as having a potent inhibitory activity against BACE-1 having a high selectivity against other enzymes etc., they can be a drug with less side effects. Moreover they can be a drug having a wide margin of safety by choosing an optically active isomer of appropriate stereochemistry. Further they have a lot of merits such as good metabolic stability, high solubility, high absorbability of oral administration, high bio-availability, good clearance and high transitivity to brain, long half-life, high ratio of non protein binding, lower inhibition of hERG channel and CYP, and/or negative result of Ames Test, and, therefore, they can be superior drugs.

A compound of the present invention may be administrated together with other agent (e.g., other agent for treating Alzheimer's disease such as acetylcholine esterase etc.). The compound can be given in combination with an antidementia drug such as donepezil hydrochloride, tacrine, galantamine, rivastigmine, zanapezil, memantine or vinpocetine, for example.

A compound of the present invention may be orally administrated as powder, granule, tablet, capsule, pill or liquid formulation, or parentally administrated as injection, suppository, formulation of transdermal absorption or inhalation. Also, an effective amount of the compound may be formulated together with medicinal additives suitable for the formulation such as an excipient, binder, moistening agent, disintegrant and/or lubricant etc.

Dose of a compounds of the present invention depends on condition of diseases, route of administration, age and body weight of a patient, but in the case of oral administration to an adult, the dose range is usually 0.1 µg to 1 g/day, preferably 0.01 to 200 mg/day and in the case of parenteral administration the dose range is usually 1 μg to 10 g/day, preferably 0.1 to 2 g/day.

EXAMPLES

The present invention is illustrated in details by examples and test examples but the present invention is not limited to these examples.

In EXAMPLES, each abbreviation has the following meaning:

Me: methyl
Et: ethyl
iPr, Pri isopropyl
tBu: t-butyl
Ph: phenyl
Bn: benzyl
Boc: tert-butoxycarbonyl
TFA: trifluoroacetic acid
THF: tetrahydrofuran
DMT-MM: 4-(4,6-dimethoxy-1,3,5-triazin-2-yl)-4-methyl-morpholinium chloride n-hydrate
DMF: N,N-dimethylformamide Reference Example 1

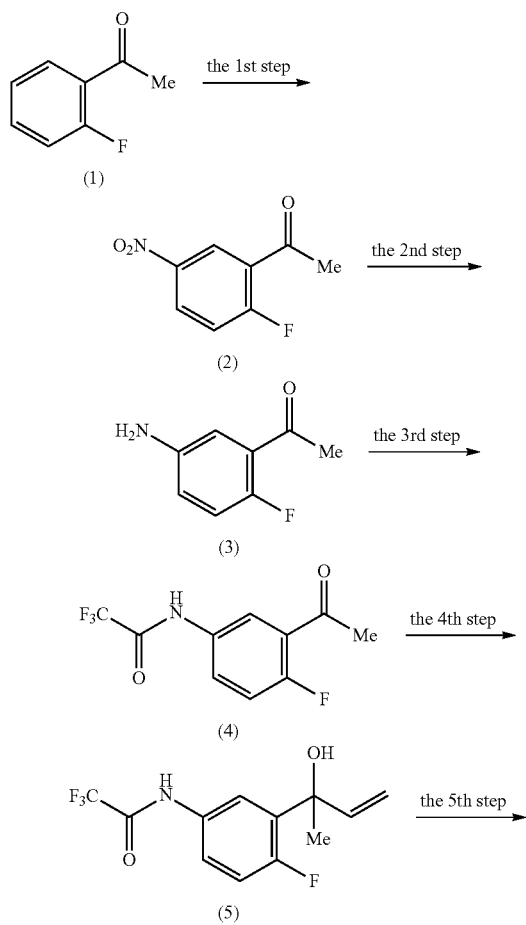

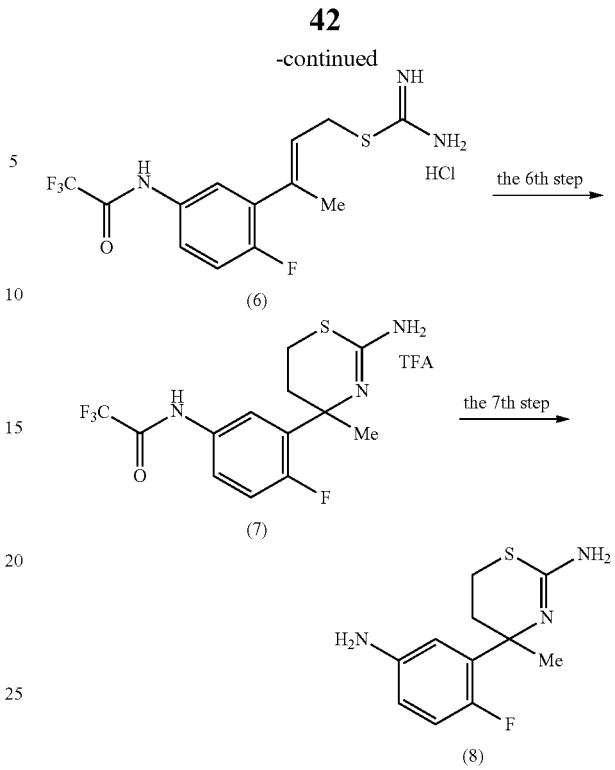

The 1$^{st}$ step: Compound (1) (101.5 g) was cooled to −18° C. and conc. sulfuric acid (400 ml) was added dropwise in 65 minutes while the inner temperature was kept at −15° C. or below. Separately fuming nitric acid (60 ml) was added to conc. sulfuric acid (180 ml) chilled to 4° C. in 45 minutes while the temperature was kept at 10° C. or below and the resulted mixed acid was added dropwise to the solution of (1) prepared before in an hour while the temperature was kept at −30° C. or below. The mixture was stirred at −20° C. or below for 1.5 hours, poured into 2.5 kg of ice-water and stirred for an hour. The precipitated crystals were filtered to give compound (2) (121.5 g).

$^1$H-NMR (CDCl$_3$): 2.71 (3H, d, J=5.1 Hz), 7.35 (1H, dd, J=9.3, 9.0 HZ), 8.41 (1H, ddd, J=9.0, 3.9, 3.0 Hz), 8.78 (1H, dd, J=6.3, 3.0 Hz).

The 2$^{nd}$ step: Compound (2) (20 g) was dissolved in ethanol (400 ml), Pd—C (10% dry) (2.0 g) was added thereto and the mixture was stirred in a hydrogen atmosphere at room temperature for 2 hours. Then Pd—C (10% dry) (1.0 g) was added and the mixture was stirred in a hydrogen atmosphere at room temperature for 1.5 hours, and further Pd—C (10% dry) (1.0 g) was added and the mixture was stirred in a hydrogen atmosphere at room temperature for 15 minutes. Pd—C was filtered off, the solvent was evaporated under reduced pressure and the residue of compound (3) (15.9 g) was obtained.

$^1$H-NMR (DMSO-d$_6$): 2.50 (3H, d, J=4.8 Hz), 5.21 (2H, brs, 1H), 6.78 (1H, ddd, J=8.7, 4.2, 3.0 Hz), 6.94 (1H, dd, J=6.3, 3.0 Hz), 6.99 (1H, dd, J=11.4, 8.7 Hz).

The 3rd step: Compound (3) (15.8 g) was dissolved in THF (79 ml), anhydrous trifluoroacetic acid (16.1 ml) and triethylamine (20.2 ml) were added under ice cooling and the mixture was stirred for 20 minutes. After the addition of water (30 ml), it was stirred under ice cooling for 20 minutes and the precipitated crystals were filtered. The filtrate was extracted with ethyl acetate (80 ml) and 50 ml, the organic layer was washed with water (60 ml), saturated brine. The crystals filtered previously were dissolved in the organic layer and dried over sodium sulfate. Sodium sulfate was filtered, the filtrate was concentrated under reduced pressure and the residue was dissolved in ethyl acetate under warming. After the addition of hexane (50 ml) and stirring under ice cooling for 20 minutes, the precipitated crystals were filtered. The mother liquid was concentrated again under reduced pressure, crystallized by the addition of ethyl acetate (8 ml) and hexane (2 ml) and compound (4) (totally 20.4 g) was obtained.

$^1$H-NMR (CDCl$_3$): 2.70 (3H, d, J=5.1 Hz), 7.24 (1H, dd, J=10.5, 9.3 Hz), 8.00 (1H, dd, J=6.2, 2.9 Hz), 8.21 (1H, m), 8.78 (1H, brs).

The 4$^{th}$ step: 1.6 M Vinyl magnesium chloride-THF solution (122 ml) was dissolved in THF (161 ml), cooled to −40° C. in a nitrogen atmosphere and a THF (81 ml) solution of compound (4) (16.1 g) was added dropwise thereto. The reaction solution was stirred at −40° C. for 20 minutes, 1.6 M vinyl magnesium chloride-THF solution (20 ml) was further added and the mixture was stirred at −40° C. for 15 minutes. The reaction solution was poured into a mixture of chilled ethyl acetate (480 ml), a saturated aqueous solution of ammonium chloride (80 and water (80 ml) with stirring, and the organic layer was separated. The aqueous layer was further extracted with ethyl acetate (200 ml), the organic layers were combined, washed with water (80 ml), and saturated brine successively, and dried over sodium sulfate. Sodium sulfate was filtered, the filtrate was concentrated under reduced pressure and the residue of compound (5) (22.4 g) was obtained.

$^1$H-NMR (CDCl$_3$): 1.74 (3H, d, J=1.2 Hz), 5.16 (1H, dd, J=10.5, 0.9 Hz), 5.27 (1H, d, J=17.3 Hz), 6.26 (1H, ddd, J=17.3, 10.5, 1.7 Hz), 7.07 (1H, dd, J=11.1, 9.6 Hz), 7.64-7.69 (2H, m), 7.94 (1H, brs).

The 5$^{th}$ step: The residue of compound (5) (22.3 g) and thiourea (5.17 g) were dissolved in acetic acid (112 ml), 1 M HCl-ethyl acetate (97 ml) was added thereto and the mixture was stirred at 40° C. for 18 hours. The solvent was evaporated under reduced pressure, toluene (150 ml) was added and again concentrated under reduced pressure. After repeating the same procedure, crystals were precipitated. Ethyl acetate (100 ml) was added to the crystalline residue, the mixture was stirred under ice cooling for an hour and the crystals were filtered to give compound (6) (15.1 g).

$^1$H-NMR (DMSO-d$_6$): 2.08 (3H, s), 4.10 (2H, d, J=7.8 Hz), 5.72 (1H, t, J=7.8 Hz), 7.23-7.32 (1H, m), 7.60-7.69 (2H, m), 9.25 (3H, brs), 11.39 (1H, brs), The 6$^{th}$ step: Compound (6) (10.0 g) was dissolved in THF (50 ml), conc. sulfuric acid (5.74 ml) was added thereto and stared at 60° C. for 2 hours. After evaporation of TFA under reduced pressure, ice-water (100 ml) was added. The mixture was stirred under ice-cooling for an hour, and the precipitated crystals were filtered to give compound (7) (11.2 g).

$^1$H-NMR (CDCl$_3$): 1.72 (3H, s), 2.02-2.18 (1H, m), 2.54-2.76 (2H, m), 3.14-3.28 (1H, m), 7.37 (1H, dd, J=11.9, 8.8 Hz), 7.62 (1H, dd, J=7.5, 3.0 Hz), 7.80 (1H, ddd, J=8.8, 3.9, 3.0 Hz), 8.77 (1H, brs), 9.38 (1H, hrs), 10.66 (1H, brs), 11.50 (1H, brs).

The 7$^{th}$ step: MeOH (28 ml), THE (35 ml) and 5 hr NaOH (10.9 ml) were added to compound (7) (7.00 g) and stirred at 50° C. for 4 hours. Toluene (50 ml) was added and extracted, and the aqueous layer was further extracted with toluene (50 ml) and ethyl acetate (60 ml). All the organic layers were combined, washed with water and saturated brine, and dried over sodium sulfate. The solvent was concentrated under reduced pressure, the resulted crystalline residue was washed with hexane (20 ml) to give compound (8) (3.45 g).

$^1$H-NMR (CDCl$_3$): 1.60 (3H, d, J=1.5 Hz), 1.76-1.87 (1H, m), 2.11-2.54 (1H, m), 2.66-2.76 (1H, m), 2.86-2.94 (1H, m), 6.50 (1H, ddd, J=8.7, 3.6, 3.0 Hz), 6.66 (1H, dd, J=7.1, 3.0 Hz), 6.81 (1H, dd, J=12.0, 8.7 Hz).

Reference Example 2

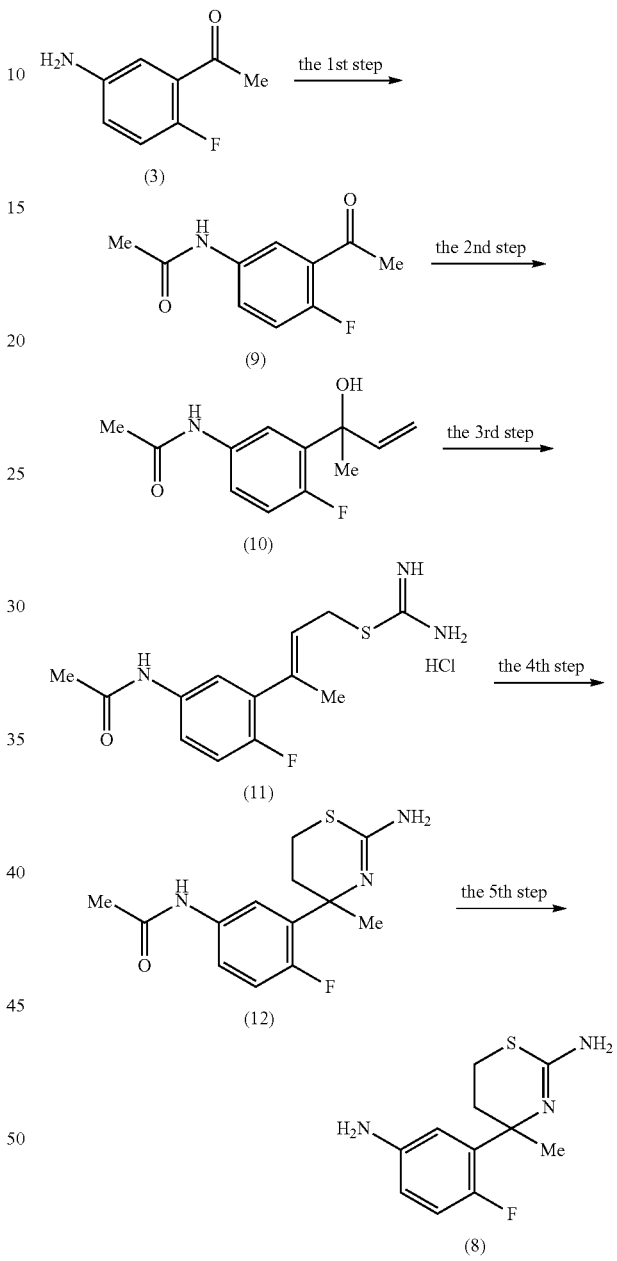

The 1$^{st}$ step: Compound (3) (15.6 g) was dissolved in ethyl acetate (78 ml), acetic anhydride (10.6 ml) and pyridine (9.07 ml) were added under ice cooling, and the mixture was stirred for 15 minutes. Ethyl acetate (100 ml) and water (50 ml) were added, extracted, and the aqueous layer was extracted with ethyl acetate (50 ml). The organic layers were combined, washed with 2 M HCl (50 ml), a saturated solution of sodium bicarbonate (50 ml) and saturated brine, dried over sodium sulfate. Sodium sulfate was filtered, the filtrate was concentrated under reduced pressure, and ethyl acetate (50 ml) and hexane (50 ml) were added to the residue. The mixture was stirred under ice cooling for 30 minutes and the precipitated crystals were filtered to give compound (9) (total 14.9 g).

¹H-NMR (CDCl₃) 2.20 (3H, s), 2.66 (3H, d, J=5.1 Hz), 7.13 (1H, dd, J=10.5, 9.0 Hz), 7.70 (1H, dd, J=6.3, 3.0 Hz), 7.79 (1H, brs), 8.11 (1H, ddd, J=9.0, 4.1, 3.0 Hz).

The 2$^{nd}$ step: Compound (9) (10.0 g) was dissolved in THF (50 ml), cooled in ice and sodium hydride (2.25 g) was added in a nitrogen atmosphere. After stirring for 15 minutes, the resulted mixture was added dropwise to a solution of 1.6 M vinyl magnesium chloride (86 ml)/THF (70 ml) cooled to −40° C. After stirring at −40° C. for 15 minutes and then 0° C. for 20 minutes, a saturated aqueous solution of ammonium chloride (50 ml)/water (50 ml) was chilled and added. The layers were separated and the aqueous layer was extracted with ethyl acetate (100 ml). Organic layers were combined, washed with water and saturated brine, dried over sodium sulfate. Sodium sulfate was filtered, the filtrate was concentrated under reduced pressure to give a residue of compound (10) (13.7 g).

¹H-NMR (CDCl₃): 1.69 (3H, s), 2.16 (3H, s), 5.12 (1H, d, J=10.5 Hz), 5.24 (1H, d, J=17.4 Hz), 6.26 (1H, ddd, J=1.7.4, 10.5, 1.5 Hz), 6.98 (1H, dd, J=11.1, 8.7 Hz), 7.33 (1H, brs), 7.50-7.59 (2H, m).

The 3$^{rd}$ step: The residue of compound (10) (6.56 g) and thiourea (1.88 g) were dissolved in acetic acid (33 ml), 1 M HCl-acetic acid (37 ml) was added and stirred at 40° C. for 7 hours. The solvent was evaporated under reduced pressure, toluene (50 ml) was added and concentrated again under reduced pressure. The same procedure was repeated again, ethyl acetate (30 ml) was added to the residue and stirred at room temperature overnight. The precipitate was filtered to give compound (11) (5.77 g).

¹H-NMR (DMSO-d₆): 2.03 (3H, s), 2.06 (3H, s), 4.09 (2H, d, J=7.5 Hz), 5.67 (1H, t, J=7.5 Hz), 7.12 (1H, dd, J=10.7, 8.9 Hz), 7.46-7.59 (2H, m), 9.24 (4H, brs), 10.11 (1H, s).

The 4$^{th}$ step: compound (11) (5.16 g) was dissolved in conc. sulfuric acid (15.5 ml) and stirred at room temperature for an hour. It was poured into ice-water (100 ml), adjusted to pH 10 by the addition of an aqueous solution of potassium hydroxide and extracted with ethyl acetate (200 ml) and a little amount of MeOH. The organic layer was washed with water and saturated brine, dried over sodium sulfate. Sodium sulfate was filtered, the filtrate was concentrated under reduced pressure, ethyl acetate (20 ml) and hexane (15 ml) were added to the residue and the precipitate was filtered. The filtrate was concentrated, ethyl acetate (5 ml) and hexane (5 ml) were added and the precipitate was filtered to give compound (12) (total 3.16 g).

¹H-NMR (CDCl₃): 1.62 (3H, d, J=0.9 Hz), 1.80-1.91 (1H, m), 2.16 (3H, s), 2.47-2.58 (1H, m), 2.62-2.73 (1H, m), 2.87-2.98 (1H, m), 4.36 (2H, brs), 6.99 (1H, dd, J=11.7, 8.7 Hz), 7.14 (1H, dd, J=7.1, 3.0 Hz), 7.80 (1H, ddd, J=8.7, 4.2, 3.0 Hz), 7.97 (1H, brs), The 5$^{th}$ step: Compound (12) (2.50 g) was suspended in ethanol (25 ml), 6 M HCl (10.2 ml) was added and the mixture was stirred at 90° C. for 3 hours. 2 M NaOH (35 ml) was added, the organic solvent was evaporated and the residue was extracted with ethyl acetate (70 ml). The aqueous layer was further extracted with ethyl acetate (30 ml), organic layers were combined, washed with water and saturated brine, and dried over sodium sulfate.

Sodium sulfate was filtered, the filtrate was concentrated under reduced pressure, and the crystalline residue was washed with ethyl acetate (3 ml) and hexane (10 ml). The crystals were filtered to give compound (8) (total 1.22 g).

Reference Example 3

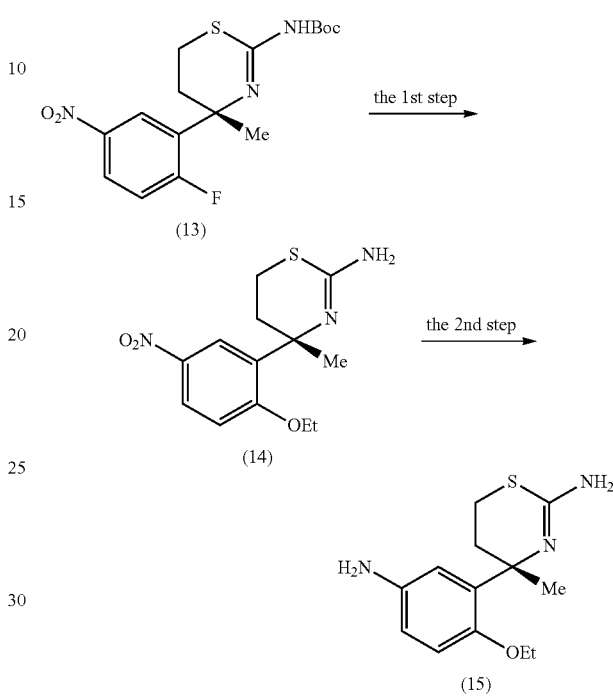

The 1$^{st}$ step: A ethanol solution of 20% sodium ethoxide (5.12 ml, 16.2 mmol, 40 eq.) was added to compound (13) (150 mg, 406 μmol) and stirred at room temperature for 6 hours. The reaction solvent was evaporated under reduced pressure, 2 M hydrochloric acid (8.12 ml, 16.2 mmol, 40 eq.) was added to the resulted residue and extracted with chloroform. The extracting solution was washed with water and dried over anhydrous sodium sulfate. The chide product (189 mg) was obtained by evaporation of the solvent under reduced pressure, to which 4 M HCl-ethyl acetate solution (1.89 ml) was added and the mixture was stirred at room temperature for 14 hours. A saturated aqueous solution of sodium bicarbonate was added to the reaction solution, extracted with ethyl acetate and dried over anhydrous sodium sulfate. The solvent was evaporated under reduced pressure to give compound (14) (90.8 mg, 76% yield) as a yellow powder.

¹H NMR (CDCl₃) δ1.52 (3H, t, 6.8 Hz), 1.67 (3H, s), 1.93-2.00 (1H, m), 2.60-2.67 (2H, m), 2.94-3.00 (1H, m), 4.19 (2H, q, J=6.8 Hz), 6.93 (1H, d, J=9.3 Hz), 8.14 (1H, dd, J=8.7, 2.4 Hz), 8.31 (1H, d, 2.5 Hz).

The 2$^{nd}$ step: A powder of 10% palladium-carbon (45.4 mg) was added to a methanol (908 μl) solution of compound (14) (90.8 mg, 307 μmol) and the mixture was stirred in a hydrogen atmosphere for 22 hours. The reaction mixture was filtered through a Celite pad and the filtrate was evaporated under reduced pressure. The residue was washed with ethyl acetate to give compound (15) (65.8 mg, 81% yield) as an yellow powder.

¹H NMR (DMSO-d₆) δ 1.29 (3H, t, J=6.9 Hz), 1.45 (3H, s), 1.51-1.58 (1H, m), 2.46-2.48 (1H, m), 2.61-2.64 (1H, m), 2.80-2.83 (1H, m), 3.85-3.91 (2H, m), 6.38 (1H, dd, J=8.3, 2.5 Hz), 6.52 (1H, d, J=2.4 Hz), 6.67 (1H, d, J=8.6 Hz)

Reference Example 4

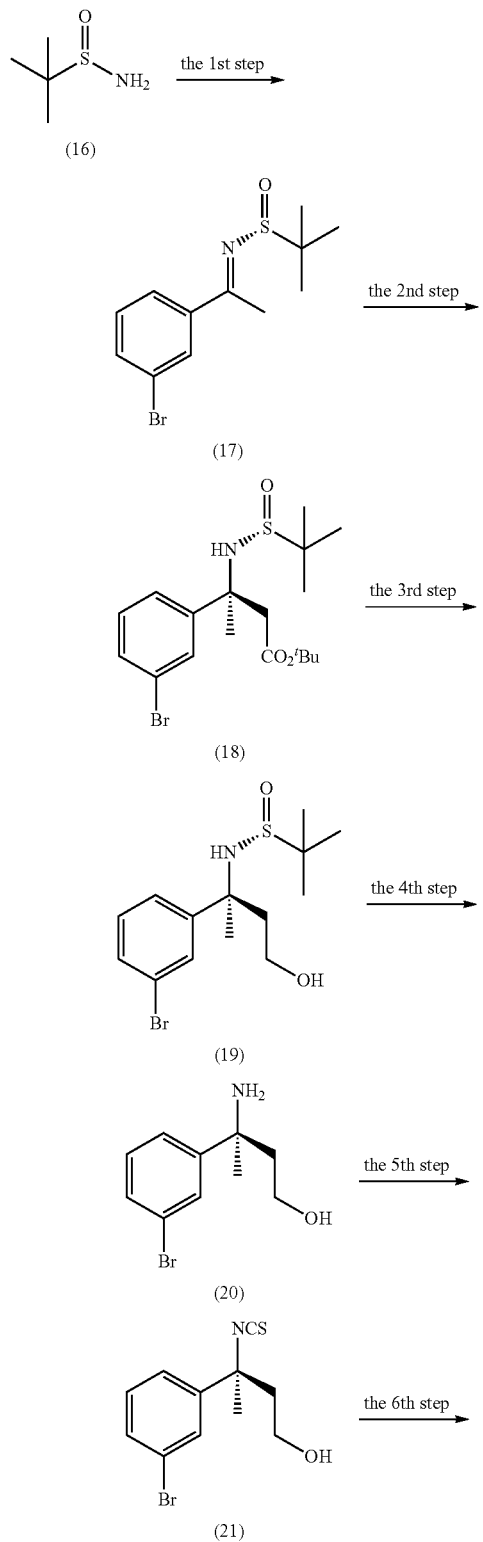

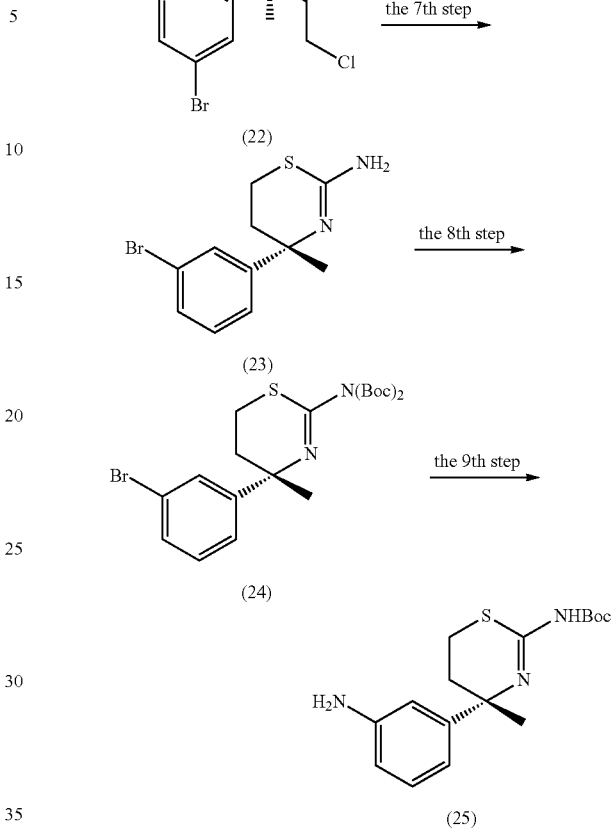

The 1st step: 3'-Bromoacetophenone (15.0 g) and compound (16) (9.13 g) were dissolved in tetrahydrofuran (250 ml), and tetraethoxy, titanium (39.5 ml) was added thereto at room temperature with stirring. Then the reaction mixture was stirred at 75° C. for 5 hours, and saturated brine was added after disappearance of compound (1) was confirmed. Titanium oxide formed in the reaction was filtered off, the filtrate was extracted with ethyl acetate, the organic layer was dried over anhydrous magnesium sulfate and the solvent was evaporated under reduced pressure. The residue was purified with a column chromatography to give compound (17) (20.1 g).

$^1$H-NMR (CDCl$_3$): 1.33 (9H, s), 2.75 (3H, s), 7.30 (1H, t, J=7.8) 7.59-7.63 (1H, m), 7.79 (1H, d, J=7.8) 8.0 (1H, s)

The 2nd step: A 2.64 M hexane solution of n-butyllithium (79.5 ml) is added dropwise to a tetrahydrofuran (100 ml) solution of diisopropylamine (42.1 ml) in a nitrogen atmosphere at −78° C. After stiffing at 0° C. for 30 minutes, the reaction solution was again cooled to −78° C. and tert-butyl acetate (26.9 ml) dissolved in tetrahydrofuran (100 ml) is added dropwise. After stirring at −78° C. for 30 minutes, chlorotriisopropoxytitanium dissolved in tetrahydrofuran (150 ml) is added dropwise. After stirring at the same temperature for 70 minutes, compound (2) (20.1 g) dissolved in tetrahydrofuran (100 ml) was added dropwise. After then, the reaction solution was stirred at −78° C. for 3 hours, and an aqueous solution of ammonium chloride was added after disappearance of compound (2) was confirmed. Titanium oxide formed in the reaction was filtered off, the filtrate was extracted with ethyl acetate, the organic layer was washed with saturated brine and dried over anhydrous magnesium sulfate. The solvent was evaporated under reduced pressure to give a crude product of compound (18) (26.4 g).

The 3$^{rd}$ step: The crude product of compound (18) (26.4 g) was dissolved in toluene (80 ml), the solution was added dropwise to a 1 M solution of aluminium diisobutyl hydride in toluene (253 ml) with stirring at 0° C. The reaction solution was stirred at room temperature for 1.5 hours and 1 N hydrochloric acid solution was added after disappearance of compound (3) was confirmed. The mixture was extracted with ethyl acetate, the organic layer was washed with saturated brine and dried over anhydrous magnesium sulfate. The solvent was evaporated under reduced pressure and the residue was purified by crystallization to give compound (19) (18.1 g).

$^1$H-NMR (CDCl$_3$): 1.28 (9H, s), 1.71 (3H, s), 2.19-2.24 (2H, m), 3.27-3.32 (1H, m), 3.54-3.66 (1H, m), 3.87-3.97 (1H, m), 5.10-5.11 (1H, m), 7.22 (1H, t, J=8.1) 7.32-7.41 (2H, m), 7.56-7.58 (1H, m)

The 4$^{th}$ step: Compound (19) (18 g) was dissolved in methanol (30 ml), and 10% hydrochloric acid in methanol (130 ml) was added dropwise therein at room temperature. The reaction solution was stirred at room temperature for 4 hours and 1 N hydrochloric acid was added after disappearance of compound (4) was confirmed. The mixture was extracted with ethyl acetate, the aqueous layer was neutralized with a 2 N aqueous solution of sodium hydroxide and extracted with ethyl acetate. The organic layer was dried over anhydrous magnesium sulfate and the solvent was evaporated under reduced pressure to give a crude product of compound (20) (14.1 g).

The 5$^{th}$ step: The crude product of compound (20) (32.8 g) and potassium carbonate (37.1 g) were dissolved in a mixed solvent of toluene (450 ml) and water (225 ml) and thiophosgene (15.3 ml) was added dropwise cooled at 0° C. with stirring. After then, the reaction solution was stirred at 0° C. for an hour and water was added when disappearance of compound (5) was confirmed. The mixture was extracted with ethyl acetate and the organic layer was washed with brine and dried over anhydrous magnesium sulfate. The solvent was evaporated under reduced pressure to give a crude product of compound (21) (38.4 g).

The 6$^{th}$ step: The crude product of (21) (38.4 g) was dissolved in toluene (384 ml), and thionyl chloride (29.4 ml) and N,N-dimethylformamide (1.04 ml) were added dropwise at 0° C. with stirring. After then, the reaction solution was stirred at 80° C. for 5 hours, and after disappearance of compound (6) was confirmed, the reaction solution was evaporated under reduced pressure to give a crude product of compound (22) (40.9 g).

The 7$^{th}$ step: The crude product of compound (22) (40.9 g) was dissolved in tetrahydrofuran (250 ml) and 25% ammonia-water (250 ml) was added with stirring at 0° C. After then the reaction solution was stirred at room temperature for 16 hours, and a saturated aqueous solution of sodium bicarbonate was added after disappearance of compound (21) was confirmed. The organic layer was separated and the aqueous solution was extracted with dichloromethane. The organic layers were combined, dried over anhydrous magnesium sulfate and evaporated under reduced pressure to give a crude product of compound (23) (38.3 g).

The 8$^{th}$ step: The crude product of compound (23) (38.3 g) is dissolved in tetrahydrofuran (383 ml), di-tert-butyl dicarbonate (61.5 g) and N,N-dimethylaminopyridine (1.64 g) are added and the mixture was stirred at room temperature for 72 hours. After disappearance of compound (23) was confirmed, the solvent was evaporated under reduced pressure. The residue was purified with a silicagel column chromatography to give compound (24) (45.3 g)

$^1$H-NMR (CDCl$_3$): 1.54 (9H, s), 1.57 (3H, s), 1.96 (2H, t, J=6.0), 2.80-2.92 (1H, 3.00-3.13 (1H, m), 7.21 (1H, t, J=8.1) 7.28-7.41 (2H, m), 7.52-7.55 (1H, m)

The 9$^{th}$ step: In a nitrogen atmosphere, compound (24) (12.1 g), trisdibenzylideneacetonedipalladium (1.14 g) and dicyclohexylbiphenylphosphine (0.88 g) were dissolved in toluene (125 ml), and a 1.6 M solution of lithium hexamethyldisilazide in tetrahydrofuran (46.9 ml) was added with stirring at room temperature. The reaction solution was warmed up to 80° C. and stirred for 16 hours. After disappearance of compound (21) was confirmed, the reaction solution was cooled at 0° C. and diethyl ether and 1 N hydrochloric acid were added. After stirring at 0° C. for 10 minutes, the solution was neutralized with a saturated aqueous solution of sodium carbonate. It was extracted with ethyl acetate, the organic layer was washed with saturated brine and dried over anhydrous magnesium sulfate. The solvent was evaporated under reduced pressure and the residue was purified with a silicagel column chromatography to give compound (25) (6.84 g).

$^1$H-NMR (CDCl$_3$) 1.51 (9H, s), 1.69 (3H, s), 2.01-2.12 (1H, m), 140-2.51 (1H, m), 2.67-2.76 (2H, m), 6.55-6.67 (3H, m), 7.15 (1H, t, J=8.1).

Reference Example 5

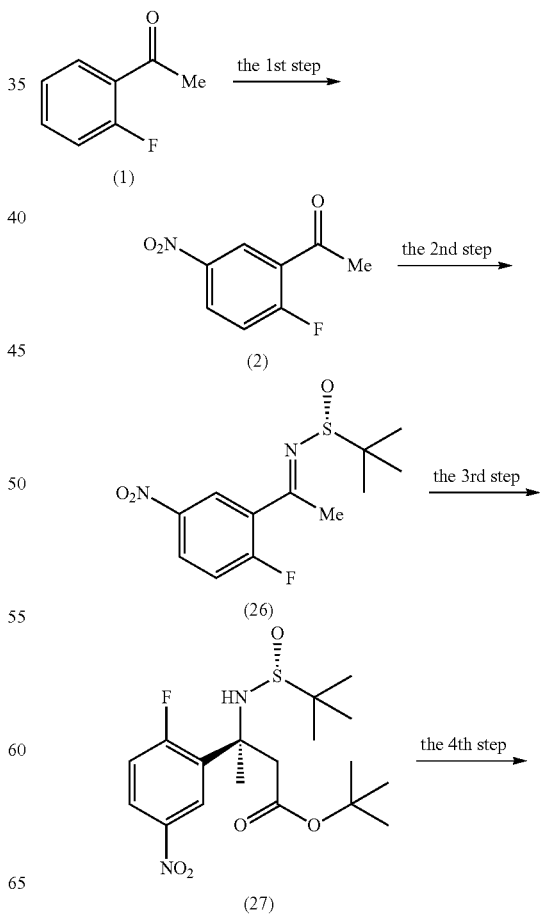

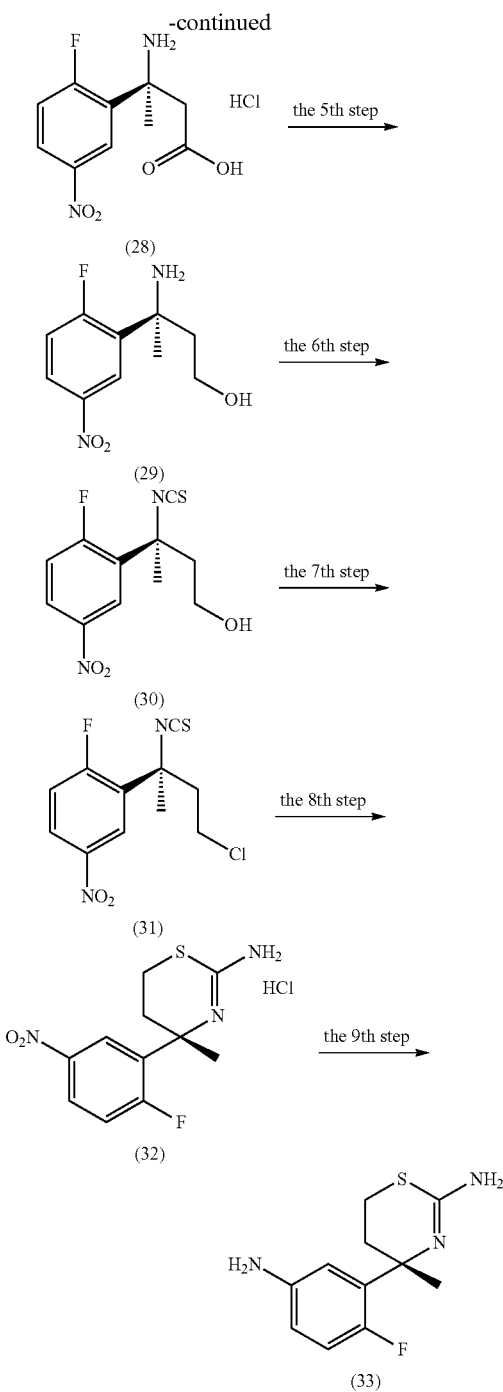

The 1st step: After the addition of compound (1) (70.00 g) to conc. sulfuric acid (279 ml) cooled in an acetonitrile/dry ice bath with stirring, a mixture of fuming nitric acid (42 ml) and conc. sulfuric acid (98 ml) were added dropwise. After stiffing for 16 minutes, the mixture was gradually poured into ice, the precipitated crystals were filtered and dried to give compound (2) (77.79 g).

$^1$H-NMR (CDCl$_3$) δ: 2.71 (3H, d, J=4.9 Hz), 7.34 (1H, t, J=9.3 Hz), 8.40 (1H, ddd, J=9.3, 6.2, 3.0 Hz), 8.78 (1H, dd, J=6.2, 3.0 Hz).

The 2nd step: A solution of compound (2) (73.94 g), (R)-(+)-2-methyl-2-propanesulfinamide (53.82 g) and tetraethyl orthotitanate (230.20 g) in tetrahydrofuran (500 ml) were reacted for 2.5 hours under heating to reflux, and then the reaction mixture was gradually poured into ice and the resulted insoluble materials were filtered. It was extracted with ethyl acetate, the organic layer was dried over anhydrous magnesium sulfate and evaporated under reduced pressure. The residue was crystallized from ethyl acetate/n-hexane to give compound (26) (85.44 g).

$^1$H-NMR (CDCl$_3$) δ: 1.34 (9H, s), 2.81 (3H, d, J=3.5 Hz), 7.29 (1H, t, J=8.9 Hz), 8.31 (1H, dt, J=8.9, 2.9 Hz), 8.55 (1H, dd, J=6.3, 2.9 Hz).

The 3rd step: A solution of tert-butyl acetate (6.08 g) in tetrahydrofuran (10 ml) was added dropwise to a 2 M solution of lithium diisopropylamide/tetrahydrofuran/n-heptane/ethylbenzene (27.9 ml) cooled in an acetone/day ice bath with stirring. After stirring for 20 minutes, a solution of chlorotitanium isopropoxide (17.5 ml) in tetrahydrofuran (30 ml) was added dropwise, the mixture was stirred for an hour and a solution of compound (26) (5.00 g) in tetrahydrofuran (10 ml) was added dropwise. After reacting for an hour, the reaction solution was gradually poured into an aqueous solution of ammonium chloride cooled in ice with stiffing, and the resulted insoluble materials were filtered. It was extracted with ethyl acetate, the organic layer was dried over anhydrous sodium sulfate. The solvent was evaporated under reduced pressure and the residue was purified with a silicagel column chromatography to give compound (27) (5.49 g).

$^1$H-NMR (CDCl$_3$) δ: 1.30 (9H, s), 1.35 (9H, s), 1.86 (3H, s), 3.11 (1H, dd, J=16.2, 2.1 Hz), 3.26 (1H, dd, J=16.2, 2.1 Hz), 5.55 (1H, s), 7.18 (1H, dd, J=11.1, 8.9 Hz), 8.18 (1H, ddd, J=8.9, 4.0, 2.9 Hz), 8.53 (1H, dd, J=7.0, 2.9 Hz).

Ratio of diastereomers (3S:3R=97:3) HPLC Column: CHIRALPAK AS-RH, Detection: 254 nm: Column temp.: 25° C., Mobile phase: 40% MeCNaq., Flow rate: 0.5 ml/min.

Note: As to the stereochemistry of compound (27) obtained above, it is known that 3S-isomer is preferentially prepared as written in the literature A etc. and it is also possible to prepare each diastereomer selectively by choosing appropriate metal species and/or a reaction condition.

Literature A: (1) T. Fujisawa et al., *Tetrahedron Lett.*, 37, 3881-3884 (1996), (2) D. H. Hua et al, *Sulfur Reports*, vol. 21, pp. 211-239 (1999), (3) Y. Koriyama et al., *Tetrahedron*, 58, 9621-9628 (2002), (4) Yong Qin et al., *J. Org. Chem.*, 71, 1588-1591 (2006).

The 4th step: A solution of 4 M HCl/1,4-dioxane (50 ml) was added to compound (27) (12.74 g) and the mixture was stirred at 80° C. for an hour, diethyl ether (50 ml) was added, the precipitated crystals were filtered and dried to give compound (28) (7.67 g).

$^1$H-NMR (DMSO-d$_6$) δ: 1.76 (3H, s), 3.25 (2H, s), 7.62 (1H, dd, J=11.4, 9.4 Hz), 8.33-8.48 (2H, m).

The 5th step: A solution of 1 M tetrahydrofuran-borane in tetrahydrofuran (2029 ml) was added dropwise to a solution of compound (28) (141.32 g) in tetrahydrofuran (707 ml) cooled in ice with stirring and it was reacted for 3 hours and 6 minutes. The reaction mixture was poured into a mixture of sodium bicarbonate (511 g), ice (1500 g) and ethyl acetate (3000 ml) stirred at room temperature, extracted with ethyl acetate and the organic layer was dried over anhydrous sodium sulfate. The solvent was evaporated under reduced pressure to give compound (29) (115.46 g) as a crude product.

The 6th step: Toluene (25 ml) and water (12.5 ml) were added to the compound (29) (3.76 g) obtained in the 5th step and stilled under ice cooling. After the addition of potassium carbonate (7.97 g), thiophosgene (2.85 g) was added dropwise. After reacting for 3 hours, water was added, extracted with toluene and the organic layer was dried over anhydrous magnesium sulfate. A part of the solvent was evaporated under reduced pressure to give compound (30) as a crude product.

The 7$^{th}$ step: Compound (30) obtained in the 6th step was dissolved in toluene (17.4 ml) and thionyl chloride (6.67 g) and N,N-dimethylformamide (0.128 ml) were added with stirring at mom temperature. The mixture was stirred at 80° C. for 2 hours, water was added, extracted with toluene and concentrated under reduced pressure to give compound (31) (4.03 g) as a crude product.

The 8$^{th}$ step: Compound (31) (4.03 g) obtained in the 7th step was dissolved in tetrahydrofuran (23.8 ml) and 28% ammonia-water (23.8 ml) was added under ice cooling with stirring. The mixture was trued at room temperature for 3 days, the reaction solution was concentrated under reduced pressure and ethyl acetate was added therein. Conc. hydrochloric acid (6 ml) was added under ice cooling with stirring, the precipitated crystals were washed with ethyl acetate and water and dried to give compound (32) (2.14 g).

$^1$H-NMR (DMSO-d$_6$) δ: 1.76 (3H, s), 2.13-2.24 (1H, m), 2.68-2.74 (2H, m), 3.19-3.25 (1H, m), 7.63 (1H, dd, J=11.4, 8.9 Hz), 8.07 (1H, dd, J=7.0, 3.5 Hz), 8.36 (1H, dt, J=8.9, 3.5 Hz), 11.22 (1H, s).

The 9$^{th}$ step: Compound (32) (100 mg) was dissolved in methanol (2 ml), 10% palladium-carbon powder (50 mg) was added, and the mixture was stirred in a hydrogen atmosphere at room temperature for 18 hours. Insoluble materials were filtered off, the filtrate was evaporated under reduced pressure, sodium carbonate and water were added therein and extracted with ethyl acetate. The organic layer was dried over anhydrous sodium sulfate and the solvent was evaporated under reduced pressure to give compound (33) (68 mg).

$^1$H-NMR (CDCl$_3$) δ: 1.59 (3H, s), 1.81 (1H, ddd, J=14.1, 10.9, 3.5 Hz), 2.47 (1H, ddd, J=14.1, 5.9, 3.5 Hz), 2.71 (1H, td, J=10.9, 3.5 Hz), 2.89 (1H, ddd, J=10.9, 5.9, 3.5 Hz), 3.57 (2H, br s), 6.49 (1H, dt, J=8.5, 3.3 Hz), 6.67 (1H, dd, J=6.9, 3.3 Hz), 6.80 (1H, dd, J=11.8, 8.5 Hz).

Reference Example 6

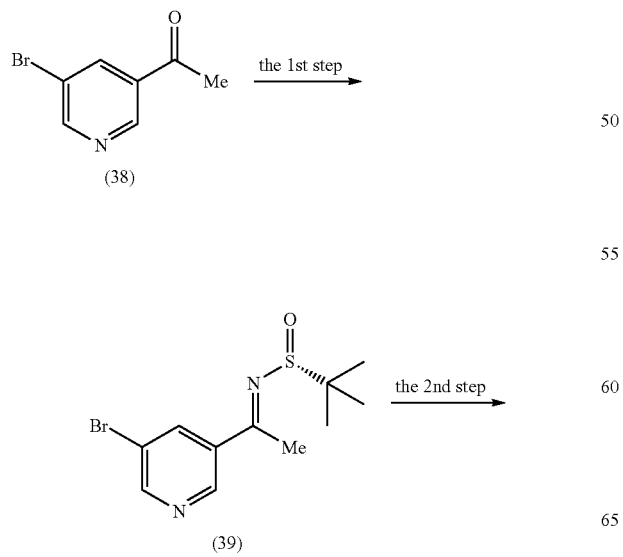

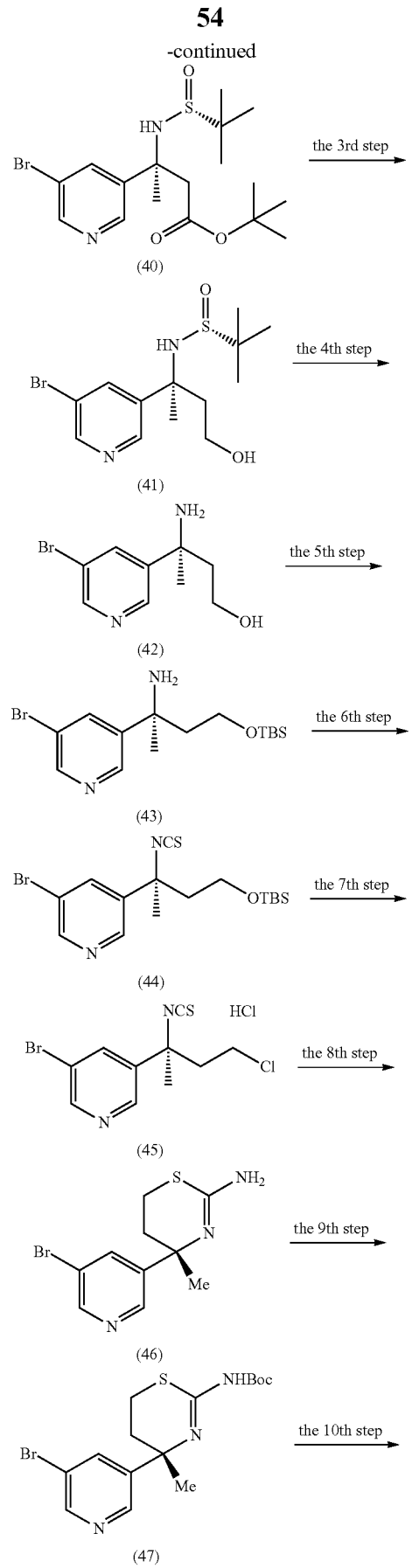

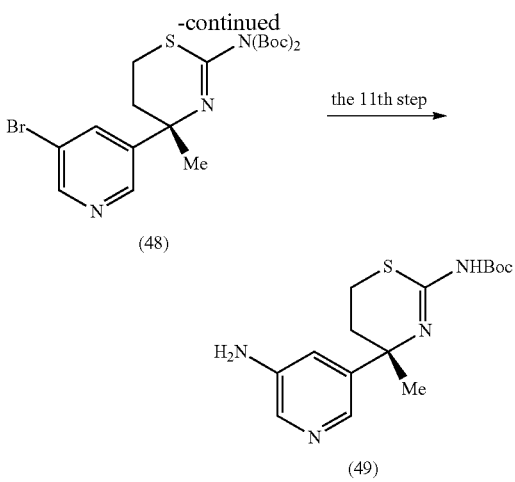

The 1st step: A solution of compound (38) (5.00 g), (R)-(+)-2-methyl-2-propanesulfinamide (3.33 g) and tetraethyl orthotitanate (17.11 g) in tetrahydrofuran (50 ml) was reacted under heating to reflux for 7 hours, and then, it was poured portionwise into saturated brine and the resulted insoluble materials were filtered off.

It was extracted with ethyl acetate, the organic layer was dried over anhydrous magnesium sulfate and concentrated under reduced pressure. The residue was purified with a silicagel column chromatography to give compound (39) (6.37 g).

$^1$H-NMR (CDCl$_3$) δ: 1.34 (9H, s), 2.79 (3H, s), 8.26 (1H, t, J=2.3 Hz), 8.76 (1H, d, J=2.3 Hz), 8.96 (1H, d, J=2.3 Hz).

The 2$^{nd}$ Step: A solution of 2.66 M n-butyllithium/n-hexane (32.4 ml) was added dropwise to a solution of diisopropylamine (9.36 g) in tetrahydrofuran (39 ml) cooled in an acetone/dry ice bath with stirring and the mixture was stirred under ice cooling for 30 minutes. The reaction solution was stirred again in an acetone/dry ice bath and a solution of tert-butyl acetate (4.88 g) in tetrahydrofuran (8 ml) was added dropwise. After stirring for 40 minutes, a solution of chlorotitanium triisopropoxide (23.00 g) in tetrahydrofuran (88 ml) was added dropwise. After stirring for 10 minutes, a solution of compound (39) (637 g) in tetrahydrofuran (65 ml) was added dropwise. After reacting for 30 minutes, the reaction solution was poured portionwise into an aqueous solution of ammonium chloride and the resulted insoluble materials were filtered off. It was extracted with ethyl acetate and the organic layer was dried over anhydrous sodium sulfate. The solvent was evaporated under reduced pressure to give compound (40) (8.03 g) as a crude product.

The 3$^{rd}$ step: Lithium aluminium hydride (2.85 g) was added portionwise to a solution of the compound (40) (8.03 g) obtained in the 2nd step in tetrahydrofuran (100 ml) cooled in ice with stirring and the mixture was stirred for 2 hours. Acetone, water, and a 1N aqueous solution of sodium hydroxide were added portionwise and the mixture was stirred at room temperature for 30 minutes. The insoluble materials were filtered off and extracted with ethyl acetate. The organic layer was dried over anhydrous magnesium sulfate and concentrated under reduced pressure to give compound (41) (5.83 g) as a crude product.

The 4$^{th}$ step: A solution of 10% HCl/methanol (60 ml) was added to a solution of the compound (41) (5.83 g) obtained in the 3rd step in methanol (60 ml) cooled in ice with stirring and stirred at room temperature for 16 hours. The reaction solution was made alkaline by the addition of water and potassium carbonate, extracted with chloroform, the organic layer was dried over anhydrous sodium sulfate and concentrated under reduced pressure to give compound (42) (5.07 g) as a elude product.

The 5th step: Imidazole (2.24 g) and t-butyldimethylsilyl chloride (3.77 g) were added to a solution of the compound (42) (5.07 g) obtained in the 4th step in N,N-dimethylformamide (26 ml) with stirring at room temperature and the mixture was stirred for 1 hour and 40 minutes. After extraction with ethyl acetate, the organic layer was washed with saturated brine and dried over anhydrous sodium sulfate. The solvent was evaporated under reduced pressure and the residue was purified with a silicagel column chromatography to give compound (43) (3.82 g).

$^1$H-NMR (CDCl$_3$) δ: −0.04 (3H, s), −0.01 (3H, s), 0.85 (9H, s), 1.51 (3H, s), 1.98 (2H, t, J=6.0 Hz), 3.49-3.54 (1H, m), 3.65 (1H, dt, J=6.0 Hz), 8.02 (1H, t, J=2.2 Hz), 8.53 (1H, d, J=2.2 Hz), 8.63 (1H, d, J=2.2 Hz).

The 6$^{th}$ step: Toluene (25 ml) and water (13 ml) were added to compound (43) (3.82 g) and stirred under ice cooling. After the addition of potassium carbonate (5.14 g), thiophosgene (1.83 g) was added dropwise. After reacting for 2 hours, water was added, extracted with chloroform and the organic layer was dried over anhydrous magnesium sulfate. A part of the solvent was evaporated under reduced pressure to give compound (44) as a crude product.

The 7$^{th}$ step: Thionyl chloride (4.43 g) and N,N-dimethylformamide (0.08 ml) were added to a solution of the compound (7) obtained in the 6th step in toluene (25 ml) with stirring at room temperature. The mixture was stirred at 80° C. for 5 hours, concentrated under reduced pressure to give compound (45) (5.03 g) as a crude product.

The 8$^{th}$ step: 28% Ammonia water (60 ml) was added to a solution of the compound (45) (5.03 g) obtained in the 7th step in tetrahydrofuran (60 ml) stirred under ice cooling and the mixture was stirred at room temperature for 14 hours. The reaction solution was concentrated under reduced pressure to give compound (46) (4.92 g) as a crude product.

The 9$^{th}$ step: A mixture of the compound (46) (4.92 g) obtained in the 8th step, di-t-butyl dicarbonate (9.28 g), triethylamine (3.23 g), 4-dimethylaminopyridine (0.13 g) and tetrahydrofuran (106 ml) was stirred at room temperature for 3 days. The insoluble materials were filtered off, water was added to the filtrate and extracted with ethyl acetate. The organic layer was dried over anhydrous sodium sulfate and concentrated under reduced pressure to give compound (47) (8.31 g) as a crude product.

The 10$^{th}$ step: A mixture of the compound (47) (8.31 g) obtained in the 9th step, di-t-butyl dicarbonate (6.96 g), triethylamine (3.23 g), 4-dimethylaminopyridine (0.13 g) and tetrahydrofuran (50 ml) was stirred at room temperature for an hour. After the addition of water, it was extracted with ethyl acetate and the organic layer was dried over anhydrous magnesium sulfate. The solvent was evaporated under reduced pressure and the residue was purified with a silicagel column chromatography to give compound (48) (1.23 g).

$^1$H-NMR (CDCl$_3$) δ: 1.53 (18H, s), 1.60 (3H, s), 1.93 (1H, ddd, J=13.8, 9.4, 3.9 Hz), 2.06 (1H, ddd, J=13.8, 3.9, 1.9 Hz), 2.91 (1H, ddd, J=12.9, 3.9, 1.9 Hz), 3.15 (1H, ddd, J=12.9, 9.4, 3.9 Hz), 7.89 (1H, t, J=2.1 Hz), 8.55-8.57 (2H, m).

The 11th step: Compound (48) (190 mg), trisdibenzylideneacetonedipalladium (54 mg), dicyclohexylbiphenylphosphine (41 mg) were dissolved in toluene (5 ml), stirred at room temperature, and 1.6 M solution of lithium hexamethyldisilazide in tetrahydrofuran (0.73 ml) was added therein. The reaction solution was warmed up to 85° C. and stirred for 9 hours, then, it was cooled in ice and diethyl ether and a 1 N solution of hydrochloric acid were added. After stirring for 10 minutes, it was neutralized by the addition of a saturated aqueous solution of sodium carbonate and extracted with dichloromethane. The organic layer was dried over anhydrous sodium sulfate, concentrated under reduced pressure and the residue was purified with a silicagel column chromatography to give compound (49) (27 mg).

$^1$H-NMR (CDCl$_3$) δ: 1.51 (9H, s), 1.68 (3H, s), 2.12 (1H, ddd, J=14.8, 11.0, 3.0 Hz), 2.38-2.47 (1H, m), 2.64-2.70 (1H, m), 2.78-2.82 (1H, m), 3.80 (2H, br s), 6.90 (1H, t, J=2.4 Hz), 7.98 (1H, dd, J=10.4, 2.4 Hz).

Reference Example 7

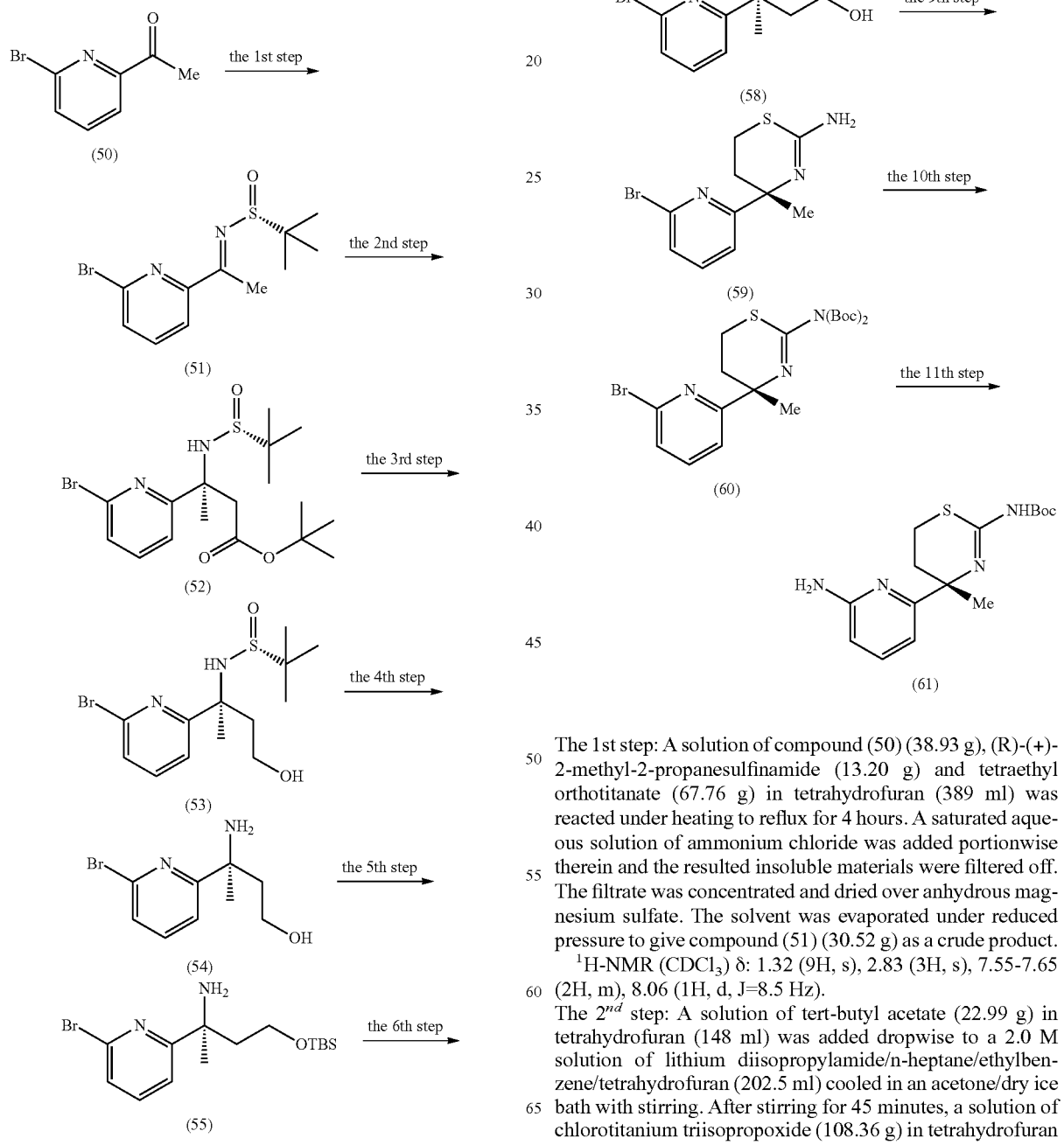

The 1st step: A solution of compound (50) (38.93 g), (R)-(+)-2-methyl-2-propanesulfinamide (13.20 g) and tetraethyl orthotitanate (67.76 g) in tetrahydrofuran (389 ml) was reacted under heating to reflux for 4 hours. A saturated aqueous solution of ammonium chloride was added portionwise therein and the resulted insoluble materials were filtered off. The filtrate was concentrated and dried over anhydrous magnesium sulfate. The solvent was evaporated under reduced pressure to give compound (51) (30.52 g) as a crude product.

$^1$H-NMR (CDCl$_3$) δ: 1.32 (9H, s), 2.83 (3H, s), 7.55-7.65 (2H, m), 8.06 (1H, d, J=8.5 Hz).

The 2$^{nd}$ step: A solution of tert-butyl acetate (22.99 g) in tetrahydrofuran (148 ml) was added dropwise to a 2.0 M solution of lithium diisopropylamide/n-heptane/ethylbenzene/tetrahydrofuran (202.5 ml) cooled in an acetone/dry ice bath with stirring. After stirring for 45 minutes, a solution of chlorotitanium triisopropoxide (108.36 g) in tetrahydrofuran (342 ml) was added dropwise and stirred for 40 minutes. A solution of the compound (51) (30.52 g) in tetrahydrofuran (342 ml) was added dropwise and reacted for an hour. The reaction solution was poured portionwise into an aqueous solution of ammonium chloride with stirring under ice cooling and the resulted insoluble materials were filtered off. It was extracted with ethyl acetate and the organic layer was dried over anhydrous magnesium sulfate. The solvent was evaporated under reduced pressure and the residue was purified with a silicagel column chromatography to give compound (52) (27.40 g).

$^1$H-NMR (CDCl$_3$) δ: 1.30 (9H, s), 1.35 (9H, s), 1.65 (3H, s), 3.01 (1H, d, J=16.5 Hz), 3.38 (1H, d, J=16.5 Hz), 5.60 (1H, s), 7.31 (1H, dd, J=5.9, 2.7 Hz), 7.48-7.50 (2H, m).

The 3$^{rd}$ step: Lithium aluminum hydride (5.67 g) was added portionwise to a solution of the compound (52) (22.40 g) in tetrahydrofuran (336 ml) stirred in an ice salt bath and stirred for 7 hours. After the addition of acetone, water and a 1 N aqueous solution of sodium hydroxide, the insoluble materials were filtered off and extracted with ethyl acetate. The organic layer was dried over anhydrous sodium sulfate and concentrated under reduced pressure to give compound (53) (18.75 g) as a crude product.

The 4$^{th}$ step: A solution of 10% HCl/methanol (94 ml) was added to a solution of the compound (53) (18.75 g) obtained in the 3rd step in methanol (94 ml) stirred under ice cooling and stirred at room temperature for 1.5 hours. The reaction solution was made alkaline by the addition of water and potassium carbonate and extracted with chloroform. The organic layer was dried over anhydrous sodium sulfate and concentrated under reduced pressure to give compound (54) (21.03 g) as a mute product.

The 5$^{th}$ step: Imidazole (5.49 g) and tert-butyldimethylsilyl chloride (10.53 g) were added to a solution of the compound (54) (21.03 g) in N,N-dimethylformamide (210 ml) stirred at room temperature and the mixture was stirred for an hour. After extraction with ethyl acetate, the organic layer was washed with saturated brine and dried over anhydrous sodium sulfate. The solvent was evaporated under reduced pressure and the residue was purified with a silicagel column chromatography to give compound (55) (20.12 g).

$^1$H-NMR (CDCl$_3$) δ: −0.04 (3H, s), −0.02 (3H, s), 0.84 (9H, s), 1.47 (3H, s), 1.95-2.15 (2H, m), 3.54-3.63 (2H, m), 7.29 (1H, dd, J=6.1, 2.6 Hz), 7.45-7.48 (2H, m).

The 6th step: Toluene (66 ml) and water (33 ml) were added to compound (55) (10.06 g) and stirred under ice cooling. After the addition of potassium carbonate (11.13 g), thiophosgene (2.86 ml) was added dropwise. After reacting for an hours, water was added, extracted with chloroform and the organic layer was dried over anhydrous sodium sulfate. The solvent was evaporated under reduced pressure and the residue was purified with a silicagel column chromatography to give compound (56) (9.43 g).

$^1$H-NMR (CDCl$_3$) δ: −0.03 (6H, s), 0.82 (9H, s), 1.80 (3H, s), 2.21-2.24 (1H, m), 2.44-2.48 (1H, m), 3.57 (1H, ddd, J=12.0, 5.8, 4.8 Hz), 3.71 (1H, ddd, J=12.0, 5.8, 4.8 Hz), 7.37 (1H, dd, J=7.5, 1.2 Hz), 7.48-7.58 (2H, m).

The 7$^{th}$ step: 28% Ammonia water (47 ml) was added to compound (56) (9.43 g) dissolved in tetrahydrofuran (94 ml) stirred at room temperature. After stilling for 16 hours, water was added, extracted with ethyl acetate and the organic layer was dried over anhydrous sodium sulfate. The solvent was evaporated under reduced pressure to give compound (57) (6.35 g) as a crude product.

The 8$^{th}$ step: Acetic acid (1.09 g) and a 1.0 M solution of tetrabutylammonium fluoride/tetrahydrofuran (18.20 ml) were added to a solution of the compound (57) (6.35 g) obtained in the 7th step in tetrahydrofuran (127 ml) stirred under ice cooling. After stirring at room temperature for 3 hours, water and potassium carbonate were added and extracted with ethyl acetate. The organic layer was dried over anhydrous sodium sulfate, concentrated under reduced pressure and the residue was purified with a silicagel column chromatography to give compound (58) (4.47 g).

$^1$H-NMR (CDCl$_3$) δ: 1.85 (3H, s), 2.27-2.31 (2H, br m), 3.73-3.83 (2H, m), 5.86 (2H, br s), 7.43 (1H, d, J=7.8 Hz), 7.52 (1H, d, J=7.8 Hz), 7.61 (1H, t, J=7.8 Hz), 7.81 (1H, br s).

The 9$^{th}$ step: 1-Chloro-N,N,2-trimethyl-1-propenylamine (2.16 g) was added to compound (58) (4.47 g) dissolved in dichloromethane (89 ml) stirred under ice cooling. After stirring at room temperature for 1.5 hours, water was added and extracted with dichloromethane. The organic layer was dried over anhydrous sodium sulfate, concentrated under reduced pressure and the residue was purified with a silicagel column chromatography to give compound (59) (2.91 g).

$^1$H-NMR (CDCl$_3$) δ: 1.53 (3H, s), 1.88 (1H, ddd, J=13.9, 10.1, 3.8 Hz), 2.40 (1H, ddd, J=13.9, 6.6, 3.8 Hz), 2.71 (1H, ddd, J=13.9, 10.1, 3.8 Hz), 2.95 (1H, tt, J=6.6, 3.8 Hz), 4.33 (2H, br s), 7.29 (1H, dd, J=7.5, 1.2 Hz), 7.41-7.50 (1H, m).

The 10$^{th}$ step: A mixture of compound (59) (2.91 g), di-tert-butyl dicarbonate (5.52 g), 4-dimethylaminopyridine (0.12 g) and tetrahydrofuran (29 ml) was stirred at room temperature for 2.5 hours. The reaction solvent was evaporated under reduced pressure and the residue was purified with a silicagel column chromatography to give compound (60) (1.23 g).

$^1$H-NMR (CDCl$_3$) δ: 1.53 (23H, s), 1.60 (3H, s), 1.93 (1H, ddd, J=13.8, 9.4, 3.9 Hz), 2.06 (1H, ddd, J=13.8, 3.7, 1.8 Hz), 2.91 (1H, ddd, J=12.7, 3.7, 1.9 Hz), 3.15 (1H, ddd, J=12.9, 9.2, 3.7 Hz), 7.89 (1H, t, J=2.1 Hz), 8.55-8.57 (2H, m).

The 11$^{th}$ step: Compound (60) (3.30 g), trisdibenzylideneacetonedipalladium (0.93 g), dicyclohexylbiphenylphosphine (0.73 g) were dissolved in toluene (66 ml), stirred at room temperature, and a 1.6 M solution of lithium hexamethyldisilazide in tetrahydrofuran (12.7 ml) was added therein. The reaction solution was warmed up to 80° C. and stirred for 8 hours, than, it was cooled in ice and diethyl ether and a 1 N solution of hydrochloric acid were added. After stirring for 5 minutes, it was neutralized by the addition of a saturated aqueous solution of sodium carbonate and extracted with ethyl acetate. The organic layer was dried over anhydrous sodium sulfate, concentrated under reduced pressure and the residue was purified with a silicagel column chromatography to give compound (61) (1.55 g).

$^1$H-NMR (CDCl$_3$) δ: 1.61 (3H, s), 1.74-1.80 (1H, n), 1.96-2.11 (1H, m), 2.64-2.82 (2H, m), 4.41 (2H, br s), 6.39 (1H, dd, J=8.1, 0.6 Hz), 6.71 (1H, dd, J=8.1, 0.6 Hz), 7.42 (1H, t, J=8.1 Hz).

Reference Example 8

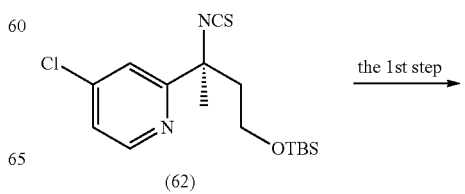

(62) the 1st step

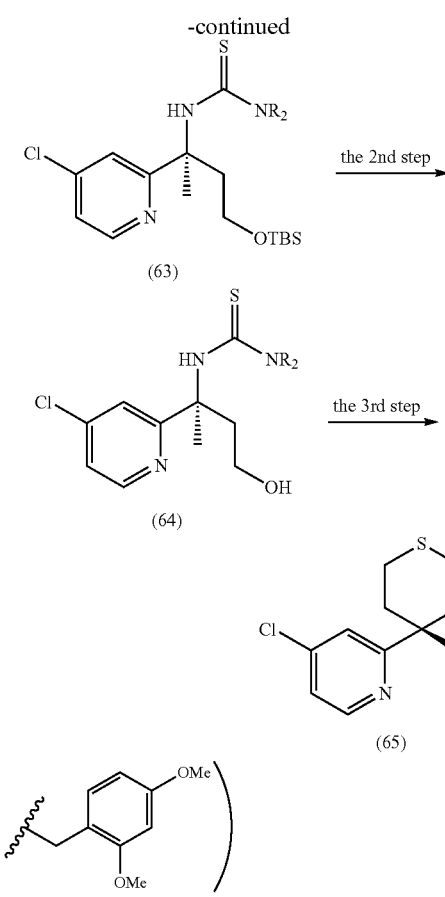

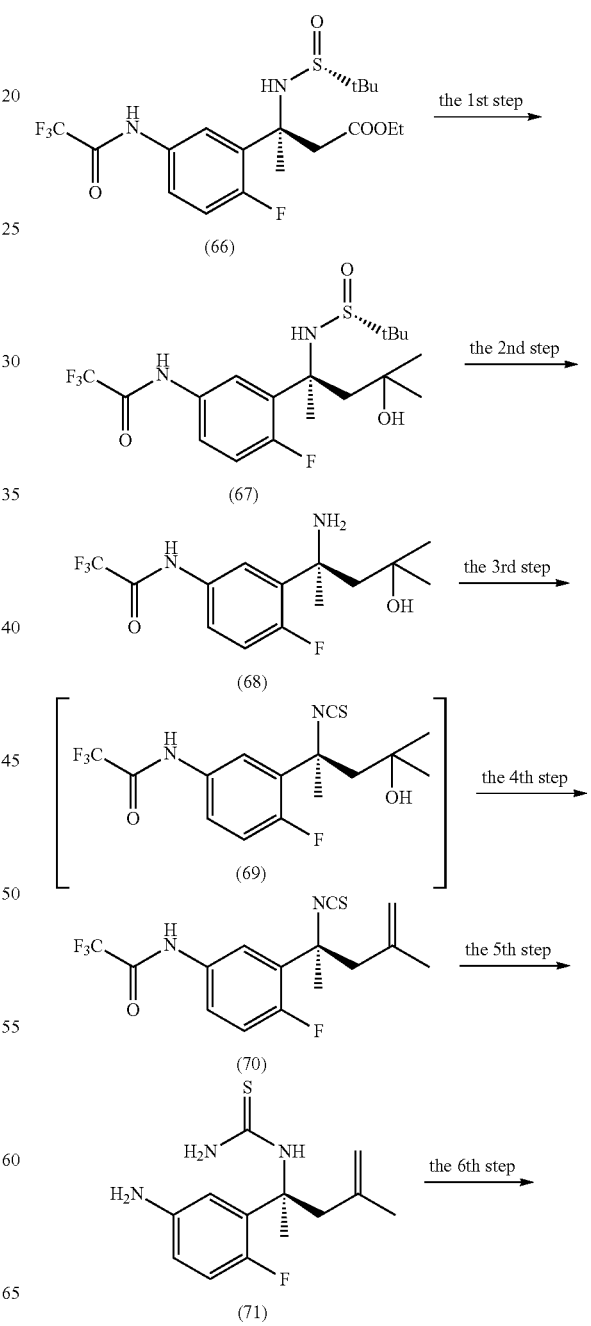

was added, extracted with chloroform and the organic layer was dried over anhydrous sodium sulfate. The solvent was evaporated under reduced pressure and the residue was purified with a silicagel column chromatography to give a compound (65) (3.41 g).

$^1$H-NMR (CDCl$_3$): 1.49 (3H, s), 1.99 (1H, ddd, J=13.3, 7.6, 3.2 Hz), 2.31 (1H, ddd, J=13.3, 8.6, 3.7), 2.78 (1H, ddd, J=12.2, 8.6, 3.2 Hz), 3.04 (1H, ddd, J=12.2, 7.6, 3.7 Hz), 3.77 (6H, s), 3.79 (6H, s), 4.60 (2H, d, J=15.8 Hz), 4.76 (2H, d, J=15.8 Hz), 6.45-6.52 (4H, m), 7.08 (1H, dd, J=5.3, 2.1 Hz), 7.17-7.27 (3H, m), 8.40 (1H, dd, J=5.3, 0.5 Hz).

Reference Example 9

The 1$^{st}$ step: Compound (63) (3.31 g) prepared in the same manner as Reference Example 6 and 7 described above was dissolved in dichloromethane (16.5 nit), bis(2,4-dimethoxybenzyl)amine (4.45 g) was added and the solvent was evaporated under reduced pressure after stirring at room temperature for an hour and standing for 15 hours. The residue was purified with silicagel chromatography to give compound (63) (5.7 g).

$^1$H-NMR (CDCl$_3$): −0.10 (3H, s), −0.07 (3H, s), 0.77 (9H, s), 1.93 (3H, s), 2.08-2.27 (1H, m), 3.06-3.28 (1H, m), 3.38 (1H, ddd, J=10.8, 6.8, 6.8 Hz), 3.55 (1H, ddd, J=10.8, 6.8, 6.8 Hz), 3.78 (6H, s), 3.79 (6H, s), 4.81-5.05 (1H, br), 6.43-6.50 (4H, m), 7.07 (1H, d, J=1.9 Hz), 7.17 (2H, d, J=7.3 Hz), 8.05-8.16 (2H, m).

The 2$^{nd}$ step: Compound (63) (5.77 g) was dissolved in tetrahydrofuran (60 ml) and acetic acid (1.01 g) and 1M tetrabutylammonium fluoride/tetrahydrofuran-solution (15 ml) were added and the mixture was stirred at room temperature for 150 minutes. Water was added, extracted with ethyl acetate and the organic layer was dried over anhydrous sodium sulfate. The solvent was evaporated under reduced pressure and the residue was purified with a silicagel chromatography to give compound (64) (3.94 g).

$^1$H-NMR (CDCl$_3$): 1.99 (3H, s), 1.91-2.02 (1H, m), 3.10 (1H, ddd, J=14.6, 6.6, 5.2), 3.36-3.51 (2H, m), 3.78 (6H, s), 3.80 (6H, s), 4.58 (2H, d, J=15.8 Hz), 4.72 (2H, d, J=15.8 Hz), 6.43-6.51 (4H, m), 7.12 (1H, dd, J=5.3, 2.0 Hz), 7.18-7.29 (3H, m), 8.20 (1H, dd, J=5.3, 0.6 Hz), 8.28-8.34 (1H, br).

The 3$^{rd}$ step: Compound (64) (3.94 g) was dissolved in dichloromethane (20 ml) and 1-chloro-N,N',2-trimethyl-1-propenylamine (1.86 ml) was added under ice cooling with stirring. After stirring at room temperature for 2 hours, water

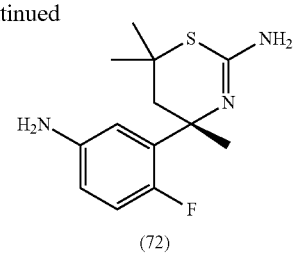

The 1st step: Compound (66) (4.72 g) derived by a conventional method from an intermediate prepared in the same manner as the compound (27) described above was dissolved in tetrahydrofuran (150 ml) and a diethylether solution of methyl magnesium bromide (3M, 37 ml) was added dropwise with stirring under ice cooling in a nitrogen stream for 12 minutes. After stirring 3 hours, a saturated aqueous solution of ammonium chloride (190 ml) was added dropwise, extracted with ethyl acetate, the organic layer was washed with saturated brine and dried over anhydrous sodium sulfate. The solvent was evaporated under reduced pressure and the residue was purified with a silicagel column chromatography to give a compound (67) (2.11 g).

$^1$H-NMR (DMSO-$d_6$) 0.75 (3H, s), 1.09 (3H, s), 1.21 (9H, s), 1.79 (3H, s), 2.06 (1H, m), 2.29 (1H, m), 4.97 (1H, s), 6.57 (1H, s), 7.17 (1H, dd, J=8.7, 12.0 Hz), 7.48-7.53 (1H, m), 7.99-8.03 (1H, m), 11.26 (1H, bs).

The 2nd step: Compound (67) (2.11 g) was dissolved in methanol (7.8 ml) and hydrochloric acid-methanol solution (5-10%) (15:6 ml) was added with stirring at room temperature, and the mixture was stirred for 1.5 hams. Then the reaction solution was poured into ice water and ethyl acetate (100 ml), a saturated aqueous solution of sodium bicarbonate (50 ml) was added and extracted with ethyl acetate. The aqueous layer was further extracted with ethyl acetate (50 ml), organic layers were combined, washed with saturated brine and dried over anhydrous sodium sulfate. The solvent was evaporated under reduced pressure and the residue was crystallized from n-hexane to give compound (68) (1.42 g).

$^1$H-NMR (DMSO-$d_6$): 0.65 (3H, s), 1.10 (3H, s), 1.43 (3H, s), 1.85 (1H, d, J=14.4 Hz), 2.17 (1H, dd, J=1.5, 14.4 Hz), 7.12 (1H, dd, J=2.7, 12.0 Hz), 7.60-7.64 (1H, m), 7.90 (1H, dd, 7.5 Hz), 11.35 (1H, bs).

The 3rd step: Toluene (9.6 ml) and water (4.8 ml) were added to compound (68) (1.42 g) and suspended, potassium carbonate (2.13 g) was added with stirring under ice cooling and 2 minutes later thiophosgene (0.51 ml) was added at once and the stirring was continued.

The temperature was back to room temperature 40 minutes later, toluene (40 ml) and water were added and extracted an hour later. The aqueous layer was further extracted with toluene, organic layers were combined, washed with saturated brine and dried over anhydrous sodium sulfate. The solvent was evaporated under reduced pressure to give a crude product (69) (2.02 g).

The 4th step: Tetrahydrofuran (17 ml) was added to triphenylphosphine (1.735 g) and N-chlorosuccinimide (833 mg), suspended in a nitrogen stream and stirred at room temperature for 10 minutes. A tetrahydrofuran (21 ml) solution of the crude product (69) (2.02 g) was added dropwise using a dropping funnel for 2 minutes. After stirring for 6 hours, the mixture was left stand at room temperature overnight. The solvent was evaporated under reduced pressure and the residue was purified with a silicagel column chromatography to give compound (70) (828 mg).

$^1$H-NMR (DMSO-$d_6$): 1.54 (3H, s), 1.86 (3H, s), 2.81 (1H, d, J=13.8 Hz), 2.92 (1H, d, J=13.8 Hz), 4.73 (1H, s), 4.85 (1H, m), 7.28-7.35 (1H, m), 7.77-7.82 (2H, m), 11.39 (1H, bs).

The 5th step: Compound (70) (828 mg) was dissolved in tetrahydrofuran (4 ml), conc. ammonia water (28%) (4 ml) was added with stirring under ice cooling and the temperature was back to room temperature after stirring for 5 minutes. After 25 hours, the reaction mixture was poured into ice water and extracted with ethyl acetate (50 ml). The organic layer was washed with saturated brine and dried over anhydrous sodium sulfate. The solvent was evaporated under reduced pressure and the residue was purified with a silicagel chromatography to give a compound (71) (260 mg).

$^1$H-NMR (DMSO-$d_6$): 1.47 (3H, bs), 1.66 (3H, bs), 2.58 (1H, d, J=12.3 Hz), 4.71 (1H, s), 4.87 (3H, bs), 6.42 (1H, bs), 6.51 (1H, dd, 7.2 Hz), 6.75 (2H, bs), 7.54 (1H, bs).

The 6th step: Compound (71) (245 mg) was dissolved in chilled conc. sulfuric acid (4.9 ml) and stirred under ice cooling for 2 hours. The reaction solution was poured into ice water with stilling and pH was adjusted to 2-3 by the addition of a 5N aqueous solution of sodium hydroxide. Ethyl acetate (100 ml) and an aqueous solution of potassium carbonate were added and extracted under alkaline condition. The alkaline layer was further extracted with ethyl acetate (50 ml). Organic layers were combined, washed with saturated brine (50 ml) and dried over anhydrous sodium sulfate. The solvent was evaporated under reduced pressure and the residue was purified with a silicagel column chromatography to give a compound (72) (101 mg) as a crystal.

$^1$H-NMR (DMSO-$d_6$): 0.83 (3H, s), 1.27 (3H, s), 1.44 (3H, s), 1.54 (1H, d, J=14.1 Hz), 2.45 (1H, d, J=14.1 Hz), 4.79 (2H, s), 5.89 (2H, bs), 6.32-6.37 (1H, m), 6.58 (1H, dd, J=2.7, 7.2 Hz), 6.72 (1H, dd, J=8.7, 12.3 Hz).

Reference Example 10

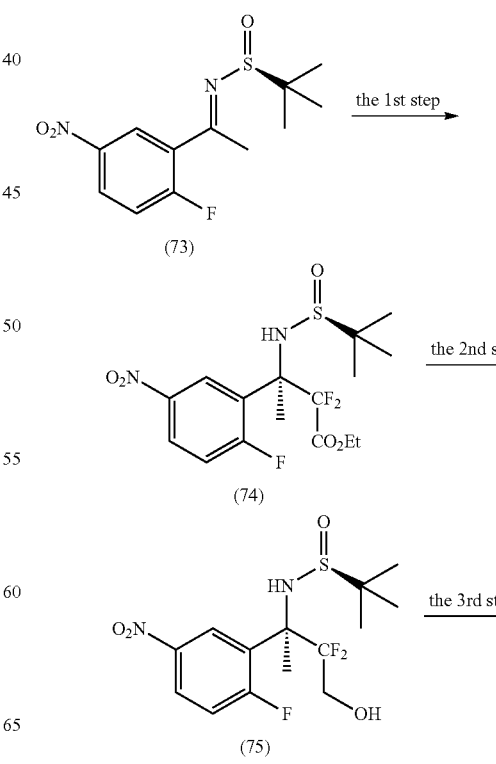

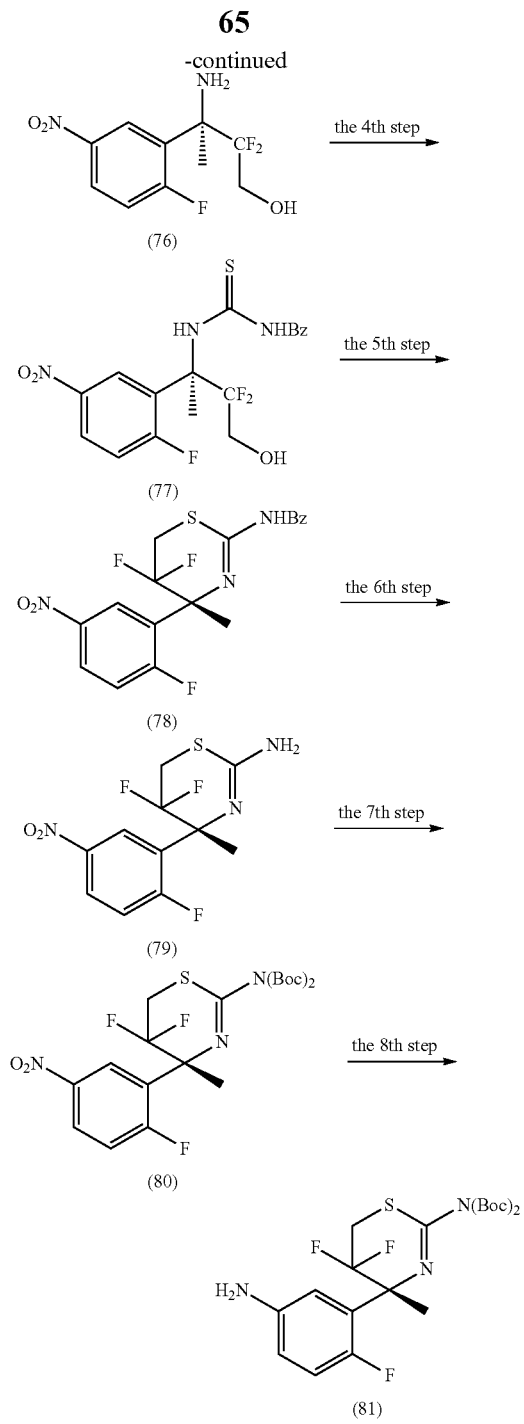

¹H-NMR (DMSO-d₆) δ: 1.17 (3H, t, J=7.2 Hz), 1.18 (9H, s), 2.00 (3H, brs), 4.24 (2H, q, J=7.2 Hz), 5.56 (1H, brs), 7.56 (dd, J=9.0, 11.7 Hz), 8.36 (1H, m), 8.49 (1H, dd, J=3.0, 6.6 Hz).

The 2$^{nd}$ step: Compound (74) (670 mg) was dissolved in tetrahydrofuran (6.7 ml) and lithium borohydride (71 mg) was added in a nitrogen stream with stirring under ice cooling. After stirring for 30 minutes, acetic acid (198 mg) and ice water were added to the reaction mixture, extracted with ethyl acetate, the organic layer was washed with brine and dried over anhydrous magnesium sulfate. The solvent was evaporated under reduced pressure and the residue was purified with a silicagel column chromatography to give a compound (75) (401 mg).

¹H-NMR (DMSO-d₆) δ: 1.20 (9H, s), 2.00 OH, d, J=3.6 Hz), 3.80 (1H, m), 4.00 (1H, m), 5.99 (1H, s), 6.34 (1H, t, J=5.7 Hz), 7.53 (1H, dd, J=9.0, 12.0 Hz), 8.31 (1H, m), 8.50 (1H, dd, J=2.7, 6.6 Hz).

The 3$^{rd}$ step: Compound (75) (394 mg) was dissolved in methanol (3 ml), and 4N—HCl/1,4-dioxane (1.35 ml) was added with stirring under ice cooling. After stirring for 30 minutes, the mixture was stirred at room temperature for 1.5 hours. Ice water was added to the reaction solution and washed with ethyl acetate. The aqueous layer was made alkaline by the addition of a 2M aqueous solution of potassium carbonate and extracted with ethyl acetate. The organic layer was dried over anhydrous magnesium sulfate, the solvent was evaporated under reduced pressure to give compound (76) (293 mg).

¹H-NMR (DMSO-d₆) δ: 1.62 (3H, d, J=2.7 Hz), 2.62 (2H, brs), 3.65-3.83 (2H, m), 5.31 (1H, brt), 7.41 (1H, dd, J=9.0, 11.4 Hz), 8.23 (1H, m), 8.59 (1H, dd, J=3.0, 6.9 Hz).

The 4$^{th}$ step: Compound (76) (266 mg) was dissolved in acetone (3 ml) and benzoyl isothiocyanate (164 mg) was added in a nitrogen stream with stirring under ice cooling. After stirring for an hour, the mixture was stirred at room temperature for an hour. The reaction solution was concentrated under reduced pressure and the residue was purified with a silicagel column chromatography to give a compound (77) (353 mg).

¹H-NMR (DMSO-d₆) δ: 2.30 (3H, brs), 3.65-3.96 (2H, m), 5.90 (1H, brt), 7.42-7.68 (4H, m), 7.93-7.96 (2H, m), 8.17-8.33 (2H, m), 11.42 (1H, brs), 12.31 (1H, brs).

The 5$^{th}$ step: Compound (77) (348 mg) was dissolved in dichloromethane (4 ml) and 1-chloro-N,N-2-trimethyl-1-propenylamine (131 mg) was added in a nitrogen stream with stirring under ice cooling. After stirring for 15 hours at room temperature, ice water was added and neutralized by the addition of potassium carbonate. It was extracted with ethyl acetate, washed with brine and dried over anhydrous magnesium sulfite. The solvent was evaporated under reduced pressure and the residue was purified with a silicagel column chromatography to give a compound (78) (308 mg).

¹H-NMR (CDCl₃) δ: 1.89 (3H, d, J=3.0 Hz), 3.17 (1H, ddd, J=8.4, 10.2, 13.2 Hz), 3.51 (1H, ddd, J=6.0, 13.2, 19.2 Hz), 7.23 (1H, dd, J=9.0, 10.8 Hz), 7.49-7.64 (3H, m), 7.91 (2H, d, J=7.2 Hz), 8.24 (1H, m), 8.43 (1H, dd, J=3.0, 6.6 Hz), 8.57 (1H, br).

The 6$^{th}$ step: Compound (78) (297 mg) was dissolved in ethanol (4 ml), water (1.5 ml) and conc, hydrochloric acid (1.5 ml) were added and the mixture was stirred at 90° C. for 2.5 hours. Water was added to the reaction solution, washed with ethyl acetate and the aqueous layer was made alkaline by the addition of a 2M aqueous solution of potassium carbonate. It was extracted with ethyl acetate, washed with brine and the organic layer was dried over anhydrous magnesium sulfate. The solvent was evaporated under reduced pressure and The 1$^{st}$ step: Ethyl bromodifluoroacetate (0.77 ml) was added to a suspension of zinc dust (392 mg) in tetrahydrofuran (4 ml) with stirring in a nitrogen stream at room temperature, stirred for 15 minutes, ethyl bromodifluoroacetate (0.29 ml) was added, stirred for 30 minutes to prepare a solution of ethyl bromozincdifluoroacetate. This solution was added to a solution of compound (73) in tetrahydrofuran (3 ml) in a nitrogen stream and stirred for 8 hours. 3% Ammonia water was added to the reaction mixture with stirring under ice cooling, extracted with ethyl acetate, the organic layer was washed with saturated brine and dried over anhydrous magnesium sulfate. The solvent was evaporated under reduced pressure and the residue was purified with a silicagel column chromatography to give a compound (74) (696 mg).

the residue was purified with a silicagel column chromatography to give a compound (79) (89 mg).

$^1$H-NMR (CDCl$_3$) δ: 1.85 (3H, d, J=3.6 Hz), 3.15 (1H, ddd, J=8.7, 10.5, 12.9 Hz), 3.50 (1H, ddd, J=5.4, 12.9, 18.3 Hz), 4.51 (2H, brs), 7.19 (1H, dd, J=9.0, 11.1 Hz), 8.20 (1H, ddd, J=3.0, 6.9, 9.0 Hz), 8.54 (1H, dd, J=3.0, 6.9 Hz).

The 7$^{th}$ step: Compound (79) (82 mg) was dissolved in dichloromethane (1 ml), di-tert-butyldicarbonate (176 mg) and 4-dimethylaminopyridine (4 mg) were added and the mixture was stirred at room temperature for 30 minutes. The reaction solution was concentrated under reduced pressure and the residue was purified with a silicagel column chromatography to give a compound (80) (101 mg).

$^1$H-NMR (CDCl$_3$) δ: 1.56 (18H, s), 1.90 (3H, d, J=3.6 Hz), 3.27 (1H, ddd, J=6.6, 9.3, 12.9 Hz), 3.69 (1H, ddd, J=4.2, 12.9, 17.4 Hz), 7.23 (1H, dd, J=9.0, 12.0 Hz), 8.24 (1H, ddd, J=3.0, 9.0, 12.0 Hz), 8.41 (1H, ddd, J=2.4, 3.0, 6.0 Hz).

The 8$^{th}$ step: Compound (80) (4.76 g) was dissolved in methanol (70 ml), 10% Pd—C (containing 50% water) (2.38 g) was added and the mixture was stirred in a hydrogen atmosphere for 20 hours. The catalyst was filtered off the solvent was evaporated under reduced pressure to give compound (81) (4.43 g)

$^1$H-NMR (CDCl$_3$) δ: 1.54 (18H, s), 1.85 (3H, d, J=2.4 Hz), 3.24 (1H, m), 3.41 (1H, m), 3.53 (2H, brs), 6.61 (1H, m), 6.82-6.89 (2H, m).

Reference Example 11

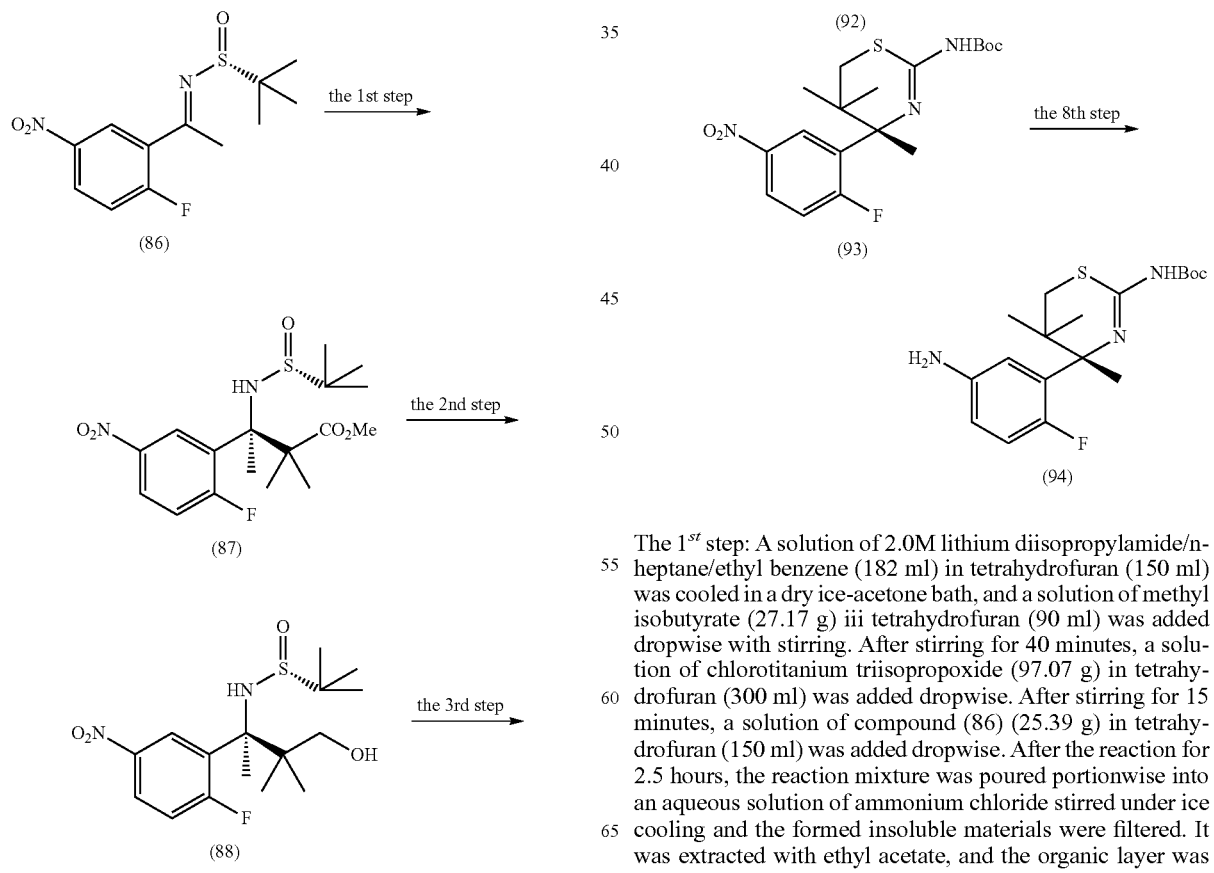

The 1$^{st}$ step: A solution of 2.0M lithium diisopropylamide/n-heptane/ethyl benzene (182 ml) in tetrahydrofuran (150 ml) was cooled in a dry ice-acetone bath, and a solution of methyl isobutyrate (27.17 g) iii tetrahydrofuran (90 ml) was added dropwise with stirring. After stirring for 40 minutes, a solution of chlorotitanium triisopropoxide (97.07 g) in tetrahydrofuran (300 ml) was added dropwise. After stirring for 15 minutes, a solution of compound (86) (25.39 g) in tetrahydrofuran (150 ml) was added dropwise. After the reaction for 2.5 hours, the reaction mixture was poured portionwise into an aqueous solution of ammonium chloride stirred under ice cooling and the formed insoluble materials were filtered. It was extracted with ethyl acetate, and the organic layer was dried over anhydrous magnesium sulfate. The solvent was evaporated under reduced pressure and the residue was purified with a silicagel column chromatography to give a compound (87) (23.98 g).

$^1$H-NMR (CDCl$_3$) δ: 1.12 (3H, s), 1.22 (3H, s), 1.35 (9H, s), 1.99 (3H, d, J=5.8 Hz), 3.75 (3H, s), 5.65 (1H, s), 7.20 (OH, dd, J=11.5, 8.9 Hz), 8.18-8.21 (1H, m), 8.45 (1H, dd, J=6.9, 2.9 Hz).

The 2$^{nd}$ step: Compound (87) (391 mg) was dissolved in tetrahydrofuran (4 ml) and lithium borohydride (44 mg) was added in 3 minutes in a nitrogen stream with stirring at room temperature. After stirring for 2 hours, lithium borohydride (22 mg) was further added and the stirring was continued. After stirring for 2 hours, a saturated aqueous solution of ammonium chloride was slowly added to the reaction solution with stirring under ice cooling, extracted with ethyl acetate 5 minutes later, the organic layer was washed with saturated brine and dried over anhydrous sodium sulfate. The solvent was evaporated under reduced pressure and the residue was purified with a silicagel column chromatography to give a compound (88) (175 mg).

$^1$H-NMR (DMSO-d$_6$) δ: 0.65 (3H, d, J=1.8 Hz), 0.93 (3H, s), 1.22 (9H, s), 1.93 (3H, d, J=6.6 Hz), 3.24 (1H, d, J=8.4 Hz), 3.74 (1H, d, J=8.4 Hz), 5.96 (1H, bs), 6.75 (1H, s), 7.47 (1H, dd, J=9.0, 12.0 Hz), 8.23 (1H, ddd, J=3.0, 3.0, 9.0 Hz), 8.39 (1H, dd, J=3.0, 6.9 Hz).

The 3$^{rd}$ step: Compound (88) (331 mg) was dissolved in methanol (1.5 ml), and a hydrogen chloride-methanol solution (5-10%) (3 ml) was added with stirring at room temperature. After stirring for 1.5 hours, the reaction solvent was evaporated under reduced pressure. The residue was dissolved in ethyl acetate-methanol (9:1), poured into ice water, and a saturated aqueous solution of sodium bicarbonate (4 ml) was added, extracted, washed with saturated brine and the organic layer was dried over anhydrous sodium sulfate. The solvent was evaporated under reduced pressure and the powder obtained by the addition of n-hexane to the solid was filtered to give a compound (89) (207 mg).

$^1$H-NMR (DMSO-d$_6$) δ: 0.80 (6H, s), 1.59 (3H, d, J=4.5 Hz), 3.16 (1H, d, J=10.8 Hz), 7.38 (1H, dd, J=9.0, 12.0 Hz), 8.17 (1H, ddd, J=3.0, 3.0, 9.0 Hz), 8.64 (1H, dd, J=3.0, 6.9 Hz).

The 4$^{th}$ step: Compound (89) (150 mg) was dissolved in acetone (3 ml) and benzoyl isothiocyanate (0.079 ml) was added in a nitrogen stream with stirring under ice cooling. After stirring for 2 hours, the reaction solvent was evaporated under reduced pressure and the residue was purified with a silicagel column chromatography to give a compound (90) (236 mg).

LCMS: 420 m/z[M+H]$^+$

The 5$^{th}$ step: Compound (90) (233 mg) was dissolved in dichloromethane (4 ml) and chloropropenylamine (0.081 ml) was added at once in a nitrogen stream with stiffing at room temperature. After stirring for 23 hours, the reaction solution was poured into ice water, extracted with ethyl acetate, washed with saturated brine and the organic layer was dried over anhydrous sodium sulfate. The solvent was evaporated under reduced pressure and the residue was purified with a silicagel column chromatography to give a compound (91) (128 mg).

$^1$H-NMR (DMSO-d$_6$) δ: 0.83 (3H, s), 1.12 (3H, s), 1.72 (3H, s), 2.69 (1H, d, J=13.2 Hz), 2.90-3.10 (1H, m), 7.44-7.58 (4H, m), 8.00 (2H, d, J=7.5 Hz), 8.23-8.35 (2H, m), 10.75 (1H, bs).

The 6$^{th}$ step: Compound (91) (20 mg) was suspended in 99.5% ethanol (0.4 ml), 6N hydrochloric acid (0.2 ad) was added and the mixture was stirred in a oil bath heated to 90° C. After stifling for 17 hours, the reaction solution was poured into water, and extracted with ethyl acetate. The aqueous layer was made alkaline by the addition of a saturated aqueous solution of potassium carbonate (pH=11), extracted with ethyl acetate, washed with saturated brine and the organic layer was dried over anhydrous sodium sulfate. The solvent was evaporated under reduced pressure to give compound (92) (14 mg).

$^1$H-NMR (DMSO-d$_6$) δ: 0.72 (3H, s), 1.00 (3H, d, J=3.6 Hz), 1.54 (3H, d, J=4.8 Hz), 2.61 (1H, d, J=12.3 Hz), 3.09 (1H, d, J=12.3 Hz), 5.98 (2H, s), 7.41 (1H, dd, J=9.0, 11.7 Hz), 8.16-8.21 (1H, m), 8.42 (1H, dd, J=3.0, 6.9 Hz).

The 7$^{th}$ step: Compound (92) (12 mg) was dissolved in dichloromethane (0.1 ml) and a di-tert-butyldicarbonate-dichloromethane solution (0.0966M, 1.2 ml) was added with stirring at room temperature. After stifling for 2 hours, the reaction solvent was evaporated under reduced pressure and the residue was purified with a silicagel column chromatography to give a compound (93) (15 mg).

$^1$H-NMR (DMSO-d$_6$) δ: 0.70 (3H, s), 1.02 (3H, s), 1.43 (9H, s), 1.56 (3H, bs), 2.61 (1H, d, J=12.9 Hz), 3.16 (1H, m), 7.45 (1H, dd, J=9.0, 11.4 Hz), 8.20-8.24 (1H, m), 8.35 (1H, m), 9.87 (1H, bs).

The 8$^{th}$ step: Methanol (4.1 ml) was added to compound (93) (823 mg), suspended, and 10% Pd—C (50% wet) (412 mg) was added. A catalytic reduction was carried out at normal pressure, and methanol (8.2 ml) was added when a solid was precipitated and the reduction was further continued. After 23 hours, the catalyst was filtered through a Celite pad, washed with warm methanol, and the washings were combined. The solvent was evaporated under reduced pressure and the powder precipitated by the addition of diisopropylether to the residue was filtered to give compound (94) (638 mg).

$^1$H-NMR (DMSO-d$_6$) δ: 0.87 (3H, bs), 1.06 (3H, bs), 1.39 (9H, s), 1.57 (3H, bs), 2.66-2.72 (2H, m), 4.97 (2H, bs), 6.45-6.47 (2H, m), 6.78 in), 9.65 (1H, bs).

Reference Example 12

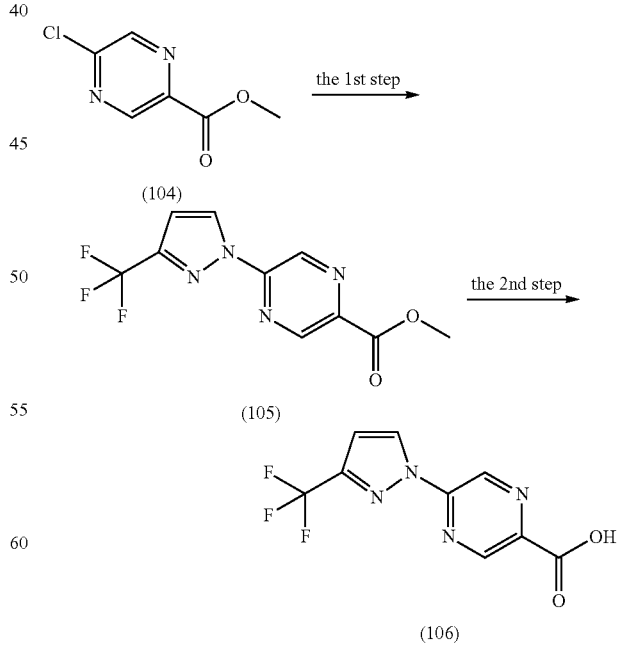

The 1$^{st}$ step: 3-(Trifluoromethyl)-1H-pyrazole (591 mg) was dissolved in dimethylformamide (7 ml), potassium carbonate (601 mg) and compound (104) (500 mg) were added thereto and stirred at room temperature overnight. The reaction was quenched by an addition of water. The insoluble materials were filtered and washed with diisopropylether. The resulted solid was dried under reduced pressure to give compound (105) (644 mg).

$^1$H-NMR (CDCl$_3$) δ: 4.08 (3H, s), 6.81 (1H, d, J=2.5 Hz), 8.65 (1H, s), 9.14 (1H, s), 9.45 (1H, s).

The 2$^{nd}$ step: Compound (105) (640 mg) was added to a mixed solvent of water-methanol (6 ml, 1:1), lithium hydroxide (84 mg) was added and the mixture was stirred at room temperature for 4 hours. The reaction solution was acidified by the addition of 2N hydrochloric acid, the insoluble materials were filtered off and washed with diisopropylether.

The resulted solid was dried under reduced pressure to give compound (106) (343 mg).

$^1$H-NMR (DMSO-d$_6$) δ: 7.20 (1H, d, 2.5 Hz), 8.93 (1H, s), 9.12 (1H, s), 9.33 (1H, s).

Reference Example 13

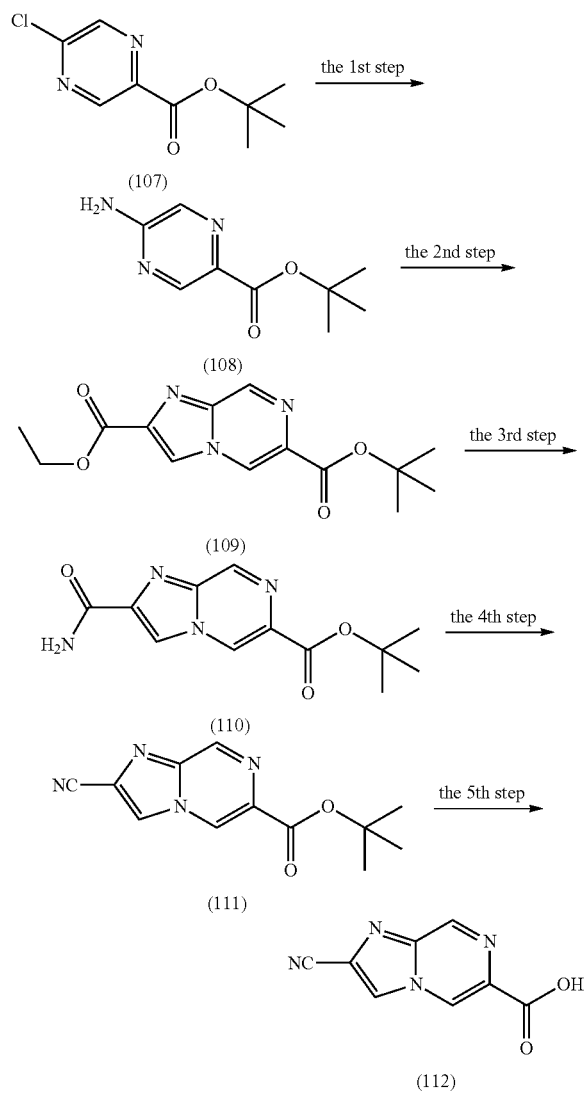

The 1$^{st}$ step: A mixture of compound (107) (1000 mg), dioxane (2 ml), and 28% ammonia water (2 ml) was stirred at 50° C. for 19 hours. The reaction solution was concentrated under reduced pressure. Water was added to the residue, extracted with ethyl acetate and dried over anhydrous magnesium sulfate. The solvent was evaporated under reduced pressure and the residue was purified with a silicagel column chromatography to give a compound (108) (476 mg).

$^1$H-NMR (CDCl$_3$) δ: 1.63 (9H, s), 5.04 (2H, br s), 8.03 (1H, s), 8.69 (1H, s).

The 2$^{nd}$ step: 3-Bromo-2-oxopropanoic acid ethyl ester (1582 mg) was added to compound (108) (475 mg) in dimethoxyethane (4 ml) and the mixture was stirred at 75° C. for 2.5 hours. The reaction solution was diluted with diisopropylether, the insoluble materials were filtered, washed with diisopropylether and hexane, and dried under reduced pressure. The residue was stirred in tert-butyl alcohol (7.5 ml) at 95° C. for 2 hours. The solvent was evaporated under reduced pressure and the residue was purified with a silicagel column chromatography to give compound (109) (709 mg).

$^1$H-NMR (CDCl$_3$) δ: 1.46 (3H, t, J=7.1 Hz), 1.66 (9H, s), 4.50 (2H, q, J=7.1 Hz), 8.35 (1H, s), 8.89 (1H, s), 9.24 (1H, s).

The 3$^{rd}$ step: A mixture of compound (09) (270 mg), dioxane (3 ml) and 28% ammonia water (2.5 ml) was stirred in a pressure bottle at 50° C. for 6 hours. The reaction solution was concentrated under reduced pressure to give a crude product of compound (110) (249 mg).

$^1$H-NMR of the crude product (CDCl$_3$) δ: 1.67 (9H, s), 5.79 (1H, br s), 8.35 (1H, s), 8.90 (1H, s), 9.15 (1H, s).

The 4$^{th}$ step: 2,2,2-Trichloroacetyl chloride (253 mg) was added at 0° C. to a mixture of compound (10) (146 mg), triethylamine (282 mg) and dimethylaminopyridine (6.8 mg) in tetrahydrofuran (9 ml), and the mixture was stirred at room temperature for 2 hours. The reaction solution was diluted with ethyl acetate and the reaction was quenched by the addition of a saturated aqueous solution of sodium bicarbonate. It was extracted with ethyl acetate, dried over anhydrous magnesium sulfate and the solvent was evaporated under reduced pressure to give compound (111) (99 mg) as a crude product.

The 5$^{th}$ step: Compound (111) (95 mg) was dissolved in chloroform (3 ml), trifluoroacetic acid (1330 mg) was added and the mixture was stirred at room temperature for 4 hours. The reaction solution was concentrated under reduced pressure to give a crude product. The residue was suspended with ethyl acetate and diisopropylether and the insoluble materials were filtered and washed with diisopropylether. The residue was dried under reduced pressure to give a composition including compound (112).

Reference Example 14

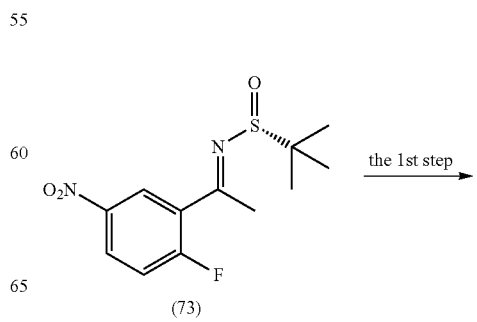

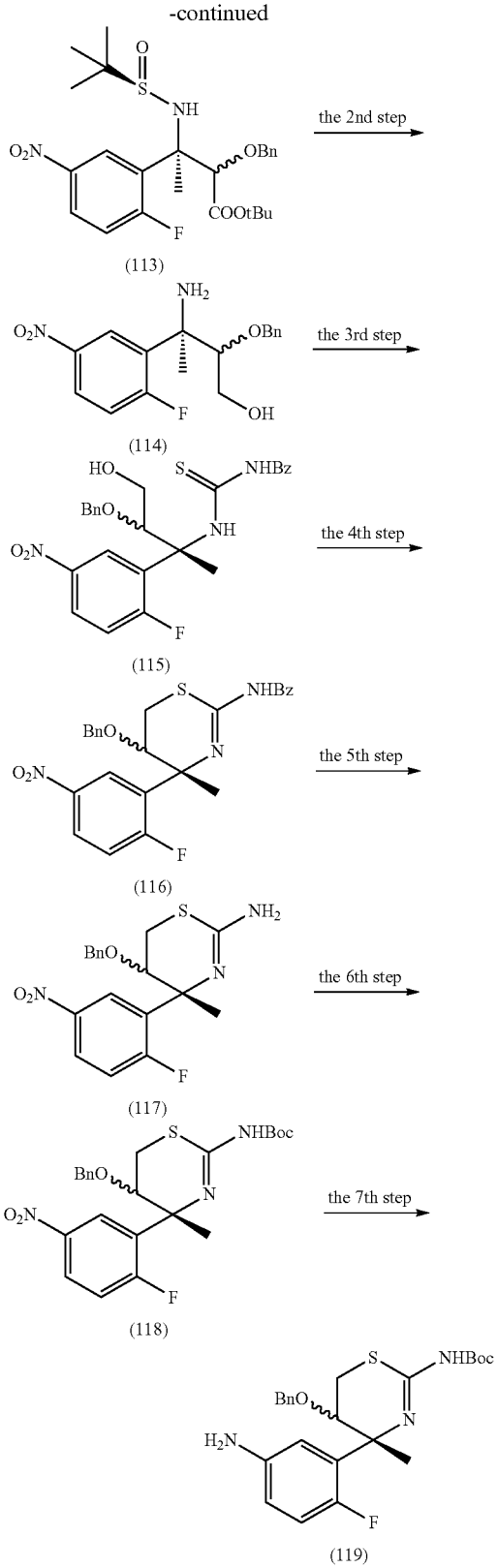

in a dry ice/acetone bath for 10 minutes, tert-butyl α-benzyloxyacetate (5.21 g) dissolved in tetrahydrofuran (25 ml) was added dropwise for 30 minutes. After stirring for 40 minutes, chlorotitaniumtriisopropoxide (6.60 g) dissolved in tetrahydrofuran (50 ml) was added dropwise. After stirring for 30 minutes, compound (73) (2.68 g) dissolved in tetrahydrofuran (50 ml) was added dropwise for 10 minutes and stirred for 90 minutes. A suspension of ammonium chloride (7.52 g) in tetrahydrofuran-water (1:1, 40 ml) was stirred at room temperature, and the reaction mixture was added thereto at once and the precipitated insoluble materials were filtered. The filtrate was extracted with ethyl acetate, the organic layer was dried over anhydrous sodium sulfate. The solvent was evaporated under reduced pressure and the residue was purified with a silicagel column chromatography to give compound (4.49 g).

$^1$H-NMR (CDCl$_3$) δ: 1.14 (3.6H, s), 1.22 (3.6H, s), 1.27 (5.4H, s), 1.39 (5.4H, s), 1.96 (1.2H, s), 1.99 (1.8H, s), 4.31 (0.4H, s), 4.34 (0.6H, d, J=11.6 Hz), 4.41 (0.4H, d, J=11.6 Hz), 4.45 (0.6H, s), 4.56 (0.4H, s), 4.68 (0.6H, d, J=11.6 Hz), 4.81 (0.41H, d, J=11.6 Hz), 5.01 (0.6H, s), 7.06-7.38 (6H, m), 8.18 (0.61H, d, J=8.8 Hz), 8.24 (0.4H, d, J=9.1 Hz), 8.42-8.47 (1H, m).

The 2$^{nd}$ step: Compound (113) (4.49 g) was dissolved in trifluoroacetic acid (44 ml), stirred at room temperature for an hour and the solvent was evaporated under reduced pressure. The resulted residue was dissolved in 10% hydrochloric acid-methanol (44 ml), stirred at room temperature overnight and the reaction solution was concentrated under reduced pressure. The residue was dissolved in tetrahydrofuran (22 ml) and a solution of 1M-borane-tetrahydrofuran complex in tetrahydrofuran (44.1 ml) was added dropwise for 15 minutes under ice cooling, and the mixture was stirred at room temperature for 2.5 hours. Water (50 ml) was added therein with stirring under ice cooling, stirred for 15 minutes and ethyl acetate (50 ml) and potassium carbonate (16 g) were added. It was extracted with ethyl acetate and the organic layer was dried over anhydrous sodium sulfate. The solvent was evaporated under reduced pressure and the obtained compound (114) (3.27 g) was used in the next step without purification.

The 3$^{rd}$ step: Benzoyl isothiocyanate (1.41 ml) was added to compound (114) (3.27 g) in methylenechloride (16.5 ml), stirred at room temperature for an hour and the solvent was evaporated under reduced pressure. The residue was purified with a silicagel column chromatography to give compound (115) (3.14 g).

$^1$H-NMR (CDCl$_3$) δ: 2.14 (1.35H, s), 2.21 (1.65H, s), 3.73-4.07 (3H, m), 4.43 (0.55H, d, J=11.5 Hz), 4.63 (0.55H, d, J=11.5 Hz), 4.74 (0.45H, d, J=11.5 Hz), 4.78 (0.45H, d, J=11.5 Hz), 7.20-7.38 (4H, 7.43-7.51 (2H, m), 7.56-7.63 (1H, m), 7.75-7.86 (2H, m), 8.08-8.17 (1H, m), 8.24-8.34 (1H, m), 8.91-9.01 (1H, m), 11.81 (0.55H, s), 11.90 (0.45H, s).

The 4th step: α-Chlorotetramethylenamine (1.67 ml) was added to compound (115) (3.14 g) methylenechloride (15.5 ml), stirred at room temperature for 30 minutes and pH was adjusted to over 11 by the addition of water (15 ml) and potassium carbonate. It was extracted with chloroform and the organic layer was dried over anhydrous sodium sulfate. The solvent was evaporated under reduced pressure and the residue was purified with a silicagel column chromatography to give compound (116) (2.66 g).

$^1$H-NMR (CDCl$_3$) δ: 1.58 (3bH, s), 1.81 (3aH, s), 2.76 (bH, dd, J=13.4, 1.8 Hz), 3.09 (bH, dd, J=13.4, 6.1 Hz), 3.16 (aH, dd, J=13.8, 3.9 Hz), 3.35 (aH, dd, J=13.8, 1.8 Hz), 4.21-4.25 (aH, m), 4.28 (aH, d, J=12.4 Hz), 4.33-4.38 (bH, m), 4.49-4.56 (a+bH, m), 4.73 (bH, d, J=11.9 Hz), 6.83-7.60 (10H, m), 7.91-8.23 (3H, m), 8.25-8.30 m), 8.74 (aH, m).

The 1 step: A 2.6M n-butyl lithium/hexane solution (9.38 ml) was added dropwise for 10 minutes to diisopropylamine (2.75 g) dissolved in tetrahydrofuran (25 ml) under stirring in a dry ice/acetone bath. After stirring in a ice bath for 10 minutes and The 5th step: Hydrazine monohydrate (0.73 ml) was added to compound (116) (1.44 g) in ethanol (7.2 ml) and stirred at room temperature for 2 hours. Water was added, extracted with ethyl acetate and the organic layer was dried over anhydrous sodium sulfate. The solvent was evaporated under reduced pressure and the obtained compound (117) (1.14 g) was used in the next step without purification.

The 6th step: A solution of di-tert-butyl dicarbonate (1.65 g) in methylenechloride (5.5 ml) and 4-dimethylaminopyridine (37 mg) were added to compound (117) (1.14 g) in methylenechloride (5.5 ml) and stirred at room temperature for an hour. The solvent was evaporated under reduced pressure and the residue was purified with a silicagel column chromatography to give compound (118) (1.52 g).

$^1$H-NMR (CDCl$_3$) δ: 1.47 (8.1H, s), 1.51 (9.9H, s), 1.53 (1.35H, s), 1.75 (1.65H, s), 3.01-3.49 (2H, m), 3.81-3.86 (0.55H, m), 4.07-4.09 (0.45H, m), 4.17 (0.45H, d, J=12.1 Hz), 4.25 (0.55H, d, J=11.6 Hz), 4.41 (0.45H, d, J=12.1 Hz), 4.49 (0.55H, d, J=11.6 Hz), 6.73-6.78 (1H, m), 6.94-7.23 (5H, m), 8.11-8.18 (1H, m), 8.22-8.27 (0.55H, m), 8.51-8.55 (0.45H, m).

The 7th step: 20 w/w % Palladium hydroxide supported by carbon (40 mg) was added to a solution of compound (118) (211.3 mg) in ethanol (2 ml), stirred in a hydrogen atmosphere of 1 atom at room temperature for 22 hours and filtered through a Celite pad. The filtrate was concentrated under reduced pressure and the residue was purified with a silicagel column chromatography to give compound (119) (149.1 mg).

$^1$H-NMR (CDCl$_3$) δ: 1.46 (8.1H, s), 1.51 (9.9H, s), 1.54 (1.35H, s), 1.74 (1.65H, s), 2.91 (0.55H, d, J=12.9 Hz), 3.02 (0.55H, dd, J=12.9, 6.3 Hz), 3.15 (0.45H, dd, J=13.3, 3.0 Hz), 3.37-3.73 (2H, hr), 3.43 (0.45H, d, J=13.3 Hz), 4.13-4.18 (1H, m), 4.22 (0.45H, d, J=11.9 Hz), 4.34 (0.45H, d, J=11.9 Hz), 4.49 (0.55H, d, J=11.6 Hz), 4.59 (0.55H, d, J=11.6 Hz), 6.45-6.61 (1H, m), 6.71-7.39 (7H, m).

Example 1

Preparation of Compound 46

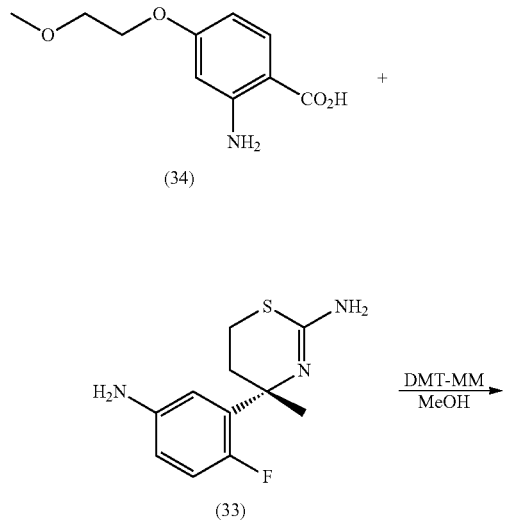

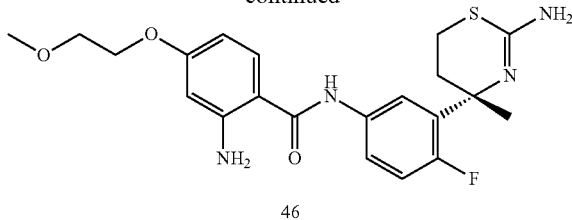

Compound (34) (125 mg) and DMT-MM (162 mg) were suspended in methanol (1.2 ml), stirred at room temperature for 30 minutes and compound (33) (117 mg) was added therein. After stirring for 5 hours, the product was isolated by a silicagel thin-layer chromatography to give the objective compound (46) (13.5 mg).

$^1$H-NMR (DMSO-d$_6$) δ: 1.47 (3H, s), 1.81 (1H, 11.6 Hz), 2.12 (1H, bs), 2.54-2.59 (1H, m), 2.97 (1H, bs), 3.28 (2H, d, 6.4 Hz), 3.52 (2H, d, 6.5 Hz), 3.88 (3H, s), 5.69 (2H, s), 7.09 (1H, dd, J=11.8, 6.8 Hz), 7.50 (1H, s), 7.60 (1H, d, 7.8 Hz), 7.67 (1H, s), 10.06 (1H, s).

Example 2

Preparation of Compound 86

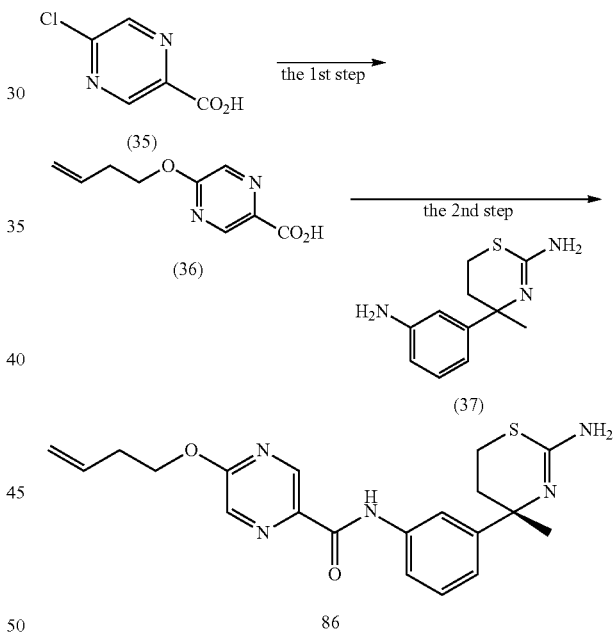

The 1st step: Sodium hydride (302 mg) is added to DMF (3.0 ml) and 3-butene alcohol (3.0 ml) under ice cooling in a nitrogen atmosphere. After stirring at room temperature for 1.0 hour, compound (35) (300 mg) was added and stirred under heating at 65° C. After 7 hours, the reaction solution was neutralized by the addition of 2M hydrochloric acid and concentrated under reduced pressure. Water was added to the resulted residue and filtered to give compound (36) (87 mg, 23.7%).

The 2$^{nd}$ step: Compound (36) (65.8 mg) and compound (37) (50 mg) were dissolved in methanol (2.0 ml), DMT-MM (93.7 mg) was added and the mixture was stirred at room temperature. After 6 hours, the solvent was evaporated under reduced pressure and the residue was purified with a column chromatography using chloroform/methanol to give compound (86) (40 mg, 44.5%).

$^1$H-NMR (DMSO-d$_6$) δ: 1.65 (3H, s), 2.03-2.09 (1H, m), 2.34-2.38 (1H, m), 2.51-2.61 (2H, m), 3.10-3.13 (1H, m), 3.57 (2H, t, J=4.4 Hz), 4.45 (2H, t, J=6.4 Hz), 5.13 (2H, dd, J=29.1, 13.9 Hz), 5.83-5.92 (1H, m), 7.08 (1H, d, J=7.8 Hz), 7.40 (1H, t, J=8.0 Hz), 7.84 (1H, s), 7.91 (1H, d, J=8.1 Hz), 8.36 (1H, s), 8.87 (1H, s), 10.56 (1H, s).

Example 3

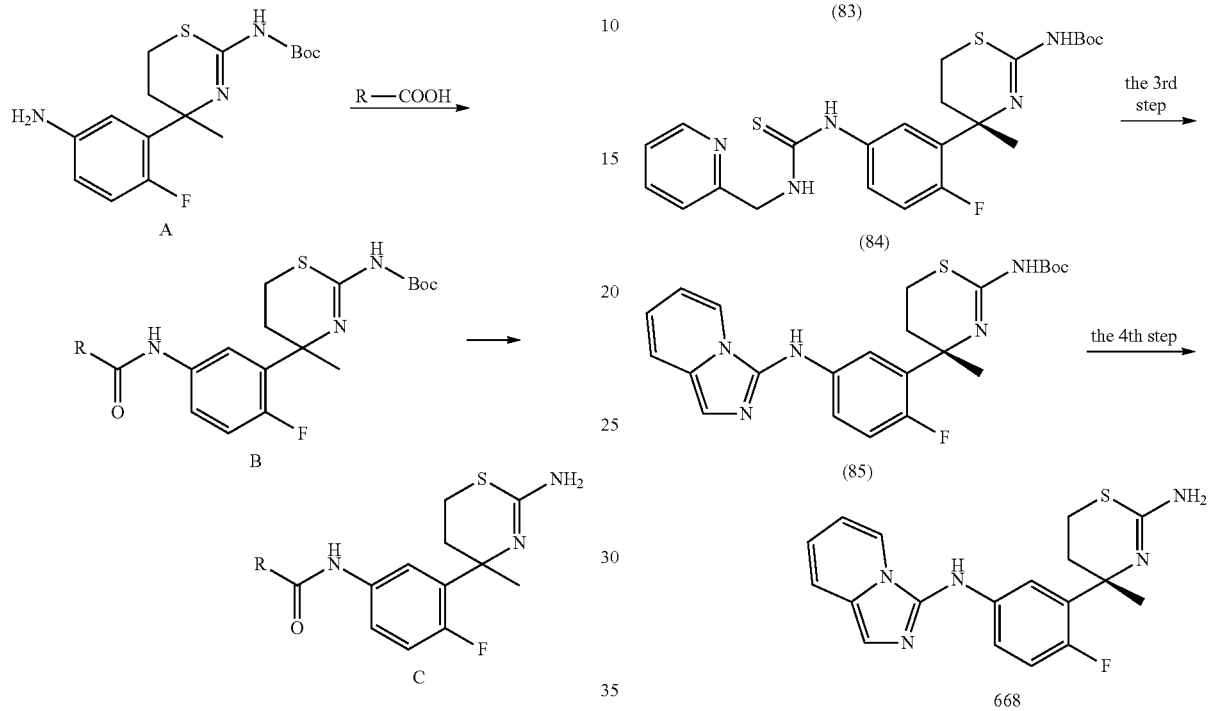

A carboxylic acid, R—COOH corresponding to the objective compound (0.115 mmol) and 4-(4,6-dimethoxy-1,3,5-triazin-2-yl)-4-methylmorpholinium chloride (0.106 mmol) were dissolved in methanol (0.4 ml) and stirred by shaking at room temperature for 1.5 hours. A solution of compound A (0.0884 mmol) in methanol (0.4 ml) was added and the mixture was stirred for 8 hours. The reaction solvent was concentrated, dissolved in ethyl acetate (1 ml) and dimethylsulfoxide (0.5 ml), a 2N aqueous solution of sodium hydroxide (1 ml) was added and stirred by shaking for 2 hours. The organic layer was separated and concentrated to give a crude product of compound B. Trifluoroacetic acid (0.3 ml) was added and stirred by shaking at room temperature for 14 hours, dimethylsulfoxide (0.4 ml) was added and the product was purified with preparative LC/MS to give the objective compound C.

Example 4

Preparation of Compound 668

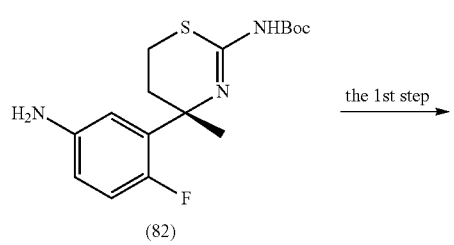

The 1$^{st}$ step: Compound (82) (506 mg) was dissolved in chloroform (30.0 ml), an aqueous solution (10.0 ml) of sodium bicarbonate (851 mg) and thiophosgene (0.111 ml) were added and stirred under ice cooling for 40 minutes. The organic layer was separated from the reaction solution and dried over anhydrous sodium sulfate. The solvent was evaporated under reduced pressure to give compound (83) (457 mg).

$^1$H-NMR (DMSO-d$_6$) δ: 1.44 (9H, s), 1.51 (3H, s), 1.60 (1H, s), 2.17 (1H, 2.68 (1H, s), 3.05 (1H, s), 7.30 (1H, t, J=10.1 Hz), 7.42 (1H, s), 7.58 (1H, s).

The 2$^{nd}$ step: Compound (83) (240 mg) was dissolved in methylenechloride (3.60 pyridine-2-ylmethanamine (74.8 mg) and triethylamine (0.192 ml) were added and the mixture was stirred at room temperature for 40 minutes. The reaction solution was washed with distilled water, the separated organic layer was dried over anhydrous sodium sulfate. The solvent was evaporated under reduced pressure to give compound (84) (210 mg).

$^1$H-NMR (DMSO-d$_6$) δ: 1.46 (9H, s), 1.65 (3H, s), 2.05 (2H, s), 2.57 (1H, s), 2.97 (1H, s), 4.86 (2H, s), 7.29 (3H, m), 7.40 (1H, d, J=7.3 Hz), 7.66 (1H, s), 7.84 (1H, s), 8.27 (1H, s), 8.58 (1H, s), 9.96 (1H, s).

The 3$^{rd}$ step: Compound (84) (95.1 ml) was dissolved in toluene (1.50 ml), dicyclohexylcarbodiimide (40.1 mg) was added and the mixture was stirred under irradiation of microwave at 100° C. for 20 minutes. The reaction solution was concentrated under reduced pressure and the residue was purified with a chromatography to give compound (85) (38.0 mg).

$^1$H-NMR (DMSO-$d_6$) δ: 1.40 (9H, s), 1.61 (3H, s), 1.94 (2H, s), 2.57 (1H, s), 2.88 (1H, s), 6.55 (1H, d, J=6.3 Hz), 6.59 (1H, d, J=8.6 Hz), 7.07 (1H, d, 8.6 Hz), 7.13 (2H, s), 7.29 (1H, s), 7.41 (1H, s, J=9.3 Hz), 7.96 (1H, d, J=6.8 Hz), 8.85 (1H, s).

The 4$^{th}$ step: Compound (85) (38.0 mg) was dissolved in chloroform (0.50 ml), trifluoroacetic acid (1.00 ml) was added and stirred at room temperature for 2 hours. The reaction solution was extracted with a mixture of chloroform/methanol and washed with an aqueous solution of potassium carbonate and distilled water. The separated organic layer was dried over anhydrous sodium sulfate and the solvent was evaporated under reduced pressure. Diisopropylether was added to the residue and the precipitated powder was filtered to give compound (668) (9.39 mg).

$^1$H-NMR (DMSO-$d_6$) δ: 1.58 (3H, s), 1.90 (1H, s), 2.44 (1H, s), 2.62 (1H, t, J=9.7 Hz), 3.06 (1H, s), 6.57 (2H, td, J-15.0, 6.3 Hz), 7.05 (1H, dd, J=12.1, 10.6 Hz), 7.15 (1H, s), 7.24 (1H, d, J=5.3 Hz), 7.31 (1H, dd, J=7.7, 3.7 Hz), 7.42 (1H, d, J-8.8 Hz), 7.99 (1H, d, J=6.8 Hz), 8.85 (1H, s).

Example 5

Preparation of Compound 674

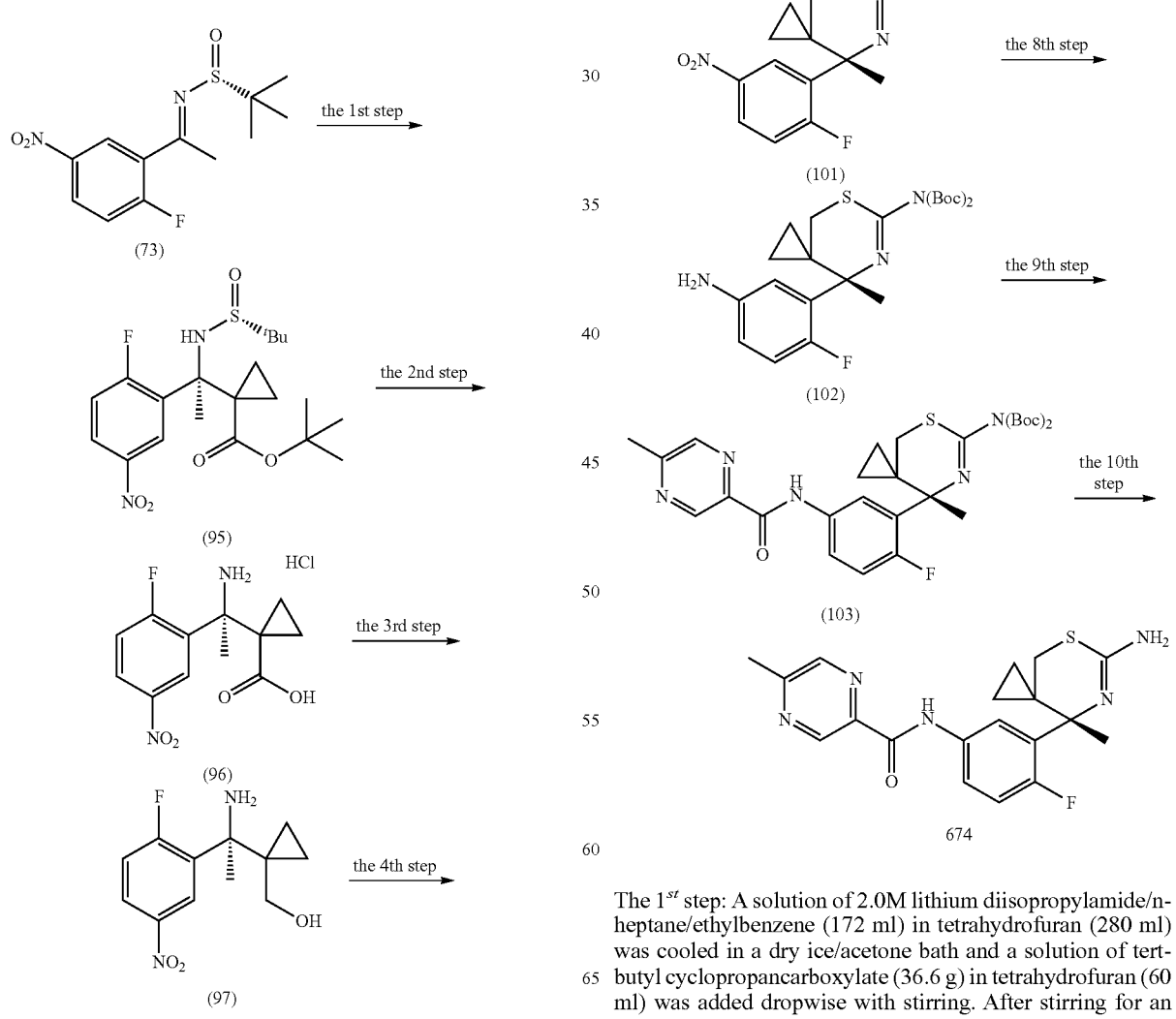

The 1$^{st}$ step: A solution of 2.0M lithium diisopropylamide/n-heptane/ethylbenzene (172 ml) in tetrahydrofuran (280 ml) was cooled in a dry ice/acetone bath and a solution of tert-butyl cyclopropancarboxylate (36.6 g) in tetrahydrofuran (60 ml) was added dropwise with stirring. After stirring for an hour, a solution of chlorotitanium tirisopropoxide (92 g) in tetrahydrofuran (190 ml) was added dropwise, stirred for 10 minutes and a solution of compound (73) (24.56 g) in tetrahydrofuran (120 ml) was added dropwise. After reaction for 2 hours, the reaction solution was added portionwise to an aqueous solution of ammonium chloride with stirring under ice cooling and the precipitated insoluble materials were filtered. It was extracted with ethyl acetate, the organic layer was dried over anhydrous sodium sulfate.

The solvent was evaporated under reduced pressure and the residue was purified with a silicagel column chromatography to give compound (95) (15.49 g).

$^1$H-NMR (CDCl$_3$) δ: 1.16-1.19 (2H, m), 1.24 (9H, s), 1.28-1.32 (2H, m), 1.36 (9H, s), 1.46 (3H, s), 1.50-1.55 (2H, m), 1.64-1.72 (2H, m), 5.45 (1H, s), 7.11-7.16 (1H, m), 8.11-8.16 (1H, m), 8.67 (1H, dd, J=6.9, 2.9 Hz).

The 2$^{nd}$ step: 2.0 M Hydrochloric acid/ethyl acetate (30 ml) was added to compound (95) (2.48 g) and stirred at 65° C. for 5.5 hours. Diisopropylether was added and the precipitated solid was filtered to give a crude product of compound (96) (1.66 g).

The 3$^{rd}$ step: A solution of compound (96) (1.66 g) in tetrahydrofuran (8.3 ml) was stirred under ice cooling and a solution of 1M borane/tetrahydrofuran (21.8 ml) was added and the mixture was stirred at room temperature for 2 hours and 45 minutes. Ice and sodium bicarbonate were added, extracted with ethyl acetate and the organic layer was dried over anhydrous magnesium sulfate. The solvent was evaporated under reduced pressure to give a crude product of compound (97) (1.36 g).

The 4th step: A solution of compound (97) (1.36 g) in acetone (20 ml) was stirred under ice cooling, a solution of benzoyl isothiocyanate (0.92 g) in acetone (6 ml) was added and the mixture was stirred for 40 minutes. After the addition of water, the reaction solution was extracted with ethyl acetate and the organic layer was dried over anhydrous magnesium sulfate. The solvent was evaporated under reduced pressure and the residue was purified with a silicagel column chromatography to give compound (98) (1.68 g).

$^1$H-NMR (CDCl$_3$) δ: 0.67-0.73 (3H, m), 0.84-0.88 (1H, m), 1.73 (1H, t, J=5.6 Hz), 2.29 (3H, d, J=2.0 Hz), 3.11 (1H, dd, J=12.2, 5.1 Hz), 3.82 (1H, J=12.2, 5.1 Hz), 7.14 (1H, dd, J=11.0, 9.0 Hz), 7.52 (2H, t, 7.6 Hz), 7.63 (1H, t, J=7.6 Hz), 7.87 (2H, d, J=7.6 Hz), 8.17 (1H, ddd, J=9.0, 3.9, 2.9 Hz), 8.27 (1H, dd, J=6.8, 2.9 Hz), 8.82 (1H, s), 11.75 (1H, s).

The 5$^{th}$ step: Compound (98) (1.68 g) was dissolved in dichloromethane (17 ml), stirred under ice cooling and 1-chloro-N,N,2-trimethyl-1-propenylamine (0.60 g) was added.

After stirring at room temperature for an hour, water was added, the reaction solution was extracted with ethyl acetate and the organic layer was dried over anhydrous magnesium sulfate. The solvent was evaporated under reduced pressure and the residue was purified with a silicagel column chromatography to give compound (99) (1.34 g).

$^1$H-NMR (CDCl$_3$) δ: 0.77-0.82 (1H, m), 0.95-1.07 (2H, m), 1.38-1.40 (1H, m), 1.52 (3H, d, J=1.1 Hz), 2.25 (1H, d, J=13.0 Hz), 3.05 (1H, d, J=13.0 Hz), 7.27 (1H, dd, J=10.8, 8.9 Hz), 7.40-7.54 (3H, m), 8.18-8.27 (3H, m), 8.36 (H, dd, J=6.7, 2.7 Hz).

The 6$^{th}$ step: Hydrazine monohydrate (038 g) was added to a solution of compound (99) (1.00 g) in ethanol (10 ml) under stifling at room temperature. After stirring for 4 hours, it was stirred under heating at 50° C. for 2 hours. The reaction solution was concentrated under reduced pressure, water was added, and the mixture was extracted with ethyl acetate and the organic layer was dried over anhydrous magnesium sulfate. The solvent was evaporated under reduced pressure to give compound (100) (0.69 g) as a crude product.

The 7$^{th}$ step: A mixture of compound (100) (0.91 g), di-tert-butyldicarbonate (1.55 g), 4-dimethylaminopyridine (0.04 g) and tetrahydrofuran (9.1 ml) was stirred at room temperature for 1 hour and 15 minutes. Water was added, the reaction solution was extracted with ethyl acetate and the organic layer was dried over anhydrous magnesium sulfate. The solvent was evaporated under reduced pressure and the residue was purified with a silicagel column chromatography to give compound (101) (1.28 g).

$^1$H-NMR (CDCl$_3$) δ: 0.37-0.41 (1H, m), 0.50-0.54 (1H, m), 0.68 (2H, t, J=7.7 Hz), 1.56 (18H, s), 1.78 (3H, d, J=4.0 Hz), 2.35 (1H, d, J=12.7 Hz), 3.57 (1H, dd, J=12.7, 1.8 Hz), 7.12-7.21 (1H, m), 8.15 (1H, ddd, J=8.9, 3.9, 3.0 Hz), 8.39 (1H, dd, J=6.7, 3.0 Hz).

The 8$^{th}$ step: Compound (101) (1.28 g) was dissolved in ethyl acetate (13 ml), 10% Pd—C (0.64 g) was added and the mixture was stirred at room temperature for 13 hours and 30 minutes. The insoluble materials were filtered the filtrate was concentrated under reduced pressure and the residue was purified with a silicagel column chromatography to give compound (102) (1.07 g).

$^1$H-NMR (CDCl$_3$) δ: 0.51-0.58 (2H, m), 0.81-0.86 (2H, m), 1.54 (18H, s), 1.64 (3H, d, J=3.0 Hz), 2.60 (1H, d, J=12.4 Hz), 3.08 (1H, d, J=12.4 Hz), 3.50 (2H, s), 6.51 (1H, ddd, J=8.6, 3.7, 3.0 Hz), 6.78-6.84 (2H, m), 7.18-7.21 (1H, m).

The 9$^{th}$ step: A solution of 5-ethylpyrazine-2-carboxylic acid (59 mg) in N,N-dimethylformamide (1.5 ml) was stirred under ice cooling, and 1-[bis(dimethylamino)methylene]-1H-1,2,3-triazolo(4,5-b)pyridinium-3-oxide hexafluorophosphate (196 mg) and triethylamine (61 mg) were added and the mixture vas stirred for 10 minutes. A solution of compound (102) (200 mg) in N,N-dimethylformamide (3 ml) was added and the mixture was stirred at room temperature for 4 hours. Water was added, extracted with ethyl acetate and the organic layer was dried over anhydrous sodium sulfate. The solvent was evaporated under reduced pressure and the residue was purified with a silicagel column chromatography to give compound (103) (170 mg).

The 10$^{th}$ step: Compound (103) (170 mg) was dissolved in dichloromethane (0.75 ml), stirred under ice cooling, trifluoroacetic acid (0.75 ml) was added and the mixture was stirred at room temperature for 3 hours. After concentration of the reaction solution under reduced pressure, ice water was added, potassium carbonate was added with stirring under ice cooling and extracted with ethyl acetate. The organic layer was dried over anhydrous sodium sulfate, the solvent was evaporated under reduced pressure and ether/hexane was added to the residue. The precipitated solid was filtered to give compound (674) (104 mg)

$^1$H-NMR (CDCl$_3$) δ: 0.53-0.59 (1H, m), 0.65-0.72 (1H, m), 0.85-0.91 (1H, m), 1.14-1.17 (1H, m), 1.47 (3H, d, J=2.0 Hz), 2.46 (1H, d, J=12.1 Hz), 2.69 (3H, s), 2.89 (1H, dd, J=12.1, 1.3 Hz), 7.06 (1H, dd, J=11.5, 8.8 Hz), 7.45 (1H, dd, J=6.8, 2.8 Hz), 7.94 (1H, ddd, J=8.8, 4.0, 2.8 Hz), 8.44 (1H, d, J=1.3 Hz), 9.36 (1H, d, J=1.3 Hz), 9.60 (1H, s).

Example 6

Reparation of Compound 687

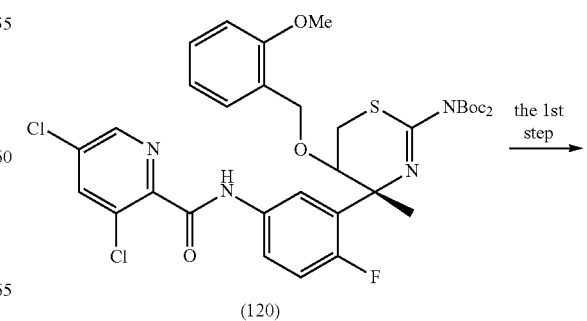

(120)

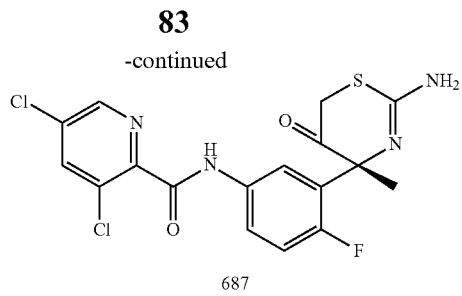

687

The 1st step: Dichloromethane-trifluoroacetic acid (1:1, 1 ml) was added to compound (120) (49 mg) and stirred at room temperature for an hour. The reaction solution was concentrated under reduced pressure, dimethyl sulfoxide-acetic anhydride (1:1, 1 ml) was added to the residue, stirred at 50° C. for 1.5 hours and the solvent was evaporated under reduced pressure. Hydrochloric acid (1M, 0.5 ml) was added to the residue and stirred at 50° C. for 1 hours. A saturated aqueous solution of sodium bicarbonate was added, extracted with chloroform, and the organic layer was dried over anhydrous sodium sulfate. The solvent was evaporated under reduced pressure and the residue was purified with a silicagel column chromatography. A mixture of chloroform-diethyl ether/ethyl acetate was added and the precipitated slid was filtered to give compound 687 (17 mg).

$^1$H-NMR (CDCl$_3$) δ: 1.78 (3H, s), 3.52 (1H, d, J=15.1 Hz), 3.73 (1H, d, 15.1 Hz), 7.06 (1H, dd, J=10.4, 8.6 Hz), 7.73 (1H, dd, J=6.6, 1.3 Hz), 7.82-7.86 (1H, m), 7.90 (1H, d, J=1.3 Hz), 8.48 (1H, d, J=1.3 Hz), 9.79 (1H, s).

Example 7

Preparation of Compound 680, 681 and 682

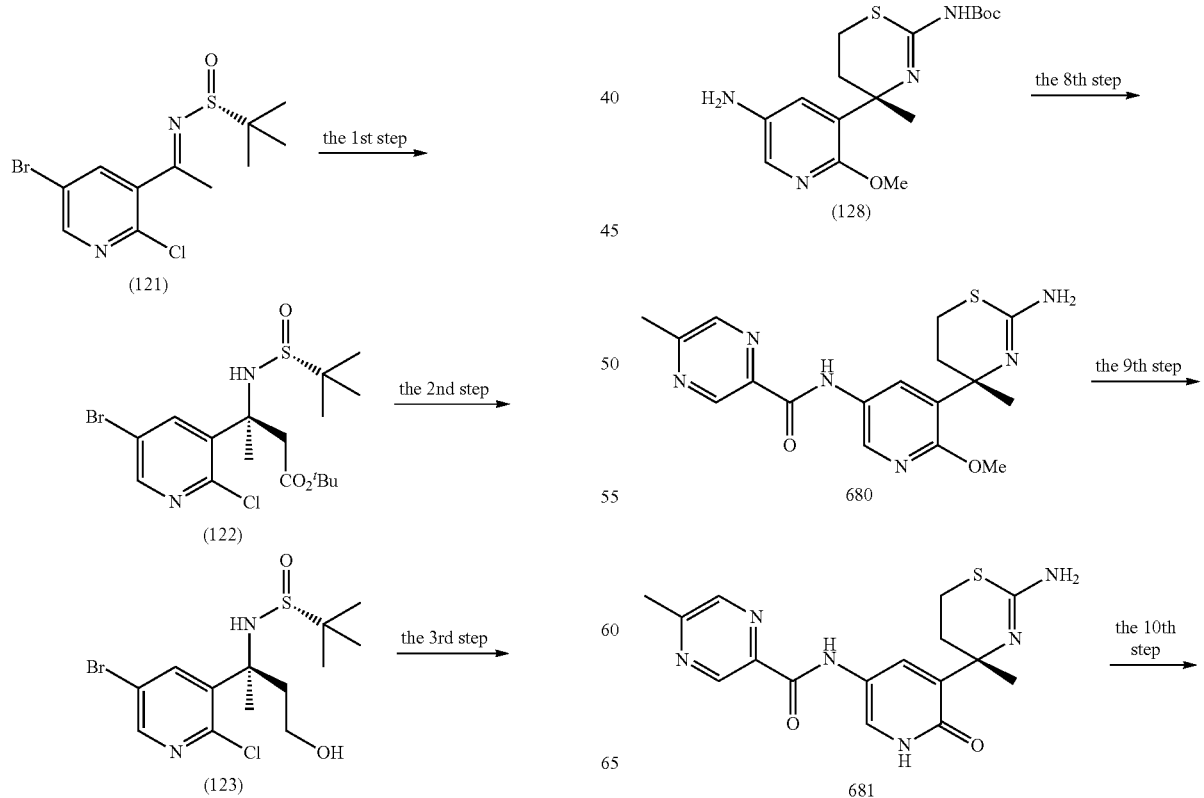

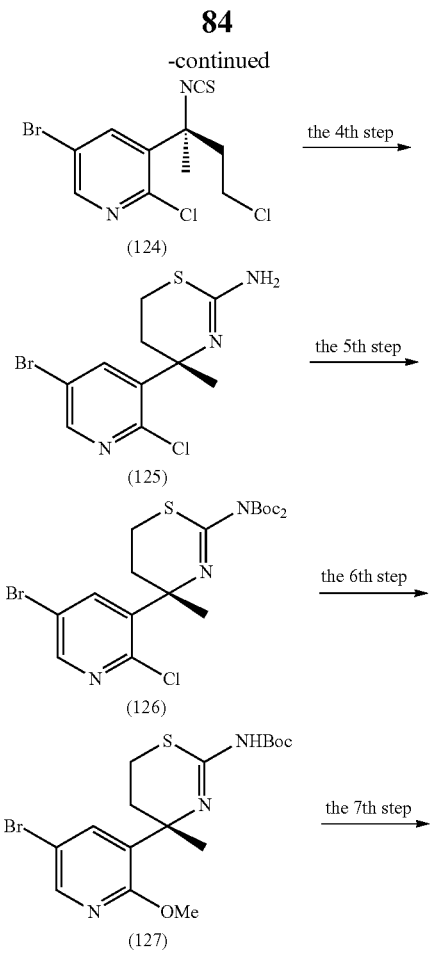

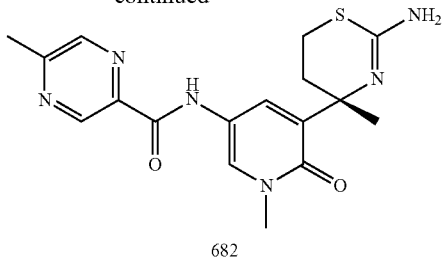

682

The 1st step: In a nitrogen atmosphere, diisopropylamine (20.3 ml) and tetrahydrofuran (83.5 ml) were added and cooled to −60° C. in an acetone/dry ice bath and a solution of 1.63M n-butyl lithium/n-hexane was added dropwise while stirring was continued until the temperature rose to 0° C. After stirring for 30 minutes, the reaction solution was cooled to −60° C. in an acetone/dry ice bath and a solution of tert-butyl acetate (16.8 ml) in tetrahydrofuran (22.2 ml) was added dropwise with stirring. After stirring for 45 minutes, a solution of compound (121) (11.1 g) in tetrahydrofuran (22.2 ml) was added dropwise. After 2.5 hours, a saturated aqueous solution of ammonium chloride (100 ml) was stirred under ice cooling and the reaction solution was poured portionwise therein, extracted with ethyl acetate, and the organic layer was dried over anhydrous magnesium sulfate. The solvent was evaporated under reduced pressure and the residue was purified with a silicagel column chromatography to give compound (122) (8.83 g).

$^1$H-NMR (CDCl$_3$) δ: 1.32 (17H, s), 1.93 (3H, s), 3.15 (1H, d, J=16.4 Hz), 3.66 (1H, d, 16.2 Hz), 5.50 (1H, s), 8.12 (1H, s), 8.36 (1H, s).

The 2$^{nd}$ step: Lithium aluminium hydride (0.76 g) and tetrahydrofuran (15 ml) were cooled in an ice-salt bath in a nitrogen atmosphere and a solution of compound (122) (3.03 g) in tetrahydrofuran (10 ml) was added dropwise with stirring. After stirring for 15 minutes, acetone (4 ml) was added, insoluble materials were filtered, extracted with ethyl acetate, and the organic layer was washed with water and dried over anhydrous magnesium sulfate. The solvent was evaporated under reduced pressure to give compound (123) (2.30 g) as a crude product.

MS: 385 m/z [M+H]$^+$

The 3$^{rd}$ step: 10% Hydrochloric acid/methanol solution (30 ml) was added to compound (123) (2.2 g) and stirred at room temperature for 1.5 hours. The solvent was evaporated under reduced pressure, the residue was basified with a 2.0M aqueous solution of potassium carbonate and extracted with ethyl acetate (100 ml). The organic layer was washed with water, dried over anhydrous magnesium sulfate and the solvent was evaporated under reduced pressure. Toluene (30 ml) and water (15 ml) were added to the resulted crude product (2.25 g), cooled in a ice bath and potassium carbonate (1.58 g) and thiophosgene (0.656 ml) were added with stirring. After stirring at room temperature for 30 minutes, the reaction solution was extracted with toluene, the organic layer was washed with water and dried over anhydrous magnesium sulfate. The solvent was evaporated under reduced pressure, toluene (30 ml), thionyl chloride (1.25 ml) and N,N-dimethylformamide (0.044 ml) were added to the resulted residue and the mixture was stirred under heating at 80° C. for 1.5 hours. The solvent was evaporated under reduced pressure, ice water was added, extracted with ethyl acetate, and the organic layer was washed with water and dried over anhydrous magnesium sulfate. The solvent was evaporated under reduced pressure and the residue was purified with a silicagel column chromatography to give compound (124) (1.26 g).

$^1$H-NMR (CDCl$_3$) δ: 1.56 (3H, s), 2.54-2.64 (1H, m), 3.07-3.17 (1H, m), 3.29-3.38 (1H, m), 3.50-3.57 (1H, m), 8.13 (1H, d, J=2.4 Hz), 8.44 (1H, d, J=2.4 Hz).

The 4$^{th}$ step: Tetrahydrofuran (12.6 ml) and 28% ammonia water (6.3 ml) were added to compound (124) (1.26 g) and stirred at room temperature for 1.5 hours. The reaction solution was extracted with ethyl acetate, the organic layer was washed with saturated brine and dried over anhydrous sodium sulfate. The solvent was evaporated under reduced pressure to give compound (125) (1.13 g) as a crude product.

$^1$H-NMR (CDCl$_3$) δ: 1.70 (3H, s), 2.15-2.21 (1H, m), 2.52-2.58 (1H, m), 2.70-2.77 (1H, m), 3.05-3.11 (1H, m), 4.44 (2H, br a), 8.12 (1H, a), 8.34 (1H, s).

The 5$^{th}$ step: Tetrahydrofuran (11.3 ml) and di-tert-butyldicarbonate (0.89 ml) were added to compound (125) (1.13 g) and stirred at room temperature for an hour. Di-tert-butyldicarbonate (1.13 ml) and 4-dimethylaminopyridine (0.086 g) were added and further stirred at room temperature for 2 hours. The solvent was evaporated under reduced pressure and the residue was purified with a silicagel column chromatography to give compound (126) (1.59 g).

$^1$H-NMR (CDCl$_3$) δ: 1.53 (18H, s), 1.73 (3H, s), 1.90-1.97 (1H, m), 2.63-2.69 (1H, m), 293-2.99 (1H, m), 3.21-3.28 (1H, m), 8.24 (1H, d, J=2.3 Hz), 8.36 (1H, d, J=2.3 Hz).

The 6$^{th}$ step: N,N-Dimethylformamide (40 ml) was added to compound (126) (2.00 g) in a nitrogen stream, cooled in an ice bath with stiffing and sodium methoxide (2.074 g) was added therein. After stifling at room temperature for 1.5 hours, the reaction solution was warmed up to 60° C. and stirred for 2 hours. It was cooled in a ice bath, neutralized by the addition of 2N hydrochloric acid and extracted with ethyl acetate. The organic layer was washed with 2M aqueous solution of potassium carbonate and brine and dried over anhydrous sodium sulfate. The solvent was evaporated under reduced pressure and the residue was purified with a silicagel column chromatography to give compound (127) (1.69 g).

$^1$H-NMR (CDCl$_3$) δ: 1.52 (9H, s), 1.70 (3H, s), 1.96-2.03 (1H, m), 2.54-2.61 (1H, m), 2.80-2.85 (1H, m), 2.97-3.00 (1H, m), 3.97 (3H, s), 7.62 (1H, 1.5 Hz), 8.15 (1H, d, J=1.5 Hz).

The 7$^{th}$ step: Compound (127) (1.571 g), trisdibenzylideneacetonedipalladium (0, 4-14 g) and butynyl-1-adamantylphosphine (0.324 g) were dissolved in toluene under a nitrogen stream, and a solution of 1.6M lithium hexamethyldisilazide/tetrahydrofuran (5.66 ml) was added at room temperature with stirring. The reaction solution was warmed up to 80° C. and stirred for 3 hours. Then diethyl ether and 1N hydrochloric acid were added with stirring under ice cooling. After stirring for 5 minutes, it was neutralized by the addition of a saturated aqueous solution of sodium carbonate, extracted with ethyl acetate and dried over anhydrous sodium sulfate. The solvent was evaporated under reduced pressure and the residue was purified with a silicagel column chromatography to give compound (128) (1.55 g).

$^1$H-NMR (CDCl$_3$) δ: 1.52 (9H, s), 1.72 (3H, s), 1.86-1.93 (1H, m), 2.02 (2H, s), 2.52-2.59 (1H, m), 2.74-2.79 (1H, m), 3.13-3.18 (1H, m), 3.90 (3H, s), 6.96 (1H, d, J=2.3 Hz), 7.59 (1H, J=1.8 Hz).

The 8$^{th}$ step: Compound (128) (0.20 g), 5-methylpyridine-2-carboxylic acid (0.10 g) and O-(7-azabenzotriazole-yl)-N,N,N',N'-tetramethyluronium hexafluorophosphate (HATU) (0.28 g) were dissolved in N,N-dimethylformamide (2 ml), triethylamine (0.119 ml) was added and the mixture was stirred at room temperature for 1.0 hours. A 2M aqueous solution of potassium carbonate was added, extracted with ethyl acetate, and the organic layer was washed with brine and dried over anhydrous sodium sulfate. The solvent was evaporated under reduced pressure and the resulted residue was dissolved in chloroform (4.0 ml), trifluoroacetic acid (1.0 ml) was added and the mixture was stirred at room temperature for 3 hours. The solvent was evaporated under reduced pressure, the residue was made basic by the addition of a 2.0M aqueous solution of potassium carbonate, extracted with ethyl acetate and the organic layer was washed with water and dried over anhydrous magnesium sulfate. The solvent was evaporated under reduced pressure and the residue was purified with a silicagel column chromatography to give compound (680) (0.096 g).

1H-NMR (DMSO-d6) δ: 1.47 (3H, s), 1.77-1.83 (1H, m), 2.34-2.39 (1H, m), 2.48-2.53 (1H, m), 2.63 (3H, s), 2.89-2.96 (1H, m), 3.90 (3H, s), 5.86 (2H, br s), 8.10 (1H, d, J=2.3 Hz), 8.47 (1H, d, J=2.5 Hz), 8.69 (1H, s), 9.14 (1H, s), 10.69 (1H, s).

The 9$^{th}$ step: Compound (680) (0.096 g) and sodium iodide (0.193 g) were dissolved in acetonitrile (5.0 ml), trimethylsilylchloride (0.164 ml) was added and the mixture was stirred at room temperature for 2.5 hours. Sodium iodide (0.193 g) and trimethyl silylchloride (0.164 ml) were added and stirring was continued at room temperature for 12 hours. A 2.0M aqueous solution of potassium carbonate, extracted with ethyl acetate and the organic layer was washed with water and dried over anhydrous magnesium sulfate. The solvent was evaporated under reduced pressure to give compound (681) (0.073 g) as a crude product.

$^1$H-NMR (DMSO-d$_6$) δ: 1.52 (3H, s), 1.80-1.85 (1H, m), 2.62 (3H, s), 2.64-2.69 (2H, m), 2.96-3.01 (1H, m), 7.77 (1H, d, J=2.5 Hz), 7.96 (1H, d, J=2.3 Hz), 8.67 (1H, s), 9.10 (1H, s), 10.58 (1H, s).

The 10$^{th}$ step: Compound (681) (0.031 g) was dissolved in tetrahydrofuran (2.0 ml), di-tert-butyldicarbonate (0.030 ml) was added and the mixture was stirred at room temperature for 1.5 hours. Di-tert-butyldicarbonate (0.030 ml) was further added and the stirring was continued at room temperature for 2.0 hours. The reaction solution was concentrated under reduced pressure, the resulted residue was dissolved in N,N-dimethylformamide (0.5 ml) and potassium carbonate (23.9 mg) was added. A solution of methyl iodide (12.2 mg) in N,N-dimethylformamide (0.5 ml) was added with stirring at room temperature. After stirring at room temperature for 3 hours, methyl iodide (11.05 mg) was added and the mixture was stirred at room temperature for 2 hours. Brine was added, extracted with ethyl acetate and the organic layer was washed with water and dried over anhydrous magnesium sulfate. The solvent was evaporated under reduced pressure, the resulted residue was dissolved in chloroform (2.0 ml), trifluoroacetic acid (0.5 ml) was added and the mixture was stirred at room temperature for 3 hours. The reaction solution was concentrated under reduced pressure, the resulted residue was made alkaline by the addition of a 2.0M aqueous solution of potassium carbonate, extracted with ethyl acetate and the organic layer was washed with water and dried over anhydrous magnesium sulfate. The solvent was evaporated under reduced pressure and the residue was purified with a silicagel column chromatography to give compound (682) (4.2 mg).

$^1$H-NMR (DMSO-d$_6$) δ: 1.46 (3H, s), 1.95-2.01 (1H, m), 2.33-2.39 (1H, m), 2.62 (3H, s), 0.64-2.69 (1H, m), 2.74 (3H, s), 2.92-2.98 (1H, m), 7.90 (1H, d, J=2.5 Hz), 7.94-7.95 (1H, m), 8.67 (1H, s), 9.09 (1H, s), 10.57 (1H, s).

The other compounds are prepared in the same manner Chemical structures and physical constants are shown below.

TABLE 1

| Compound No. | Structure |
| --- | --- |
| 1 | 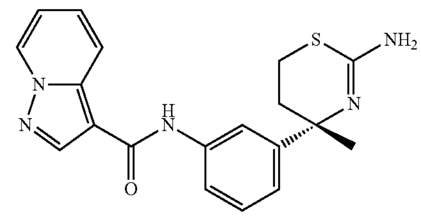 |
| 2 | 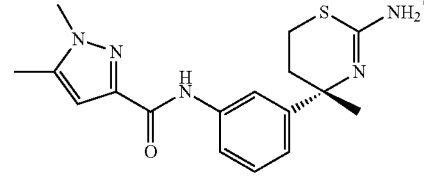 |
| 3 | 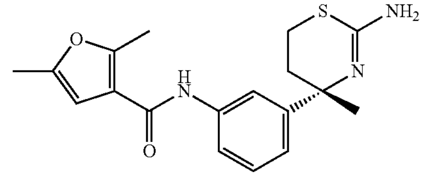 |
| 4 | 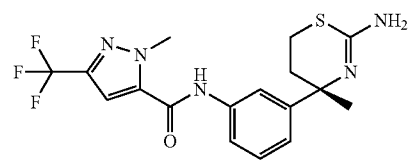 |
| 5 | 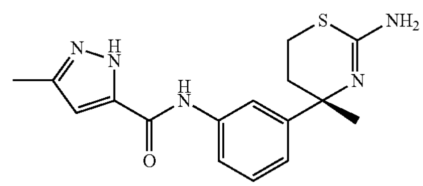 |

TABLE 2

| Compound No. | Structure |
| --- | --- |
| 6 | 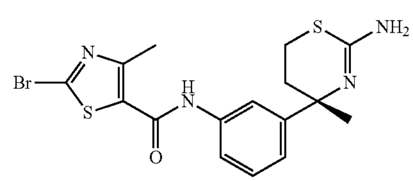 |

TABLE 2-continued
| Compound No. | Structure |
|---|---|
| 7 | 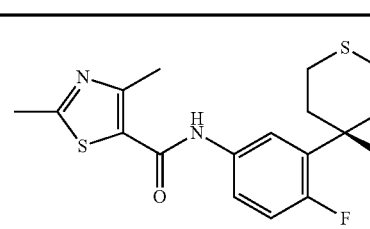 |
| 8 | 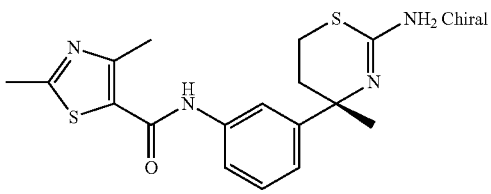 [SMILES: Cc1nc(C)c(C(=O)Nc2cccc([C@]3(C)CCSC(N)=N3)c2)s1] |
| 9 | 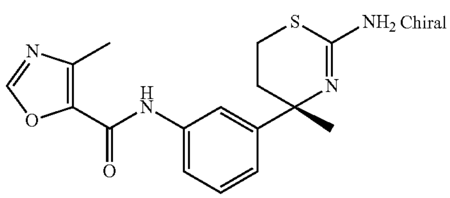 [SMILES: Cc1ncoc1C(=O)Nc1cccc([C@]2(C)CCSC(N)=N2)c1] |
| 10 | 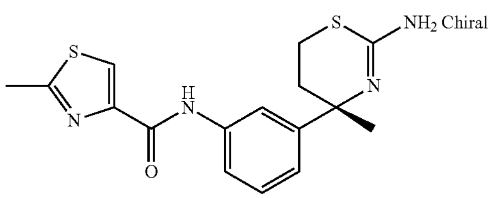 [SMILES: Cc1nc(C(=O)Nc2cccc([C@]3(C)CCSC(N)=N3)c2)cs1] |
TABLE 3
| Compound No. | Structure |
|---|---|
| 11 | 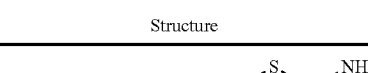 |
TABLE 3-continued
| Compound No. | Structure |
|---|---|
| 12 | 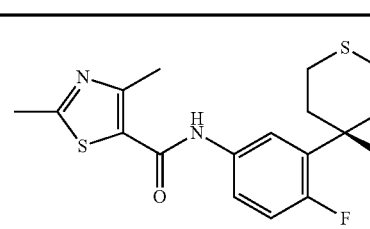 |
| 13 | 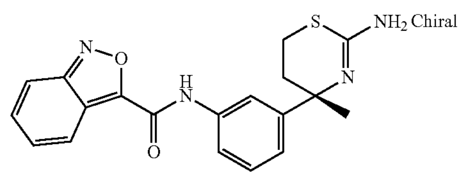 [SMILES: C[C@@]1(c2cccc(NC(=O)c3onc4ccccc34)c2)CCSC(N)=N1] |
| 14 | 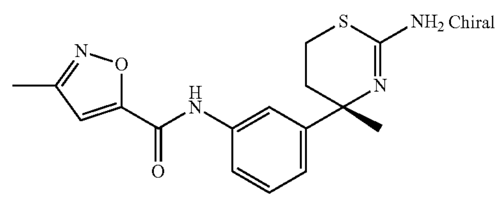 [SMILES: Cc1cc(C(=O)Nc2cccc([C@]3(C)CCSC(N)=N3)c2)on1] |
| 15 | 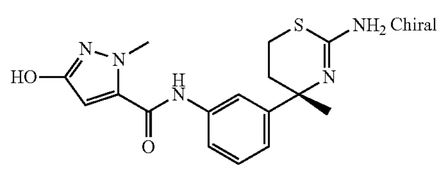 [SMILES: Cn1nc(O)cc1C(=O)Nc1cccc([C@]2(C)CCSC(N)=N2)c1] |
TABLE 4
| Compound No. | Structure |
|---|---|
| 16 | 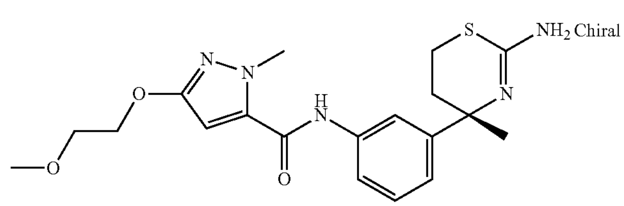 [SMILES: COCCOc1cc(C(=O)Nc2cccc([C@]3(C)CCSC(N)=N3)c2)n(C)n1] |

TABLE 4-continued

| Compound No. | Structure |
|---|---|
| 17 | (structure) |
| 18 | (structure) |
| 19 | (structure) |
| 20 | (structure) |

TABLE 5

| Compound No. | Structure |
|---|---|
| 21 | (structure) |
| 22 | (structure) |
| 23 | (structure) |
| 24 | (structure) |

TABLE 5-continued

| Compound No. | Structure |
|---|---|
| 26 | (structure: 3,5-dichloropyridine-2-carboxamidoxime linked via N-H to phenyl bearing 2-amino-4-methyl-5,6-dihydro-4H-1,3-thiazine) |

TABLE 6

| Compound No. | Structure |
|---|---|
| 27 | (3-fluoropyridine-2-carboxamide linked to phenyl bearing (chiral) 2-amino-4-methyl-5,6-dihydro-4H-1,3-thiazine) |
| 28 | (2-methoxypyrimidine-5-carboxamide linked to phenyl bearing 2-amino-4-methyl-5,6-dihydro-4H-1,3-thiazine) |

TABLE 6-continued

| Compound No. | Structure |
|---|---|
| 29 | (3-amino-6-methoxypyrazine-2-carboxamide linked to phenyl bearing (chiral) 2-amino-4-methyl-5,6-dihydro-4H-1,3-thiazine) |
| 30 | (2-methoxypyrimidine-5-carboxamide linked to 4-fluorophenyl bearing (chiral) 2-amino-4-methyl-5,6-dihydro-4H-1,3-thiazine) |
| 31 | (2-methylpyrimidine-5-carboxamide linked to phenyl bearing (chiral) 2-amino-4-methyl-5,6-dihydro-4H-1,3-thiazine), ClH |

TABLE 7

| Compound No. | Structure |
|---|---|
| 32 | (5-methylpyrazine-2-carboxamide linked to 4-methoxyphenyl bearing (chiral) 2-amino-4-methyl-5,6-dihydro-4H-1,3-thiazine), ClH |
| 33 | (5-methylthiopyridine-2-carboxamide linked to phenyl bearing (chiral) 2-amino-4-methyl-5,6-dihydro-4H-1,3-thiazine), ClH |
| 34 | (5-(but-2-enyloxy)pyridine-2-carboxamide linked to phenyl bearing (chiral) 2-amino-4-methyl-5,6-dihydro-4H-1,3-thiazine) |

TABLE 7-continued
| Compound No. | Structure |
|---|---|
| 35 | 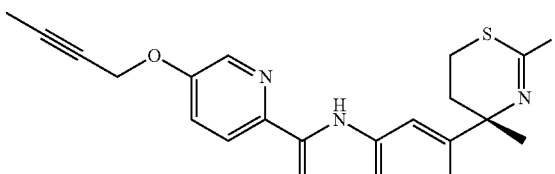 |
| 36 | 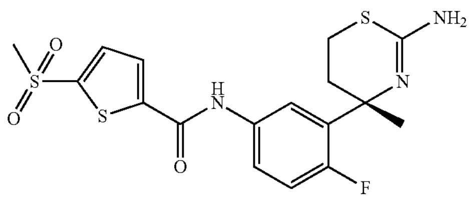 |
TABLE 8
| Compound No. | Structure |
|---|---|
| 37 | 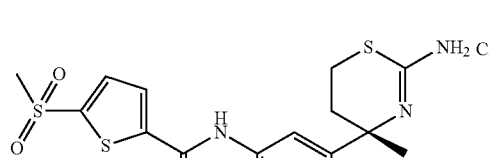 |
| 38 | 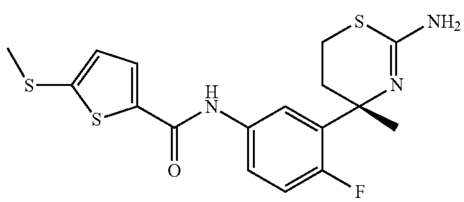 |
| 39 | 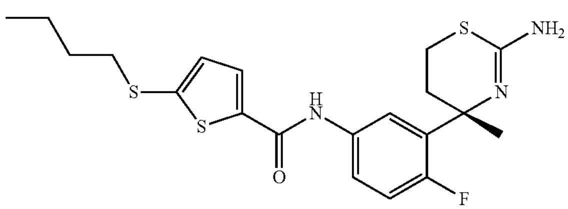 |
| 40 | 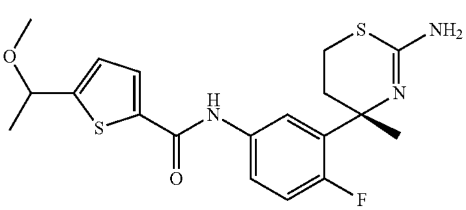 |

TABLE 8-continued

| Compound No. | Structure |
|---|---|
| 41 | (5-bromothiophene-2-carboxamide linked to 3-(2-amino-5,6-dihydro-4H-1,3-thiazin-4-yl)-4-fluorophenyl, 4-methyl, Chiral) |

TABLE 9

| Compound No. | Structure |
|---|---|
| 42 | (4,6-dimethoxypyrimidine-2-carboxamide linked to 3-(2-amino-5,6-dihydro-4H-1,3-thiazin-4-yl)phenyl, 4-methyl, Chiral; ClH) |
| 43 | (3-ethoxypyrazine-2-carboxamide linked to 3-(2-amino-5,6-dihydro-4H-1,3-thiazin-4-yl)-4-fluorophenyl, 4-methyl, Chiral) |
| 44 | (5-methylpyrazine-2-carboxamide linked to 3-(2-amino-5,6-dihydro-4H-1,3-thiazin-4-yl)-4-ethoxyphenyl, 4-methyl, Chiral) |

TABLE 9-continued

| Compound No. | Structure |
|---|---|
| 45 | (3-(2-methoxyethoxy)pyrazine-2-carboxamide linked to 3-(2-amino-5,6-dihydro-4H-1,3-thiazin-4-yl)-4-fluorophenyl, 4-methyl, Chiral) |
| 46 | (5-(2-methoxyethoxy)-3-aminopyrazine-2-carboxamide linked to 3-(2-amino-5,6-dihydro-4H-1,3-thiazin-4-yl)-4-fluorophenyl, 4-methyl, Chiral) |

TABLE 10

| Compound No. | Structure |
|---|---|
| 47 | (5-((2-aminoethyl)amino)pyrazine-2-carboxamide linked to 3-(2-amino-5,6-dihydro-4H-1,3-thiazin-4-yl)phenyl, 4-methyl) |
| 48 | (5-((3-aminopropyl)amino)pyrazine-2-carboxamide linked to 3-(2-amino-5,6-dihydro-4H-1,3-thiazin-4-yl)phenyl, 4-methyl) |

TABLE 10-continued
| Compound No. | Structure |
|---|---|
| 49 | 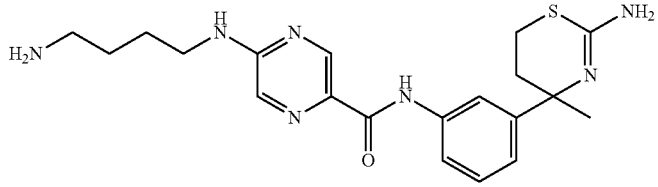 [SMILES: CC1(c2cccc(NC(=O)c3cnc(NCCCCN)cn3)c2)CCSC(N)=N1] |
| 50 | 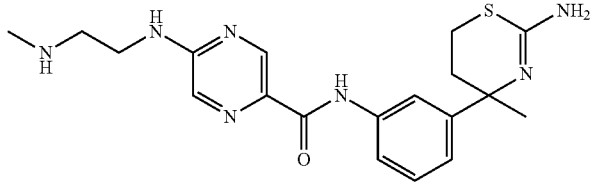 |
| 51 | 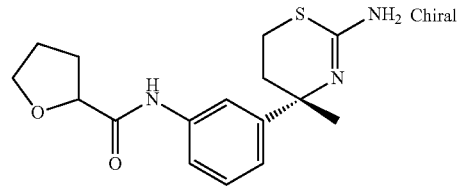 |
TABLE 11
| Compound No. | Structure |
|---|---|
| 52 | 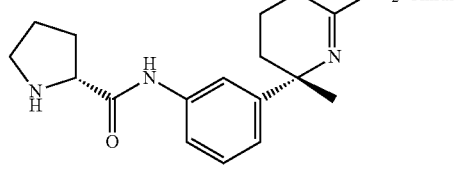 |
| 53 | 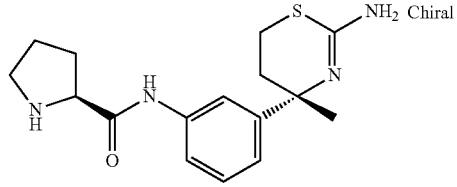 |
| 54 | 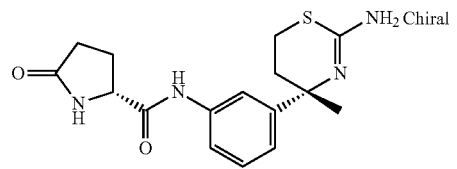 |
| 55 | 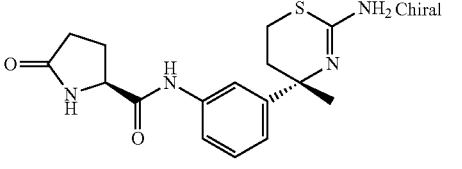 |
| 56 | 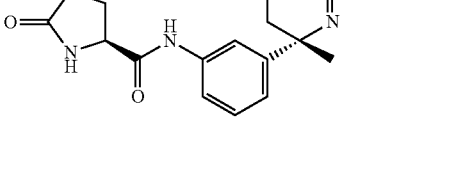 |

TABLE 12

| Compound No. | Structure |
|---|---|
| 57 | (5-oxotetrahydrofuran-2-carboxamide, chiral) linked to N-H-phenyl-(2-amino-5,6-dihydro-4H-1,3-thiazin-4-yl with methyl, chiral) |
| 58 | 5-chloropyrazine-2-carboxamide linked to N-H-phenyl-(2-amino-5,6-dihydro-4H-1,3-thiazin-4-yl with methyl, chiral) |
| 59 | 3-chloropyrazine-2-carboxamide linked to N-H-phenyl-(2-amino-5,6-dihydro-4H-1,3-thiazin-4-yl with methyl, chiral) |
| 60 | 3-methoxypyrazine-2-carboxamide linked to N-H-phenyl-(2-amino-5,6-dihydro-4H-1,3-thiazin-4-yl with methyl, chiral) |
| 61 | 5-(butylamino)pyrazine-2-carboxamide linked to N-H-phenyl-(2-amino-5,6-dihydro-4H-1,3-thiazin-4-yl with methyl) |

TABLE 13

| Compound No. | Structure |
|---|---|
| 62 | 5-(2-methoxyethoxy)pyrazine-2-carboxamide linked to N-H-phenyl-(2-amino-5,6-dihydro-4H-1,3-thiazin-4-yl with methyl) |
| 63 | 5-ethylpyrazine-2-carboxamide linked to N-H-phenyl-(2-amino-5,6-dihydro-4H-1,3-thiazin-4-yl with methyl, chiral) |

TABLE 13-continued
| Compound No. | Structure |
|---|---|
| 64 | 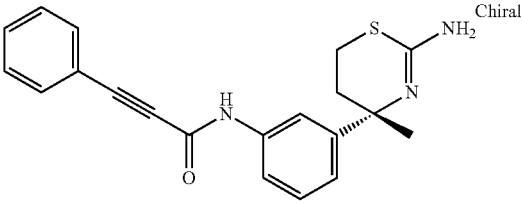 |
| 65 | 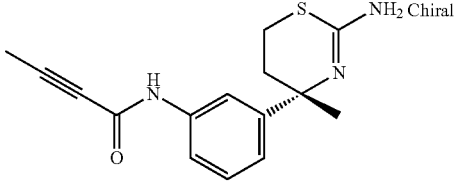 |
| 66 | 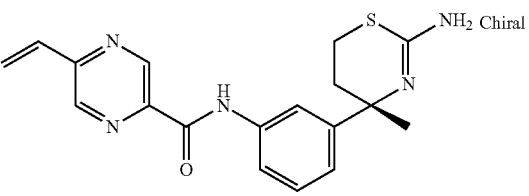 |
TABLE 14
| Compound No. | Structure |
|---|---|
| 67 | 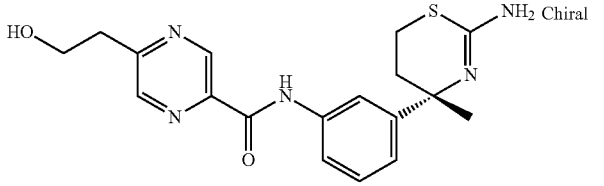 |
| 68 | 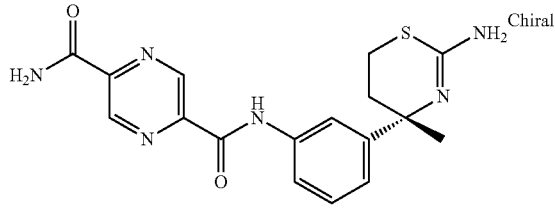 |
| 69 | 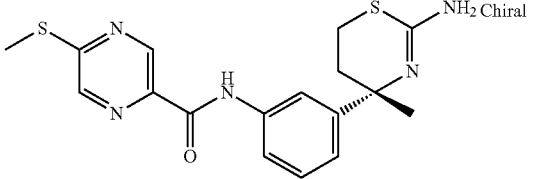 |
| 70 | 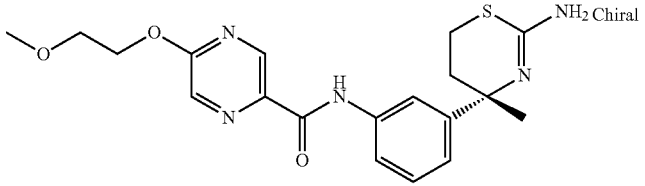 |

TABLE 14-continued

| Compound No. | Structure |
|---|---|
| 71 | (structure) |

TABLE 15

| Compound No. | Structure |
|---|---|
| 72 | (structure) |
| 73 | (structure) |
| 74 | (structure) |
| 75 | (structure) |
| 76 | (structure) |

TABLE 16

| Compound No. | Structure |
|---|---|
| 77 | (5-(methylthio)pyrazine-2-carboxamide linked to N-H of 4-fluoro-3-[(chiral) 2-amino-4-methyl-5,6-dihydro-4H-1,3-thiazin-4-yl]phenyl) |
| 78 | (5-chloropyrazine-2-carboxamide linked to N-H of 4-fluoro-3-[(chiral) 2-amino-4-methyl-5,6-dihydro-4H-1,3-thiazin-4-yl]phenyl) |
| 79 | (5-azidopyrazine-2-carboxamide linked to N-H of 4-fluoro-3-[(chiral) 2-amino-4-methyl-5,6-dihydro-4H-1,3-thiazin-4-yl]phenyl) |
| 80 | (5-(ethylthio)pyrazine-2-carboxamide linked to N-H of 3-[(chiral) 2-amino-4-methyl-5,6-dihydro-4H-1,3-thiazin-4-yl]phenyl) |
| 81 | (5-(2-ethoxyethoxy)pyrazine-2-carboxamide linked to N-H of 3-[(chiral) 2-amino-4-methyl-5,6-dihydro-4H-1,3-thiazin-4-yl]phenyl) |

TABLE 17

| Compound No. | Structure |
|---|---|
| 82 | (5-(2,2,2-trifluoroethoxy)pyrazine-2-carboxamide linked to N-H of 3-[(chiral) 2-amino-4-methyl-5,6-dihydro-4H-1,3-thiazin-4-yl]phenyl) |
| 83 | (5-(but-2-en-1-yloxy)pyrazine-2-carboxamide linked to N-H of 3-[(chiral) 2-amino-4-methyl-5,6-dihydro-4H-1,3-thiazin-4-yl]phenyl) |

TABLE 17-continued

| Compound No. | Structure |
|---|---|
| 84 | (3-chloropyrazine-2-carboxamide linked to 4-fluoro-3-(2-amino-5,6-dihydro-4-methyl-4H-1,3-thiazin-4-yl)phenyl), Chiral |
| 85 | (3-methoxypyrazine-2-carboxamide linked to 4-fluoro-3-(2-amino-5,6-dihydro-4-methyl-4H-1,3-thiazin-4-yl)phenyl), Chiral |
| 86 | (5-(but-3-en-1-yloxy)pyrazine-2-carboxamide linked to 3-(2-amino-5,6-dihydro-4-methyl-4H-1,3-thiazin-4-yl)phenyl), Chiral |

TABLE 18

| Compound No. | Structure |
|---|---|
| 87 | (5-isobutoxypyrazine-2-carboxamide linked to 3-(2-amino-5,6-dihydro-4-methyl-4H-1,3-thiazin-4-yl)phenyl), Chiral |
| 88 | (5-(2,2,2-trifluoroethoxy)pyrazine-2-carboxamide linked to 4-fluoro-3-(2-amino-5,6-dihydro-4-methyl-4H-1,3-thiazin-4-yl)phenyl), Chiral |
| 89 | (5-(3,3,3-trifluoropropoxy)pyrazine-2-carboxamide linked to 3-(2-amino-5,6-dihydro-4-methyl-4H-1,3-thiazin-4-yl)phenyl), Chiral |
| 90 | (5-(2-(2-methoxyethoxy)ethoxy)pyrazine-2-carboxamide linked to 3-(2-amino-5,6-dihydro-4-methyl-4H-1,3-thiazin-4-yl)phenyl), Chiral |

TABLE 18-continued

| Compound No. | Structure |
|---|---|
| 91 | (structure: 5-(but-2-yn-1-yloxy)-N-(3-((R)-2-amino-4-methyl-5,6-dihydro-4H-1,3-thiazin-4-yl)phenyl)pyrazine-2-carboxamide), Chiral |

TABLE 19

| Compound No. | Structure |
|---|---|
| 92 | (structure: 5-(2,2-difluoroethoxy)pyrazine-2-carboxamide derivative), Chiral |
| 93 | (structure: 5-(2-methoxyethoxy)pyridine-2-carboxamide with fluorophenyl), Chiral |
| 94 | (structure: 5-(oxetan-2-ylmethoxy)pyrazine-2-carboxamide derivative), Chiral |
| 95 | (structure: 5-(2-methoxyethoxy)pyridine-2-carboxamide derivative), Chiral |
| 96 | (structure: 5-(3-methoxypropoxy)pyridine-2-carboxamide derivative), Chiral |

TABLE 20

| Compound No. | Structure |
|---|---|
| 97 | (structure) |
| 98 | (structure) |
| 99 | (structure) |
| 100 | (structure) |
| 101 | (structure) |

TABLE 21

| Compound No. | Structure |
|---|---|
| 102 | (structure) |

TABLE 21-continued

| Compound No. | Structure |
|---|---|
| 103 | (chemical structure) |
| 104 | (chemical structure) |
| 105 | (chemical structure) |
| 106 | (chemical structure) |

TABLE 22

| Compound No. | Structure |
|---|---|
| 107 | (chemical structure) |
| 108 | (chemical structure) |
| 109 | (chemical structure) |

TABLE 22-continued
| Compound No. | Structure |
|---|---|
| 110 | 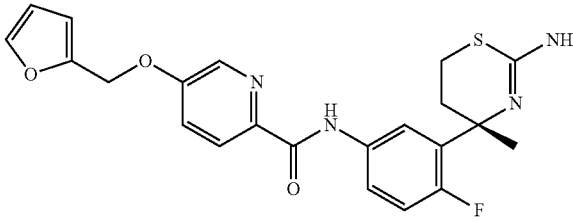 |
| 111 | 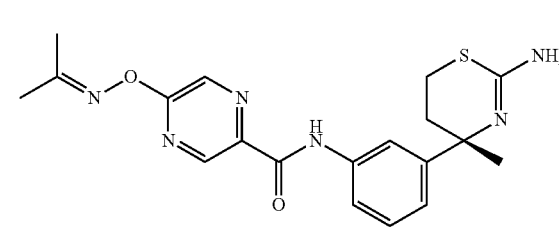 |
TABLE 23
| Compound No. | Structure |
|---|---|
| 112 | 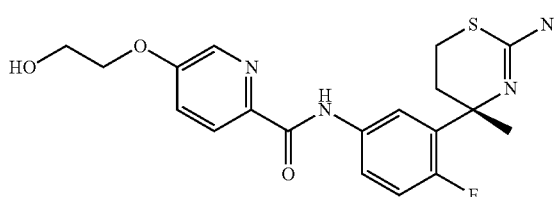 |
| 113 | 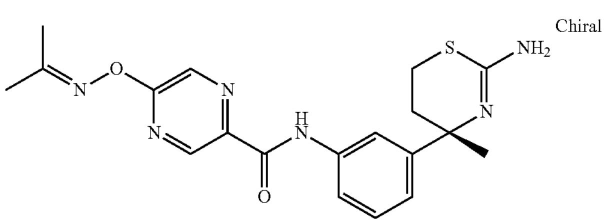 [SMILES: CC(C)=NOc1cnc(C(=O)Nc2cccc([C@]3(C)CCSC(N)=N3)c2)cn1] |
| 114 | 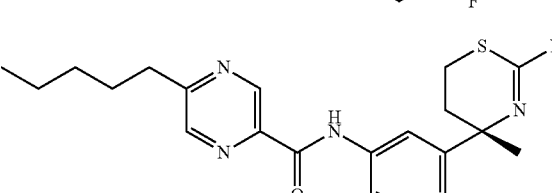 |
| 115 | 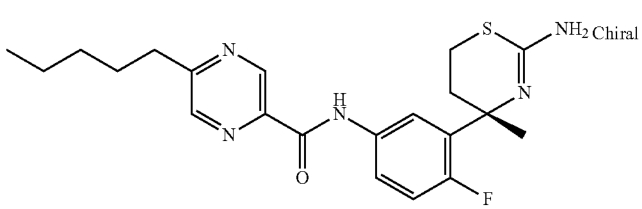 [SMILES: CCCCCc1cnc(C(=O)Nc2ccc(F)c([C@]3(C)CCSC(N)=N3)c2)cn1] |

TABLE 23-continued

| Compound No. | Structure |
|---|---|
| 116 | 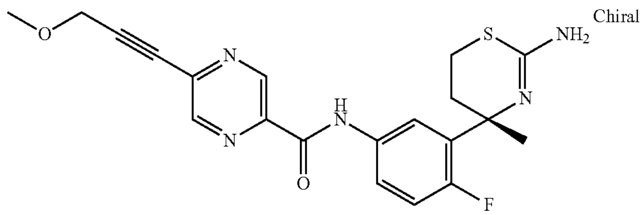 [SMILES: COCC#Cc1cnc(C(=O)Nc2ccc(F)c([C@]3(C)CCSC(N)=N3)c2)cn1] |

TABLE 24

| Compound No. | Structure |
|---|---|
| 117 | 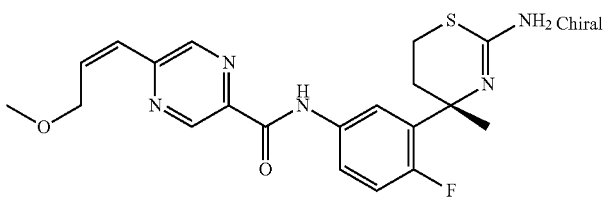 [SMILES: COC/C=C\c1cnc(C(=O)Nc2ccc(F)c([C@]3(C)CCSC(N)=N3)c2)cn1] |
| 118 | 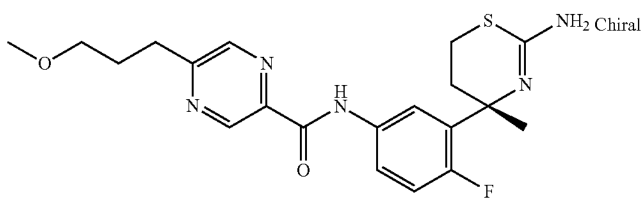 [SMILES: COCCCc1cnc(C(=O)Nc2ccc(F)c([C@]3(C)CCSC(N)=N3)c2)cn1] |
| 119 | 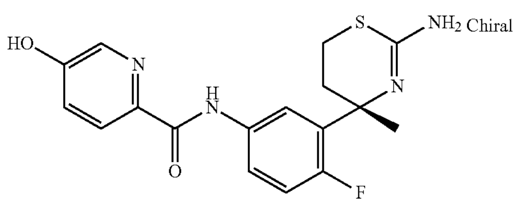 [SMILES: C[C@@]1(c2cc(NC(=O)c3ccc(O)cn3)ccc2F)CCSC(N)=N1] |
| 120 | 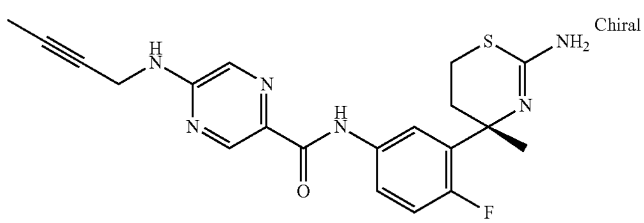 [SMILES: CC#CCNc1cnc(C(=O)Nc2ccc(F)c([C@]3(C)CCSC(N)=N3)c2)cn1] |
| 121 | 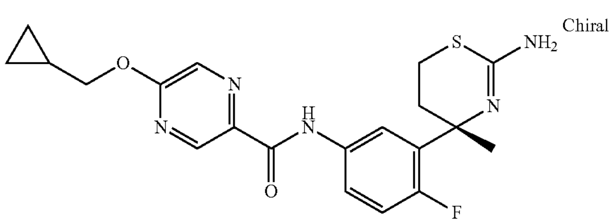 [SMILES: C[C@@]1(c2cc(NC(=O)c3cnc(OCC4CC4)cn3)ccc2F)CCSC(N)=N1] |

TABLE 25

| Compound No. | Structure |
|---|---|
| 122 | 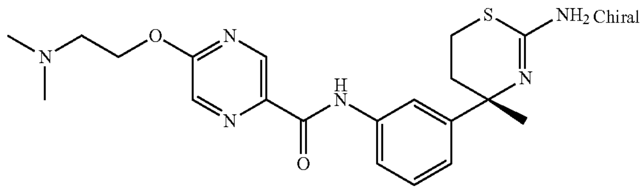 [SMILES: CN(C)CCOc1cnc(C(=O)Nc2cccc([C@]3(C)CCSC(N)=N3)c2)cn1] |
| 123 | 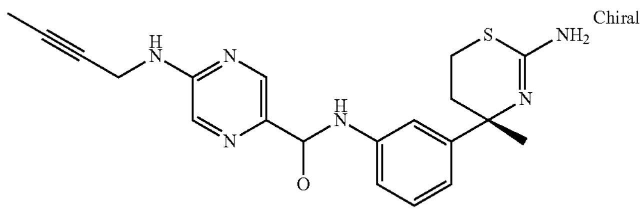 [SMILES: CC#CCNc1cnc(C(O)Nc2cccc([C@]3(C)CCSC(N)=N3)c2)cn1] |
| 124 | 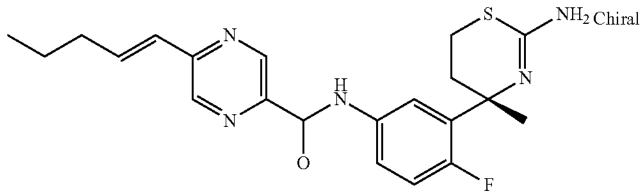 [SMILES: CCC/C=C/c1cnc(C(O)Nc2ccc(F)c([C@]3(C)CCSC(N)=N3)c2)cn1] |
| 125 | 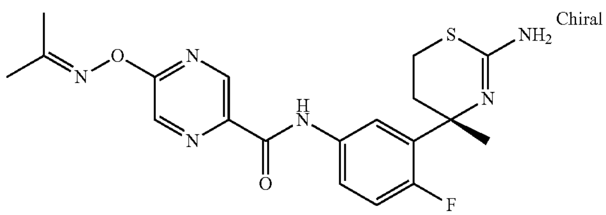 [SMILES: CC(C)=NOc1cnc(C(=O)Nc2ccc(F)c([C@]3(C)CCSC(N)=N3)c2)cn1] |
| 126 | 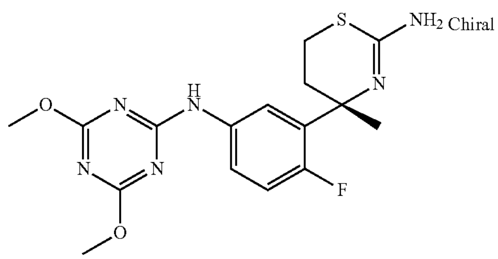 [SMILES: COc1nc(Nc2ccc(F)c([C@]3(C)CCSC(N)=N3)c2)nc(OC)n1] |

TABLE 26

| Compound No. | Structure |
|---|---|
| 127 | 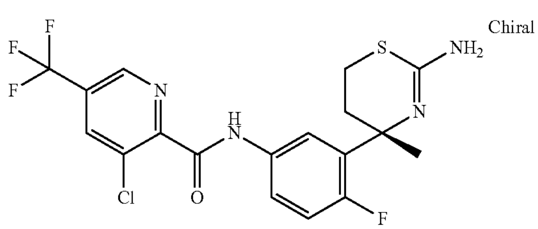 [SMILES: C[C@@]1(c2cc(NC(=O)c3ncc(C(F)(F)F)cc3Cl)ccc2F)CCSC(N)=N1] |

TABLE 26-continued
| Compound No. | Structure |
|---|---|
| 128 | 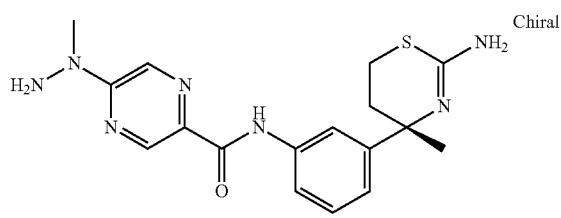 [SMILES: CN(N)c1cnc(C(=O)Nc2cccc([C@]3(C)CCSC(N)=N3)c2)cn1] |
| 129 | 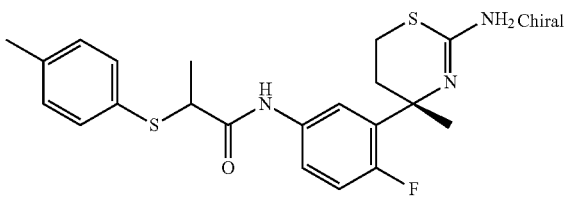 [SMILES: Cc1ccc(SC(C)C(=O)Nc2ccc(F)c([C@]3(C)CCSC(N)=N3)c2)cc1] |
| 130 | 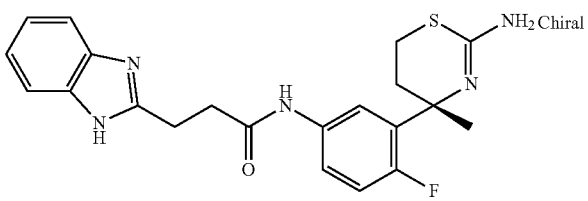 [SMILES: C[C@@]1(c2cc(NC(=O)CCc3nc4ccccc4[nH]3)ccc2F)CCSC(N)=N1] |
| 131 | 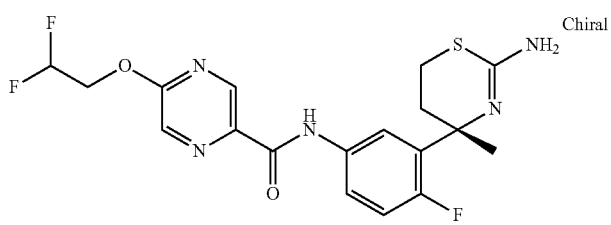 [SMILES: C[C@@]1(c2cc(NC(=O)c3cnc(OCC(F)F)cn3)ccc2F)CCSC(N)=N1] |
TABLE 27
| Compound No. | Structure |
|---|---|
| 132 | 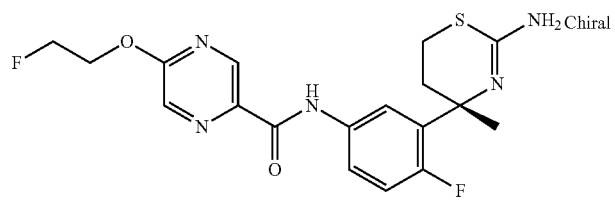 [SMILES: C[C@@]1(c2cc(NC(=O)c3cnc(OCCF)cn3)ccc2F)CCSC(N)=N1] |
| 133 | 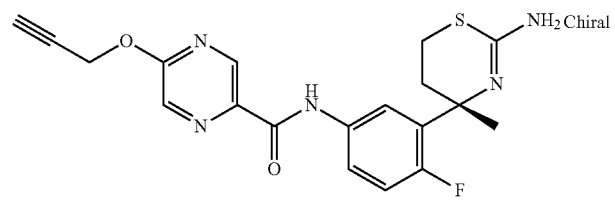 [SMILES: C#CCOc1cnc(C(=O)Nc2ccc(F)c([C@]3(C)CCSC(N)=N3)c2)cn1] |

TABLE 27-continued
| Compound No. | Structure |
|---|---|
| 134 | 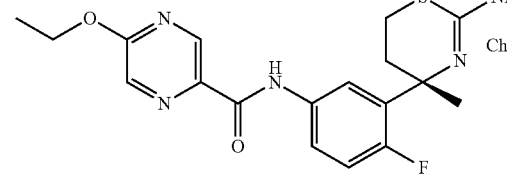 |
| 135 | 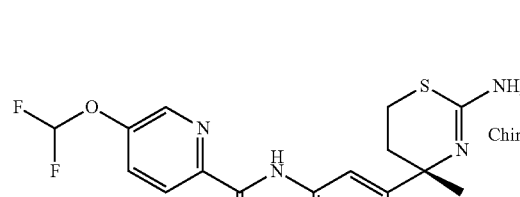 |
| 136 | 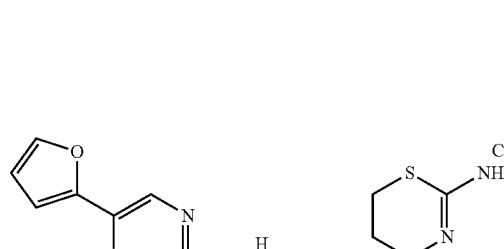 |
TABLE 28
| Compound No. | Structure |
|---|---|
| 137 | 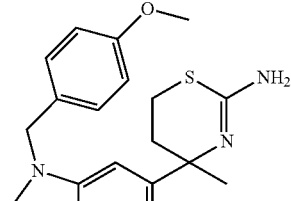 |
| 138 | 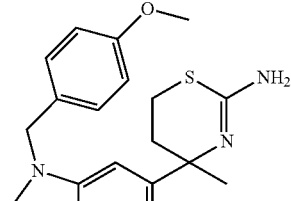 |
| 139 | 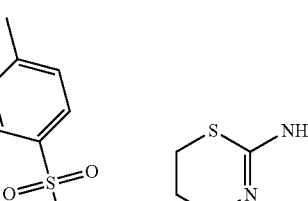 |
| 140 | 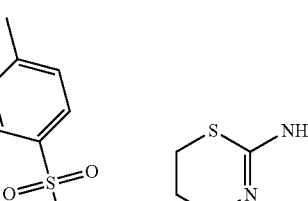 |

TABLE 29

| Compound No. | Structure |
|---|---|
| 141 | (5-chloropyrazine-2-carboxamide linked to 3-(2-amino-4-methyl-5,6-dihydro-4H-1,3-thiazin-4-yl)-4-methylphenyl) |
| 142 | (5-(but-2-yn-1-yloxy)pyrazine-2-carboxamide linked to 3-(2-amino-4-methyl-5,6-dihydro-4H-1,3-thiazin-4-yl)-4-methylphenyl) |
| 143 | (5-methylpyrazine-2-carboxamide linked to 3-(2-amino-4-methyl-5,6-dihydro-4H-1,3-thiazin-4-yl)-4,5-difluorophenyl) |
| 144 | (5-chloropyrazine-2-carboxamide linked to 3-(2-imino-4-methyl-1,3-thiazinan-4-yl)-4,5-difluorophenyl) |
| 145 | (5-(but-2-yn-1-yloxy)pyrazine-2-carboxamide linked to 3-(2-imino-4-methyl-1,3-thiazinan-4-yl)-4,5-difluorophenyl) |

TABLE 30
| Compound No. | Structure |
|---|---|
| 146 | 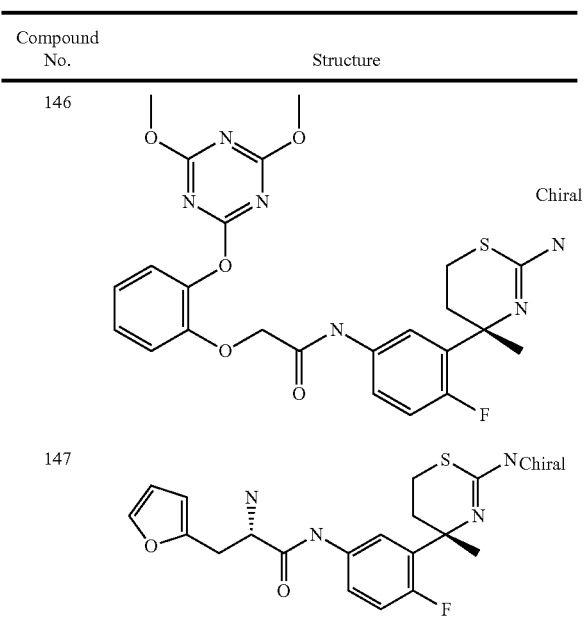 |
| 147 | 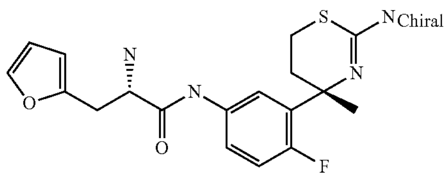 [SMILES: C[C@@]1(c2cc(NC(=O)[C@@H](N)Cc3ccco3)ccc2F)CCSC(N)=N1] |
TABLE 30-continued
| Compound No. | Structure |
|---|---|
| 148 | 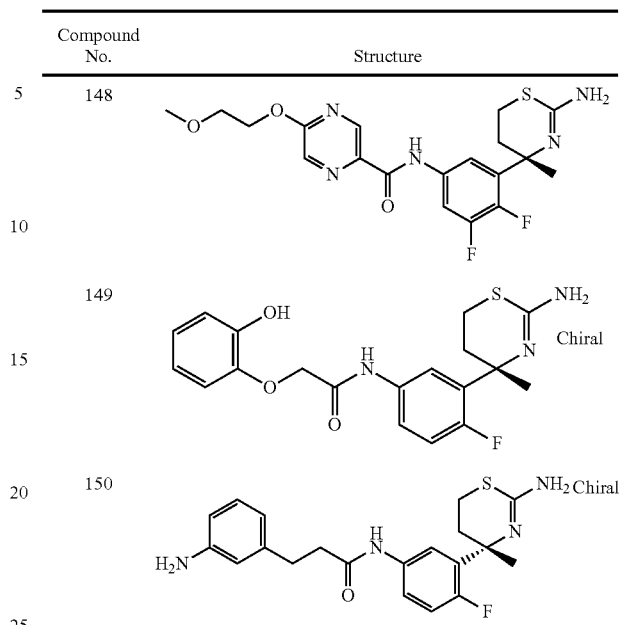 |
| 149 | 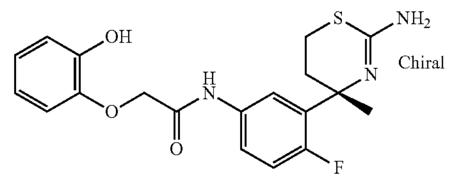 [SMILES: C[C@@]1(c2cc(NC(=O)COc3ccccc3O)ccc2F)CCSC(N)=N1] |
| 150 | 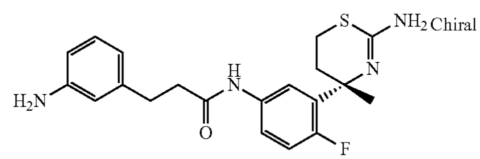 [SMILES: C[C@@]1(c2cc(NC(=O)CCc3cccc(N)c3)ccc2F)CCSC(N)=N1] |
TABLE 31
| Compound No. | Structure |
|---|---|
| 151 | 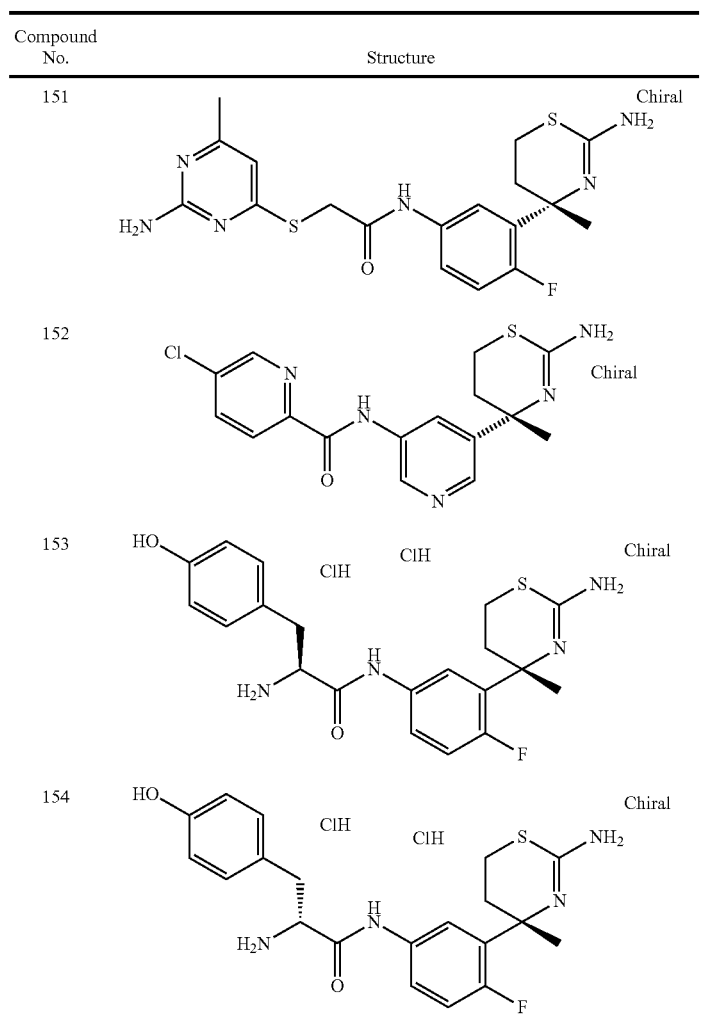 |
| 152 | 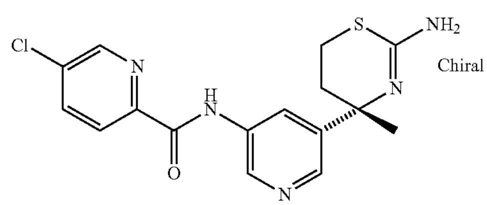 |
| 153 | 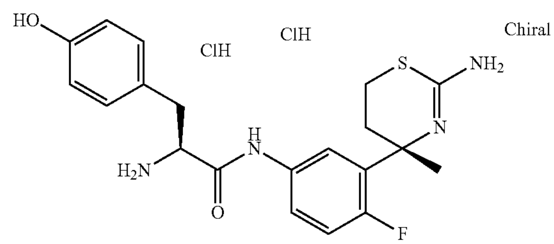 |
| 154 | 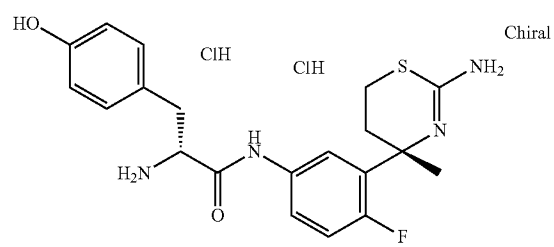 |

TABLE 31-continued
| Compound No. | Structure |
|---|---|
| 155 | 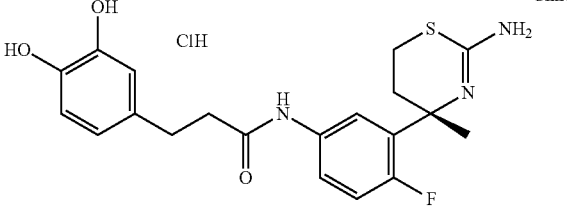 |
TABLE 32
| Compound No. | Structure |
|---|---|
| 156 | 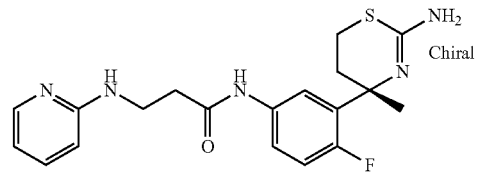 [SMILES: C[C@@]1(c2cc(NC(=O)CCNc3ccccn3)ccc2F)CCSC(N)=N1] |
| 157 | 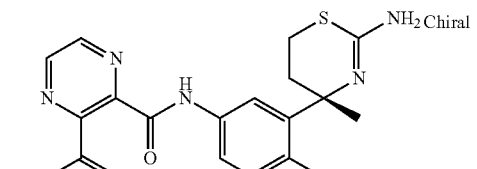 |
| 158 | 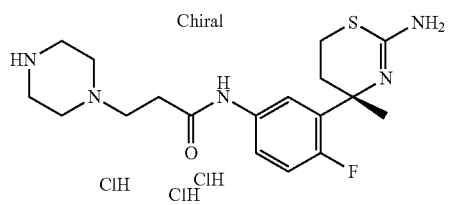 |
TABLE 32-continued
| Compound No. | Structure |
|---|---|
| 159 | 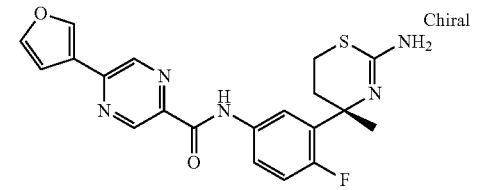 [SMILES: C[C@@]1(c2cc(NC(=O)c3cnc(-c4ccoc4)cn3)ccc2F)CCSC(N)=N1] |
| 160 | 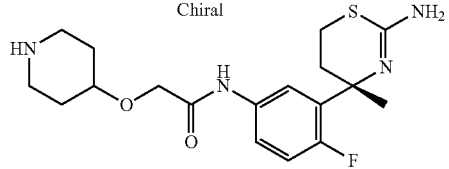 [SMILES: C[C@@]1(c2cc(NC(=O)COC3CCNCC3)ccc2F)CCSC(N)=N1] |
TABLE 33
| Compound No. | Structure |
|---|---|
| 161 | 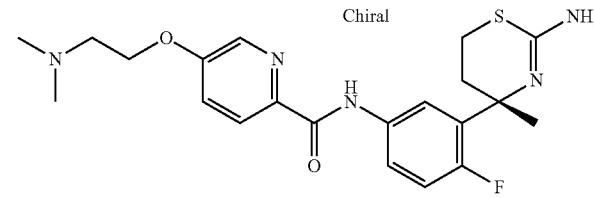 |
| 162 | 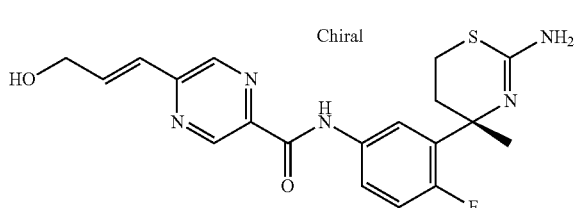 |

TABLE 33-continued
| Compound No. | Structure |
|---|---|
| 163 | 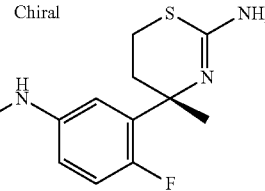 |
| 164 | 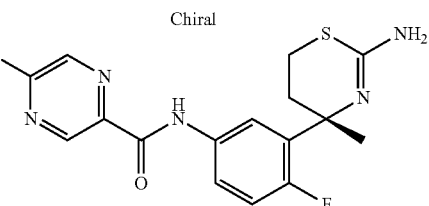 |
| 165 | 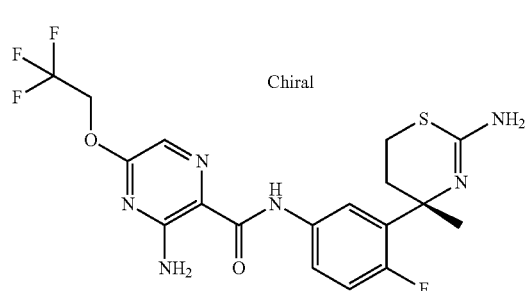 |
TABLE 34
| Compound No. | Structure |
|---|---|
| 166 | 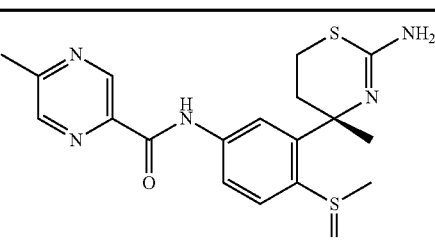 |
| 167 | 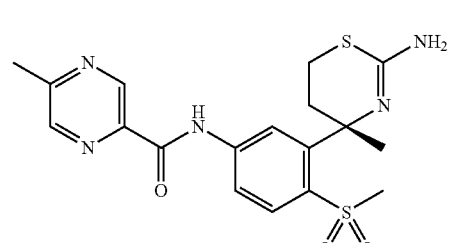 |
| 168 | 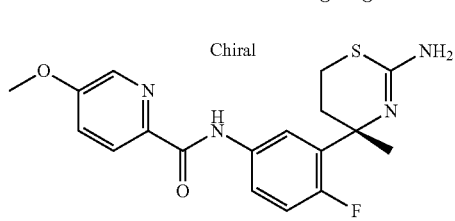 |
| 169 | 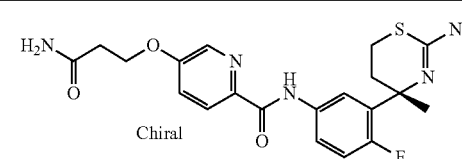 |
| 170 | 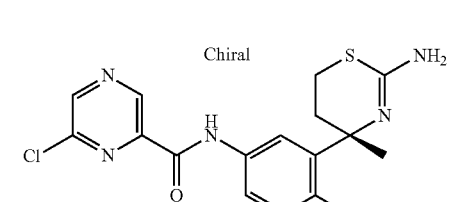 |
| 171 | 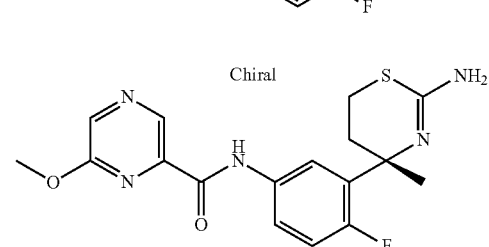 |

TABLE 35

| Compound No. | MS (M + 1) | MP | NMR (solvent, shift value ascending order) | uv |
|---|---|---|---|---|
| 1 | | | 1H-NMR (CDCl3) δ: 8.69 (1.0H, br s), 8.57 (1.0H, s), 8.53-8.41 (1.0H, m), 8.36-8.33 (1.0H, m), 7.90-7.81 (1.0H, m), 7.56 (1.0H, br s), 7.41-7.29 (2.0H, m), 7.00-6.88 (2.0H, m), 2.88-2.63 (2.0H, m), 2.50-2.38 (1.0H, m), 2.06-2.00 (1.0H, m), 1.66 (3.0H, | |
| 2 | 344 | | | |
| 3 | | | 1H-NMR (CDCl3) δ: 7.79 (1.0H, br s), 7.65-7.64 (1.0H, m), 7.48-7.41 (1.0H, m), 7.31 (1.0H, t, J = 8.01 Hz), 7.04-7.01 (1.0H, m), 6.23 (1.0H, br s), 2.93-2.65 (2.0H, m), 2.57 (3.0H, br s), 2.40 (1.0H, ddd, J = 14.11, 5.34, 3.43 Hz), 2.27 (3.0H, br s), 2.09-1.92 (1.0H, m), 1.67 (3.0H, s). | |
| 4 | | | 1H-NMR (CDCl3) δ: 7.86-7.83 (1.0H, m), 7.45-7.42 (1.0H, m), 7.35 (1.0H, t, J = 12.96 Hz), 7.21 (1.0H, br s), 7.04-7.01 (1.0H, m), 4.23 (3.0H, s), 2.90-2.86 (1.0H, m), 2.77-2.61 (1.0H, m), 2.38-2.30 (1.0H, m), 1.99-1.89 (1.0H, m), 1.60 (3.0H, s). | |
| 5 | | | 1H-NMR (DMSO-d6) δ: 9.81 (1.0H, br s), 7.70-7.65 (2.0H, m), 7.22 (1.0H, t, J = 7.85 Hz), 7.06-7.03 (1.0H, m), 6.53 (1.0H, s), 2.92-2.85 (1.0H, m), 2.61-2.52 (1.0H, m), 2.28 (3.0H, s), 2.02-1.97 (1.0H, m), 1.73-1.67 (1.0H, m), 1.39 (3.0H, s). | |
| 6 | 425 | | | |
| 7 | 415 | | | |
| 8 | 361 | | | |
| 9 | 331 | | | |
| 10 | 347 | | | |
| 11 | 360 | | | |
| 12 | 379 | | | |
| 13 | 367 | | | |
| 14 | 331 | | | |
| 15 | | | 1H-NMR (DMSO-d6) δ: 10.02 (1.0H, s), 7.61-7.55 (2.0H, m), 7.25 (1.0H, t, J = 7.93 Hz), 7.09 (1.0H, d, J = 7.78 Hz), 6.26 (1.0H, s), 3.86 (3.0H, s), 2.91-2.87 (1.0H, m), 2.59-2.54 (1.0H, m), 2.00-1.96 (1.0H, m), 1.75-1.62 (1.0H, m), 1.39 (3.0H, s). | |
| 16 | 404 | | | |
| 17 | 422 | | | |
| 18 | 360 | | | |
| 19 | 349 | | | |
| 20 | 349 | | | |
| 21 | 388 | | | |
| 22 | 365 | | | |
| 23 | 392 | | | |
| 24 | 385 | | | |
| 26 | | | 1H-NMR (MeOD) δ: 1.73 (1H, s), 1.98 (1H, s), 2.29 (1H, s), 2.76 (1H, s), 6.58 (1H, s), 6.79 (1H, s), 6.92 (1H, s), 7.13 (1H, s), 8.01 (1H, s), 8.55 (1H, s) | |
| 27 | | | 1H-NMR (DMSO-d6) δ: 1.65 (1H, s), 2.07 (1H, t, J = 13.1 Hz), 2.57 (1H, d, J = 11.6 Hz), 3.10 (1H, d, J = 7.1 Hz), 7.42 (1H, t, J = 7.5 Hz), 7.72 (2H, s), 7.84 (1H, d, J = 8.3 Hz), 7.92 (1H, t, J = 9.5 Hz), 8.55 (1H, s), 10.74 (1H, s) | |
| 28 | 358 | | | |
| 29 | | | 1H-NMR (CDCl3) δ: 1.71 (s3H, s), 2.00 (1H, d, J = 8.8 Hz), 2.45 (1H, d, J = 12.4 Hz), 2.78 (1H, t, J = 12.5 Hz), 2.88 (aH, s, J = 13.6 Hz), 3.94 (3H, s), 5.30 (1H, s) 7.05 (1H, d, J = 7.8 Hz), 7.35 (1H, t, J = 8.2 Hz), 7.48 (1H, s), 7.56 (1H, s), 7.65 (1H, d, J = 7.8 Hz), 9.58 (1H, s) | |

TABLE 36

| Compound No | MS (M + 1) | MP | NMR (solvent, shift value: ascending order) | uv |
|---|---|---|---|---|
| 30 | 376 | | | |
| 31 | | | 1H-NMR (MeOD) δ: 1.75 (3H, s), 2.10-2.13 (1H, m), 2.49-2.62 (1H, m), 2.65-2.71 (2H, m), 2.80 (3H, s), 7.02 (1H, d, J = 8.6 Hz), 7.41 (1H, t, J = 7.8 Hz), 7.53 (1H, s), 8.12 (1H, d, J = 8.1 Hz), 9.34 (2H, s), 9.79 (1H, s) | |
| 32 | 372 | | | |
| 33 | 373 | | | |
| 34 | | | 1H-NMR (DMSO-d6) δ: 1.63 (3H, s), 1.70 (3H, s, J = 5.3 Hz), 1.99-2.02 (1H, br m), 2.28 (1H, s), 2.57-2.60 (1H, dr m), 3.07 (1H, d, J = 10.1 Hz), 4.65 (2H, s), 5.70 (1H, d, 14.1 Hz), 5.91 (1H, d, 7.3 Hz), 7.06 (1H, s), 7.36 (1H, s), 7.59 (1H, d, J = 5.1 Hz), 7.82 (1H, s), 7.89 (1H, s, J 5.1 Hz), 8.36 (1H, s), 10.48 (1H, s) | |
| 35 | 395 | | | |
| 36 | 428 | | | |
| 37 | 412 | | | |

TABLE 36-continued

| Compound No | MS (M + 1) | MP | NMR (solvent, shift value: ascending order) | uv |
|---|---|---|---|---|
| 38 | 396 | | | |
| 39 | 238 | | | |
| 40 | 408 | | | |
| 41 | 428 | | | |
| 42 | 379 | | | |
| 43 | 390 | | | |
| 44 | 386 | | | |
| 45 | 420 | | | |
| 46 | 435 | | | |
| 47 | | | 1H-NMR (DMSO-d6) δ: 1.41 (3H, s), 1.69-1.75 (1H, m), 2.01-2.05 (1H, m), 2.55-2.58 (1H, m), 2.74-2.76 (2H, m), 2.88-2.91 (1H, m), 7.06 (1H, d, J = 7.8 Hz), 7.26 (1H, t, J = 7.8 Hz), 7.70-7.73 (2H, m), 7.91 (1H, br s), 7.99 (1H, s), 8.63 (1H, s), 9.97 (1H, s). | |
| 48 | | | 1H-NMR (DMSO-d6) δ: 1.42 (3H, s), 1.71-1.85 (3H, m), 2.04-2.08 (1H, m), 2.56-2.58 (1H, m), 2.82 (2H, t, J = 7.2 Hz), 2.88-2.93 (1H, m), 3.41-3.43 (2H, m), 7.06 (1H, d, J = 7.8 Hz), 7.26 (1H, t, J = 7.6 Hz), 7.70-7.73 (2H, m), 7.99 (2H, s), 8.65 (1H, s), 10.00 (1H, s). | |
| 49 | | | 1H-NMR (DMSO-d6) δ: 1.57 (3H, s), 1.62 (3H, s), 1.94-1.97 (1H, m), 2.37-2.40 (1H, m), 2.56-2.60 (1H, m), 2.80-2.82 (2H, m), 3.03-3.06 (1H, m), 7.04 (1H, d, J = 7.6 Hz), 7.34 (1H, t, J = 7.6 Hz), 7.78-7.82 (2H, m), 8.01 (1H, s), 8.06 (1H, br s), 8.64 (1H, s), 10.13 (1H, s). | |
| 50 | | | 1H-NMR (DMSO-d6) δ: 1.45 (3H, s), 1.76-1.79 (1H, m), 2.09-2.13 (1H, m), 2.40 (3H, br s), 2.57-2.60 (1H, m), 2.83 (2H, t, J = 5.9 Hz), 2.93-2.94 (1H, m), 3.49-3.51 (2H, m), 5.74 (1H, s), 7.06 (1H, d, J = 7.6 Hz), 7.27 (1H, t, J = 7.8 Hz), 7.74 (1H, br s), 7.77 (1H, s), 7.95 (2H, br s), 8.02 (1H, s), 8.66 (1H, s), 10.02 (1H, s). | |
| 51 | | | 1H-NMR (DMSO-d6) δ: 1.40 (3H, s), 1.70-1.75 (1H, m), 1.85-1.90 (2H, m), 1.93-2.02 (2H, m), 2.14-2.21 (1H, m), 2.53-2.60 (1H, m), 2.86-2.94 (1H, m), 3.82 (1H, q, J = 7.1 Hz), 3.98 (1H, q, J = 7.2 Hz), 4.35-4.39 (1H, m), 7.06 (1H, d, J = 7.6 Hz), 7.23 (1H, t, J = 7.8 Hz), 7.56-7.60 (2H, m), 9.57 (1H, s). | |

TABLE 37

| Compound No | MS (M + 1) | MP | NMR (solvent, shift value: ascending order) | uv |
|---|---|---|---|---|
| 52 | | | 1H-NMR (DMSO-d6) δ: 1.38 (3H, s), 1.61-1.81 (5H, m), 1.95-2.08 (2H, m), 2.53-2.58 (1H, m), 2.88 (4H, t, J = 6.6 Hz), 3.65-3.68 (1H, m), 5.67-5.85 (2H, m), 7.04 (1H, d, J = 7.8 Hz), 7.22 (1H, t, J = 7.8 Hz), 7.48 (1H, s), 7.59 (1H, d, J = 7.8 Hz), 9.87 (1H, s). | |
| 53 | | | 1H-NMR (DMSO-d6) δ: 1.39 (3H, s), 1.62-1.80 (5H, m), 1.99-2.07 (2H, m), 2.52-2.58 (1H, m), 2.87-2.91 (3H, m), 3.68 (2H, dd, J = 8.7, 5.9 Hz), 7.04 (1H, d, J = 7.6 Hz), 7.23 (1H, t, J = 8.0 Hz), 7.47 (1H, s), 7.61 (1H, d, J = 7.8 Hz), 9.90 (1H, s). | |
| 54 | | | 1H-NMR (DMSO-d6) δ: 1.40 (3H, s), 1.70-1.75 (1H, m), 1.95-2.05 (2H, m), 2.09-2.37 (2H, m), 2.52-2.57 (1H, m), 2.87-2.94 (1H, m), 4.03 (1H, q, J = 7.1 Hz), 4.19 (1H, dd, J = 8.6, 4.3 Hz), 7.06 (1H, d, J = 7.3 Hz), 7.25 (1H, t, J = 8.0 Hz), 7.49 (1H, s), 7.56 (1H, d, J = 7.8 Hz), 7.86 (1H, s), 10.01 (1H, s). | |
| 55 | | | 1H-NMR (DMSO-d6) δ: 1.40 (3H, s), 1.69-1.75 (1H, m), 1.97-2.03 (2H, m), 2.09-2.36 (4H, m), 2.52-2.57 (1H, m), 2.87-2.93 (1H, m), 4.17-4.20 (1H, m), 7.06 (1H, d, J = 7.8 Hz), 7.25 (1H, t, J = 8.0 Hz), 7.54 (2H, t, J = 8.0 Hz), 7.87 (1H, s), 10.00 (1H, s). | |
| 56 | | | 1H-NMR (DMSO-d6) δ: 1.40 (3H, s), 1.71-1.76 (1H, m), 2.00-2.03 (1H, m), 2.19-2.26 (1H, m), 2.46-2.58 (5H, m), 2.88-2.94 (1H, m), 5.03-5.06 (1H, m), 7.09 (1H, d, J = 7.1 Hz), 7.27 (1H, t, J = 8.1 Hz), 7.50 (1H, s), 7.56 (1H, d, J = 8.1 Hz), 10.22 (1H, s). | |
| 57 | | | 1H-NMR (DMSO-d6) δ: 1.40 (3H, s), 1.69-1.75 (1H, m), 2.00-2.04 (1H, m), 2.19-2.27 (1H, m), 2.46-2.57 (6H, m), 2.87-2.94 (1H, m), 5.03-5.06 (1H, m), 7.09 (1H, d, J = 8.3 Hz), 7.26 (1H, t, J = 8.0 Hz), 7.51 (1H, s), 7.56 (1H, d, J = 8.3 Hz), 10.22 (1H, s). | |
| 58 | | | 1H-NMR (DMSO-d6) δ: 1.48 (3H, s), 1.78-1.84 (1H, m), 2.11-2.18 (1H, m), 2.55-2.61 (1H, m), 2.93-2.99 (1H, m), 7.14 (1H, d, J = 7.8 Hz), 7.34 (1H, t, J = 8.0 Hz), 7.77-7.82 (2H, m), 8.93 (1H, s), 9.11 (1H, s). | |

TABLE 37-continued

| Compound No | MS (M + 1) | MP | NMR (solvent, shift value: ascending order) | uv |
|---|---|---|---|---|
| 59 | | | 1H-NMR (DMSO-d6) δ: 1.43 (3H, s), 1.73-1.78 (1H, m), 2.01-2.08 (1H, m), 2.54-2.59 (1H, m), 2.89-2.96 (1H, m), 7.16 (1H, d, J = 8.1 Hz), 7.34 (1H, t, J = 8.0 Hz), 7.57 (1H, s), 7.68 (1H, d, J = 7.1 Hz), 8.70 (1H, d, J = 2.5 Hz), 8.77 (1H, d, J = 2.3 Hz), 10.80 (1H, s). | |
| 50 | | | 1H-NMR (DMSO-d6) δ: 1.42 (3H, s), 1.70-1.76 (1H, m) 2.01-2.06 (1H, m), 2.54-2.60 (1H, m), 2.88-2.95 (1H, m), 3.97 (3H, s), 7.12 (1H, d, J = 7.8 Hz), 7.30 (1H, t, J = 7.8 Hz), 7.62-7.68 (2H, m), 8.29 (1H, d, J = 2.3 Hz), 8.40 (1H, d, J = 2.5 Hz), 10.53 (1H, s). | |
| 61 | | | 1H-NMR (DMSO-d6) δ: 0.91 (3H, t, J = 7.2 Hz), 1.32-1.40 (5H, m), 1.51-1.58 (2H, m), 1.68-1.73 (1H, m), 1.97-2.05 (0H, m), 2.55-2.60 (1H, m), 2.85-2.92 (1H, m), 5.77 (2H, br s), 7.07 (1H, d, J = 7.6 Hz), 7.25 (1H, t, J = 8.0 Hz), 7.73 (2H, t, J = 6.7 Hz), 7.83-7.87 (1H, m), 7.96 (1H, s), 8.64 (1H, s), 9.95 (1H, s). | |
| 62 | | | 1H-NMR (DMSO-d6) δ: 1.43 (3H, s), 1.71-1.77 (1H, m), 2.02-2.09 (1H, m), 2.55-2.61 (1H, m), 2.87-2.95 (1H, m), 3.31 (3H, s), 3.70-3.74 (2H, m), 4.51-4.54 (2H, m), 7.11 (1H, d, J = 7.1 Hz), 7.29 (1H, t, J = 7.7 Hz), 7.75 (1H, d, J = 8.3 Hz), 7.80 (1H, s), 8.43 (1H, s), 8.87 (1H, s), 10.35 (1H, s). | |

TABLE 38

| Compound No. | MS (M + 1) | MP | NMR (solvent, shift value: ascending order) | uv |
|---|---|---|---|---|
| 63 | | | 1H-NMR (DMSO-d6) δ: 1.29 (3H, t, J = 7.5 Hz), 1.43 (3H, s), 1.71-1.77 (1H, m), 2.01-2.09 (1H, m), 2.55-2.61 (1H, m), 2.90-2.96 (3H, m), 7.12 (1H, d, J = 7.8 Hz), 7.30 (1H, t, J = 7.8 Hz), 7.76 (1H, d, J = 8.1 Hz), 7.82 (1H, s), 8.70 (1H, s), 9.18 (1H, s), 10.53 (1H, s). | |
| 64 | | | 1H-NMR (DMSO-d6) δ: 1.41 (3H, s), 1.70-1.75 (1H, m), 1.99-2.06 (1H, m), 2.52-2.57 (1H, m), 2.87-2.94 (1H, m), 7.11 (1H, d, J = 7.6 Hz), 7.28 (1H, t, J = 7.8 Hz), 7.47-7.59 (5H, m), 7.65 (2H, d, J = 7.6 Hz), 8.30 (0H, s). | |
| 65 | | | 1H-NMR (DMSO-d6) δ: 1.38 (3H, s), 1.67-1.72 (1H, m), 1.94-2.00 (1H, m), 2.03 (3H, s), 2.50-2.55 (1H, m), 2.85-2.92 (1H, m), 7.06 (1H, d, J = 7.1 Hz), 7.23 (1H, t, J = 7.7 Hz), 7.48 (2H, t, J = 8.3 Hz), 10.55 (1H, s). | |
| 66 | 707.0 (2M + 1) | | | |
| 67 | 743.1 (2M + 1) | | | |
| 68 | | | 1H-NMR (DMSO-d6) δ: 1.45 (3H, s), 1.74-1.80 (1H, m), 2.06-2.13 (1H, m), 2.56-2.61 (1H, m), 2.90-2.97 (1H, m), 7.15 (1H, d, J = 7.6 Hz), 7.33 (1H, t, J = 7.7 Hz), 7.79 (1H, d, J = 7.8 Hz), 7.87 (1H, s), 8.04 (1H, s), 8.45 (1H, s), 9.29 (2H, d, J = 8.3 Hz), 10.79 (1H, s). | |
| 69 | | | 1H-NMR (DMSO-d6) δ: 1.43 (3H, s), 1.71-1.76 (1H, m), 2.02-2.09 (1H, m), 2.55-2.63 (4H, m), 2.88-2.94 (1H, m), 7.12 (1H, d, J = 8.1 Hz), 7.29 (1H, t, J = 7.8 Hz), 7.74 (1H, d, J = 8.1 Hz), 7.81 (1H, s), 8.70 (1H, s), 9.08 (1H, s), 10.45 (1H, s). | |
| 70 | | | 1H-NMR (DMSO-d6) δ: 1.43 (3H, s), 1.71-1.77 (1H, m), 2.02-2.09 (1H, m), 2.55-2.61 (1H, m), 2.87-2.95 (1H, m), 3.31 (3H, s), 3.70-3.74 (2H, m), 4.51-4.54 (2H, m), 7.11 (1H, d, J = 7.1 Hz), 7.29 (1H, t, J = 7.7 Hz), 7.75 (1H, d, J = 8.3 Hz), 7.80 (1H, s), 8.43 (1H, s), 8.87 (1H, s), 10.35 (1H, s). | |
| 71 | | | 1H-NMR (DMSO-d6) δ: 0.94 (3H, t, J = 7.3 Hz), 1.43-1.47 (4H, m), 1.72-1.79 (3H, m), 2.02-2.09 (1H, m), 2.58 (1H, t, J = 9.7 Hz), 2.91 (1H, s), 4.40 (2H, t, J = 6.6 Hz), 7.11 (1H, d, J = 7.8 Hz), 7.29 (1H, t, J = 8.1 Hz), 7.75 (1H, d, J = 7.3 Hz), 7.80 (1H, s), 8.37 (1H, s), 8.86 (1H, s), 10.34 (1H, s). | |
| 72 | 771.1 (2M + 1) | | | |
| 73 | | | 1H-NMR (DMSO-d6) δ: 1.40 (3H, s) 1.68-1.73 (1H, m), 1.98-2.05 (1H, m), 2.11 (3H, s), 2.55-2.60 (1H, m), 2.69 (2H, t, J = 6.8 Hz), 2.86-2.92 (1H, m), 3.55-3.59 (2H, m), 5.77 (2H, br s), 7.07 (1H, d, J = 8.1 Hz), 7.25 (1H, t, J = 8.0 Hz), 7.71-7.75 (2H, m), 8.00 (2H, s), 8.65 (1H, s), 9.98 (1H, s). | |
| 74 | | | 1H-NMR (DMSO-d6) δ: 0.99 (3H, t, J = 7.5 Hz), 1.39 (3H, s), 1.56 (2H, td, J = 14.3, 7.2 Hz), 1.67-1.73 (1H, m), 1.95-2.02 (1H, m), 2.38 (2H, t, J = 6.8 Hz), 2.50-2.55 (1H, m), 2.86-2.93 (1H, m), 7.06 (1H, d J = 7.8 Hz), 7.23 (1H, t, J = 8.3 Hz), 7.47-7.51 (2H, m). | |
| 75 | 839.1 (2M + 1) | | | |
| 76 | 835.1 (2M + 1) | | | |
| 77 | 782.9 (2M + 1) | | | |

TABLE 38-continued

| Compound No. | MS (M + 1) | MP | NMR (solvent, shift value: ascending order) | uv |
|---|---|---|---|---|
| 78 | | | 1H-NMR (DMSO-d6) δ: 1.50 (3H, s), 1.79-1.84 (1H, m), 2.23-2.30 (1H, m), 2.55-2.60 (1H, m), 2.96-3.02 (1H, m), 7.16 (1H, dd, J = 11.6, 8.8 Hz), 7.75-7.78 (2H, m), 8.89 (1H, s), 9.07 (1H, s), 10.74 (1H, br s). | |

TABLE 39

| Compound No | MS (M + 1) | MP | NMR (solvent, shift value: ascending order) | uv |
|---|---|---|---|---|
| 79 | | | 1H-NMR (DMSO-d6) δ: 1.49 (4H, s), 1.77-1.83 (1H, m), 2.16-2.23 (1H, m), 2.56-2.62 (1H, m), 2.95-3.01 (1H, m), 5.87 (2H, br s), 7.17 (1H, dd, J = 11.7, 8.5 Hz), 7.76-7.82 (2H, m), 9.96 (2H, d, J = 3.8 Hz), 10.82 (1H, s). | |
| 80 | | | 1H-NMR (DMSO-d6) δ: 1.33 (3H, t, J = 7.2 Hz), 1.42 (3H, s), 1.71-1.76 (1H, m), 2.03-2.07 (1H, m), 2.55-2.59 (1H, m), 2.89-2.92 (1H, m), 3.25 (2H, q, J = 7.3 Hz), 7.11 (1H, d, J = 7.8 Hz), 7.29 (1H, t, J = 7.8 Hz), 7.74 (1H, d, J = 8.1 Hz), 7.79 (1H, s), 8.66 (1H, s), 9.07 (1H, s), 10.45 (1H, s). | |
| 81 | 831.1 (2M + 1) | | | |
| 82 | 850.9 (2M + 1) | | | |
| 83 | 795.0 (2M + 1) | | | |
| 84 | 758.8 (2M + 1) | | | |
| 85 | 750.9 (2M + 1) | | | |
| 86 | 795.1 (2M + 1) | | | |
| 87 | | | 1H-NMR (DMSO-d6) δ: 1.01 (6H, d, J = 6.8 Hz), 1.44 (3H, s), 1.73-1.78 (1H, m), 2.05-2.13 (2H, m), 2.56-2.61 (1H, m), 2.89-2.95 (1H, m), 4.19 (2H, d, J = 6.6 Hz), 7.12 (1H, d, J = 8.1 Hz), 7.29 (1H, t, J = 7.8 Hz), 7.76 (1H, d, J = 7.8 Hz), 7.82 (1H, s), 8.41 (1H, d, J = 1.3 Hz), 8.87 (1H, s), 10.36 (1H, s). | |
| 88 | | | 1H-NMR (DMSO-d6) δ: 1.70 (3H, s), 2.02-2.08 (1H, m), 2.58-2.64 (2H, m), 3.15-3.19 (1H, m), 5.16 (2H, q, J = 8.8 Hz), 7.27 (1H, dd, J = 11.9, 8.8 Hz), 7.85-7.98 (2H, m), 8.62 (1H, s), 8.92 (1H, s), 10.83 (1H, s). | |
| 89 | | | 1H-NMR (DMSO-d6) δ: 1.65 (3H, s), 2.04-2.11 (1H, m), 2.54-2.62 (3H, m), 2.83-2.95 (2H, m), 3.11-3.14 (1H, m), 4.65 (2H, t, J = 5.8 Hz), 7.09 (1H, d, J = 7.6 Hz), 7.42 (1H, t, J = 8.0 Hz), 7.87-7.92 (2H, m), 8.48 (1H, s), 8.91 (1H, s), 10.62 (1H, s). | |
| 90 | | | 1H-NMR (DMSO-d6) d: 1.41 (3H, s), 1.69-1.74 (1H, m), 2.00-2.04 (1H, m), 2.56-2.61 (1H, m), 2.87-2.92 (1H, m), 3.24 (6H, s), 3.37-3.52 (12H, m), 3.59 (2H, t, J = 4.5 Hz), 3.80 (2H, t, J = 4.3 Hz), 4.52 (2H, t, J = 4.4 Hz), 5.81 (2H, br s), 7.12 (1H, d, J = 7.6 Hz), 7.28 (1H, t, J = 8.0 Hz), 7.75 (1H, d, J = 8.3 Hz), 7.81 (1H, s), 8.42 (1H, s), 8.87 (1H, s), 10.33 (1H, s). | |
| 91 | | | 1H-NMR (DMSO-d6) δ: 1.41 (3H, s), 1.69-1.75 (1H, m), 1.85 (3H, s), 1.98-2.05 (1H, m), 2.55-2.61 (1H, m), 2.86-2.93 (1H, m), 5.09 (2H, d, J = 2.0 Hz), 5.79 (2H, br s), 7.12 (1H, d, J = 7.8 Hz), 7.28 (1H, t, J = 7.8 Hz), 7.74 (1H, d, J = 8.3 Hz), 7.80 (1H, s), 8.45 (1H, s), 8.90 (1H, s), 10.36 (1H, s). | |
| 92 | | | 1H-NMR (DMSO-d6) δ: 1.41 (4H, s), 1.69-1.74 (1H, m), 1.98-2.05 (1H, m), 2.56-2.61 (1H, m), 2.87-2.93 (1H, m), 4.74 (2H, td, J = 15.0, 3.1 Hz), 5.79 (2H, br s), 6.34-6.61 (1H, m), 7.12 (1H, d, J = 7.8 Hz), 7.29 (1H, t, J = 8.0 Hz), 7.74 (1H, d, J = 8.1 Hz), 7.81 (1H, s), 8.54 (1H, s), 8.90 (1H, s), 10.40 (1H, s). | |
| 93 | 837.0 (2M + 1) | | | |
| 94 | | | 1H-NMR (DMSO-d6) δ: 1.41 (4H, s), 1.69-1.74 (1H, m), 1.98-2.05 (1H, m), 2.55-2.61 (2H, m), 2.71-2.75 (1H, m), 2.87-2.93 (1H, m), 4.49-4.61 (4H, m), 5.05-5.11 (1H, m), 5.79 (2H, br s), 7.12 (1H, d, J = 7.3 Hz), 7.26 (1H, t, J = 8.0 Hz), 7.74 (1H, d, J = 8.6 Hz), 7.81 (1H, s), 8.47 (1H, s), 8.88 (1H, s), 10.36 (1H, s). | |
| 95 | 801.0 (2M + 1) | | | |

TABLE 40

| Compound No. | MS (M + 1) | MP | NMR (solvent, shift value: ascending order) | uv |
|---|---|---|---|---|
| 96 | | | 1H-NMR (DMSO-d6) δ: 1.42 (3H, s), 1.70-1.78 (1H, m), 1.97-2.04 (3H, m), 2.55-2.60 (1H, m), 2.87-2.93 (1H, m), 3.26 (3H, s), 3.49 (2H, t, J = 6.2 Hz), 4.20 (2H, t, J = 6.4 Hz), 5.86 (2H, br s), 7.10 (1H, d, J = 7.8 Hz), 7.28 (1H, t, J = 8.1 Hz), 7.61 (1H, dd, J = 8.8, 2.8 Hz), 7.77-7.78 (2H, m), 8.11 (1H, d, J = 8.6 Hz), 8.38 (1H, d, J = 2.8 Hz), 10.32 (1H, s). | |
| 97 | | | 1H-NMR (DMSO-d6) δ: 1.41 (3H, s), 1.70-1.75 (1H, m), 1.99-2.06 (1H, m), 2.56-2.61 (1H, m), 2.87-2.93 (1H, m), 4.40-4.50 (2H, m), 4.74-4.88 (2H, m), 5.81 (2H, br s) 7.10 (1H, d, J = 7.6 Hz), 7.28 (1H, t, J = 8.2 Hz), 7.66 (1H, dd, J = 8.8, 2.8 Hz), 7.77-7.78 (2H, m), 8.13 (1H, d, J = 8.8 Hz), 8.43 (1H, d, J = 2.5 Hz), 10.33 (1H, s). | |
| 98 | | | 1H-NMR (DMSO-d6) δ: 1.41 (3H, s), 1.74-1.76 (7H, m), 1.99-2.06 (1H, m), 2.56-2.61 (1H, m), 2.86-2.93 (1H, m), 4.71 (2H, d, J = 6.3 Hz), 5.44-5.49 (1H, m), 5.81 (2H, br s), 7.10 (1H, d, J = 7.3 Hz), 7.28 (1H, t, J = 8.1 Hz), 7.60 (1H, d, J = 8.8 Hz), 7.77 (2H, s), 8.11 (1H, d, J = 8.6 Hz), 8.36 (1H, d), 10.30 (1H, s). | |
| 99 | 799.0 (2M + 1) | | | |
| 100 | 827.0 (2M + 1) | | | |
| 101 | 867.1 (2M + 1) | | | |
| 102 | 885.1 (2M + 1) | | | |
| 103 | 382 | | | |
| 104 | 412 | | | |
| 105 | | | 1H-NMR (DMSO-d6) δ: 1.41 (4H, s), 1.69-1.74 (1H, m), 1.98-2.05 (1H, m), 2.55-2.60 (1H, m), 2.69-2.75 (2H, m), 2.86-2.93 (2H, m), 4.49 (2H, t, J = 6.4 Hz), 5.82 (2H, br s), 7.12 (1H, d, J = 7.3 Hz), 7.28 (1H, t, J = 7.7 Hz), 7.74 (1H, d, J = 7.8 Hz), 7.80 (1H, s), 8.42 (1H, s), 8.88 (1H, s), 10.34 (1H, s). | |
| 106 | | | 1H-NMR (DMSO-d6) δ: 1.41 (3H, s), 1.69-1.76 (3H, m), 1.98-2.05 (1H, m), 2.56-2.61 (1H, m), 2.64-2.69 (2H, m), 2.87-2.93 (1H, m), 4.45 (2H, t, J = 6.4 Hz), 5.80 (2H, br s), 7.12 (1H, d, J = 7.8 Hz), 7.28 (1H, t, J = 7.8 Hz), 7.74 (1H, d, J = 8.3 Hz), 7.80 (1H, s), 8.42 (1H, s), 8.88 (1H, s), 10.34 (1H, s). | |
| 107 | | | 1H-NMR (DMSO-d6) δ: 1.47-1.54 (1H, m), 1.86 (3H, s), 2.03-2.09 (1H, m), 2.88-2.94 (1H, m), 3.09-3.15 (1H, m), 4.43-4.47 (1H, m), 5.08-5.11 (2H, m), 5.76 (2H, br s), 7.04-7.06 (1H, m), 7.27-7.31 (1H, m), 7.68-7.70 (1H, m), 7.79 (1H, s), 8.45 (1H, s), 8.89 (1H, s), 10.39 (1H, s). | |
| 108 | 412 | | | |
| 109 | 398 | | | |
| 110 | | | 1H-NMR (DMSO-d6) δ: 1.45 (3H, s), 1.75-1.81 (1H, m), 2.08-2.14 (1H, m), 2.56-2.61 (1H, m), 2.90-2.97 (1H, m), 7.08 (1H, d, J = 6.8 Hz), 7.27-7.36 (2H, m), 7.77-7.79 (2H, m), 8.01 (1H, d, J = 8.6 Hz), 8.22 (1H, d, J = 2.8 Hz), 10.27 (1H, s). | |
| 111 | | | 1H-NMR (DMSO-d6) δ: 1.45 (3H, s), 1.75-1.80 (1H, m), 2.07-2.14 (1H, m), 2.56-2.61 (1H, m), 2.90-2.97 (1H, m), 5.28 (2H, s), 7.09 (1H, d, J = 7.8 Hz), 7.23-7.32 (3H, m), 7.57 (2H, dd, J = 8.3, 5.6 Hz), 7.70 (1H, dd, J = 8.7, 2.7 Hz), 7.78-7.81 (2H, m), 8.13 (1H, d, J = 8.6 Hz), 8.45 (1H, d, J = 2.8 Hz), 10.36 (1H, s). | |
| 112 | 441 | | | |

TABLE 41

| Compound No. | MS (M + 1) | MP | NMR (solvent, shift value: ascending order) | uv |
|---|---|---|---|---|
| 113 | | | 1H-NMR (DMSO-d6) δ: 1.43 (3H, s), 1.71-1.77 (1H, m), 2.05-2.13 (7H, m), 2.56-2.61 (1H, m), 2.88-2.94 (1H, m), 5.75 (2H, s), 7.12 (1H, d, J = 8.1 Hz), 7.30 (1H, t, J = 7.8 Hz), 7.74-7.80 (2H, m), 8.66 (1H, s), 8.93 (1H, s), 10.44 (1H, s). | |
| 114 | | | 1H-NMR (DMSO-d6) δ: 1.47 (3H, s), 1.77-1.82 (1H, m), 2.13-2.20 (1H, m), 2.57-2.62 (1H, m), 2.93-3.00 (1H, m), 3.75-3.79 (2H, m), 4.18 (2H, t, J = 4.4 Hz), 5.00 (1H, br s), 5.89 (2H, br s), 7.12 (1H, dd, J = 11.4, 8.8 Hz), 7.58-7.63 (1H, m), 7.72-7.82 (2H, m), 8.09 (1H, d, J = 8.6 Hz), 8.39 (1H, s), 10.34 (1H, s). | |
| 115 | 416 | | | |
| 116 | | | 1H-NMR (DMSO-d6) δ: 1.47 (4H, s), 1.76-1.81 (1H, m), 2.15-2.22 (1H, m), 2.55-2.60 (1H, m), 2.93-2.99 (1H, m), 4.47 (3H, s), 5.87 (2H, br s), 7.13 (1H, dd, J = 12.0, 8.7 Hz), 7.79 (2H, ddd, J = 18.3, 8.0, 3.1 Hz), 8.89 (1H, s), 9.23 (1H, s), 10.72 (1H, s). | |

TABLE 41-continued

| Compound No. | MS (M + 1) | MP | NMR (solvent, shift value: ascending order) | uv |
|---|---|---|---|---|
| 117 | | | 1H-NMR (DMSO-d6) δ: 1.48 (3H, s), 1.77-1.82 (1H, m), 2.14-2.21 (1H, m), 2.57-2.62 (1H, m), 2.93-3.00 (1H, m), 3.32 (3H, s), 4.56-4.59 (2H, m), 5.87 (2H, br s), 6.27-6.33 (1H, m), 6.75 (1H, d, J = 12.4 Hz), 7.13 (1H, dd, J = 11.9, 8.8 Hz), 7.77-7.83 (2H, m), 8.77 (1H, s), 9.25 (1H, s), 10.64 (1H, s). | |
| 118 | 418 | | | |
| 119 | 361 | | | |
| 120 | 825.1 (2M + 1) | | | |
| 121 | 416 | | | |
| 122 | | | 1H-NMR (DMSO-d6) δ: 1.41 (3H, s), 1.68-1.74 (1H, m), 1.98-2.05 (1H, m), 2.21 (6H, s), 2.55-2.60 (1H, m), 2.67 (2H, t, J = 5.6 Hz), 2.86-2.93 (1H, m), 4.48 (2H, t, J = 5.4 Hz), 5.79 (2H, br s), 7.11 (1H, d, J = 7.8 Hz), 7.28 (1H, t, J = 7.8 Hz), 7.73 (1H, d, J = 7.6 Hz), 7.79 (1H, s), 8.39 (1H, s), 8.86 (1H, s), 10.33 (1H, s). | |
| 123 | 395 | | | |
| 124 | 414 | | | |
| 125 | 417 | | | |
| 126 | | | 1H-NMR (DMSO-d6) δ: 1.45 (3H, s), 1.75-1.81 (1H, m), 2.13-2.20 (1H, m), 2.55-2.60 (1H, m), 2.92-2.99 (1H, m), 3.88 (6H, s), 5.81 (2H, br s), 7.08 (1H, dd, J = 11.6, 8.8 Hz), 7.50-7.55 (1H, m), 7.66-7.69 (1H, m), 10.07 (1H, s). | |
| 127 | 380 | | | |
| 128 | 372 | | | |
| 129 | 418 | | | |
| 130 | 412 | | | |
| 131 | | | 1H-NMR (DMSO-d6) δ: 1.48 (3H, s), 1.77-1.82 (1H, m), 2.18-2.25 (1H, m), 2.55-2.60 (1H, m), 2.94-3.01 (1H, m), 4.72 (2H, t, J = 13.8 Hz), 6.45 (1H, t, J = 53.9 Hz), 7.10-7.15 (1H, m), 7.74-7.79 (2H, m), 8.50 (1H, s), 8.87 (1H, s), 10.47 (1H, s). | |
| 132 | | | 1H-NMR (DMSO-d6) δ: 1.49 (3H, s), 1.78-1.83 (1H, m), 2.19-2.26 (1H, m), 2.56-2.60 (1H, m), 2.94-3.01 (1H, m), 4.61-4.86 (4H, m), 7.09-7.14 (1H, m), 7.75-7.79 (2H, m), 8.43 (1H, s), 8.84 (1H, s), 10.43 (1H, s). | |
| 133 | 400 | | | |

TABLE 42

| Compound No. | MS (M + 1) | MP | NMR (solvent, shift value: ascending order) | uv |
|---|---|---|---|---|
| 134 | | | 1H-NMR (DMSO-d6) δ: 1.37 (3H, t, J = 7.1 Hz), 1.49 (3H, s), 1.78-1.83 (1H, m), 2.19-2.26 (1H, m), 2.56-2.61 (1H, m), 2.95-3.01 (1H, m), 4.44 (2H, q, J = 7.0 Hz), 7.13 (1H, dd, J = 11.6, 9.1 Hz), 7.73-7.78 (2H, m), 8.35 (1H, s), 8.83 (1H, s), 10.41 (1H, s) | |
| 135 | 411 | | | |
| 136 | 412 | | | |
| 137 | | | 1H-NMR (CDCl3) δ: 1.63 (3H, s), 1.81-1.91 (1H, m), 2.21-2.32 (1H, m), 2.56-2.67 (1H, m), 2.75-2.83 (1H, m), 3.77 (3H, s), 5.24 (2H, s), 6.47 (1H, dd, J = 3.2, 0.6 Hz), 6.83 (2H, d, J = 8.9 Hz), 7.02 (1H, dd, 8.0, 1.8 Hz), 7.07 (1H, d, J = 3.2 Hz), 7.12 (2H, d, J = 8.9 Hz), 7.26 (1H, dd, 1.8, 0.6 Hz), 7.57 (1H, d, J = 8.0 Hz). | |
| 138 | 400 | | | |
| 139 | 246 | | | |
| 140 | 356 | | | |
| 141 | 376 | | | |
| 142 | 410 | | | |
| 143 | 378 | | | |
| 144 | 398 | | | |
| 145 | 432 | | | |
| 146 | 529 | | | |
| 147 | 377 | | | |
| 148 | 438 | | | |
| 149 | 390 | | | |
| 150 | | | | 212.2 |
| 151 | | | | 211.0, 266.3, 301.8 |
| 152 | | | | 285.2 |
| 153 | 403 | | | |
| 154 | 403 | | | |
| 155 | 404 | | | |
| 156 | 388 | | | |
| 157 | 389 | | | |

TABLE 42-continued

| Compound No. | MS (M + 1) | MP | NMR (solvent, shift value: ascending order) | uv |
|---|---|---|---|---|
| 158 | 412 | | | |
| 159 | 380 | | | |
| 160 | 381 | | | |
| 161 | | | 1H-NMR (DMSO-d6) δ: 1.47 (3H, s), 1.77-1.82 (1H, m), 2.15-2.21 (8H, m), 2.56-2.67 (3H, m), 2.93-3.00 (1H, m), 4.21 (2H, t, J = 5.4 Hz), 5.88 (2H, br s), 7.11 (1H, dd, J = 11.6, 9.3 Hz), 7.59-7.61 (1H, m), 7.73-7.80 (2H, m), 8.09 (1H, d, J = 8.6 Hz), 8.37 (1H, s), 10.33 (1H, s). | |
| 162 | 402 | | | |
| 163 | 408 | | | |
| 164 | 464 | | | |
| 165 | 459 | | | |
| 166 | 404 | | | |
| 167 | 420 | | | |
| 168 | 375 | | | |
| 169 | 432 | | | |
| 170 | 380 | | | |
| 171 | 376 | | | |

TABLE 43

| Compound No. | Structure | MS (M + 1) |
|---|---|---|
| 172 | 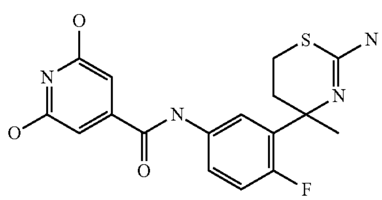 [SMILES: CC1(c2cc(NC(=O)c3cc(O)nc(O)c3)ccc2F)CCSC(N)=N1] | |
| 173 | 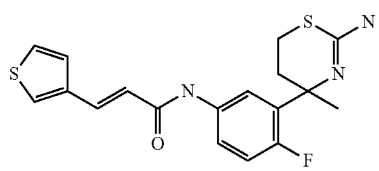 [SMILES: CC1(c2cc(NC(=O)/C=C/c3ccsc3)ccc2F)CCSC(N)=N1] | 459 |
| 174 | 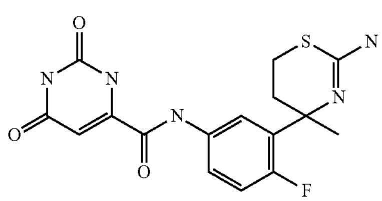 [SMILES: CC1(c2cc(NC(=O)c3cc(=O)[nH]c(=O)[nH]3)ccc2F)CCSC(N)=N1] | 403 |
| 175 | 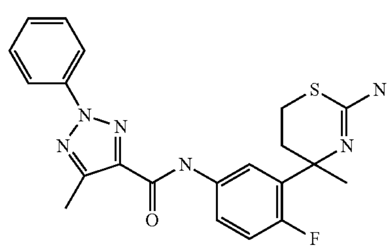 [SMILES: Cc1nn(-c2ccccc2)nc1C(=O)Nc1ccc(F)c(C2(C)CCSC(N)=N2)c1] | 426 |
| 176 | 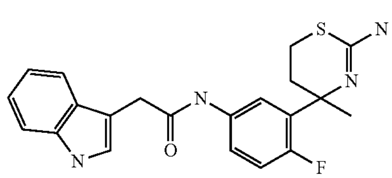 [SMILES: CC1(c2cc(NC(=O)Cc3c[nH]c4ccccc34)ccc2F)CCSC(N)=N1] | 393 |

TABLE 44

| Compound No. | Structure | MS (M + 1) |
|---|---|---|
| 177 | 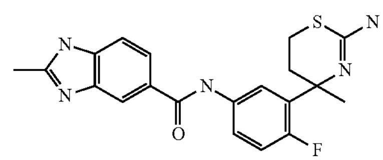 [SMILES: Cc1nc2cc(C(=O)Nc3ccc(F)c(C4(C)CCSC(N)=N4)c3)ccc2[nH]1] | 359 |
| 178 | 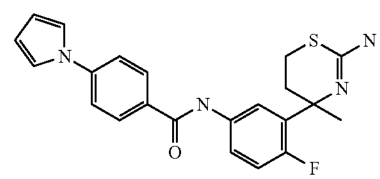 [SMILES: CC1(c2cc(NC(=O)c3ccc(-n4cccc4)cc3)ccc2F)CCSC(N)=N1] | 402 |
| 179 | 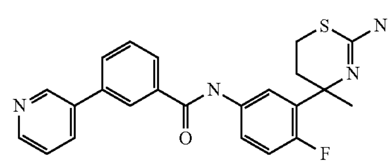 [SMILES: CC1(c2cc(NC(=O)c3cccc(-c4cccnc4)c3)ccc2F)CCSC(N)=N1] | 447 |
| 180 | 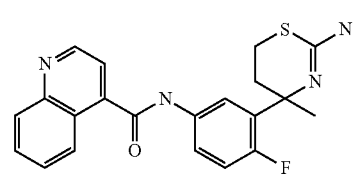 [SMILES: CC1(c2cc(NC(=O)c3ccnc4ccccc34)ccc2F)CCSC(N)=N1] | 435 |
| 181 | 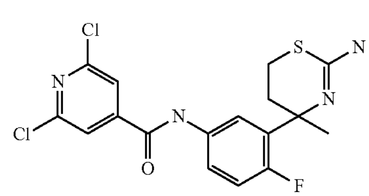 [SMILES: CC1(c2cc(NC(=O)c3cc(Cl)nc(Cl)c3)ccc2F)CCSC(N)=N1] | 396 |

TABLE 45

| Compound No. | Structure | MS (M + 1) |
|---|---|---|
| 182 | 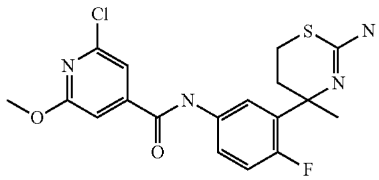 [SMILES: COc1cc(C(=O)Nc2ccc(F)c(C3(C)CCSC(N)=N3)c2)cc(Cl)n1] | 376 |
| 183 | 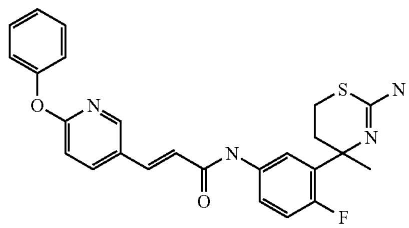 [SMILES: CC1(c2cc(NC(=O)/C=C/c3ccc(Oc4ccccc4)nc3)ccc2F)CCSC(N)=N1] | 385 |
| 184 | 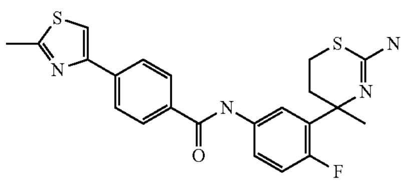 [SMILES: Cc1nc(-c2ccc(C(=O)Nc3ccc(F)c(C4(C)CCSC(N)=N4)c3)cc2)cs1] | 375 |
| 185 | 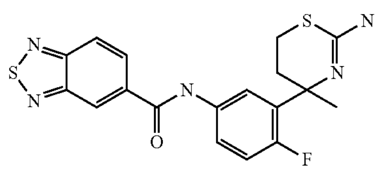 [SMILES: CC1(c2cc(NC(=O)c3ccc4nsnc4c3)ccc2F)CCSC(N)=N1] | 378 |
| 186 | 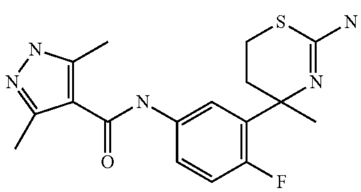 [SMILES: Cc1n[nH]c(C)c1C(=O)Nc1ccc(F)c(C2(C)CCSC(N)=N2)c1] | 412 |

TABLE 46

| Compound No. | Structure | MS (M + 1) |
|---|---|---|
| 187 | | 366 |
| 188 | | 429 |
| 189 | 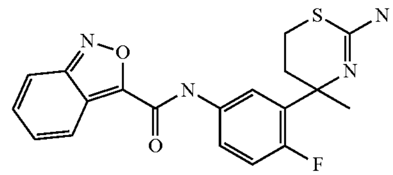 [SMILES: CC1(c2cc(NC(=O)c3onc4ccccc34)ccc2F)CCSC(N)=N1] | 364 |
| 190 | 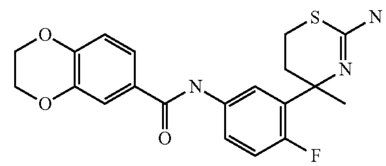 [SMILES: CC1(c2cc(NC(=O)c3ccc4c(c3)OCCO4)ccc2F)CCSC(N)=N1] | 404 |
| 191 | 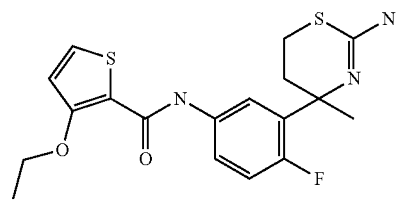 [SMILES: CCOc1ccsc1C(=O)Nc1ccc(F)c(C2(C)CCSC(N)=N2)c1] | 439 |

TABLE 47

| Compound No. | Structure | MS (M + 1) |
|---|---|---|
| 192 | 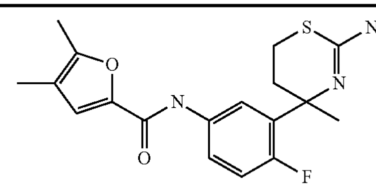 | 412 |
| 193 | 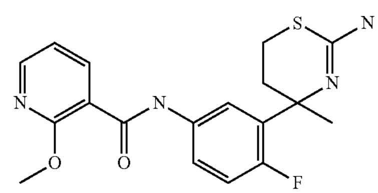 [SMILES: COc1ncccc1C(=O)Nc1ccc(F)c(C2(C)CCSC(N)=N2)c1] | 426 |
| 194 | 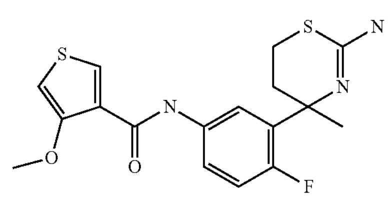 [SMILES: COc1cscc1C(=O)Nc1ccc(F)c(C2(C)CCSC(N)=N2)c1] | 393 |
| 195 | 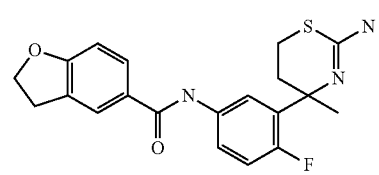 [SMILES: CC1(c2cc(NC(=O)c3ccc4c(c3)CCO4)ccc2F)CCSC(N)=N1] | 352 |

TABLE 47-continued

| Compound No. | Structure | MS (M + 1) |
|---|---|---|
| 196 | 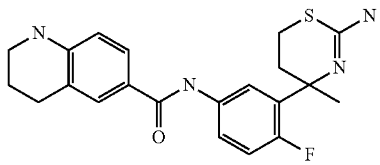 [SMILES: CC1(c2cc(NC(=O)c3ccc4c(c3)CCCN4)ccc2F)CCSC(N)=N1] | 414 |

TABLE 48

| Compound No. | Structure | MS (M + 1) |
|---|---|---|
| 197 | 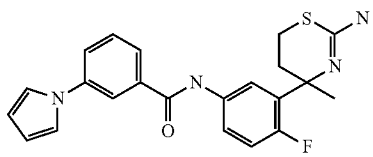 [SMILES: CC1(c2cc(NC(=O)c3cccc(-n4cccc4)c3)ccc2F)CCSC(N)=N1] | |
| 198 | 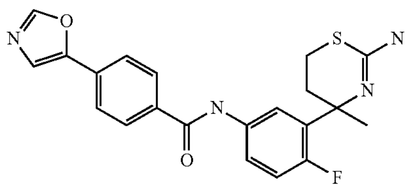 [SMILES: CC1(c2cc(NC(=O)c3ccc(-c4cnco4)cc3)ccc2F)CCSC(N)=N1] | 414 |
| 199 | 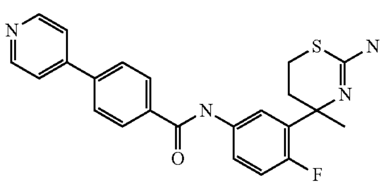 [SMILES: CC1(c2cc(NC(=O)c3ccc(-c4ccncc4)cc3)ccc2F)CCSC(N)=N1] | 364 |
| 200 | 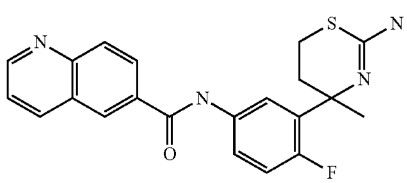 [SMILES: CC1(c2cc(NC(=O)c3ccc4ncccc4c3)ccc2F)CCSC(N)=N1] | 397 |
| 201 | 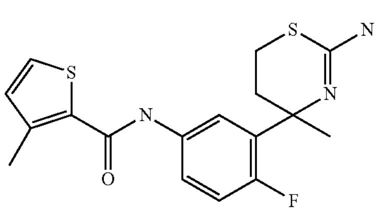 [SMILES: Cc1ccsc1C(=O)Nc1ccc(F)c(C2(C)CCSC(N)=N2)c1] | 428 |

TABLE 49

| Compound No. | Structure | MS (M + 1) |
|---|---|---|
| 202 | 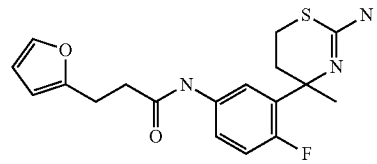 [SMILES: CC1(c2cc(NC(=O)CCc3ccco3)ccc2F)CCSC(N)=N1] | |
| 203 | 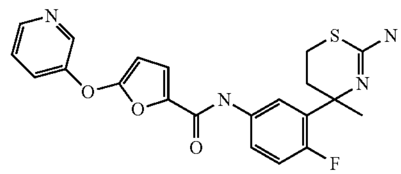 [SMILES: CC1(c2cc(NC(=O)c3ccc(Oc4cccnc4)o3)ccc2F)CCSC(N)=N1] | 398 |
| 204 | 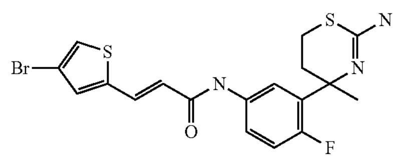 [SMILES: CC1(c2cc(NC(=O)/C=C/c3cc(Br)cs3)ccc2F)CCSC(N)=N1] | 410 |
| 205 | 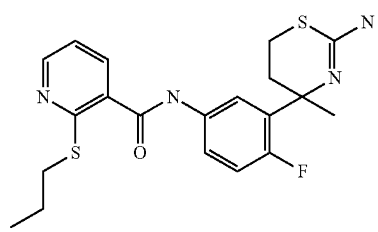 [SMILES: CCCSc1ncccc1C(=O)Nc1ccc(F)c(C2(C)CCSC(N)=N2)c1] | 422 |
| 206 | 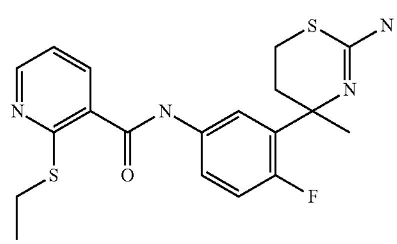 [SMILES: CCSc1ncccc1C(=O)Nc1ccc(F)c(C2(C)CCSC(N)=N2)c1] | 395 |

TABLE 50

| Compound No. | Structure | MS(M + 1) |
|---|---|---|
| 207 | 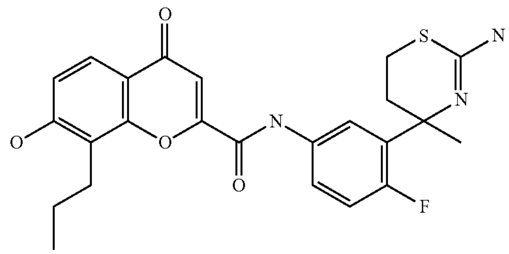 [SMILES: CCCc1c(O)ccc2c(=O)cc(C(=O)Nc3ccc(F)c(C4(C)CCSC(N)=N4)c3)oc12] | 414 |
| 208 | 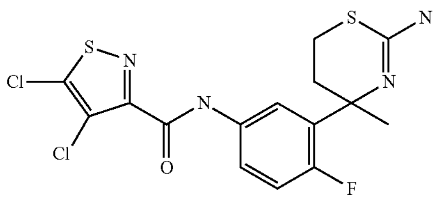 [SMILES: CC1(c2cc(NC(=O)c3nsc(Cl)c3Cl)ccc2F)CCSC(N)=N1] | 410 |
| 209 | 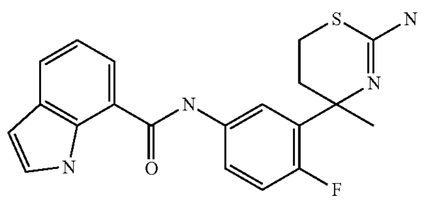 [SMILES: CC1(c2cc(NC(=O)c3cccc4cc[nH]c34)ccc2F)CCSC(N)=N1] | 402 |
| 210 | 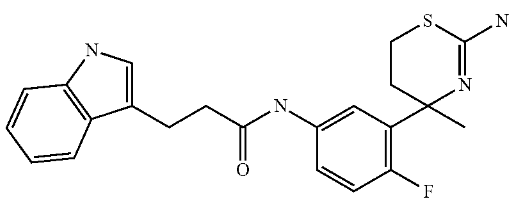 [SMILES: CC1(c2cc(NC(=O)CCc3c[nH]c4ccccc34)ccc2F)CCSC(N)=N1] | |
| 211 | 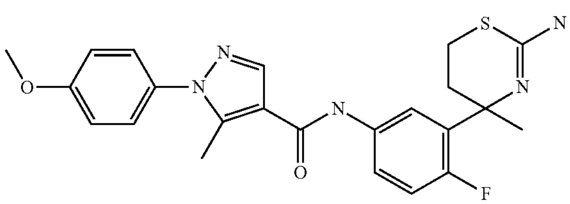 [SMILES: COc1ccc(-n2ncc(C(=O)Nc3ccc(F)c(C4(C)CCSC(N)=N4)c3)c2C)cc1] | |

TABLE 51

| Compound No. | Structure | MS(M + 1) |
|---|---|---|
| 212 | 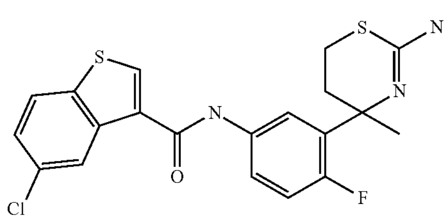 [SMILES: CC1(c2cc(NC(=O)c3csc4ccc(Cl)cc34)ccc2F)CCSC(N)=N1] | 433 |

TABLE 51-continued
| Compound No. | Structure | MS(M + 1) |
|---|---|---|
| 213 | 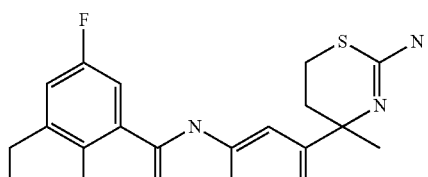 | 466 |
| 214 | 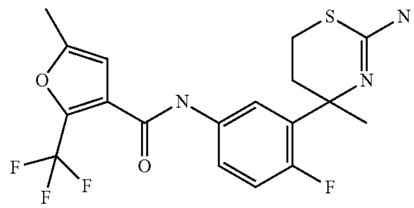 [SMILES: Cc1cc(C(=O)Nc2ccc(F)c(C3(C)CCSC(N)=N3)c2)c(C(F)(F)F)o1] | 464 |
| 215 | 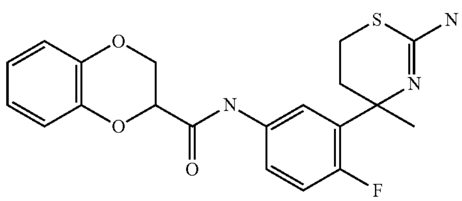 | 427 |
| 216 | 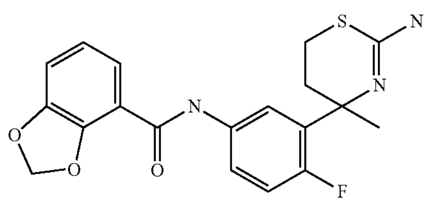 [SMILES: CC1(c2cc(NC(=O)c3cccc4c3OCO4)ccc2F)CCSC(N)=N1] | 400 |
TABLE 52
| Compound No. | Structure | MS(M + 1) |
|---|---|---|
| 217 | 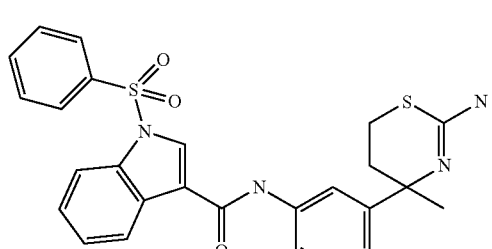 | 442 |
| 218 | 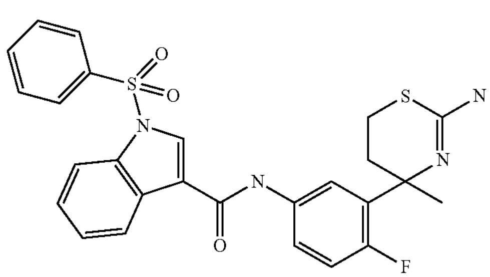 [SMILES: CC1(c2cc(NC(=O)c3cn(S(=O)(=O)c4ccccc4)c4ccccc34)ccc2F)CCSC(N)=N1] | 386 |

TABLE 52-continued

| Compound No. | Structure | MS(M + 1) |
|---|---|---|
| 219 | 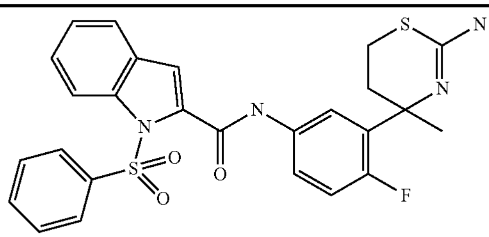 | 402 |
| 220 | 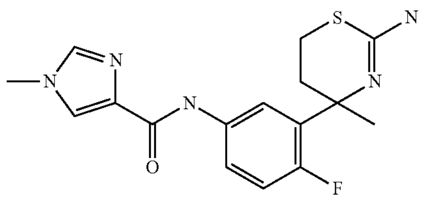 [SMILES: Cn1cnc(C(=O)Nc2ccc(F)c(C3(C)CCSC(N)=N3)c2)c1] | 362 |
| 221 | 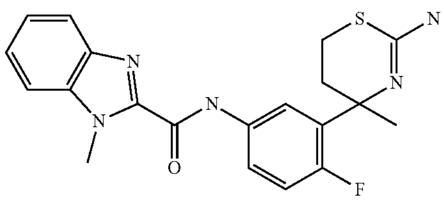 [SMILES: Cn1c(C(=O)Nc2ccc(F)c(C3(C)CCSC(N)=N3)c2)nc2ccccc21] | |

TABLE 53

| Compound No. | Structure | MS(M + 1) |
|---|---|---|
| 222 | 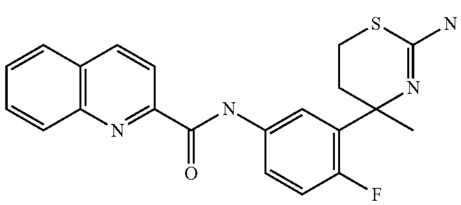 [SMILES: CC1(c2cc(NC(=O)c3ccc4ccccc4n3)ccc2F)CCSC(N)=N1] | 399 |
| 223 | 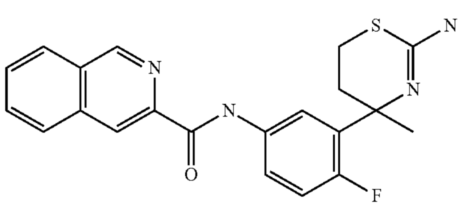 [SMILES: CC1(c2cc(NC(=O)c3cc4ccccc4cn3)ccc2F)CCSC(N)=N1] | |
| 224 | 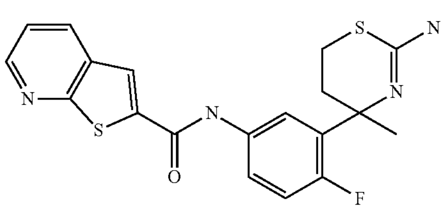 [SMILES: CC1(c2cc(NC(=O)c3cc4cccnc4s3)ccc2F)CCSC(N)=N1] | 352 |

TABLE 53-continued

| Compound No. | Structure | MS(M + 1) |
|---|---|---|
| 225 | 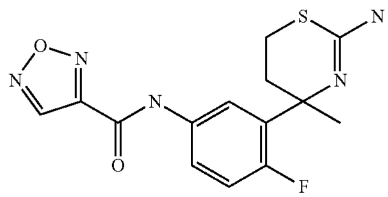 [SMILES: CC1(c2cc(NC(=O)c3cnon3)ccc2F)CCSC(N)=N1] | 402 |
| 226 | 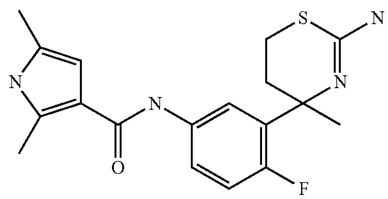 [SMILES: Cc1cc(C(=O)Nc2ccc(F)c(C3(C)CCSC(N)=N3)c2)c(C)[nH]1] | 395 |

TABLE 54

| Compound No. | Structure | MS(M + 1) |
|---|---|---|
| 227 | 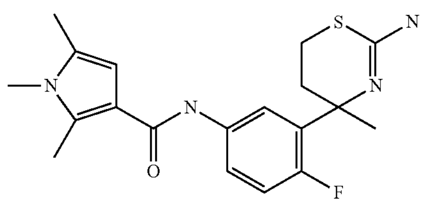 [SMILES: Cc1cc(C(=O)Nc2ccc(F)c(C3(C)CCSC(N)=N3)c2)c(C)n1C] | 362 |
| 228 | 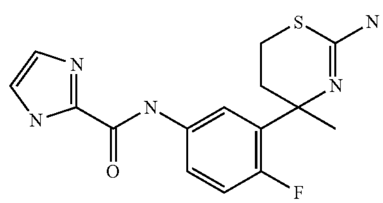 [SMILES: CC1(c2cc(NC(=O)c3ncc[nH]3)ccc2F)CCSC(N)=N1] | 375 |
| 229 | 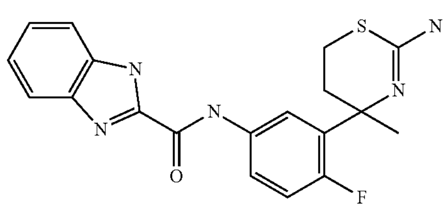 [SMILES: CC1(c2cc(NC(=O)c3nc4ccccc4[nH]3)ccc2F)CCSC(N)=N1] | 380 |
| 230 | 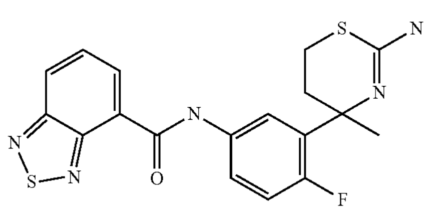 [SMILES: CC1(c2cc(NC(=O)c3cccc4nsnc34)ccc2F)CCSC(N)=N1] | |

TABLE 54-continued

| Compound No. | Structure | MS(M + 1) |
|---|---|---|
| 231 | 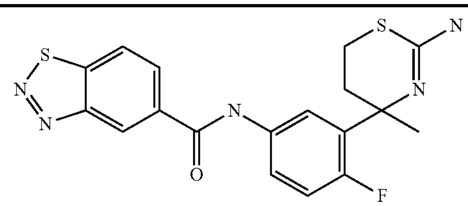 | 400 |

TABLE 55

| Compound No. | Structure | MS(M + 1) |
|---|---|---|
| 232 | 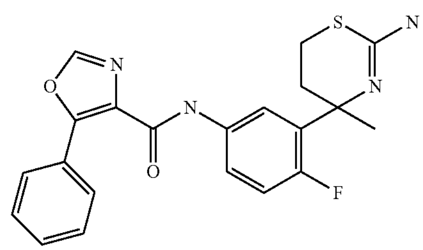 [SMILES: CC1(c2cc(NC(=O)c3ncoc3-c3ccccc3)ccc2F)CCSC(N)=N1] | |
| 233 | 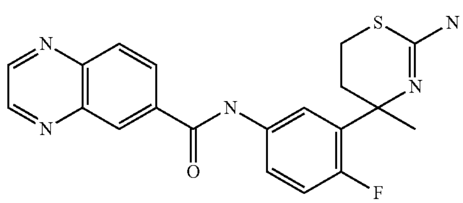 [SMILES: CC1(c2cc(NC(=O)c3ccc4nccnc4c3)ccc2F)CCSC(N)=N1] | |
| 234 | 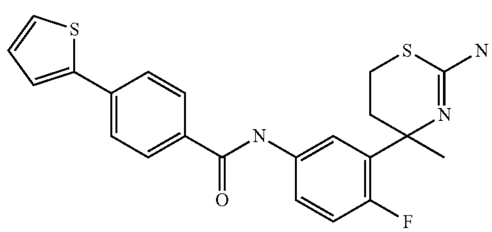 | 422 |
| 235 | 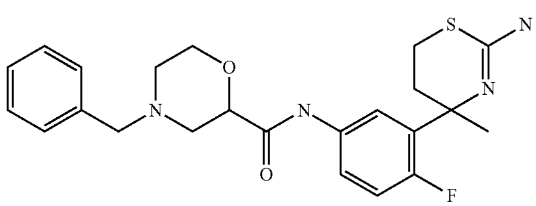 [SMILES: CC1(c2cc(NC(=O)C3CN(Cc4ccccc4)CCO3)ccc2F)CCSC(N)=N1] | 395 |
| 236 | 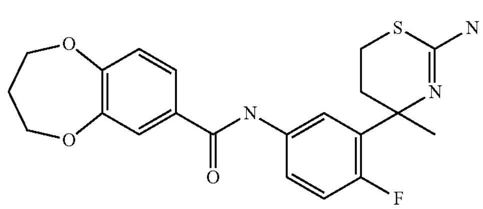 [SMILES: CC1(c2cc(NC(=O)c3ccc4c(c3)OCCCO4)ccc2F)CCSC(N)=N1] | 364 |

TABLE 56

| Compound No. | Structure | MS(M + 1) |
| --- | --- | --- |
| 237 | 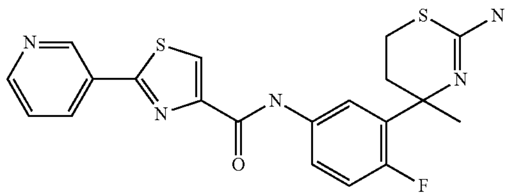 [SMILES: CC1(c2cc(NC(=O)c3csc(-c4cccnc4)n3)ccc2F)CCSC(N)=N1] | 362 |
| 238 | 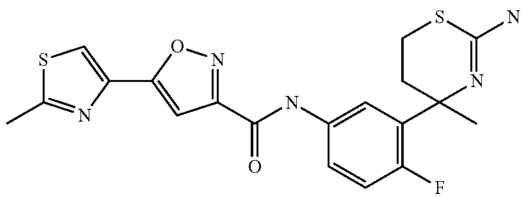 [SMILES: Cc1nc(-c2cc(C(=O)Nc3ccc(F)c(C4(C)CCSC(N)=N4)c3)no2)cs1] | 427 |
| 239 | 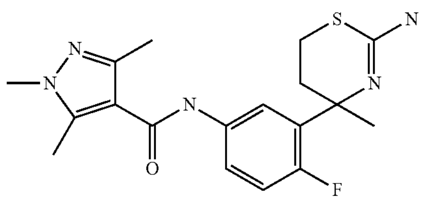 [SMILES: Cc1nn(C)c(C)c1C(=O)Nc1ccc(F)c(C2(C)CCSC(N)=N2)c1] | 455 |
| 240 | 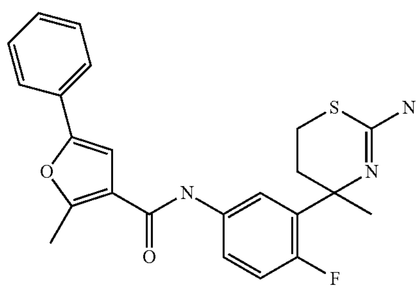 [SMILES: Cc1oc(-c2ccccc2)cc1C(=O)Nc1ccc(F)c(C2(C)CCSC(N)=N2)c1] | 420 |
| 241 | 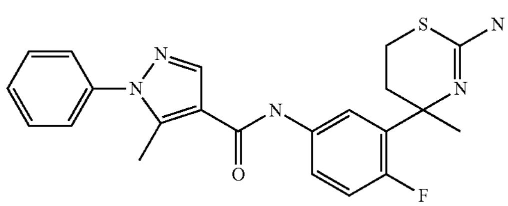 [SMILES: Cc1c(C(=O)Nc2ccc(F)c(C3(C)CCSC(N)=N3)c2)cnn1-c1ccccc1] | 406 |

TABLE 57

| Compound No. | Structure | MS(M + 1) |
| --- | --- | --- |
| 242 | 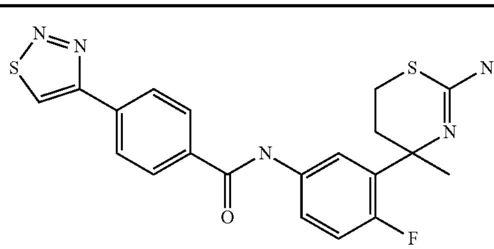 | 471 |

TABLE 57-continued

| Compound No. | Structure | MS(M + 1) |
|---|---|---|
| 243 | 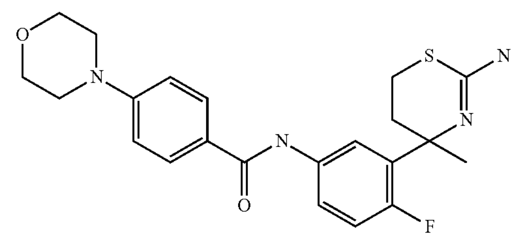 [SMILES: CC1(c2cc(NC(=O)c3ccc(N4CCOCC4)cc3)ccc2F)CCSC(N)=N1] | 406 |
| 244 | 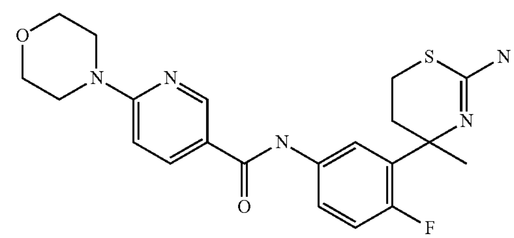 [SMILES: CC1(c2cc(NC(=O)c3ccc(N4CCOCC4)nc3)ccc2F)CCSC(N)=N1] | 420 |
| 245 | 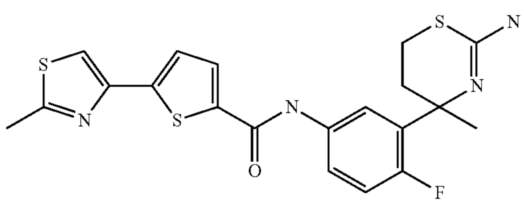 [SMILES: Cc1nc(-c2ccc(C(=O)Nc3ccc(F)c(C4(C)CCSC(N)=N4)c3)s2)cs1] | 383 |
| 246 | 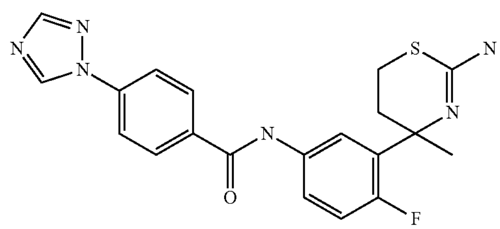 [SMILES: CC1(c2cc(NC(=O)c3ccc(-n4cncn4)cc3)ccc2F)CCSC(N)=N1] | 398 |

TABLE 58

| Compound No. | Structure | MS(M + 1) |
|---|---|---|
| 247 | 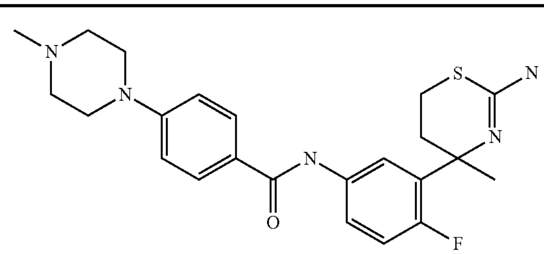 | 455 |

TABLE 58-continued
| Compound No. | Structure | MS(M + 1) |
|---|---|---|
| 248 | 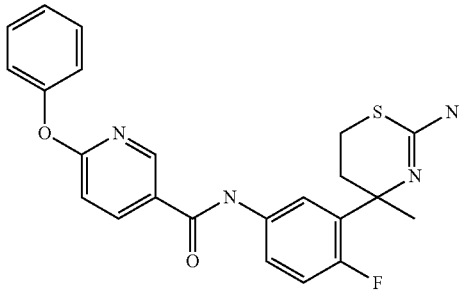 [SMILES: CC1(c2cc(NC(=O)c3ccc(Oc4ccccc4)nc3)ccc2F)CCSC(N)=N1] | 435 |
| 249 | 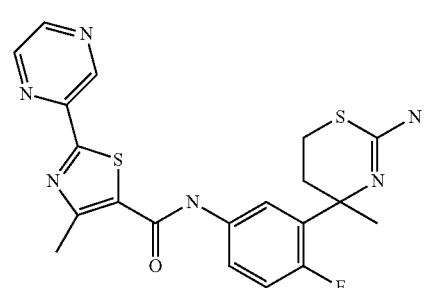 | 416 |
| 250 | 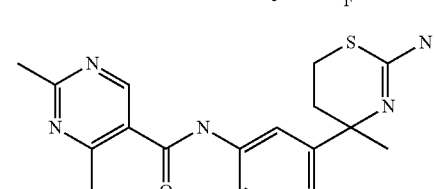 | 416 |
TABLE 59
| Compound No. | Structure | MS(M + 1) |
|---|---|---|
| 251 | 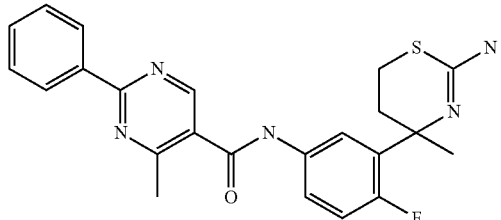 | 402 |
| 252 | 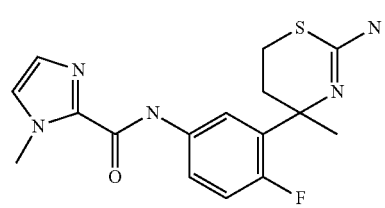 [SMILES: Cn1ccnc1C(=O)Nc1ccc(F)c(C2(C)CCSC(N)=N2)c1] | 388 |

TABLE 59-continued
| Compound No. | Structure | MS(M + 1) |
|---|---|---|
| 253 | 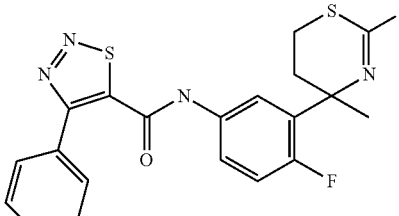 | 420 |
| 254 | 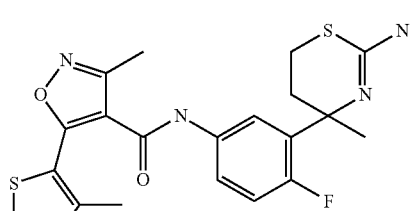 | |
| 255 | 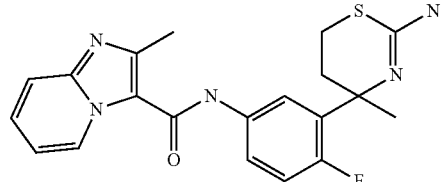 | 524 |
TABLE 60
| Compound No. | Structure | MS(M + 1) |
|---|---|---|
| 256 | 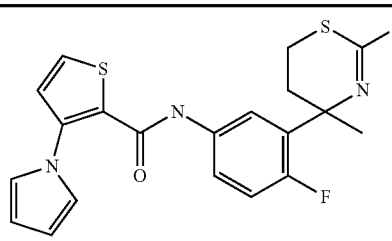 | 348 |
| 257 | 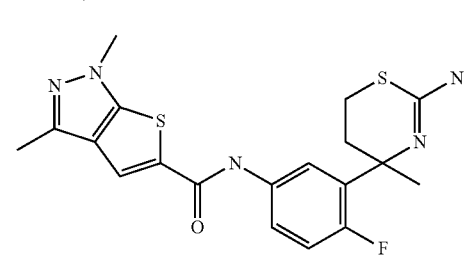 [SMILES: Cc1nn(C)c2sc(C(=O)Nc3ccc(F)c(C4(C)CCSC(N)=N4)c3)cc12] | |
| 258 | 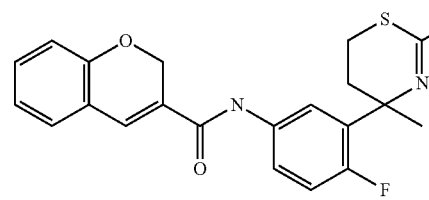 | 395 |

TABLE 60-continued

| Compound No. | Structure | MS(M + 1) |
|---|---|---|
| 259 | 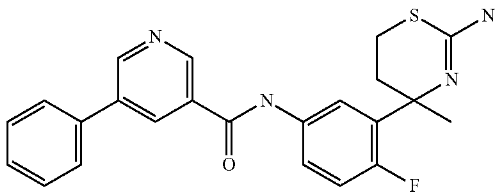 [SMILES: CC1(c2cc(NC(=O)c3cncc(-c4ccccc4)c3)ccc2F)CCSC(N)=N1] | 395 |
| 260 | 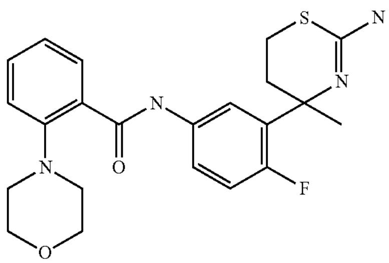 [SMILES: CC1(c2cc(NC(=O)c3ccccc3N3CCOCC3)ccc2F)CCSC(N)=N1] | 402 |

TABLE 61

| Compound No. | Structure | MS(M + 1) |
|---|---|---|
| 261 | 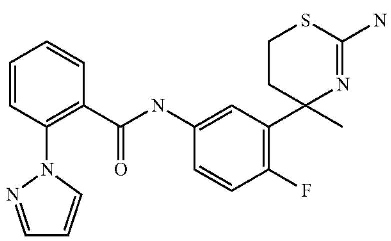 [SMILES: CC1(c2cc(NC(=O)c3ccccc3-n3cccn3)ccc2F)CCSC(N)=N1] | 336 |
| 262 | 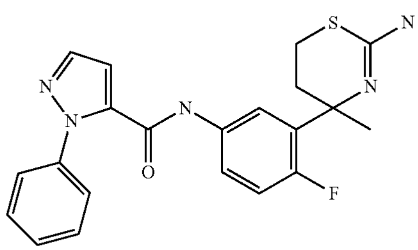 [SMILES: CC1(c2cc(NC(=O)c3ccnn3-c3ccccc3)ccc2F)CCSC(N)=N1] | |
| 263 | 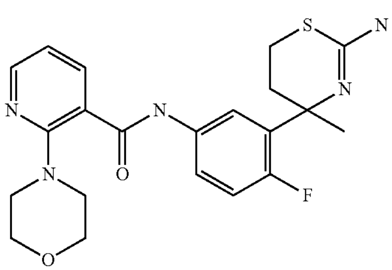 [SMILES: CC1(c2cc(NC(=O)c3cccnc3N3CCOCC3)ccc2F)CCSC(N)=N1] | |

TABLE 61-continued

| Compound No. | Structure | MS(M + 1) |
|---|---|---|
| 264 | 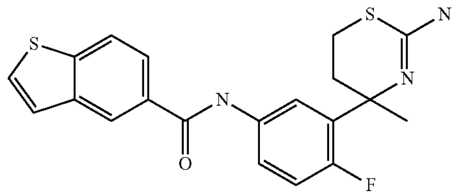 [SMILES: CC1(c2cc(NC(=O)c3ccc4sccc4c3)ccc2F)CCSC(N)=N1] | 334 |
| 265 | 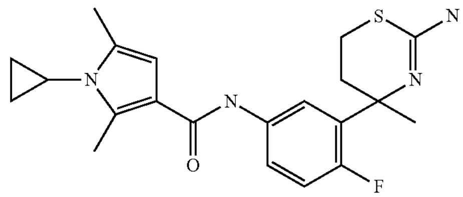 [SMILES: Cc1cc(C(=O)Nc2ccc(F)c(C3(C)CCSC(N)=N3)c2)c(C)n1C1CC1] | 384 |

TABLE 62

| Compound No. | Structure | MS(M + 1) |
|---|---|---|
| 266 | 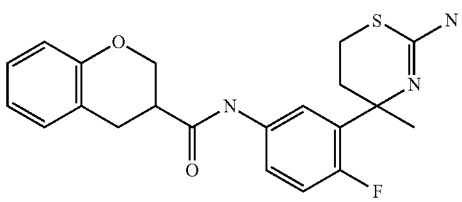 [SMILES: CC1(c2cc(NC(=O)C3COc4ccccc4C3)ccc2F)CCSC(N)=N1] | 402 |
| 267 | 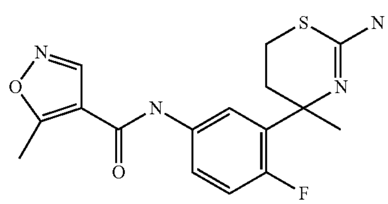 [SMILES: Cc1oncc1C(=O)Nc1ccc(F)c(C2(C)CCSC(N)=N2)c1] | 402 |
| 268 | 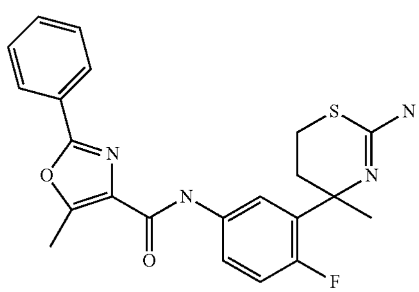 [SMILES: Cc1oc(-c2ccccc2)nc1C(=O)Nc1ccc(F)c(C2(C)CCSC(N)=N2)c1] | |
| 269 | 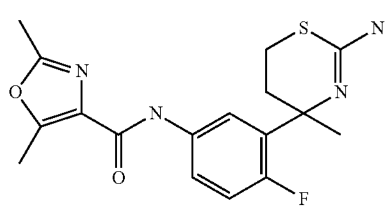 [SMILES: Cc1nc(C(=O)Nc2ccc(F)c(C3(C)CCSC(N)=N3)c2)c(C)o1] | 396 |

TABLE 62-continued

| Compound No. | Structure | MS(M + 1) |
|---|---|---|
| 270 | 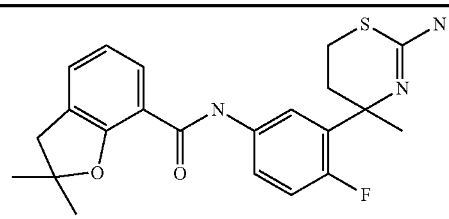 | 427 |

TABLE 63

| Compound No. | Structure | MS(M + 1) |
|---|---|---|
| 271 | 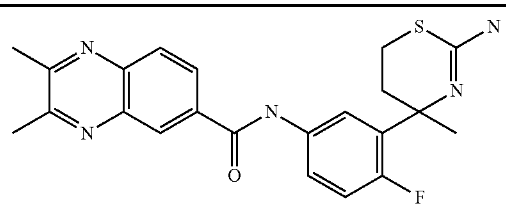 | 444 |
| 272 | 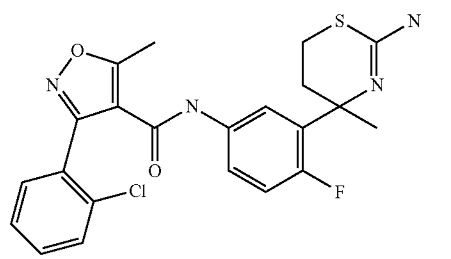 [SMILES: Cc1onc(-c2ccccc2Cl)c1C(=O)Nc1ccc(F)c(C2(C)CCSC(N)=N2)c1] | 416 |
| 273 | 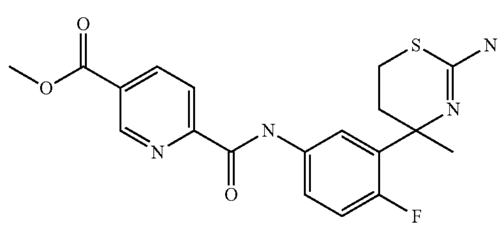 [SMILES: COC(=O)c1ccc(C(=O)Nc2ccc(F)c(C3(C)CCSC(N)=N3)c2)nc1] | 429 |
| 274 | 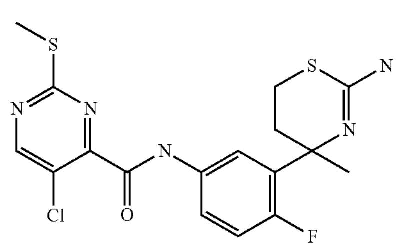 [SMILES: CSc1ncc(Cl)c(C(=O)Nc2ccc(F)c(C3(C)CCSC(N)=N3)c2)n1] | 429 |
| 275 | 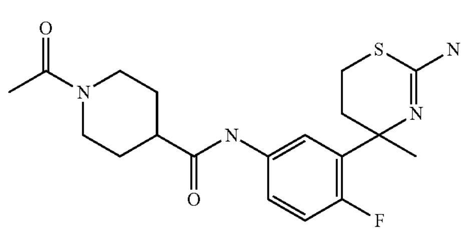 [SMILES: CC(=O)N1CCC(C(=O)Nc2ccc(F)c(C3(C)CCSC(N)=N3)c2)CC1] | 376 |

TABLE 64
| Compound No | Structure | MS(M + 1) |
|---|---|---|
| 276 | 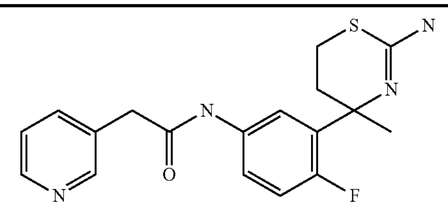 | 425 |
| 277 | 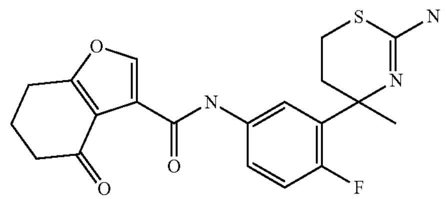 [SMILES: CC1(c2cc(NC(=O)c3coc4c3C(=O)CCC4)ccc2F)CCSC(N)=N1] | 425 |
| 278 | 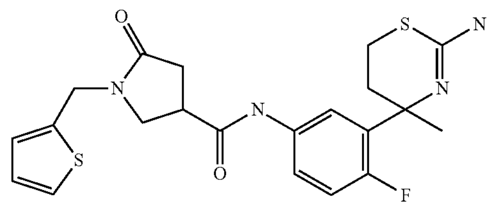 [SMILES: CC1(c2cc(NC(=O)C3CC(=O)N(Cc4cccs4)C3)ccc2F)CCSC(N)=N1] | 429 |
| 279 | 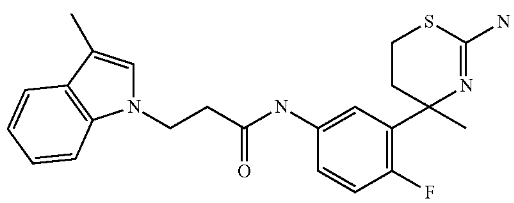 [SMILES: Cc1cn(CCC(=O)Nc2ccc(F)c(C3(C)CCSC(N)=N3)c2)c2ccccc12] | 430 |
| 280 | 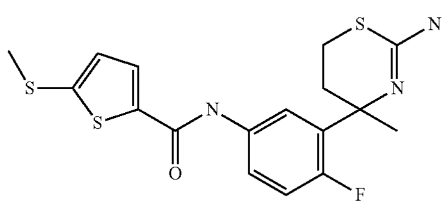 [SMILES: CSc1ccc(C(=O)Nc2ccc(F)c(C3(C)CCSC(N)=N3)c2)s1] | 425 |
TABLE 65
| Compound No | Structure | MS (M + 1) |
|---|---|---|
| 281 | 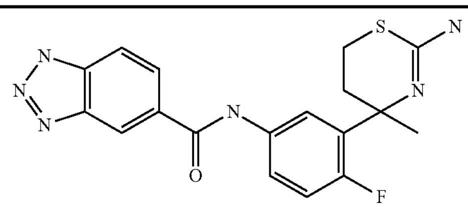 | 448 |
| 282 | 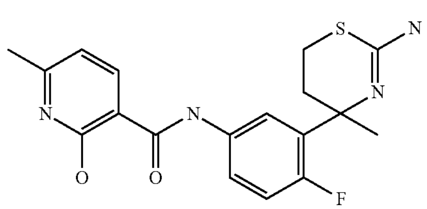 [SMILES: Cc1ccc(C(=O)Nc2ccc(F)c(C3(C)CCSC(N)=N3)c2)c(O)n1] | 411 |
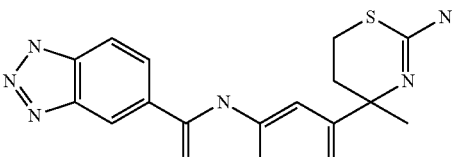

TABLE 65-continued

| Compound No | Structure | MS (M + 1) |
|---|---|---|
| 283 | 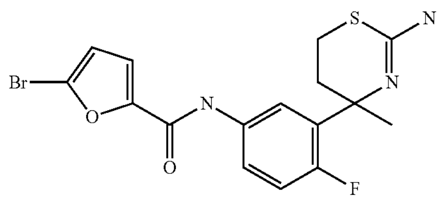 [SMILES: CC1(c2cc(NC(=O)c3ccc(Br)o3)ccc2F)CCSC(N)=N1] | |
| 284 | 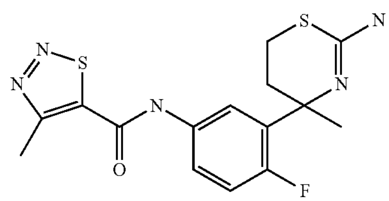 [SMILES: Cc1nnsc1C(=O)Nc1ccc(F)c(C2(C)CCSC(N)=N2)c1] | 438 |
| 285 | 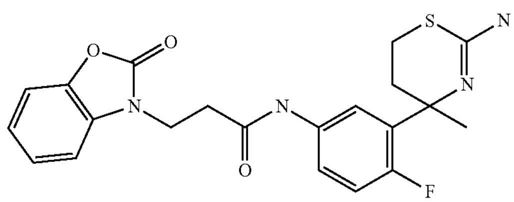 [SMILES: CC1(c2cc(NC(=O)CCn3c(=O)oc4ccccc43)ccc2F)CCSC(N)=N1] | 30 |

TABLE 66

| Compound No. | Structure | MS (M + 1) |
|---|---|---|
| 286 | 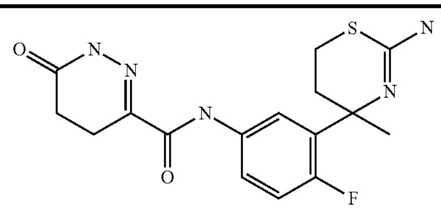 | 437 |
| 287 | 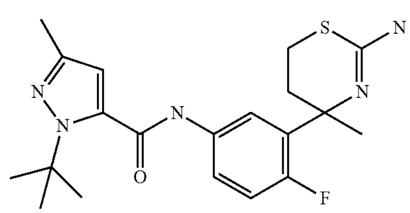 [SMILES: Cc1cc(C(=O)Nc2ccc(F)c(C3(C)CCSC(N)=N3)c2)n(C(C)(C)C)n1] | 437 |
| 288 | 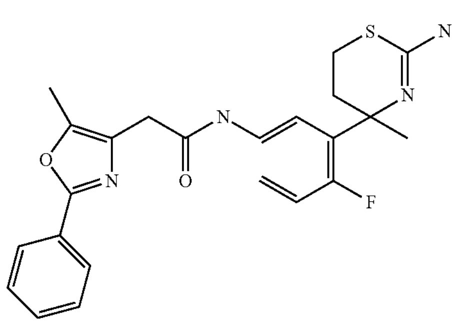 [SMILES: C=C/C(F)=C(\C=C\NC(=O)Cc1nc(-c2ccccc2)oc1C)C1(C)CCSC(N)=N1] | 348 |

TABLE 66-continued

| Compound No. | Structure | MS (M + 1) |
|---|---|---|
| 289 | 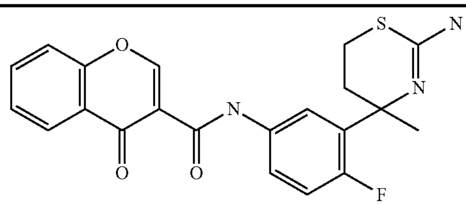 | 429 |
| 290 | 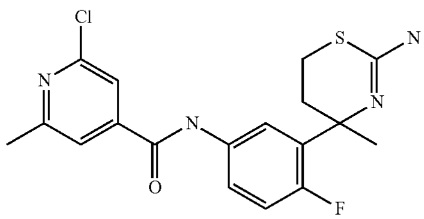 | 448 |

TABLE 67

| Compound No. | Structure | MS (M + 1) |
|---|---|---|
| 291 | 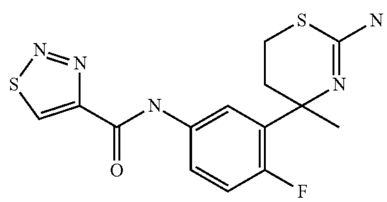 [SMILES: CC1(c2cc(NC(=O)c3csnn3)ccc2F)CCSC(N)=N1] | 398 |
| 292 | 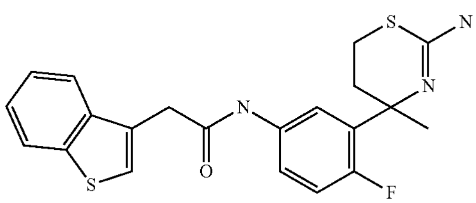 [SMILES: CC1(c2cc(NC(=O)Cc3csc4ccccc34)ccc2F)CCSC(N)=N1] | |
| 293 | 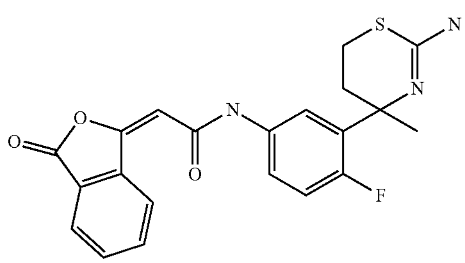 [SMILES: CC1(c2cc(NC(=O)/C=C3/OC(=O)c4ccccc43)ccc2F)CCSC(N)=N1] | 419 |
| 294 | 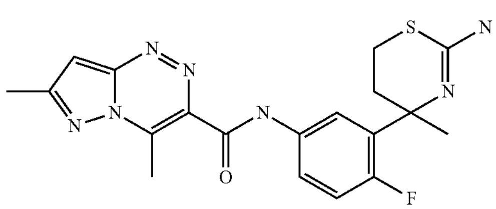 [SMILES: Cc1cc2nnc(C(=O)Nc3ccc(F)c(C4(C)CCSC(N)=N4)c3)c(C)n2n1] | |

TABLE 67-continued

| Compound No. | Structure | MS (M + 1) |
|---|---|---|
| 295 | 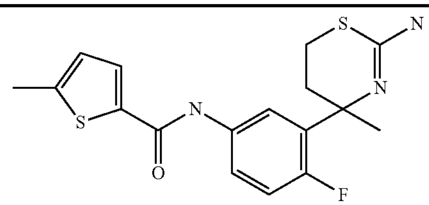 | 422 |

TABLE 68

| Compound No. | Structure | MS (M + 1) |
|---|---|---|
| 296 | 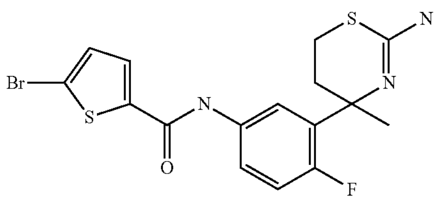 [SMILES: CC1(c2cc(NC(=O)c3ccc(Br)s3)ccc2F)CCSC(N)=N1] | 430 |
| 297 | 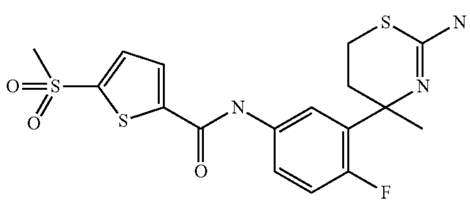 [SMILES: CC1(c2cc(NC(=O)c3ccc(S(C)(=O)=O)s3)ccc2F)CCSC(N)=N1] | 410 |
| 298 | 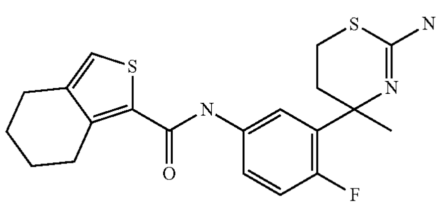 [SMILES: CC1(c2cc(NC(=O)c3scc4c3CCCC4)ccc2F)CCSC(N)=N1] | 410 |
| 299 | 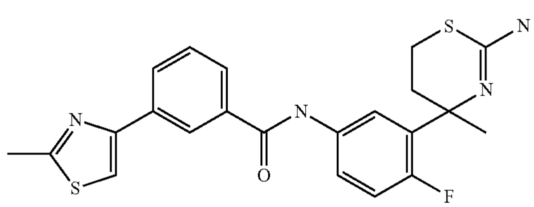 [SMILES: Cc1nc(-c2cccc(C(=O)Nc3ccc(F)c(C4(C)CCSC(N)=N4)c3)c2)cs1] | |
| 300 | 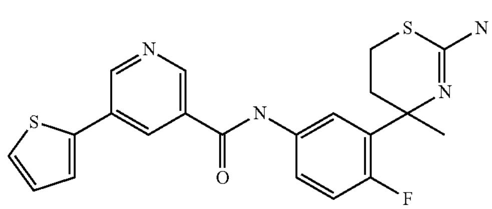 [SMILES: CC1(c2cc(NC(=O)c3cncc(-c4cccs4)c3)ccc2F)CCSC(N)=N1] | 401 |

TABLE 69

| Compound No. | Structure | MS (M + 1) |
| --- | --- | --- |
| 301 | 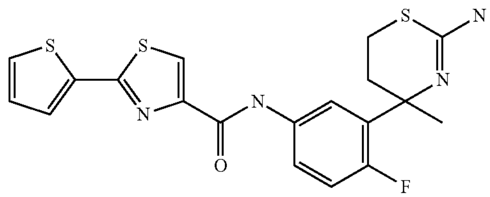 [SMILES: CC1(c2cc(NC(=O)c3csc(-c4cccs4)n3)ccc2F)CCSC(N)=N1] | |
| 302 | 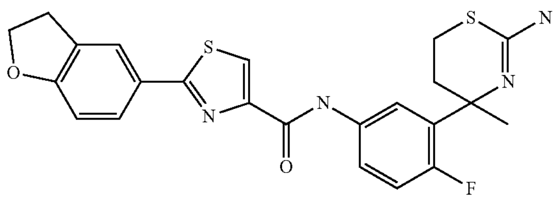 [SMILES: CC1(c2cc(NC(=O)c3csc(-c4ccc5c(c4)CCO5)n3)ccc2F)CCSC(N)=N1] | 400 |
| 303 | 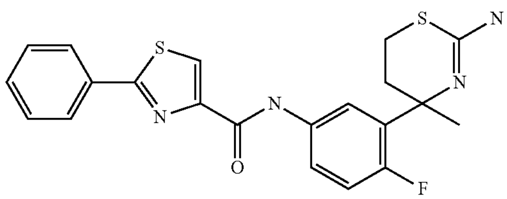 [SMILES: CC1(c2cc(NC(=O)c3csc(-c4ccccc4)n3)ccc2F)CCSC(N)=N1] | 349 |
| 304 | 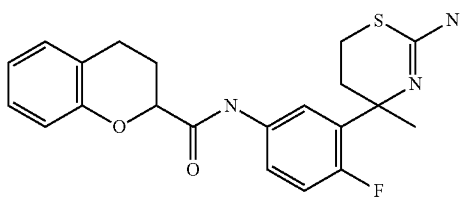 [SMILES: CC1(c2cc(NC(=O)C3CCc4ccccc4O3)ccc2F)CCSC(N)=N1] | 426 |
| 305 | 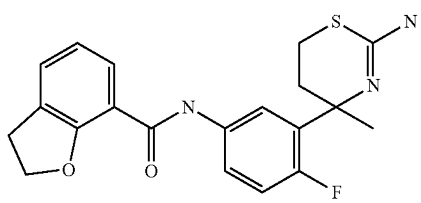 [SMILES: CC1(c2cc(NC(=O)c3cccc4c3OCC4)ccc2F)CCSC(N)=N1] | 363 |

TABLE 70

| Compound No. | Structure | MS (M + 1) |
| --- | --- | --- |
| 306 | 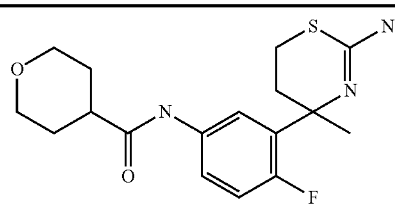 | 415 |
| 307 | 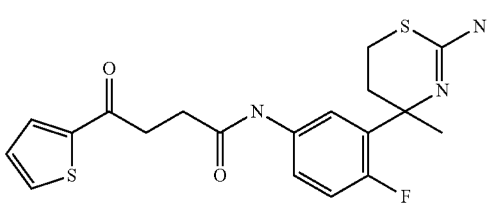 [SMILES: CC1(c2cc(NC(=O)CCC(=O)c3cccs3)ccc2F)CCSC(N)=N1] | |

TABLE 70-continued

| Compound No. | Structure | MS (M + 1) |
|---|---|---|
| 308 | 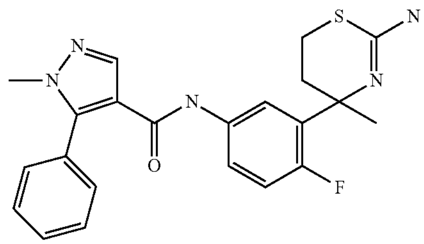 [SMILES: Cn1ncc(C(=O)Nc2ccc(F)c(C3(C)CCSC(N)=N3)c2)c1-c1ccccc1] | 424 |
| 309 | 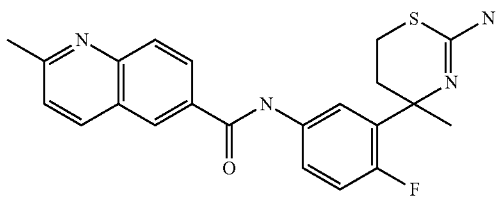 [SMILES: Cc1ccc2cc(C(=O)Nc3ccc(F)c(C4(C)CCSC(N)=N4)c3)ccc2n1] | 406 |
| 310 | 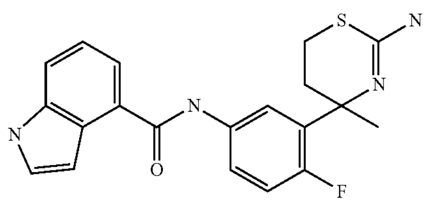 [SMILES: CC1(c2cc(NC(=O)c3cccc4[nH]ccc34)ccc2F)CCSC(N)=N1] | 383 |

TABLE 71

| Compound No. | Structure | MS (M + 1) |
|---|---|---|
| 311 | 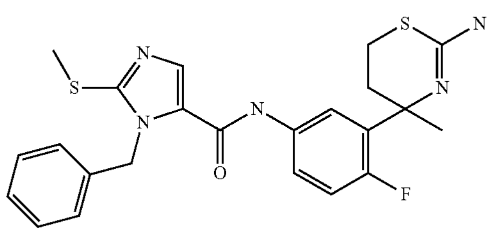 [SMILES: CSc1ncc(C(=O)Nc2ccc(F)c(C3(C)CCSC(N)=N3)c2)n1Cc1ccccc1] | 470 |
| 312 | 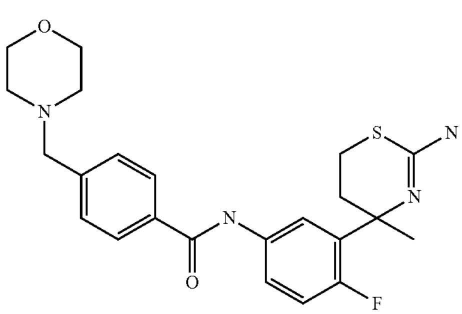 [SMILES: CC1(c2cc(NC(=O)c3ccc(CN4CCOCC4)cc3)ccc2F)CCSC(N)=N1] | 422 |

TABLE 71-continued

| Compound No. | Structure | MS (M + 1) |
|---|---|---|
| 313 | 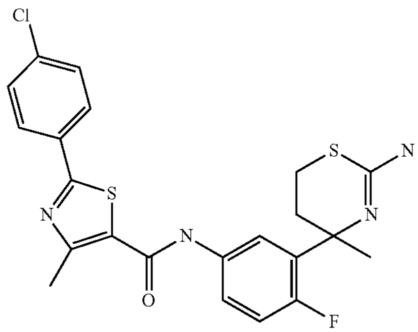 [SMILES: Cc1nc(-c2ccc(Cl)cc2)sc1C(=O)Nc1ccc(F)c(C2(C)CCSC(N)=N2)c1] | 476 |
| 314 | 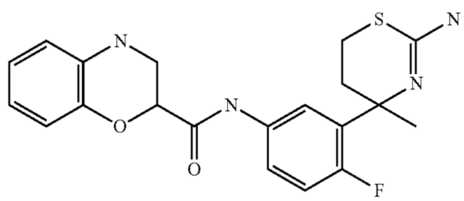 [SMILES: CC1(c2cc(NC(=O)C3CNc4ccccc4O3)ccc2F)CCSC(N)=N1] | 401 |
| 315 | 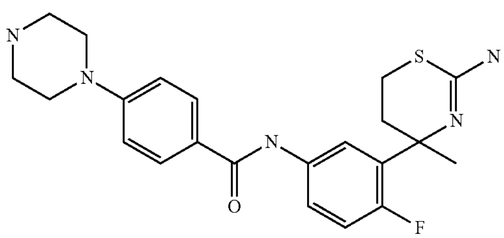 [SMILES: CC1(c2cc(NC(=O)c3ccc(N4CCNCC4)cc3)ccc2F)CCSC(N)=N1] | 428 |

TABLE 72

| Compound No. | Structure | MS (M + 1) |
|---|---|---|
| 316 | 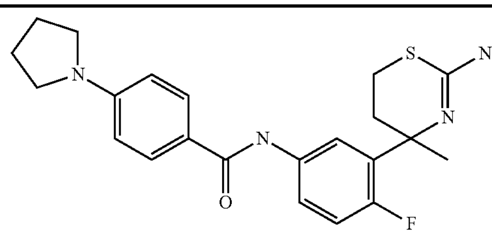 | 413 |
| 317 | 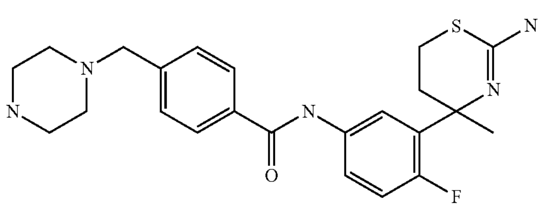 [SMILES: CC1(c2cc(NC(=O)c3ccc(CN4CCNCC4)cc3)ccc2F)CCSC(N)=N1] | 442 |
| 318 | 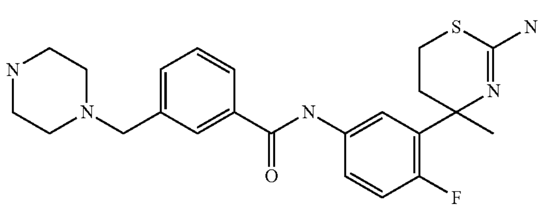 | 442 |

TABLE 72-continued

| Compound No. | Structure | MS (M + 1) |
|---|---|---|
| 319 | 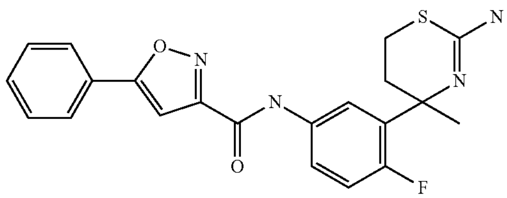 [SMILES: CC1(c2cc(NC(=O)c3cc(-c4ccccc4)on3)ccc2F)CCSC(N)=N1] | 411 |
| 320 | 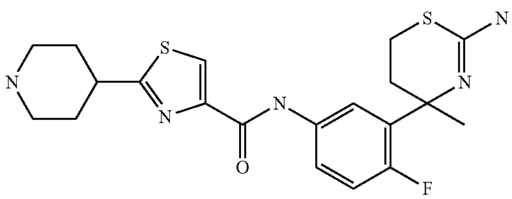 [SMILES: CC1(c2cc(NC(=O)c3csc(C4CCNCC4)n3)ccc2F)CCSC(N)=N1] | 434 |

TABLE 73

| Compound No. | Structure | MS (M + 1) |
|---|---|---|
| 321 | 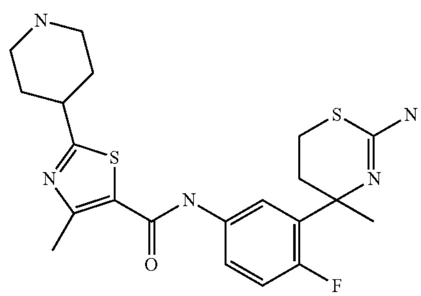 [SMILES: Cc1nc(C2CCNCC2)sc1C(=O)Nc1ccc(F)c(C2(C)CCSC(N)=N2)c1] | |
| 322 | 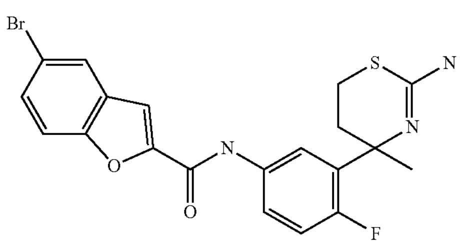 [SMILES: CC1(c2cc(NC(=O)c3cc4cc(Br)ccc4o3)ccc2F)CCSC(N)=N1] | 463 |
| 323 | 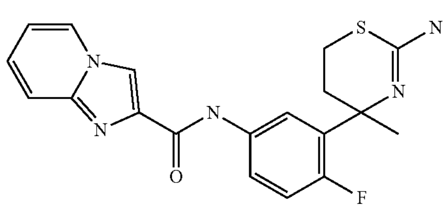 [SMILES: CC1(c2cc(NC(=O)c3cn4ccccc4n3)ccc2F)CCSC(N)=N1] | |
| 324 | 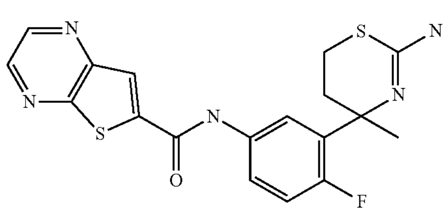 [SMILES: CC1(c2cc(NC(=O)c3cc4nccnc4s3)ccc2F)CCSC(N)=N1] | |

TABLE 73-continued

| Compound No. | Structure | MS (M + 1) |
|---|---|---|
| 325 | 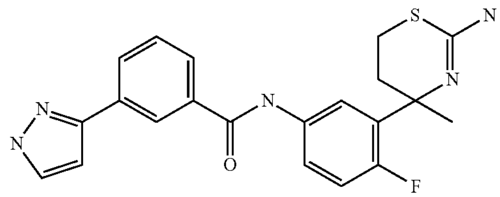 [SMILES: CC1(c2cc(NC(=O)c3cccc(-c4cc[nH]n4)c3)ccc2F)CCSC(N)=N1] | 410 |

TABLE 74

| Compound No. | Structure | MS (M + 1) |
|---|---|---|
| 326 | 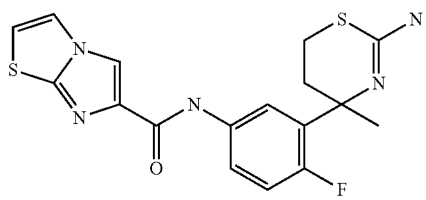 [SMILES: CC1(c2cc(NC(=O)c3cn4ccsc4n3)ccc2F)CCSC(N)=N1] | 390 |
| 327 | 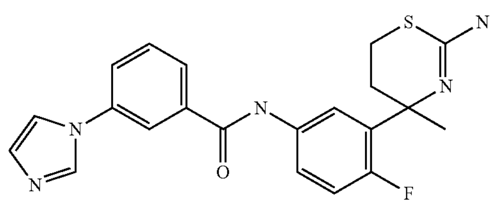 [SMILES: CC1(c2cc(NC(=O)c3cccc(-n4ccnc4)c3)ccc2F)CCSC(N)=N1] | 410 |
| 328 | 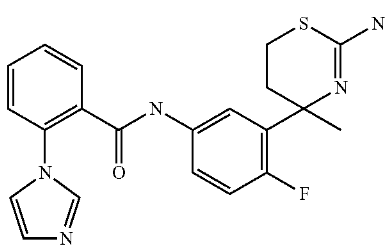 [SMILES: CC1(c2cc(NC(=O)c3ccccc3-n3ccnc3)ccc2F)CCSC(N)=N1] | 410 |
| 329 | 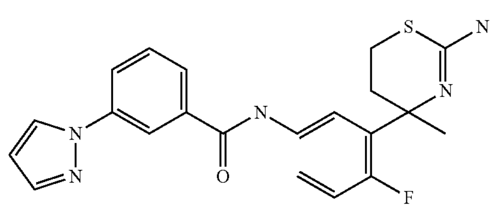 [SMILES: C=C/C(F)=C(\C=C\NC(=O)c1cccc(-n2cccn2)c1)C1(C)CCSC(N)=N1] | 410 |
| 330 | 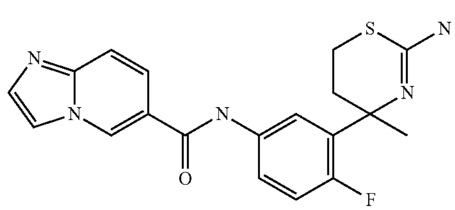 [SMILES: CC1(c2cc(NC(=O)c3ccc4nccn4c3)ccc2F)CCSC(N)=N1] | 384 |

TABLE 75

| Compound No. | Structure | MS (M + 1) |
|---|---|---|
| 331 | 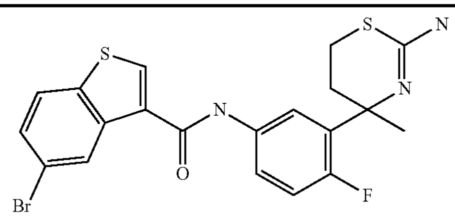 | 479 |
| 332 | 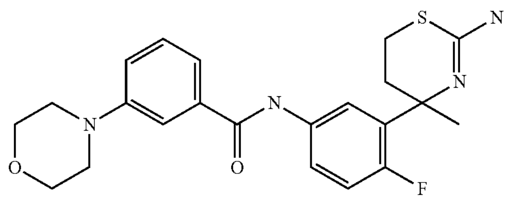 [SMILES: CC1(c2cc(NC(=O)c3cccc(N4CCOCC4)c3)ccc2F)CCSC(N)=N1] | 429 |
| 333 | 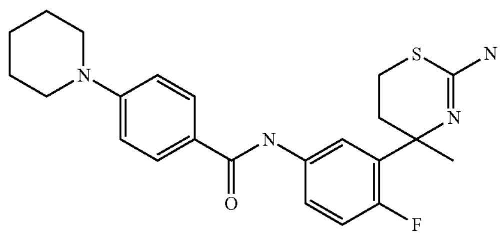 [SMILES: CC1(c2cc(NC(=O)c3ccc(N4CCCCC4)cc3)ccc2F)CCSC(N)=N1] | 427 |
| 334 | 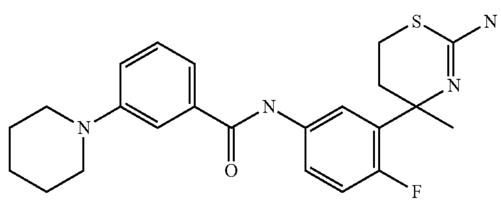 [SMILES: CC1(c2cc(NC(=O)c3cccc(N4CCCCC4)c3)ccc2F)CCSC(N)=N1] | 427 |
| 335 | 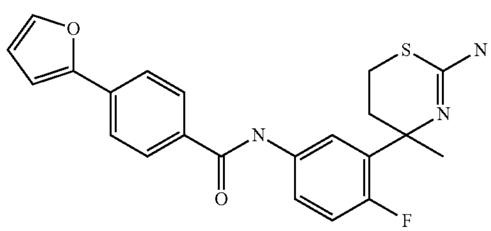 [SMILES: CC1(c2cc(NC(=O)c3ccc(-c4ccco4)cc3)ccc2F)CCSC(N)=N1] | 410 |

TABLE 76

| Compound No. | Structure | MS (M + 1) |
|---|---|---|
| 336 | 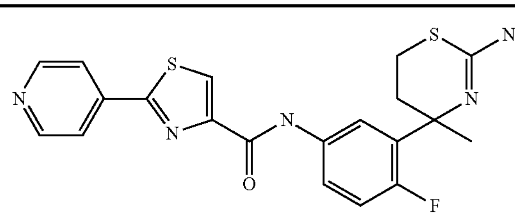 | 428 |

TABLE 76-continued
| Compound No. | Structure | MS (M + 1) |
|---|---|---|
| 337 | 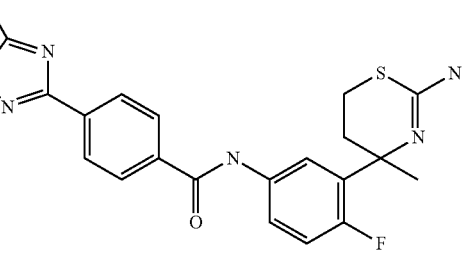 | 426 |
| 338 | 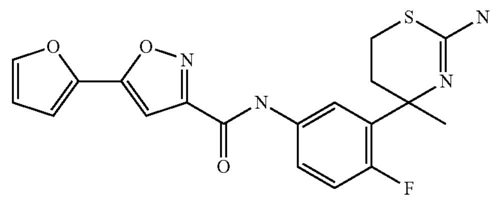 [SMILES: CC1(c2cc(NC(=O)c3cc(-c4ccco4)on3)ccc2F)CCSC(N)=N1] | 401 |
| 339 | 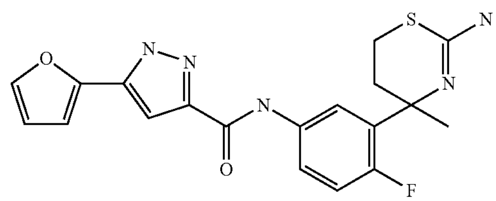 [SMILES: CC1(c2cc(NC(=O)c3cc(-c4ccco4)[nH]n3)ccc2F)CCSC(N)=N1] | 400 |
| 340 | 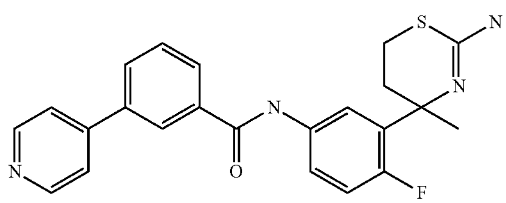 [SMILES: CC1(c2cc(NC(=O)c3cccc(-c4ccncc4)c3)ccc2F)CCSC(N)=N1] | 40 |
TABLE 77
| Compound No. | Structure | MS (M + 1) |
|---|---|---|
| 341 | 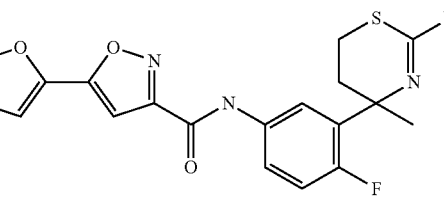 | 441 |
| 342 | 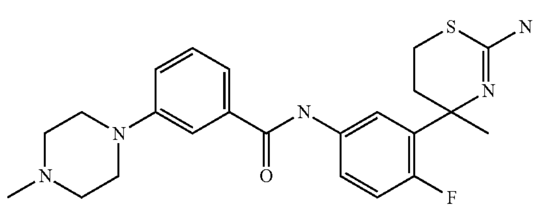 [SMILES: CN1CCN(c2cccc(C(=O)Nc3ccc(F)c(C4(C)CCSC(N)=N4)c3)c2)CC1] | 442 |

TABLE 77-continued

| Compound No. | Structure | MS (M + 1) |
|---|---|---|
| 343 | 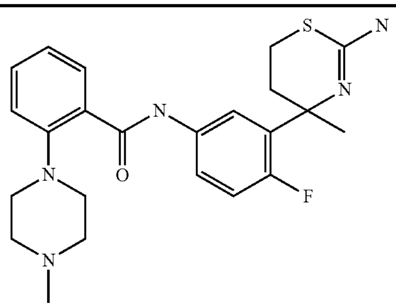 | 442 |
| 344 | 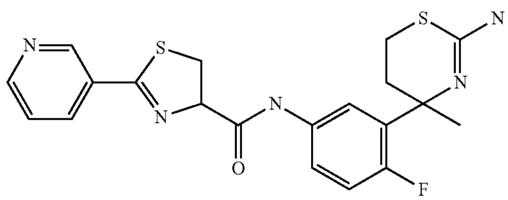 [SMILES: CC1(c2cc(NC(=O)C3CSC(c4cccnc4)=N3)ccc2F)CCSC(N)=N1] | 430 |
| 345 | 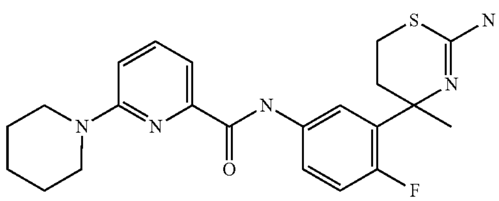 [SMILES: CC1(c2cc(NC(=O)c3cccc(N4CCCCC4)n3)ccc2F)CCSC(N)=N1] | 428 |

TABLE 78

| Compound No. | Structure | MS (M + 1) |
|---|---|---|
| 346 | 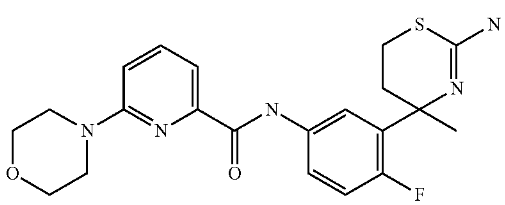 [SMILES: CC1(c2cc(NC(=O)c3cccc(N4CCOCC4)n3)ccc2F)CCSC(N)=N1] | 430 |
| 347 | 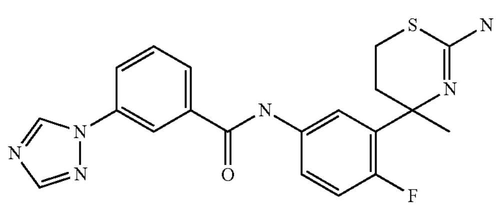 [SMILES: CC1(c2cc(NC(=O)c3cccc(-n4cncn4)c3)ccc2F)CCSC(N)=N1] | 411 |
| 348 | 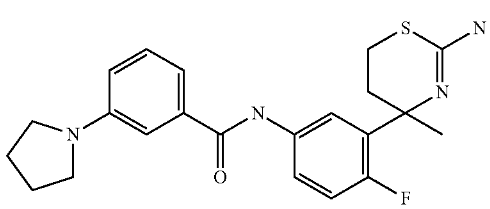 [SMILES: CC1(c2cc(NC(=O)c3cccc(N4CCCC4)c3)ccc2F)CCSC(N)=N1] | 413 |

TABLE 78-continued

| Compound No. | Structure | MS (M + 1) |
|---|---|---|
| 349 | 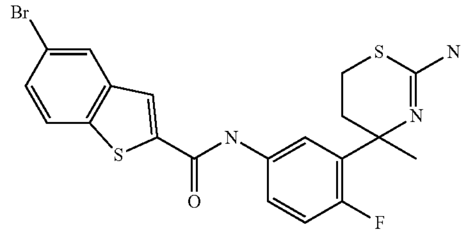 [SMILES: CC1(c2cc(NC(=O)c3cc4cc(Br)ccc4s3)ccc2F)CCSC(N)=N1] | 478 |
| 350 | 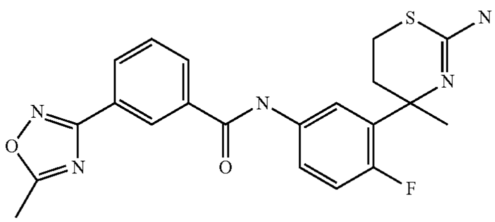 [SMILES: Cc1nc(-c2cccc(C(=O)Nc3ccc(F)c(C4(C)CCSC(N)=N4)c3)c2)no1] | |

TABLE 79

| Compound No. | Structure | MS (M + 1) |
|---|---|---|
| 351 | 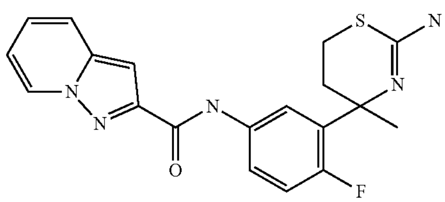 [SMILES: CC1(c2cc(NC(=O)c3cc4ccccn4n3)ccc2F)CCSC(N)=N1] | 384 |
| 352 | 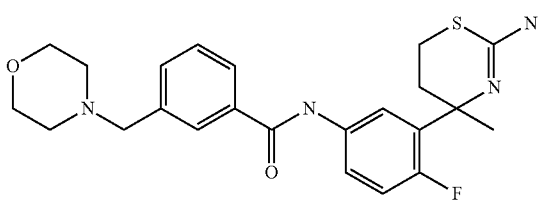 [SMILES: CC1(c2cc(NC(=O)c3cccc(CN4CCOCC4)c3)ccc2F)CCSC(N)=N1] | 443 |
| 353 | 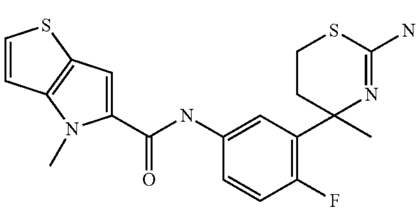 [SMILES: Cn1c(C(=O)Nc2ccc(F)c(C3(C)CCSC(N)=N3)c2)cc2sccc21] | 403 |
| 354 | 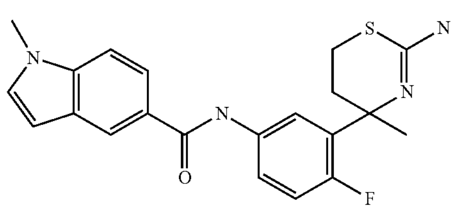 [SMILES: Cn1ccc2cc(C(=O)Nc3ccc(F)c(C4(C)CCSC(N)=N4)c3)ccc21] | |

TABLE 79-continued

| Compound No. | Structure | MS (M + 1) |
|---|---|---|
| 355 | 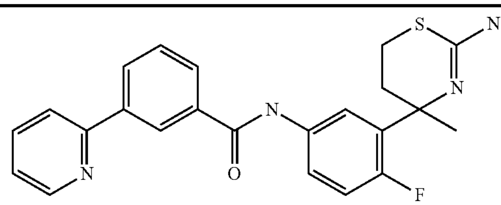 | 421 |

TABLE 8

| Compound No. | Structure | MS (M + 1) |
|---|---|---|
| 356 | 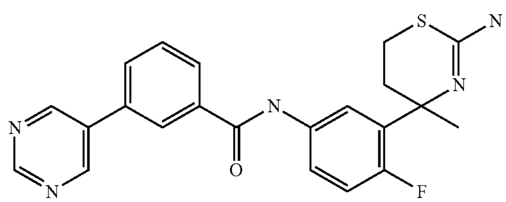 [SMILES: CC1(c2cc(NC(=O)c3cccc(-c4cncnc4)c3)ccc2F)CCSC(N)=N1] | 422 |
| 357 | 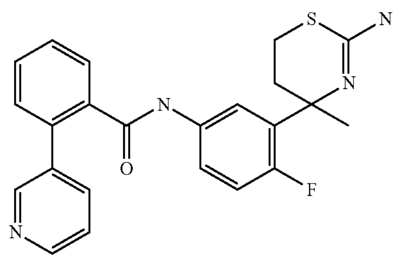 [SMILES: CC1(c2cc(NC(=O)c3ccccc3-c3cccnc3)ccc2F)CCSC(N)=N1] | 421 |
| 358 | 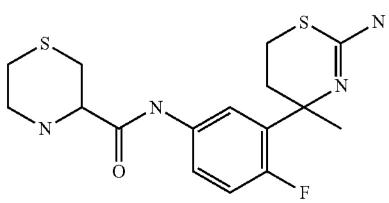 [SMILES: CC1(c2cc(NC(=O)C3CSCCN3)ccc2F)CCSC(N)=N1] | 369 |
| 359 | 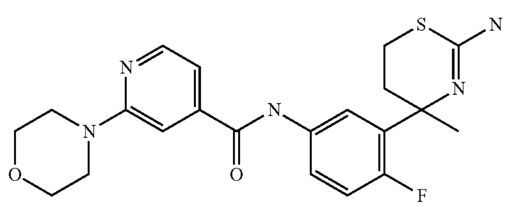 | 430 |
| 360 | 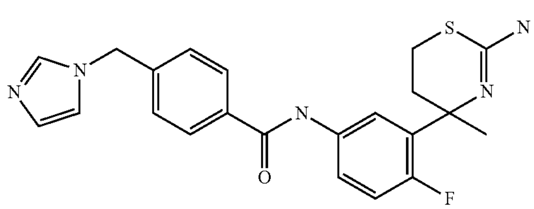 [SMILES: CC1(c2cc(NC(=O)c3ccc(Cn4ccnc4)cc3)ccc2F)CCSC(N)=N1] | 424 |

TABLE 81
| Compound No. | Structure | MS (M + 1) |
|---|---|---|
| 361 | 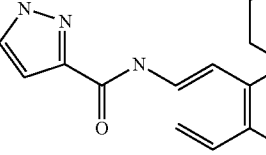 | 416 |
| 362 | 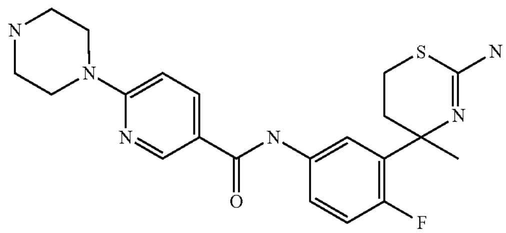 | 429 |
| 363 | 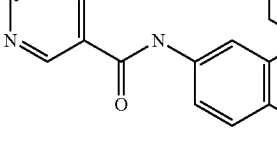 | |
| 364 | 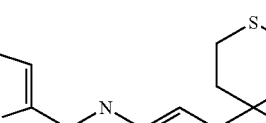 | |
| 365 | 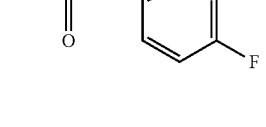 | 398 |
TABLE 82
| Compound No. | Structure | MS (M + 1) |
|---|---|---|
| 366 | 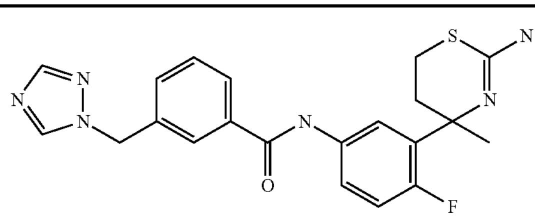 | 425 |

TABLE 82-continued

| Compound No. | Structure | MS (M + 1) |
| --- | --- | --- |
| 367 | 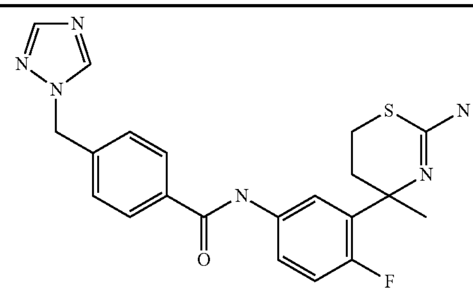 | 425 |
| 368 | 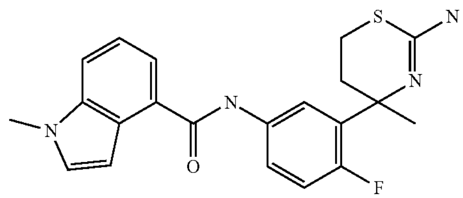 [SMILES: Cn1ccc2c(C(=O)Nc3ccc(F)c(C4(C)CCSC(N)=N4)c3)cccc21] | |
| 369 | 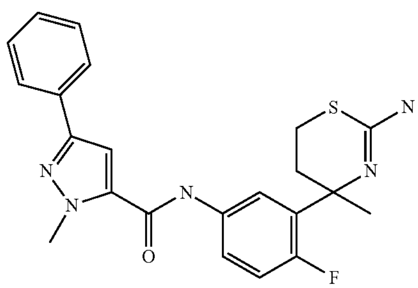 [SMILES: Cn1nc(-c2ccccc2)cc1C(=O)Nc1ccc(F)c(C2(C)CCSC(N)=N2)c1] | 424 |

TABLE 83

| Compound No. | Structure | MS (M + 1) |
| --- | --- | --- |
| 370 | 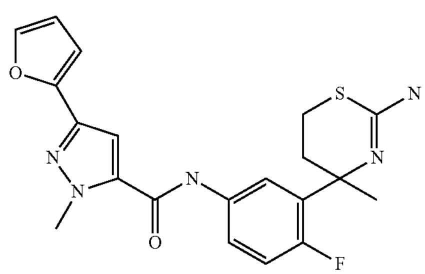 [SMILES: Cn1nc(-c2ccco2)cc1C(=O)Nc1ccc(F)c(C2(C)CCSC(N)=N2)c1] | 413 |
| 371 | 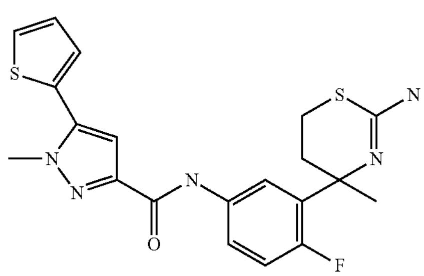 [SMILES: Cn1nc(C(=O)Nc2ccc(F)c(C3(C)CCSC(N)=N3)c2)cc1-c1cccs1] | 430 |

TABLE 83-continued

| Compound No. | Structure | MS (M + 1) |
|---|---|---|
| 372 | 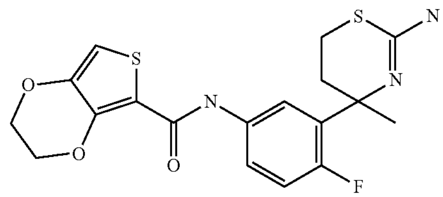 [SMILES: CC1(c2cc(NC(=O)c3scc4c3OCCO4)ccc2F)CCSC(N)=N1] | 408 |
| 373 | 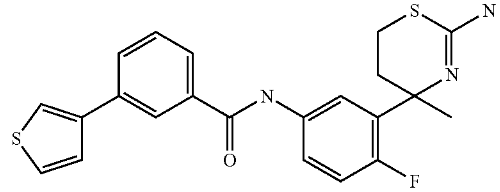 [SMILES: CC1(c2cc(NC(=O)c3cccc(-c4ccsc4)c3)ccc2F)CCSC(N)=N1] | 426 |
| 374 | 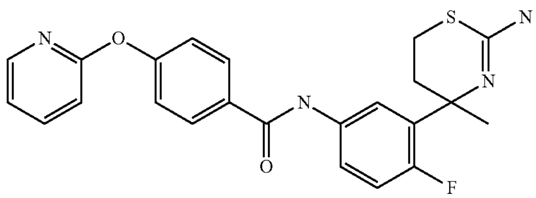 [SMILES: CC1(c2cc(NC(=O)c3ccc(Oc4ccccn4)cc3)ccc2F)CCSC(N)=N1] | 437 |

TABLE 84

| Compound No. | Structure | MS (M + 1) |
|---|---|---|
| 375 | 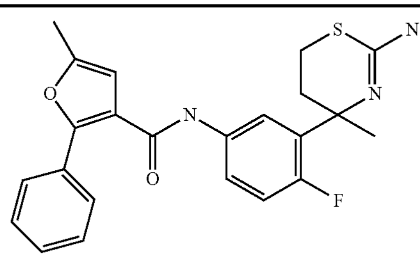 | 424 |
| 376 | 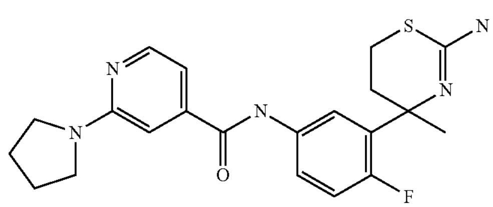 [SMILES: CC1(c2cc(NC(=O)c3ccnc(N4CCCC4)c3)ccc2F)CCSC(N)=N1] | |
| 377 | 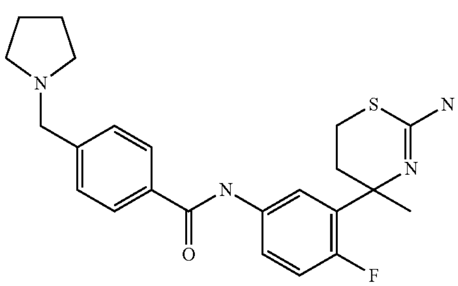 [SMILES: CC1(c2cc(NC(=O)c3ccc(CN4CCCC4)cc3)ccc2F)CCSC(N)=N1] | 427 |

TABLE 84-continued

| Compound No. | Structure | MS (M + 1) |
|---|---|---|
| 378 | 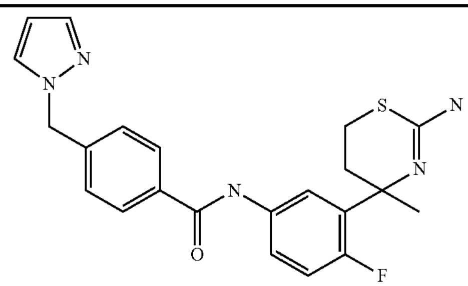 | 424 |

TABLE 85

| Compound No. | Structure | MS (M + 1) |
|---|---|---|
| 379 | 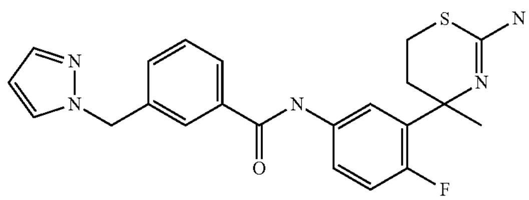 [SMILES: CC1(c2cc(NC(=O)c3cccc(Cn4cccn4)c3)ccc2F)CCSC(N)=N1] | 424 |
| 380 | 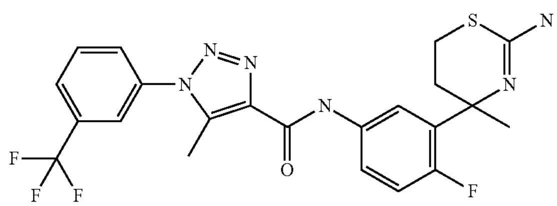 [SMILES: Cc1c(C(=O)Nc2ccc(F)c(C3(C)CCSC(N)=N3)c2)nnn1-c1cccc(C(F)(F)F)c1] | 493 |
| 381 | 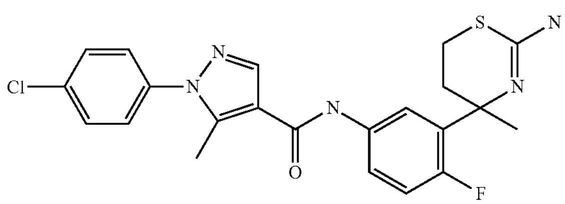 [SMILES: Cc1c(C(=O)Nc2ccc(F)c(C3(C)CCSC(N)=N3)c2)cnn1-c1ccc(Cl)cc1] | 458 |
| 382 | 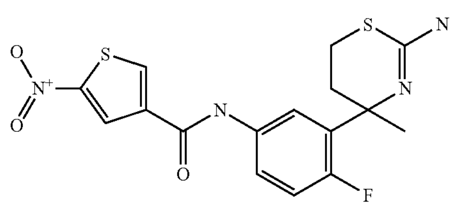 | 395 |
| 383 | 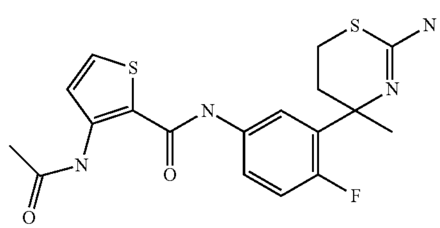 [SMILES: CC(=O)Nc1ccsc1C(=O)Nc1ccc(F)c(C2(C)CCSC(N)=N2)c1] | 407 |

TABLE 86
| Compound No. | Structure | MS (M + 1) |
|---|---|---|
| 384 | 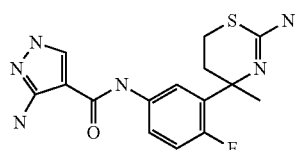 | 416 |
| 385 | 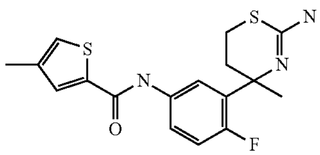 [SMILES: Cc1csc(C(=O)Nc2ccc(F)c(C3(C)CCSC(N)=N3)c2)c1] | 364 |
| 386 | 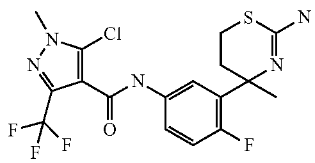 [SMILES: Cn1nc(C(F)(F)F)c(C(=O)Nc2ccc(F)c(C3(C)CCSC(N)=N3)c2)c1Cl] | |
TABLE 86-continued
| Compound No. | Structure | MS (M + 1) |
|---|---|---|
| 387 | 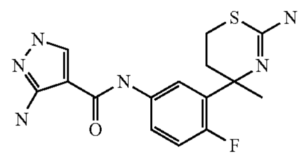 [SMILES: CC1(c2cc(NC(=O)c3c[nH]nc3N)ccc2F)CCSC(N)=N1] | |
| 388 | 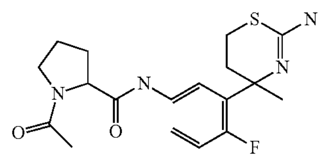 [SMILES: C=C/C(F)=C(\C=C\NC(=O)C1CCCN1C(C)=O)C1(C)CCSC(N)=N1] | |
TABLE 87
| Compound No. | Structure | MS (M + 1) |
|---|---|---|
| 389 | 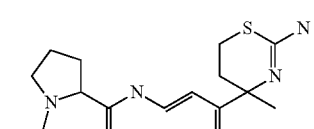 | |
| 390 | 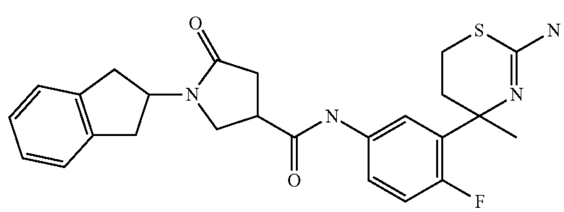 [SMILES: CC1(c2cc(NC(=O)C3CC(=O)N(C4Cc5ccccc5C4)C3)ccc2F)CCSC(N)=N1] | |
| 391 | 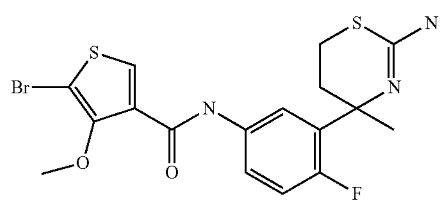 [SMILES: COc1c(C(=O)Nc2ccc(F)c(C3(C)CCSC(N)=N3)c2)csc1Br] | |
| 392 | 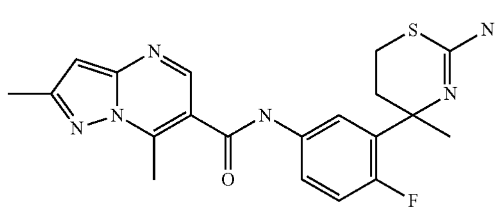 [SMILES: Cc1cc2ncc(C(=O)Nc3ccc(F)c(C4(C)CCSC(N)=N4)c3)c(C)n2n1] | 413 |

TABLE 87-continued

| Compound No. | Structure | MS (M + 1) |
|---|---|---|
| 393 | 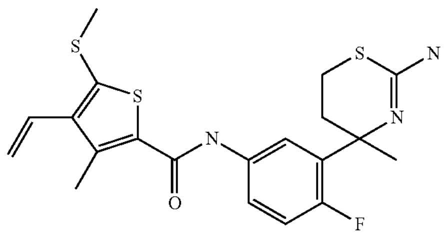 [SMILES: C=Cc1c(SC)sc(C(=O)Nc2ccc(F)c(C3(C)CCSC(N)=N3)c2)c1C] | 446 |

TABLE 88

| Compound No. | Structure | MS (M + 1) |
|---|---|---|
| 394 | 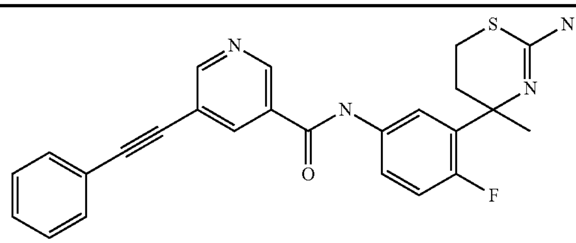 | 445 |
| 395 | 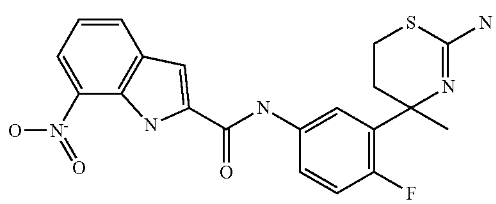 | 428 |
| 396 | 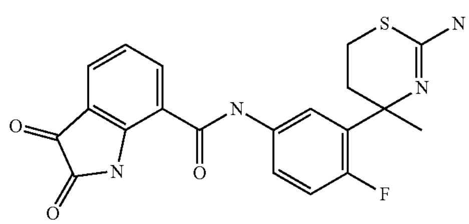 [SMILES: CC1(c2cc(NC(=O)c3cccc4c3NC(=O)C4=O)ccc2F)CCSC(N)=N1] | 413 |
| 397 | 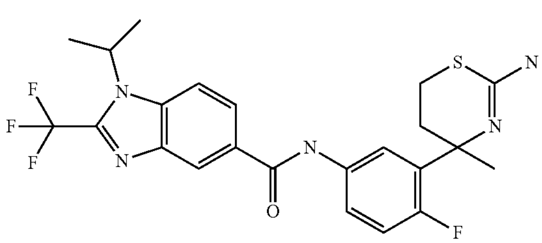 [SMILES: CC(C)n1c(C(F)(F)F)nc2cc(C(=O)Nc3ccc(F)c(C4(C)CCSC(N)=N4)c3)ccc21] | 494 |
| 398 | 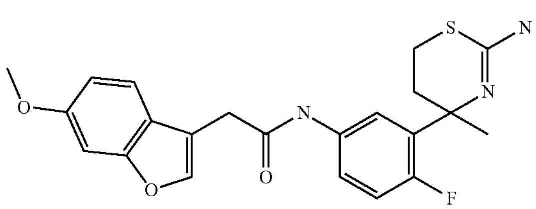 [SMILES: COc1ccc2c(CC(=O)Nc3ccc(F)c(C4(C)CCSC(N)=N4)c3)coc2c1] | 428 |

TABLE 89

| Compound No. | Structure | MS (M + 1) |
|---|---|---|
| 399 | 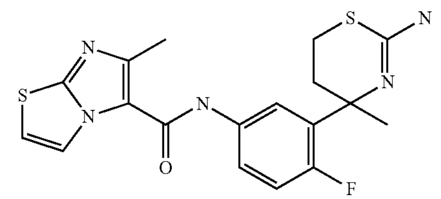 [SMILES: Cc1nc2sccn2c1C(=O)Nc1ccc(F)c(C2(C)CCSC(N)=N2)c1] | 404 |
| 400 | 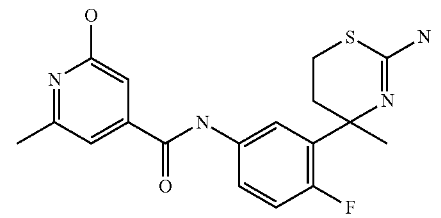 [SMILES: Cc1cc(C(=O)Nc2ccc(F)c(C3(C)CCSC(N)=N3)c2)cc(O)n1] | 375 |
| 401 | 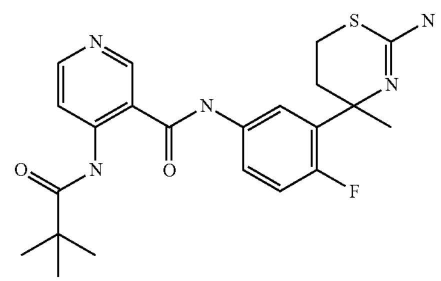 [SMILES: CC(C)(C)C(=O)Nc1ccncc1C(=O)Nc1ccc(F)c(C2(C)CCSC(N)=N2)c1] | 444 |
| 402 | 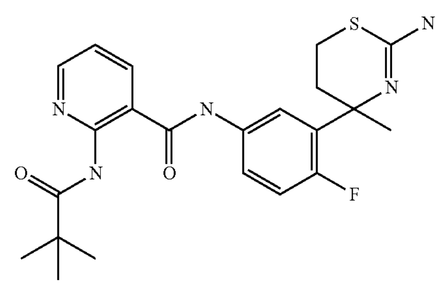 [SMILES: CC(C)(C)C(=O)Nc1ncccc1C(=O)Nc1ccc(F)c(C2(C)CCSC(N)=N2)c1] | 444 |
| 403 | 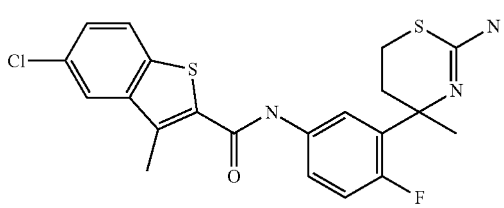 [SMILES: Cc1c(C(=O)Nc2ccc(F)c(C3(C)CCSC(N)=N3)c2)sc2ccc(Cl)cc12] | 448 |

TABLE 90

| Compound No. | Structure | MS (M + 1) |
|---|---|---|
| 404 | 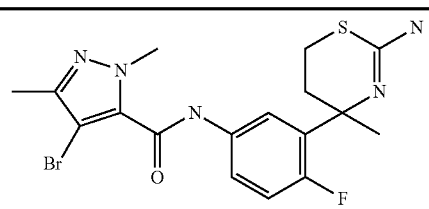 | 440 |

TABLE 90-continued

| Compound No. | Structure | MS (M + 1) |
|---|---|---|
| 405 | 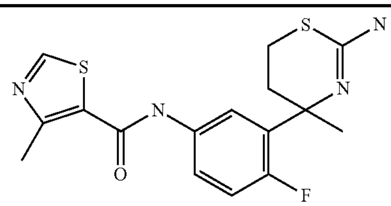 | 365 |
| 406 | 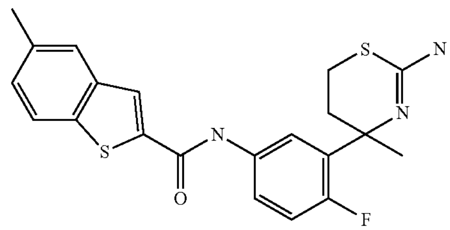 [SMILES: Cc1ccc2sc(C(=O)Nc3ccc(F)c(C4(C)CCSC(N)=N4)c3)cc2c1] | 414 |
| 407 | 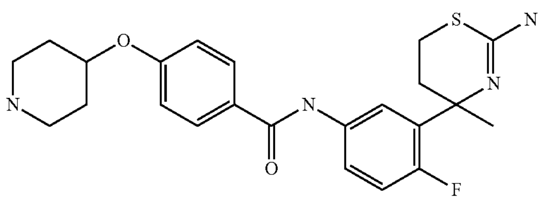 [SMILES: CC1(c2cc(NC(=O)c3ccc(OC4CCNCC4)cc3)ccc2F)CCSC(N)=N1] | 443 |
| 408 | 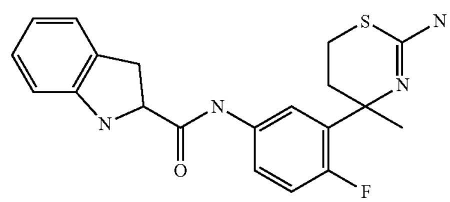 [SMILES: CC1(c2cc(NC(=O)C3Cc4ccccc4N3)ccc2F)CCSC(N)=N1] | 385 |

TABLE 91

| Compound No. | Structure | MS (M + 1) |
|---|---|---|
| 409 | 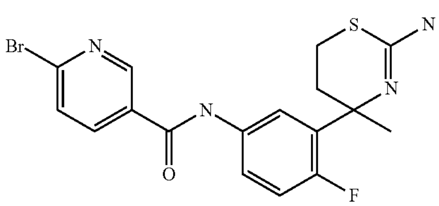 [SMILES: CC1(c2cc(NC(=O)c3ccc(Br)nc3)ccc2F)CCSC(N)=N1] | 423 |
| 410 | 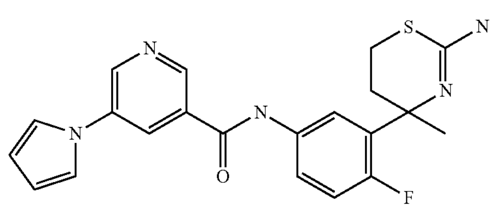 [SMILES: CC1(c2cc(NC(=O)c3cncc(-n4cccc4)c3)ccc2F)CCSC(N)=N1] | 410 |

TABLE 91-continued

| Compound No. | Structure | MS (M + 1) |
|---|---|---|
| 411 | 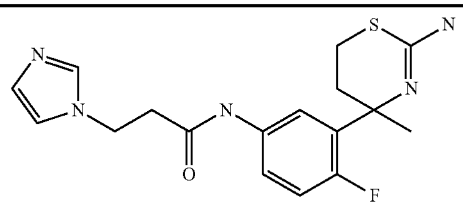 | |
| 412 | 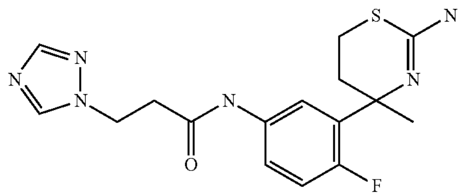 [SMILES: CC1(c2cc(NC(=O)CCn3cncn3)ccc2F)CCSC(N)=N1] | 393 |
| 413 | 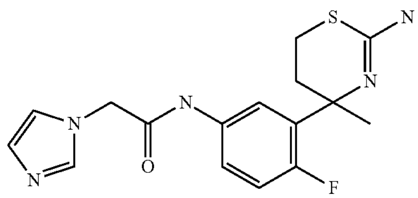 [SMILES: CC1(c2cc(NC(=O)Cn3ccnc3)ccc2F)CCSC(N)=N1] | 348 |

TABLE 92

| Compound No. | Structure | MS (M + 1) |
|---|---|---|
| 414 | 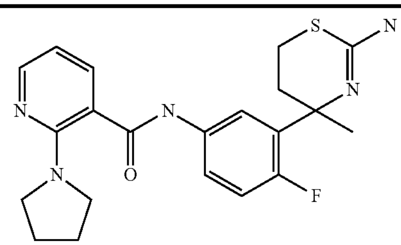 | 414 |
| 415 | 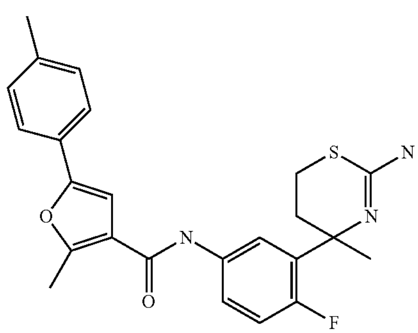 [SMILES: Cc1ccc(-c2cc(C(=O)Nc3ccc(F)c(C4(C)CCSC(N)=N4)c3)c(C)o2)cc1] | 438 |
| 416 | 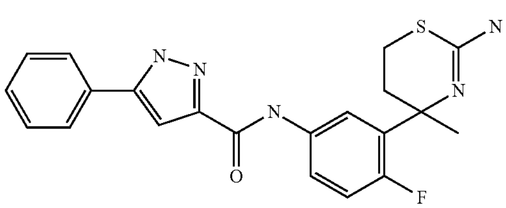 [SMILES: CC1(c2cc(NC(=O)c3cc(-c4ccccc4)[nH]n3)ccc2F)CCSC(N)=N1] | 410 |

TABLE 92-continued

| Compound No. | Structure | MS (M + 1) |
|---|---|---|
| 417 | 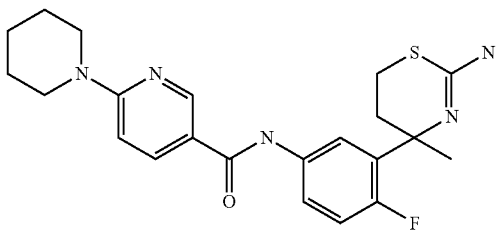 [SMILES: CC1(c2cc(NC(=O)c3ccc(N4CCCCC4)nc3)ccc2F)CCSC(N)=N1] | |
| 418 | 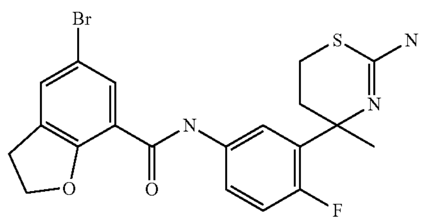 [SMILES: CC1(c2cc(NC(=O)c3cc(Br)cc4c3OCC4)ccc2F)CCSC(N)=N1] | 464 |

TABLE 93

| Compound No. | Structure | MS (M + 1) |
|---|---|---|
| 419 | 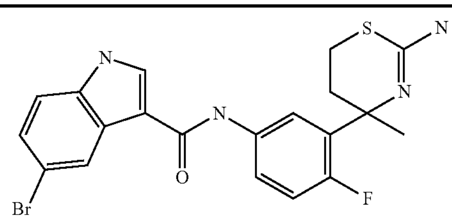 | 461 |
| 420 | 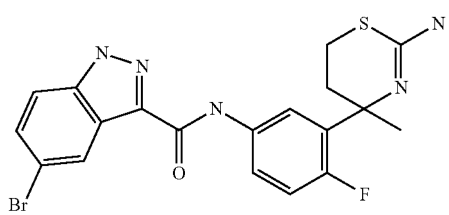 | 462 |
| 421 | 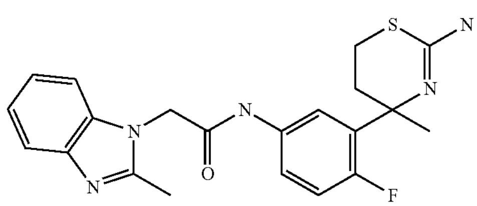 [SMILES: Cc1nc2ccccc2n1CC(=O)Nc1ccc(F)c(C2(C)CCSC(N)=N2)c1] | 412 |
| 422 | 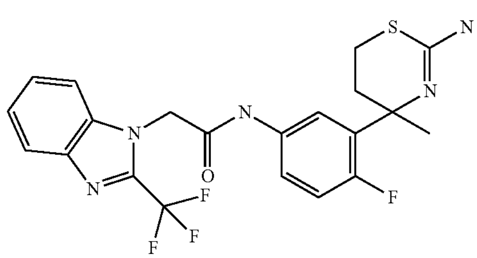 [SMILES: CC1(c2cc(NC(=O)Cn3c(C(F)(F)F)nc4ccccc43)ccc2F)CCSC(N)=N1] | 466 |

225

TABLE 93-continued

| Compound No. | Structure | MS (M + 1) |
|---|---|---|
| 423 | 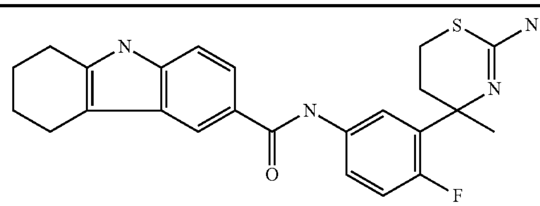 | 437 |

TABLE 94

| Compound No. | Structure | MS (M + 1) |
|---|---|---|
| 424 | 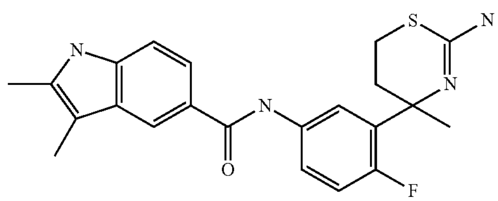 [SMILES: Cc1[nH]c2ccc(C(=O)Nc3ccc(F)c(C4(C)CCSC(N)=N4)c3)cc2c1C] | 411 |
| 425 | 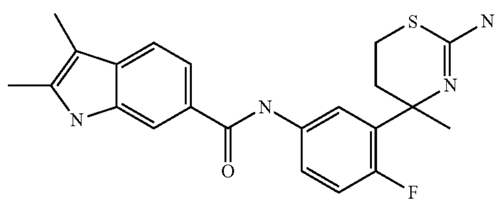 [SMILES: Cc1[nH]c2cc(C(=O)Nc3ccc(F)c(C4(C)CCSC(N)=N4)c3)ccc2c1C] | 411 |
| 426 | 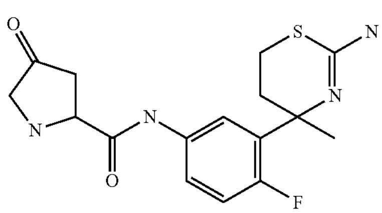 [SMILES: CC1(c2cc(NC(=O)C3CC(=O)CN3)ccc2F)CCSC(N)=N1] | 351 |
| 427 | 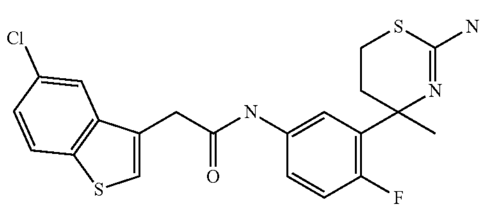 [SMILES: CC1(c2cc(NC(=O)Cc3csc4ccc(Cl)cc34)ccc2F)CCSC(N)=N1] | 478 |
| 428 | 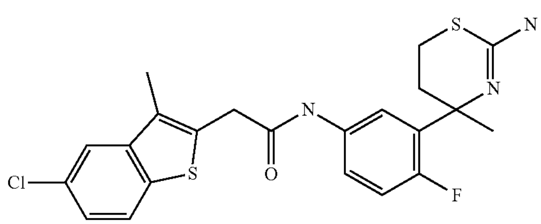 [SMILES: Cc1c(CC(=O)Nc2ccc(F)c(C3(C)CCSC(N)=N3)c2)sc2ccc(Cl)cc12] | 462 |

226

TABLE 95
| Compound No. | Structure | MS (M + 1) |
|---|---|---|
| 429 | 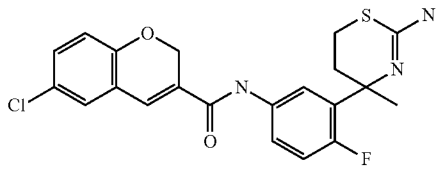 [SMILES: CC1(c2cc(NC(=O)C3=Cc4cc(Cl)ccc4OC3)ccc2F)CCSC(N)=N1] | |
| 430 | 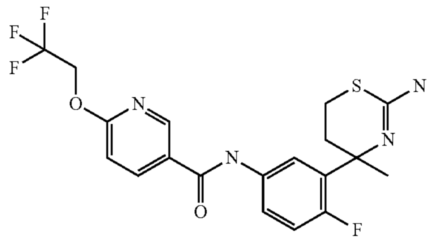 [SMILES: CC1(c2cc(NC(=O)c3ccc(OCC(F)(F)F)nc3)ccc2F)CCSC(N)=N1] | 443 |
| 431 | 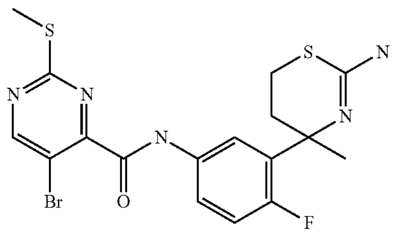 [SMILES: CSc1ncc(Br)c(C(=O)Nc2ccc(F)c(C3(C)CCSC(N)=N3)c2)n1] | 470 |
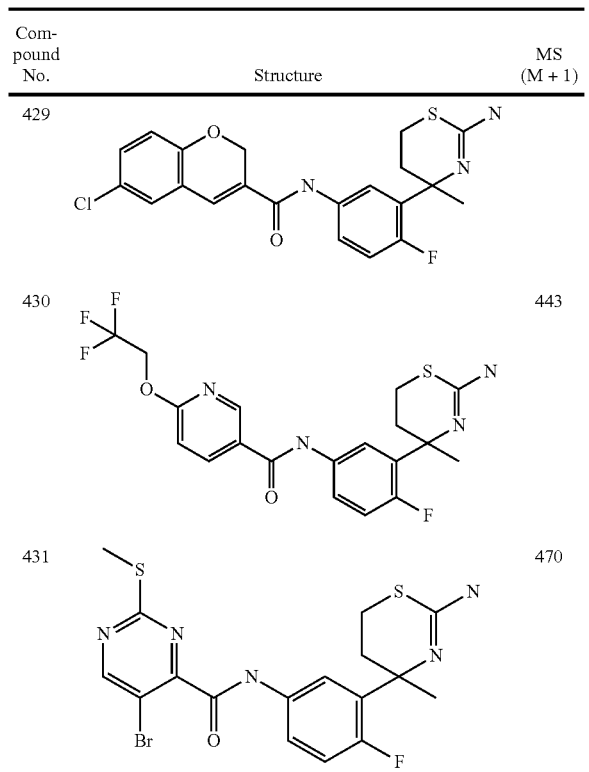
TABLE 95-continued
| Compound No. | Structure | MS (M + 1) |
|---|---|---|
| 432 | 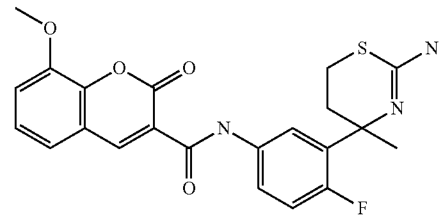 [SMILES: COc1cccc2cc(C(=O)Nc3ccc(F)c(C4(C)CCSC(N)=N4)c3)c(=O)oc12] | |
| 433 | 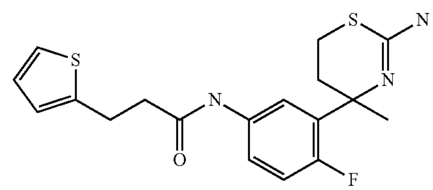 [SMILES: CC1(c2cc(NC(=O)CCc3cccs3)ccc2F)CCSC(N)=N1] | 378 |
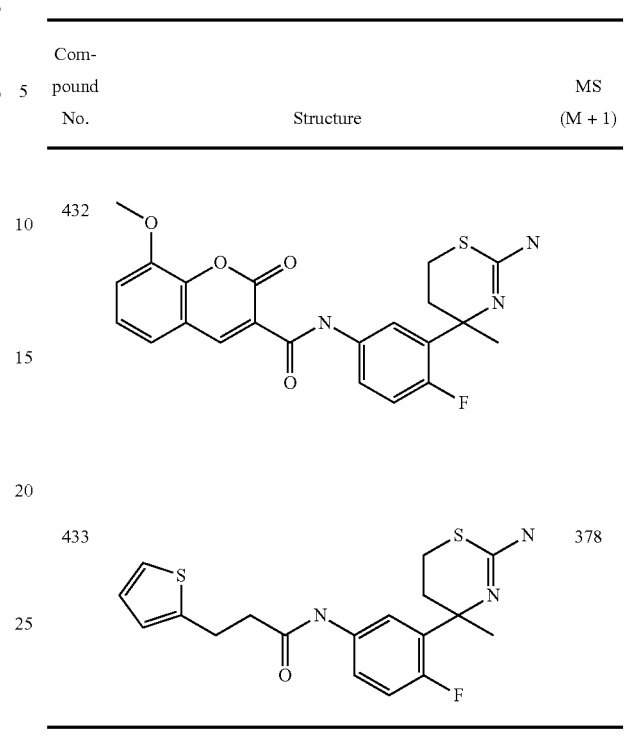
TABLE 96
| Compound No. | Structure | MS (M + 1) |
|---|---|---|
| 434 | 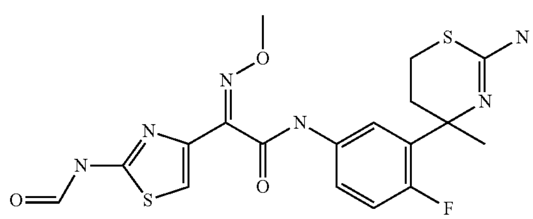 [SMILES: CO/N=C(\C(=O)Nc1ccc(F)c(C2(C)CCSC(N)=N2)c1)c1csc(NC=O)n1] | 451 |
| 435 | 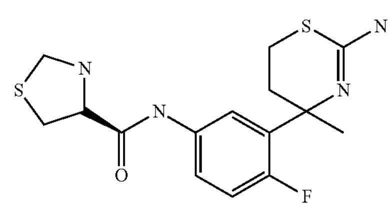 | 355 |
| 436 | 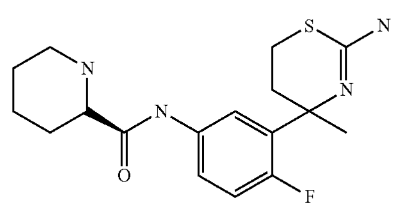 | 351 |
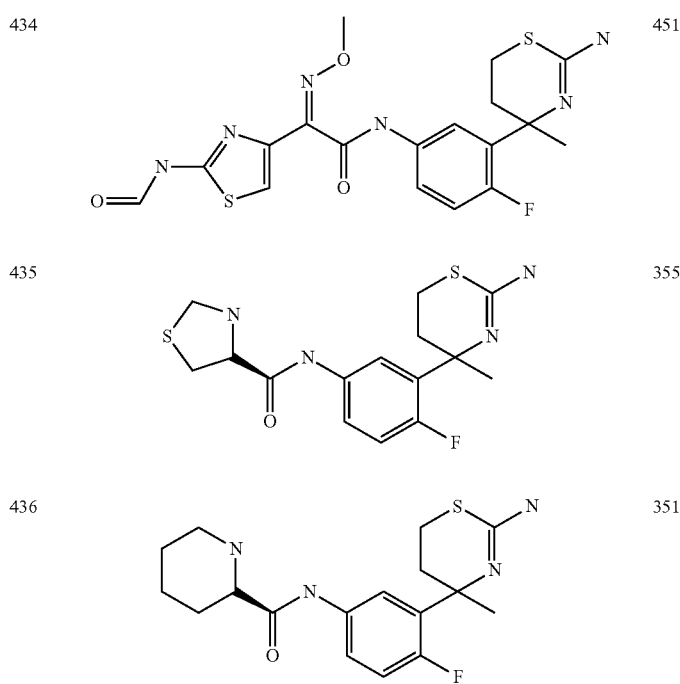

TABLE 96-continued

| Compound No. | Structure | MS (M + 1) |
|---|---|---|
| 437 | 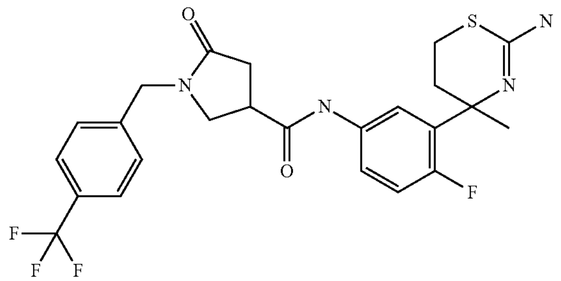 [SMILES: CC1(c2cc(NC(=O)C3CC(=O)N(Cc4ccc(C(F)(F)F)cc4)C3)ccc2F)CCSC(N)=N1] | 509 |
| 438 | 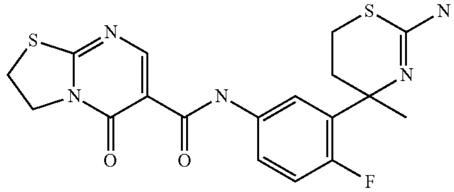 [SMILES: CC1(c2cc(NC(=O)c3cnc4n(c3=O)CCS4)ccc2F)CCSC(N)=N1] | 420 |

TABLE 97

| Compound No. | Structure | MS (M + 1) |
|---|---|---|
| 439 | 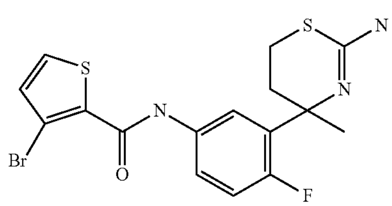 [SMILES: CC1(c2cc(NC(=O)c3sccc3Br)ccc2F)CCSC(N)=N1] | 429 |
| 440 | 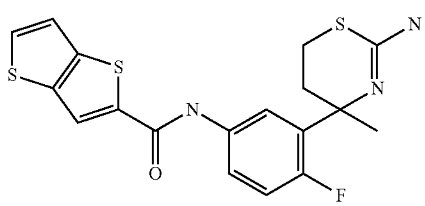 [SMILES: CC1(c2cc(NC(=O)c3cc4sccc4s3)ccc2F)CCSC(N)=N1] | 406 |
| 441 | 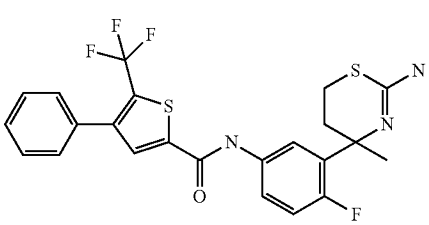 [SMILES: CC1(c2cc(NC(=O)c3cc(-c4ccccc4)c(C(F)(F)F)s3)ccc2F)CCSC(N)=N1] | 494 |
| 442 | | 458 |
| 443 | | 483 |

TABLE 98

| Compound No | Structure | MS (M + 1) |
|---|---|---|
| 444 | 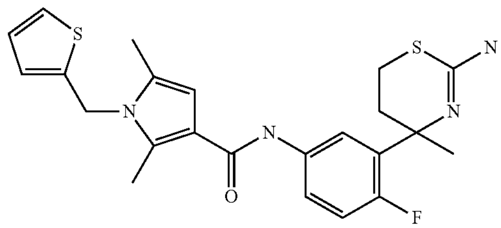 [SMILES: Cc1cc(C(=O)Nc2ccc(F)c(C3(C)CCSC(N)=N3)c2)c(C)n1Cc1cccs1] | 457 |
| 445 | 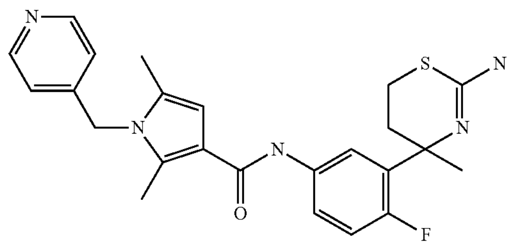 [SMILES: Cc1cc(C(=O)Nc2ccc(F)c(C3(C)CCSC(N)=N3)c2)c(C)n1Cc1ccncc1] | 452 |
| 446 | 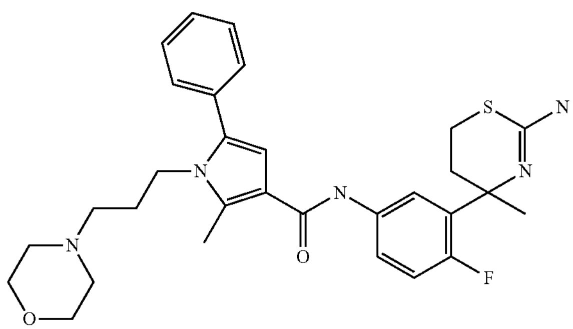 [SMILES: Cc1c(C(=O)Nc2ccc(F)c(C3(C)CCSC(N)=N3)c2)cc(-c2ccccc2)n1CCCN1CCOCC1] | 550 |
| 447 | 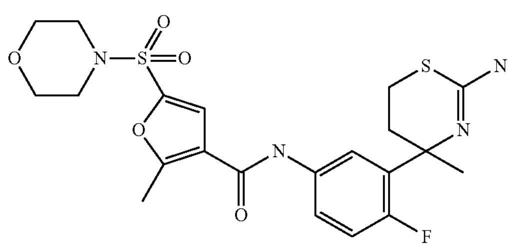 [SMILES: Cc1oc(S(=O)(=O)N2CCOCC2)cc1C(=O)Nc1ccc(F)c(C2(C)CCSC(N)=N2)c1] | 437 |

TABLE 99

| Compound No. | Structure | MS (M + 1) |
|---|---|---|
| 448 | 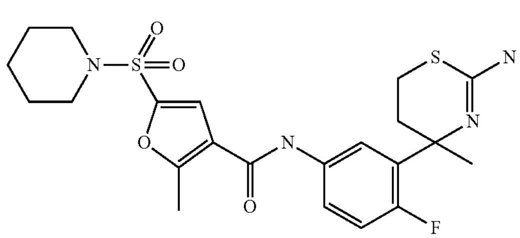 [SMILES: Cc1oc(S(=O)(=O)N2CCCCC2)cc1C(=O)Nc1ccc(F)c(C2(C)CCSC(N)=N2)c1] | 495 |

TABLE 99-continued

| Compound No. | Structure | MS (M + 1) |
|---|---|---|
| 449 | 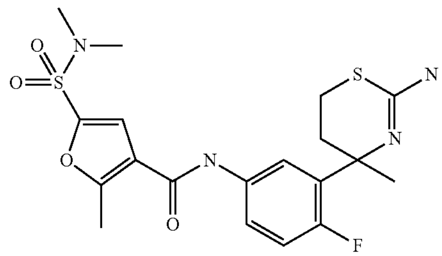 [SMILES: Cc1oc(S(=O)(=O)N(C)C)cc1C(=O)Nc1ccc(F)c(C2(C)CCSC(N)=N2)c1] | 455 |
| 450 | 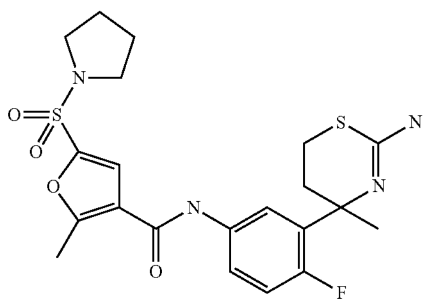 [SMILES: Cc1oc(S(=O)(=O)N2CCCC2)cc1C(=O)Nc1ccc(F)c(C2(C)CCSC(N)=N2)c1] | 481 |
| 451 | 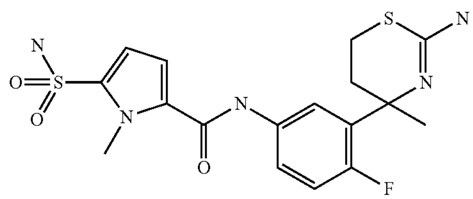 [SMILES: Cn1c(C(=O)Nc2ccc(F)c(C3(C)CCSC(N)=N3)c2)ccc1S(N)(=O)=O] | 426 |

TABLE 100

| Compound No. | Structure | MS (M + 1) |
|---|---|---|
| 452 | 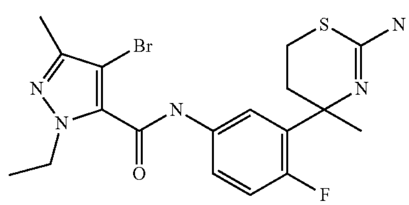 [SMILES: CCn1nc(C)c(Br)c1C(=O)Nc1ccc(F)c(C2(C)CCSC(N)=N2)c1] | 454 |
| 453 | 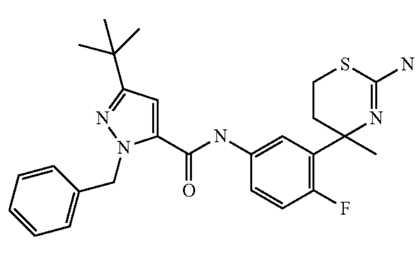 [SMILES: CC(C)(C)c1cc(C(=O)Nc2ccc(F)c(C3(C)CCSC(N)=N3)c2)n(Cc2ccccc2)n1] | 480 |
| 454 | | 404 |
| 455 | | 441 |

TABLE 101

| Compound No. | Structure | MS (M + 1) |
|---|---|---|
| 456 | 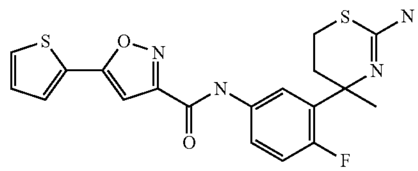 [SMILES: CC1(c2cc(NC(=O)c3cc(-c4cccs4)on3)ccc2F)CCSC(N)=N1] | 417 |
| 457 | 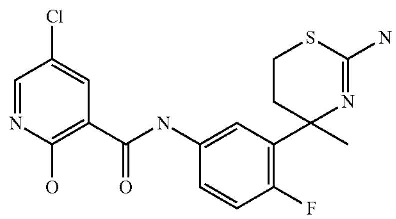 [SMILES: CC1(c2cc(NC(=O)c3cc(Cl)cnc3O)ccc2F)CCSC(N)=N1] | 395 |
| 458 | 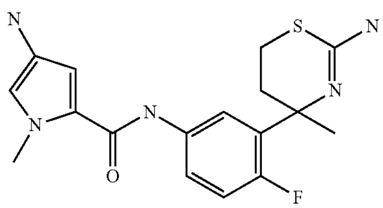 [SMILES: Cn1cc(N)cc1C(=O)Nc1ccc(F)c(C2(C)CCSC(N)=N2)c1] | 362 |

TABLE 101-continued

| Compound No. | Structure | MS (M + 1) |
|---|---|---|
| 459 | 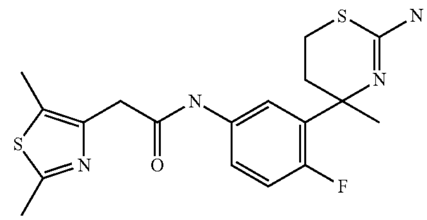 [SMILES: Cc1nc(CC(=O)Nc2ccc(F)c(C3(C)CCSC(N)=N3)c2)c(C)s1] | 393 |
| 460 | 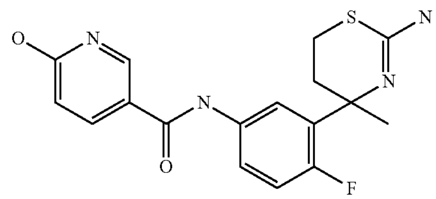 [SMILES: CC1(c2cc(NC(=O)c3ccc(O)nc3)ccc2F)CCSC(N)=N1] | |

TABLE 102

| Compound No. | Structure | MS (M + 1) | MP | NMR (solvent,) shift value: ascending order) | uv |
|---|---|---|---|---|---|
| 461 | 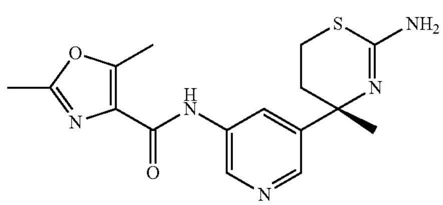 [SMILES: Cc1nc(C(=O)Nc2cncc([C@]3(C)CCSC(N)=N3)c2)c(C)o1] | 346 | | | |
| 462 | 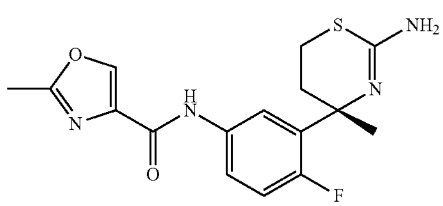 [SMILES: Cc1nc(C(=O)Nc2ccc(F)c([C@]3(C)CCSC(N)=N3)c2)co1] | 349 | | 1H-NMR (DMSO-d6) d: 10.02 (1.0H, s), 8.59 (1.0H, s), 7.73-7.66 (2.0H, m), 7.09 (1.0H, dd, J = 12.00, 8.97 Hz), 5.83 (2.0H, br s), 2.97-2.95 (1.0H, m), 2.59-2.56 (1.0H, m), 2.17-2.16 (1.0H, m), 1.79-1.76 (1.0H, m), 1.47 (3.0H, s). | |
| 463 | 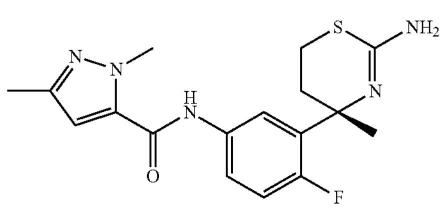 [SMILES: Cc1cc(C(=O)Nc2ccc(F)c([C@]3(C)CCSC(N)=N3)c2)n(C)n1] | 362 | | | |

TABLE 102-continued

| Compound No. | Structure | MS (M + 1) | MP | NMR (solvent,) shift value: ascending order) | uv |
|---|---|---|---|---|---|
| 464 | 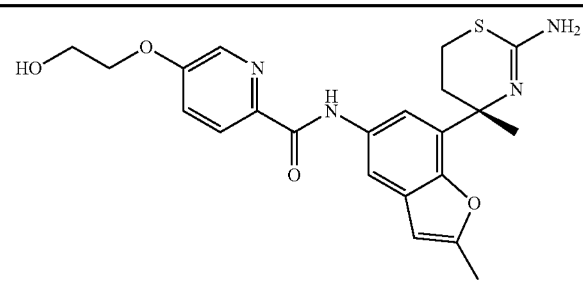 | 441 | | | |
| 465 | 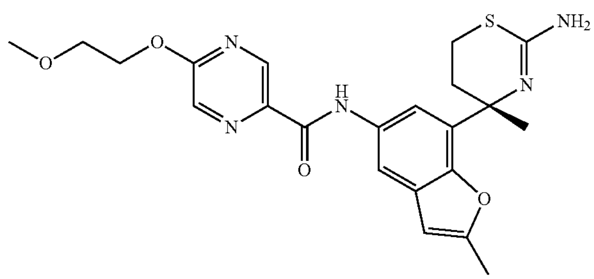 [SMILES: COCCOc1cnc(C(=O)Nc2cc([C@]3(C)CCSC(N)=N3)c3oc(C)cc3c2)cn1] | 456 | | | |
| 466 | 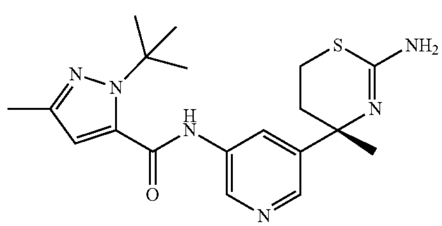 [SMILES: Cc1cc(C(=O)Nc2cncc([C@]3(C)CCSC(N)=N3)c2)n(C(C)(C)C)n1] | | | 1H-NMR (DMSO-d6) d: 10.70 (1.0H, s), 8.76 (1.0H, s), 8.36 (1.0H, s), 8.03 (1.0H, s), 6.44 (1.0H, s), 5.93 (2.0H, br s), 3.00-2.97 (1.0H, m), 2.63-2.61 (1.0H, m), 2.19 (3.0H, s), 2.00-1.98 (1.0H, m), 1.82-1.80 (1.0H, m), 1.60 (9.0H, s), 1.43 (3.0H, s). | |

TABLE 103

| Compound No | Structure | MS (M + 1) | MP | NMR (solvent, shift value: ascending order) | uv |
|---|---|---|---|---|---|
| 467 | 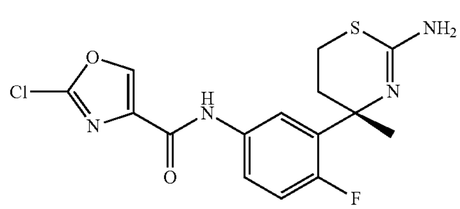 [SMILES: C[C@@]1(c2cc(NC(=O)c3coc(Cl)n3)ccc2F)CCSC(N)=N1] | 369 | | | |
| 468 | 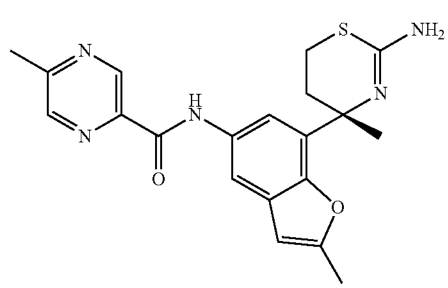 [SMILES: Cc1cnc(C(=O)Nc2cc([C@]3(C)CCSC(N)=N3)c3oc(C)cc3c2)cn1] | 396 | | | |

TABLE 103-continued

| Compound No | Structure | MS (M + 1) | MP | NMR (solvent, shift value: ascending order) | uv |
|---|---|---|---|---|---|
| 469 | 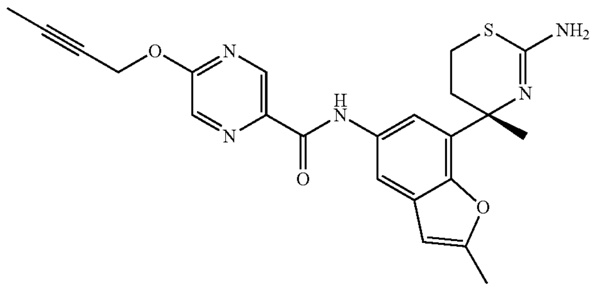 [SMILES: CC#CCOc1cnc(C(=O)Nc2cc([C@]3(C)CCSC(N)=N3)c3oc(C)cc3c2)cn1] | 450 | | | |
| 470 | 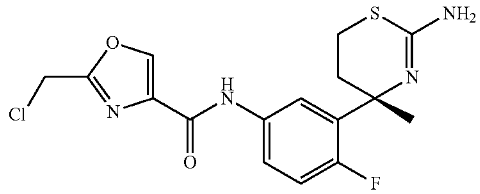 [SMILES: C[C@@]1(c2cc(NC(=O)c3coc(CCl)n3)ccc2F)CCSC(N)=N1] | 383 | | | |
| 471 | 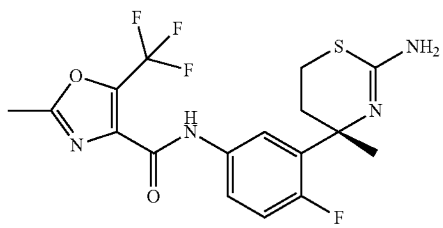 [SMILES: Cc1nc(C(=O)Nc2ccc(F)c([C@]3(C)CCSC(N)=N3)c2)c(C(F)(F)F)o1] | 417 | | | |
| 472 | 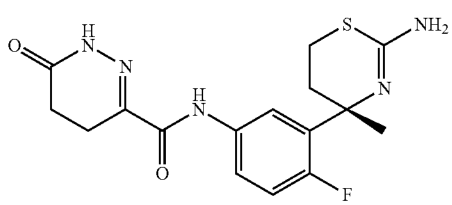 [SMILES: C[C@@]1(c2cc(NC(=O)C3=NNC(=O)CC3)ccc2F)CCSC(N)=N1] | 364 | | | |

TABLE 104

| Compound No. | Structure | MS (M + 1) | MP | NMR (solvent, shift value ascending order) | uv |
|---|---|---|---|---|---|
| 473 | 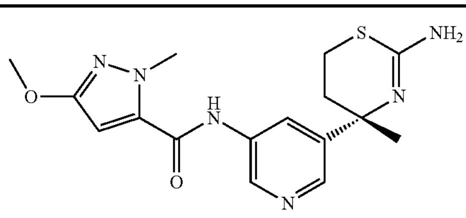 | 361 | | | |
| 474 | 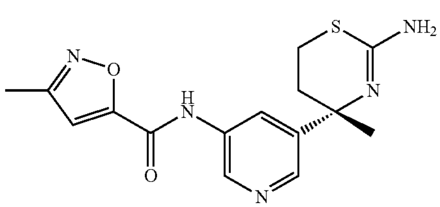 [SMILES: Cc1cc(C(=O)Nc2cncc([C@]3(C)CCSC(N)=N3)c2)on1] | 332 | | | |

TABLE 104-continued

| Compound No. | Structure | MS (M + 1) | MP | NMR (solvent, shift value ascending order) | uv |
|---|---|---|---|---|---|
| 475 | 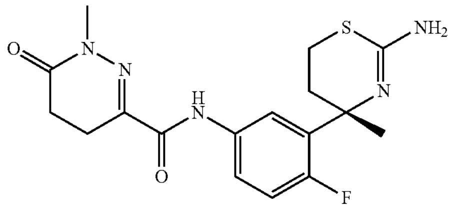 [SMILES: CN1N=C(C(=O)Nc2ccc(F)c([C@]3(C)CCSC(N)=N3)c2)CCC1=O] | 378 | | | |
| 476 | 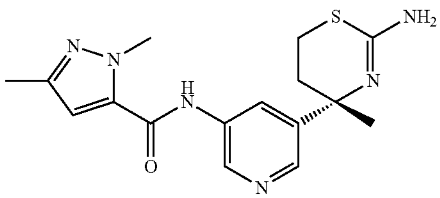 [SMILES: Cc1cc(C(=O)Nc2cncc([C@]3(C)CCSC(N)=N3)c2)n(C)n1] | 345 | | | |
| 477 | 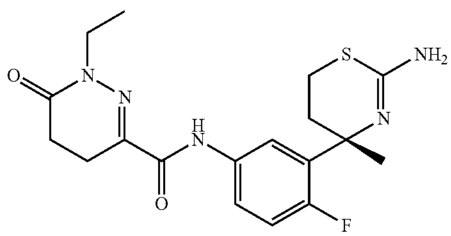 [SMILES: CCN1N=C(C(=O)Nc2ccc(F)c([C@]3(C)CCSC(N)=N3)c2)CCC1=O] | 392 | | | |
| 478 | 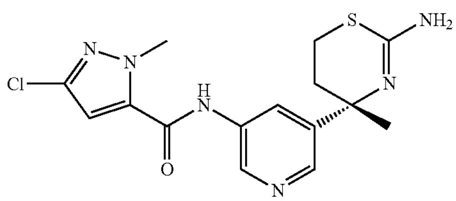 [SMILES: Cn1nc(Cl)cc1C(=O)Nc1cncc([C@]2(C)CCSC(N)=N2)c1] | 365 | | | |
| 479 | 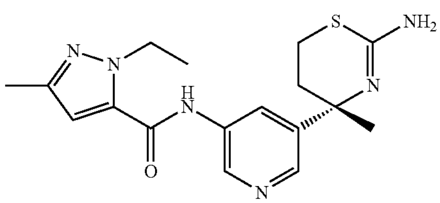 [SMILES: CCn1nc(C)cc1C(=O)Nc1cncc([C@]2(C)CCSC(N)=N2)c1] | 359 | | | |

TABLE 105

| Compound No | Structure | MS (M + 1) | MP | NMR (solvent, shift value: ascending order) | uv |
|---|---|---|---|---|---|
| 480 | 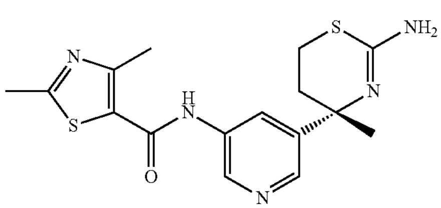 [SMILES: Cc1nc(C)c(C(=O)Nc2cncc([C@]3(C)CCSC(N)=N3)c2)s1] | 360 | | | |

TABLE 105-continued
| Compound No | Structure | MS (M + 1) | MP | NMR (solvent, shift value: ascending order) | uv |
|---|---|---|---|---|---|
| 481 | 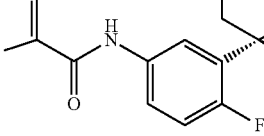 Cl—I | 366 | | | |
| 482 | 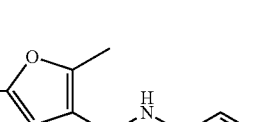 | 345 | | | |
| 483 | 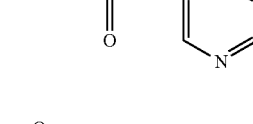 | 394 | | | |
| 484 | 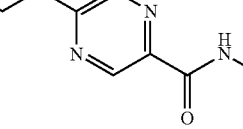 ClH | 385 | | | |
| 485 | 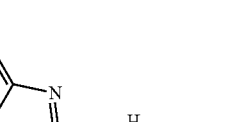 | 347 | | | |
| 486 | 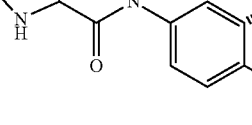 | 347 | | | |
TABLE 106
| Compound No | Structure | MS (M + 1) | MP | NMR (solvent, shift value: ascending order) | uv |
|---|---|---|---|---|---|
| 487 | 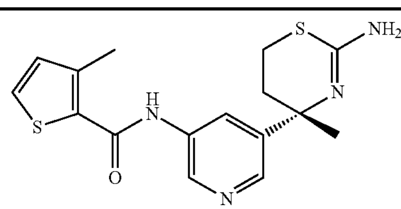 | 347 | | | |

TABLE 106-continued

| Compound No | Structure | MS (M + 1) | MP | NMR (solvent, shift value: ascending order) | uv |
|---|---|---|---|---|---|
| 488 | 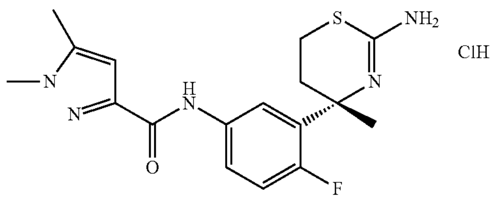 [SMILES: CN/C(C)=C\C(=N)C(=O)Nc1ccc(F)c([C@]2(C)CCSC(N)=N2)c1 ; Cl] | 362 ClH | | | |
| 489 | 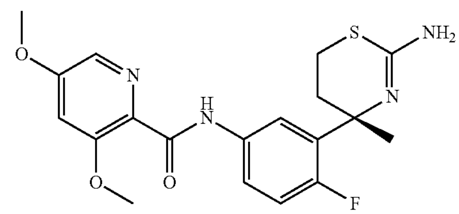 [SMILES: COc1cnc(C(=O)Nc2ccc(F)c([C@]3(C)CCSC(N)=N3)c2)c(OC)c1] | 405 | | | |
| 490 | 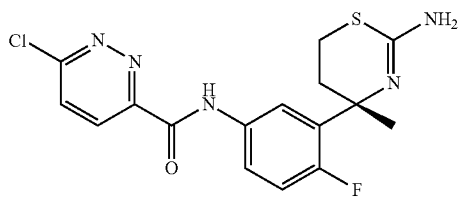 [SMILES: C[C@@]1(c2cc(NC(=O)c3ccc(Cl)nn3)ccc2F)CCSC(N)=N1] | 381 | | | |
| 491 | 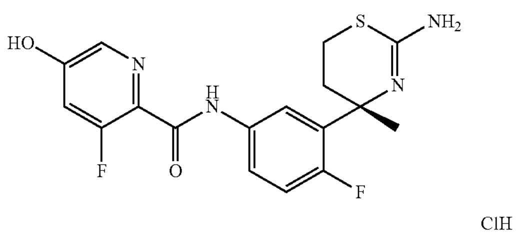 [SMILES: C[C@@]1(c2cc(NC(=O)c3ncc(O)cc3F)ccc2F)CCSC(N)=N1 ; Cl] | 379 ClH | | | |
| 492 | 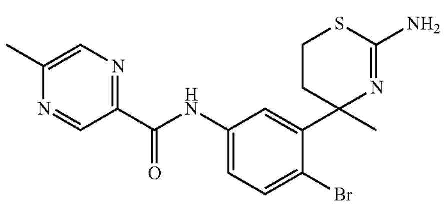 [SMILES: Cc1cnc(C(=O)Nc2ccc(Br)c(C3(C)CCSC(N)=N3)c2)cn1] | 421 | | | |
| 493 | 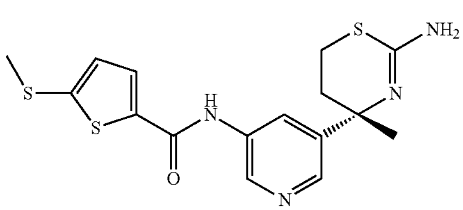 [SMILES: CSc1ccc(C(=O)Nc2cncc([C@]3(C)CCSC(N)=N3)c2)s1] | 379 | | | |

TABLE 107

| Compound No | Structure | MS (M+1) | MP | NMR (solvent, shift value: ascending order) | uv |
|---|---|---|---|---|---|
| 494 | 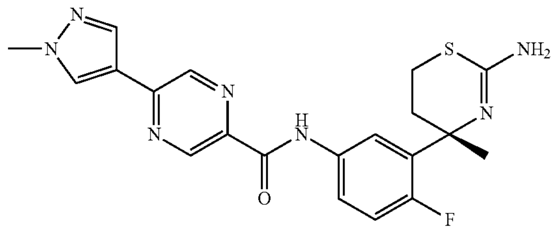 [SMILES: Cn1cc(-c2cnc(C(=O)Nc3ccc(F)c([C@]4(C)CCSC(N)=N4)c3)cn2)cn1] | 426 | | | |
| 495 | ClH | 363 | | | |
| 496 | 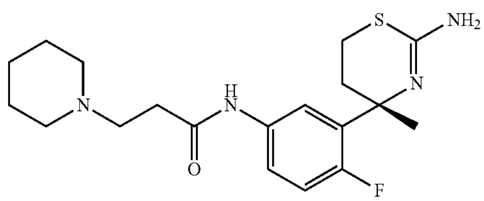 [SMILES: C[C@@]1(c2cc(NC(=O)CCN3CCCCC3)ccc2F)CCSC(N)=N1] | 378 | | | |
| 497 | 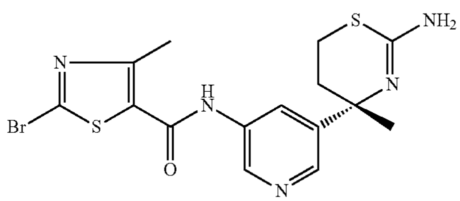 [SMILES: Cc1nc(Br)sc1C(=O)Nc1cncc([C@]2(C)CCSC(N)=N2)c1] | 426 | | | |
| 498 | ClH | 374 | | | |
| 499 | ClH | 374 | | | |
| 500 | ClH | 363 | | | |

TABLE 108
| Compound No | Structure | MS (M + 1) | MP | NMR (solvent, shift value: ascending order) | uv |
|---|---|---|---|---|---|
| 501 | 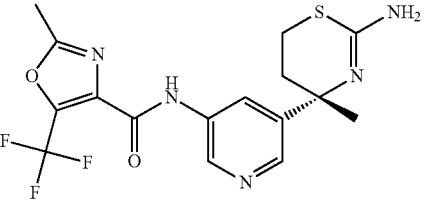 [SMILES: Cc1nc(C(=O)Nc2cncc([C@]3(C)CCSC(N)=N3)c2)c(C(F)(F)F)o1] | 400 | | | |
| 502 | 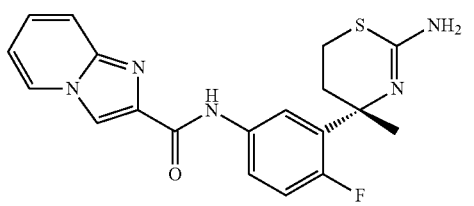 ClH | 384 | | | |
| 503 | 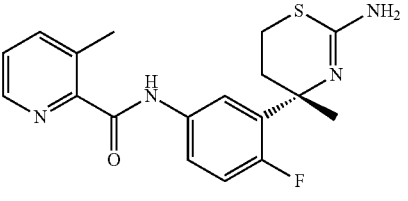 ClH | 359 | | | |
| 504 | 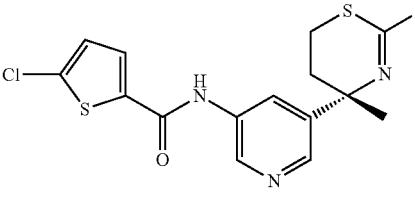 | 367 | | | |
| 505 | 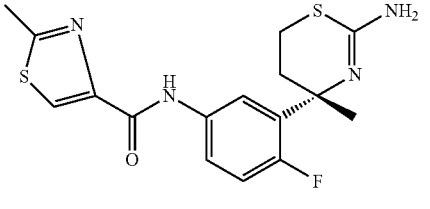 Cl—I | 365 | | | |
| 506 | 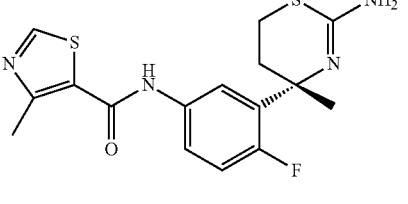 ClH | 365 | | | |
| 507 | 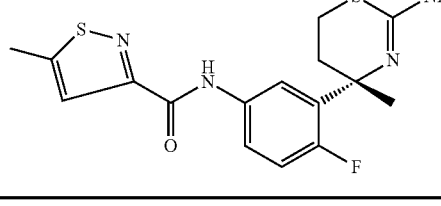 ClH | 365 | | | |

TABLE 109

| Compound No | Structure | MS (M + 1) | MP | NMR (solvent, shift value: ascending order) | uv |
|---|---|---|---|---|---|
| 508 | 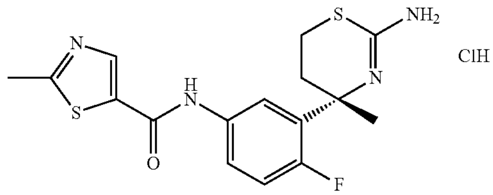 [SMILES: Cc1ncc(C(=O)Nc2ccc(F)c([C@]3(C)CCSC(N)=N3)c2)s1 ; Cl] | 365 ClH | | | |
| 509 | 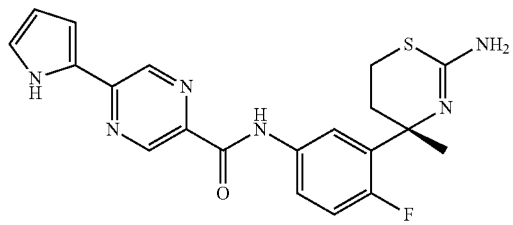 [SMILES: C[C@@]1(c2cc(NC(=O)c3cnc(-c4ccc[nH]4)cn3)ccc2F)CCSC(N)=N1] | 411 | | | |
| 510 | 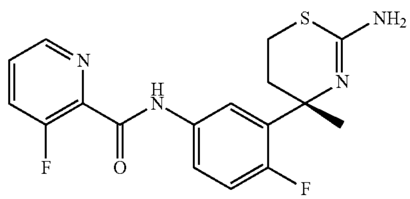 [SMILES: C[C@@]1(c2cc(NC(=O)c3ncccc3F)ccc2F)CCSC(N)=N1] | 363 | | | |
| 511 | 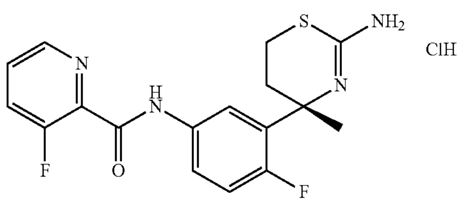 [SMILES: C[C@@]1(c2cc(NC(=O)c3ncccc3F)ccc2F)CCSC(N)=N1 ; Cl] | 363 ClH | | | |
| 512 | 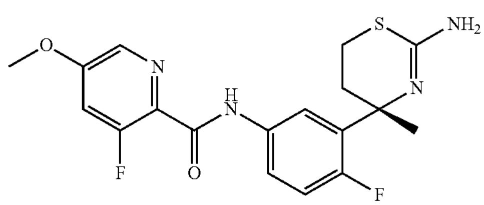 [SMILES: COc1cnc(C(=O)Nc2ccc(F)c([C@]3(C)CCSC(N)=N3)c2)c(F)c1] | 393 | | | |
| 513 | 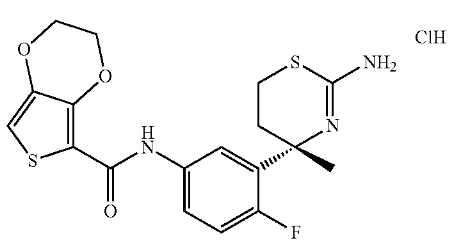 [SMILES: C[C@@]1(c2cc(NC(=O)c3scc4c3OCCO4)ccc2F)CCSC(N)=N1 ; Cl] | 408 ClH | | | |
| 514 | 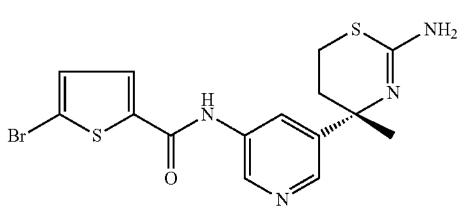 [SMILES: C[C@@]1(c2cncc(NC(=O)c3ccc(Br)s3)c2)CCSC(N)=N1] | 413 | | | |

TABLE 110

| Compound No | Structure | MS (M + 1) | NMR (solvent, MP shift value: ascending order) | uv |
|---|---|---|---|---|
| 515 | 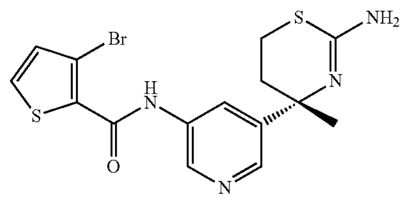 [SMILES: C[C@@]1(c2cncc(NC(=O)c3sccc3Br)c2)CCSC(N)=N1] | 411 | | |
| 516 | 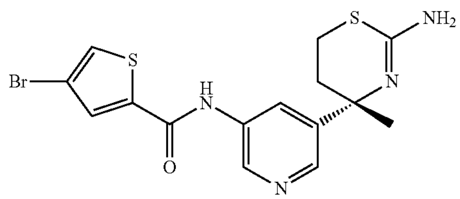 [SMILES: C[C@@]1(c2cncc(NC(=O)c3cc(Br)cs3)c2)CCSC(N)=N1] | 413 | | |
| 517 | 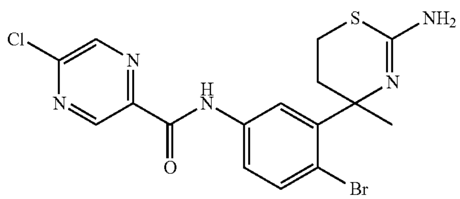 [SMILES: CC1(c2cc(NC(=O)c3cnc(Cl)cn3)ccc2Br)CCSC(N)=N1] | 441 | | |
| 518 | ClH | 348 | | |
| 519 | 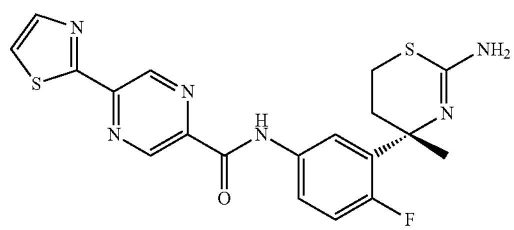 [SMILES: C[C@@]1(c2cc(NC(=O)c3cnc(-c4nccs4)cn3)ccc2F)CCSC(N)=N1] | 429 | | |
| 520 | ClH | 394 | | |
| 521 | ClH | 402 | | |

TABLE 111
| Compound No | Structure | MS (M + 1) | NMR (solvent, MP shift value: ascending order) | uv |
|---|---|---|---|---|
| 522 | 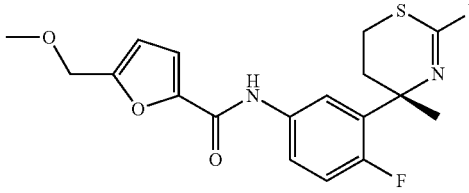 | 378 | | |
| 523 | 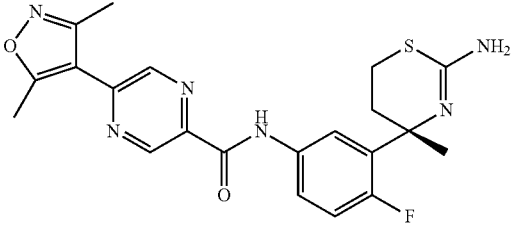 [SMILES: Cc1noc(C)c1-c1cnc(C(=O)Nc2ccc(F)c([C@]3(C)CCSC(N)=N3)c2)cn1] | 441 | | |
| 524 | 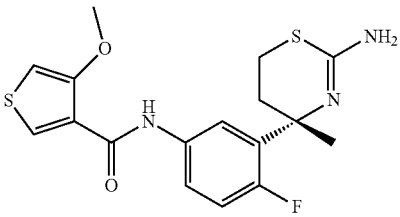 ClH | 380 | | |
| 525 | 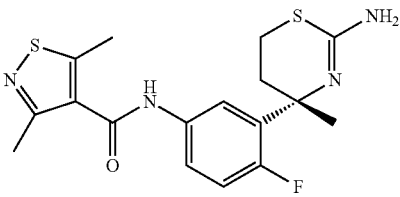 ClH | 379 | | |
| 526 | 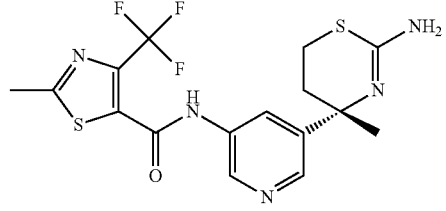 [SMILES: Cc1nc(C(F)(F)F)c(C(=O)Nc2cncc([C@]3(C)CCSC(N)=N3)c2)s1] | 414 | | |
| 527 | 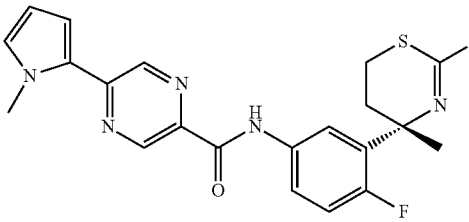 | 428 | | |

TABLE 112

| Compound No | Structure | MS (M + 1) | NMR (solvent, MP shift value: ascending order) | uv |
|---|---|---|---|---|
| 528 | 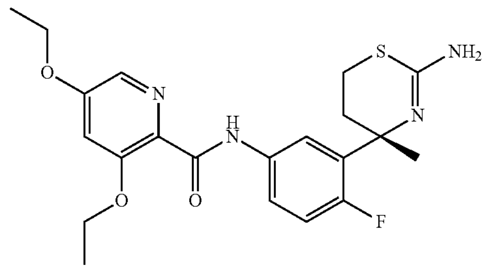 [SMILES: CCOc1cnc(C(=O)Nc2ccc(F)c([C@]3(C)CCSC(N)=N3)c2)c(OCC)c1] | 433 | | |
| 529 | ClH | 362 | | |
| 530 | ClH | 392 | | |
| 531 | 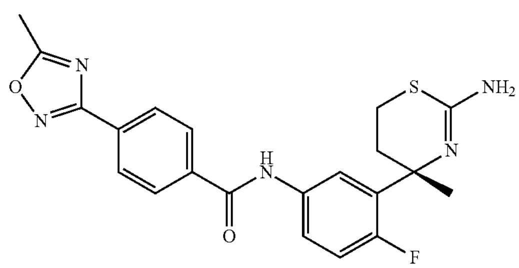 [SMILES: Cc1nc(-c2ccc(C(=O)Nc3ccc(F)c([C@]4(C)CCSC(N)=N4)c3)cc2)no1] | 426 | | |
| 532 | ClH | 364 | | |
| 533 | ClH | 364 | | |

TABLE 113
| Compound No | Structure | MS (M + 1) | NMR (solvent, MP shift value: ascending order) | uv |
|---|---|---|---|---|
| 534 | 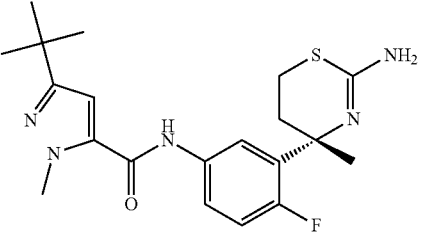 ClH | 404 | | |
| 535 | 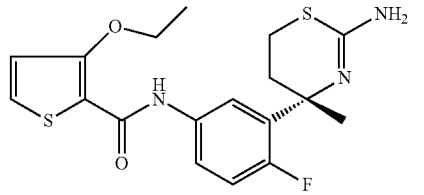 ClH | 394 | | |
| 536 | 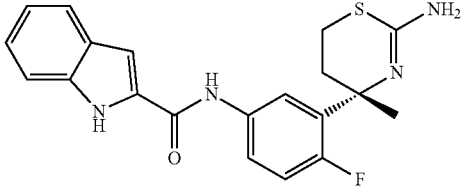 ClH | 383 | | |
| 537 | 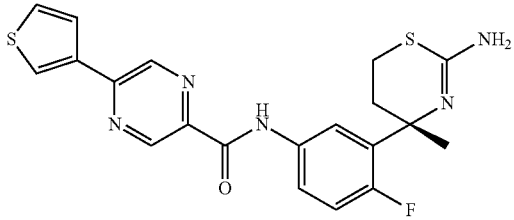 [SMILES: C[C@@]1(c2cc(NC(=O)c3cnc(-c4ccsc4)cn3)ccc2F)CCSC(N)=N1] | 428 | | |
| 538 | 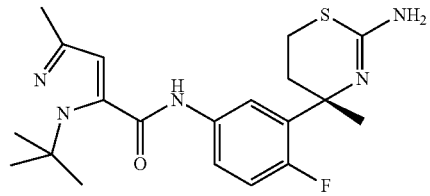 [SMILES: CC(=N)/C=C(\NC(C)(C)C)C(=O)Nc1ccc(F)c([C@]2(C)CCSC(N)=N2)c1] | 404 | | |
| 539 | 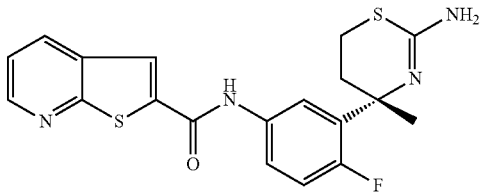 ClH | 401 | | |

TABLE 114

| Compound No. | Structure | MS (M + 1) | NMR (solvent, MP shift value: ascending order) | uv |
|---|---|---|---|---|
| 540 | 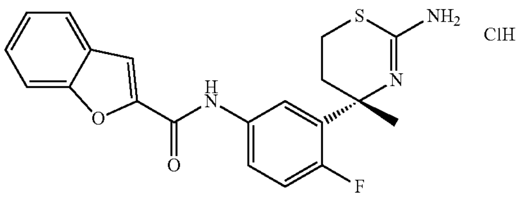 [SMILES: C[C@@]1(c2cc(NC(=O)c3cc4ccccc4o3)ccc2F)CCSC(N)=N1 ; Cl] | 384 | | |
| 541 | 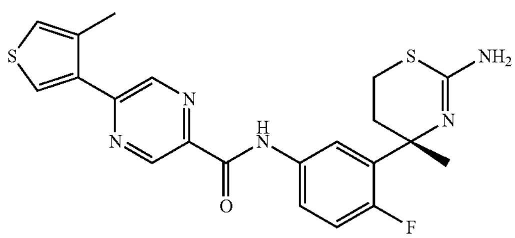 [SMILES: Cc1cscc1-c1cnc(C(=O)Nc2ccc(F)c([C@]3(C)CCSC(N)=N3)c2)cn1] | 442 | | |
| 542 | 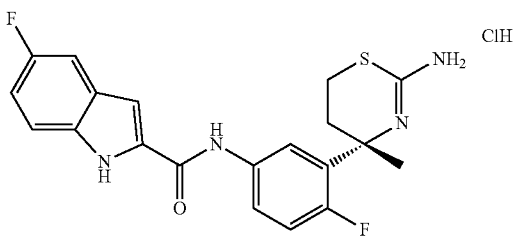 [SMILES: C[C@@]1(c2cc(NC(=O)c3cc4cc(F)ccc4[nH]3)ccc2F)CCSC(N)=N1 ; Cl] | 401 | | |
| 543 | 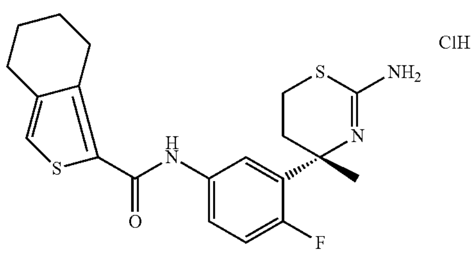 [SMILES: C[C@@]1(c2cc(NC(=O)c3scc4c3CCCC4)ccc2F)CCSC(N)=N1 ; Cl] | 404 | | |
| 544 | 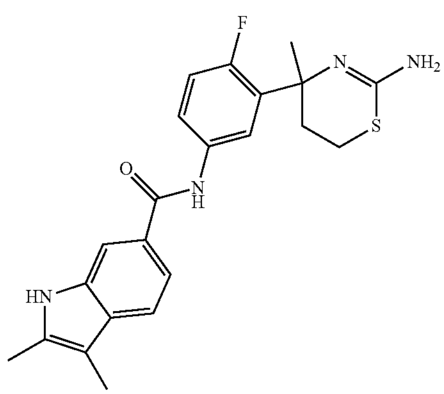 [SMILES: Cc1[nH]c2cc(C(=O)Nc3ccc(F)c(C4(C)CCSC(N)=N4)c3)ccc2c1C] | 511 | | |
| 545 | 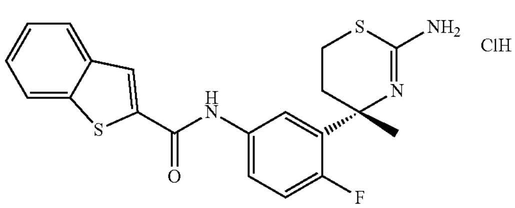 [SMILES: C[C@@]1(c2cc(NC(=O)c3cc4ccccc4s3)ccc2F)CCSC(N)=N1 ; Cl] | 400 | | |

TABLE 115

| Compound No | Structure | MS (M + 1) | NMR (solvent, MP shift value: ascending order) | uv |
|---|---|---|---|---|
| 546 | (structure with trifluoromethyl benzothiophene, ClH salt) | | 1H-NMR (DMSO-d6) d: 10.92 (1H, s), 10.45 (1H, s), 8.45 (1H, s), 8.42 (1H, s), 8.30 (1H, d, J = 8.8 Hz), 7.79-7.78 (3H, m), 7.31 (1H, dd, J = 12.3, 9.2 Hz), 3.22 (1H, d, J = 13.4 Hz), 2.72-2.65 (2H, m), 2.11 (1H, t, J = 11.5 Hz), 1.73 (3H, s). | |
| 547 | 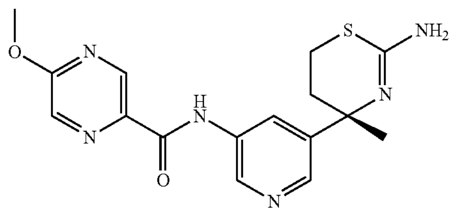 [SMILES: COc1cnc(C(=O)Nc2cncc([C@]3(C)CCSC(N)=N3)c2)cn1] | 359 | | |
| 548 | 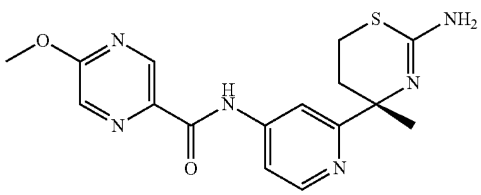 [SMILES: COc1cnc(C(=O)Nc2ccnc([C@]3(C)CCSC(N)=N3)c2)cn1] | 359 | | |
| 549 | 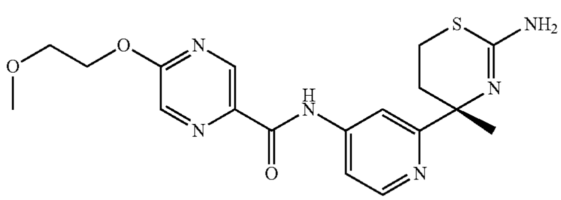 [SMILES: COCCOc1cnc(C(=O)Nc2ccnc([C@]3(C)CCSC(N)=N3)c2)cn1] | 403 | | |
| 550 | 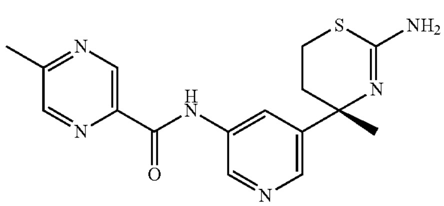 [SMILES: Cc1cnc(C(=O)Nc2cncc([C@]3(C)CCSC(N)=N3)c2)cn1] | 343 | | |
| 551 | 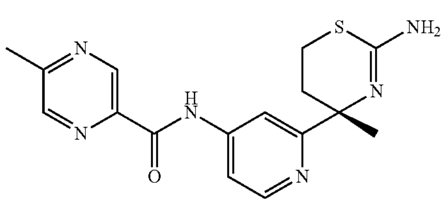 [SMILES: Cc1cnc(C(=O)Nc2ccnc([C@]3(C)CCSC(N)=N3)c2)cn1] | 343 | | |

TABLE 116

| Compound No. | Structure | MS (M + 1) | MP | NMR (solvent, shift value: ascending order) | uv |
|---|---|---|---|---|---|
| 552 | 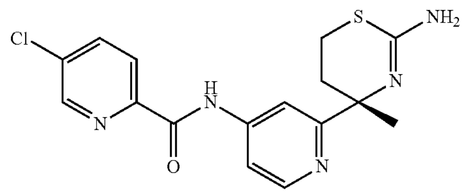 [SMILES: C[C@@]1(c2cc(NC(=O)c3ccc(Cl)cn3)ccn2)CCSC(N)=N1] | 363 | | | |
| 553 | 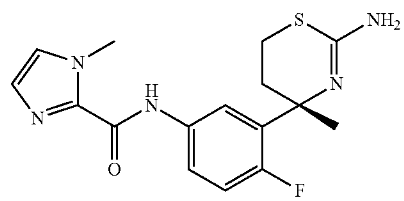 [SMILES: Cn1ccnc1C(=O)Nc1ccc(F)c([C@]2(C)CCSC(N)=N2)c1] | 348 | | | |
| 554 | 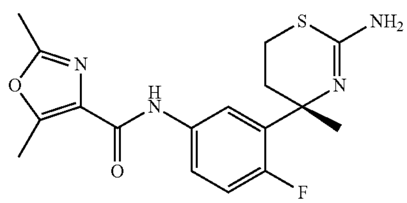 [SMILES: Cc1nc(C(=O)Nc2ccc(F)c([C@]3(C)CCSC(N)=N3)c2)c(C)o1] | 363 | | | |
| 555 | 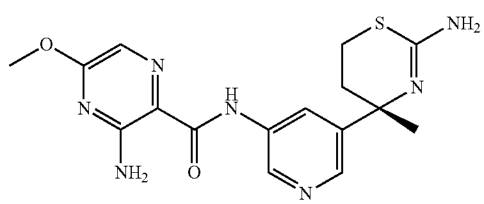 [SMILES: COc1cnc(C(=O)Nc2cncc([C@]3(C)CCSC(N)=N3)c2)c(N)n1] | 374 | | | |
| 556 | 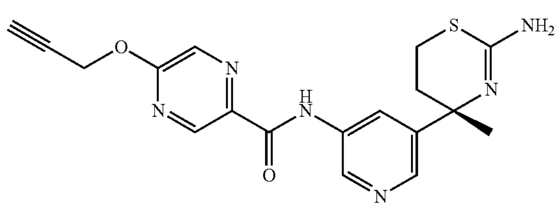 [SMILES: C#CCOc1cnc(C(=O)Nc2cncc([C@]3(C)CCSC(N)=N3)c2)cn1] | 383 | | | |
| 557 | 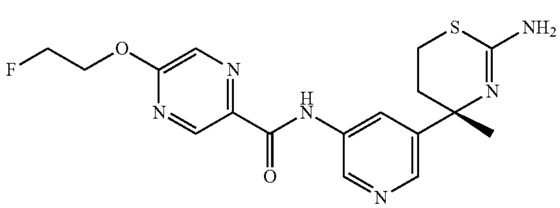 [SMILES: C[C@@]1(c2cncc(NC(=O)c3cnc(OCCF)cn3)c2)CCSC(N)=N1] | | | 1H-NMR (DMSO-d6) δ: 10.72 (1H, s), 8.93 (1H, s), 8.90 (1H, s), 8.49 (1H, s), 8.36 (1H, s), 8.24 (1H, s), 4.88-4.64 (4H, m), 3.03-2.97 (1H, m), 2.65-2.58 (1H, m), 2.13-2 07 (1H, m), 1.89-1.81 (1H, m), 1.48 (3H, s). | |
| 558 | 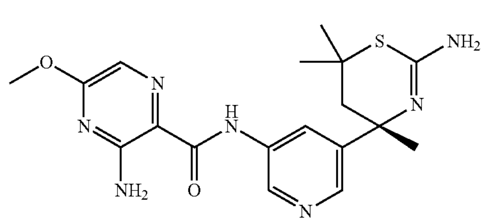 [SMILES: COc1cnc(C(=O)Nc2cncc([C@]3(C)CC(C)(C)SC(N)=N3)c2)c(N)n1] | 402 | | | |

TABLE 117

| Compound No. | Structure | MS (M + 1) | NMR (solvent, MP shift value: ascending order) | uv |
|---|---|---|---|---|
| 559 | 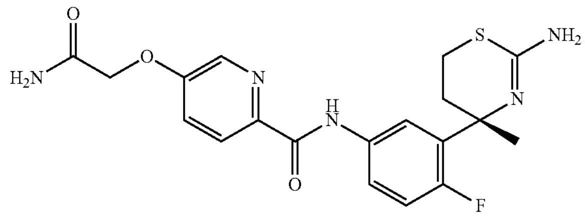 [SMILES: C[C@@]1(c2cc(NC(=O)c3ccc(OCC(N)=O)cn3)ccc2F)CCSC(N)=N1] | 418 | | |
| 560 | 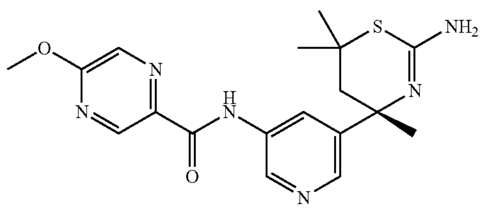 [SMILES: COc1cnc(C(=O)Nc2cncc([C@]3(C)CC(C)(C)SC(N)=N3)c2)cn1] | 387 | | |
| 561 | 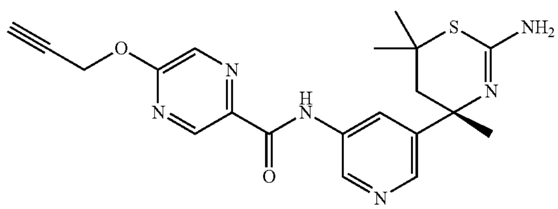 [SMILES: C#CCOc1cnc(C(=O)Nc2cncc([C@]3(C)CC(C)(C)SC(N)=N3)c2)cn1] | 411 | | |
| 562 | 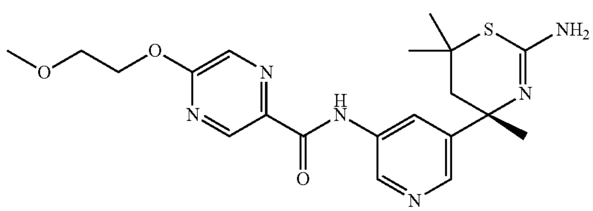 [SMILES: COCCOc1cnc(C(=O)Nc2cncc([C@]3(C)CC(C)(C)SC(N)=N3)c2)cn1] | 431 | | |
| 563 | 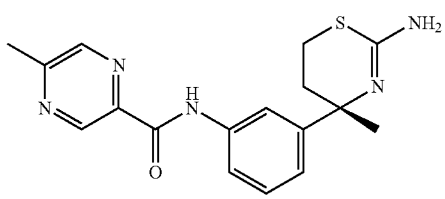 | 342 | | |
| 564 | 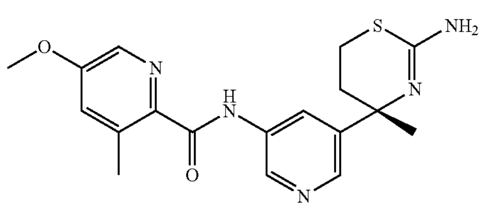 [SMILES: COc1cnc(C(=O)Nc2cncc([C@]3(C)CCSC(N)=N3)c2)c(C)c1] | 372 | | |
| 565 | 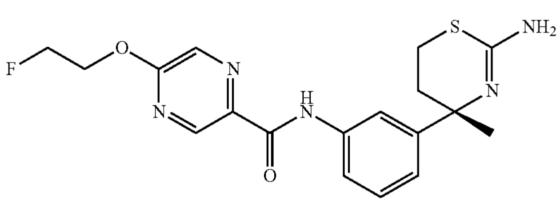 [SMILES: C[C@@]1(c2cccc(NC(=O)c3cnc(OCCF)cn3)c2)CCSC(N)=N1] | 390 | | |

TABLE 118

| Compound No | Structure | MS (M + 1) | NMR (solvent, MP shift value: ascending order) | uv |
|---|---|---|---|---|
| 566 | 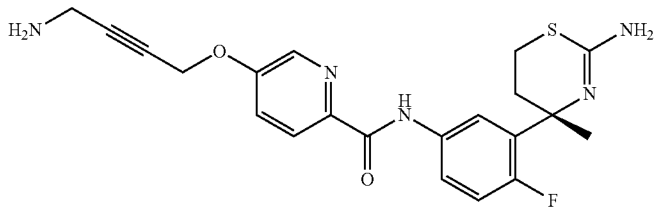 [SMILES: C[C@@]1(c2cc(NC(=O)c3ccc(OCC#CCN)cn3)ccc2F)CCSC(N)=N1] | 428 | | |
| 567 | 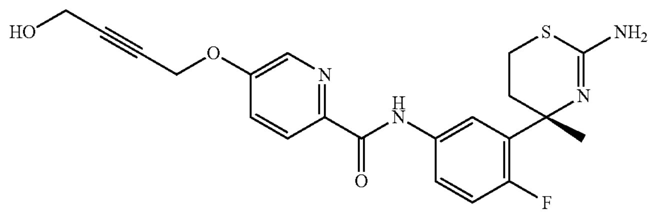 [SMILES: C[C@@]1(c2cc(NC(=O)c3ccc(OCC#CCO)cn3)ccc2F)CCSC(N)=N1] | 429 | | |
| 568 | 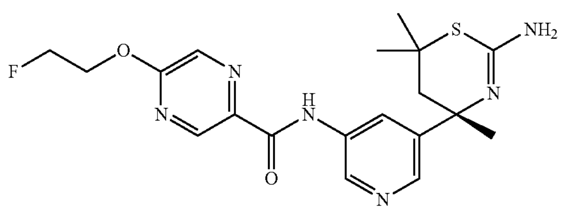 [SMILES: CC1(C)C[C@@](C)(c2cncc(NC(=O)c3cnc(OCCF)cn3)c2)N=C(N)S1] | 419 | | |
| 569 | 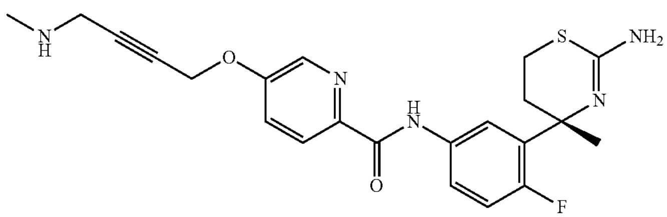 [SMILES: CNCC#CCOc1ccc(C(=O)Nc2ccc(F)c([C@]3(C)CCSC(N)=N3)c2)nc1] | 442 | | |
| 570 | 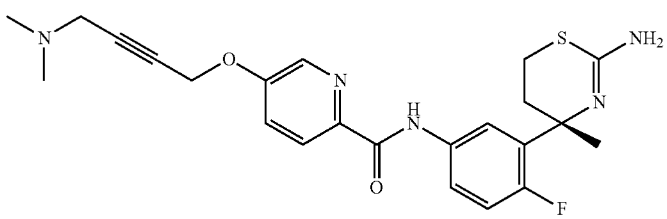 [SMILES: CN(C)CC#CCOc1ccc(C(=O)Nc2ccc(F)c([C@]3(C)CCSC(N)=N3)c2)nc1] | 456 | | |
| 571 | 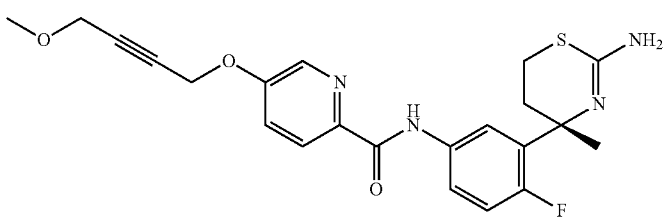 [SMILES: COCC#CCOc1ccc(C(=O)Nc2ccc(F)c([C@]3(C)CCSC(N)=N3)c2)nc1] | 443 | | |
| 572 | 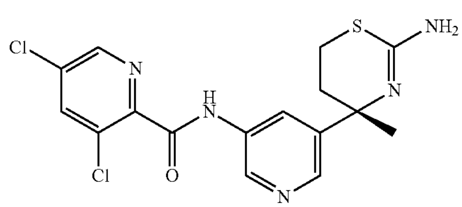 [SMILES: C[C@@]1(c2cncc(NC(=O)c3ncc(Cl)cc3Cl)c2)CCSC(N)=N1] | 396 | | |

TABLE 119

| Compound No. | Structure | MS (M + 1) | MP | NMR (solvent, shift value: ascending order) | uv |
|---|---|---|---|---|---|
| 573 | 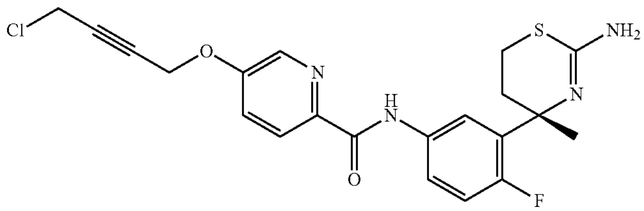 [SMILES: C[C@@]1(c2cc(NC(=O)c3ccc(OCC#CCCl)cn3)ccc2F)CCSC(N)=N1] | 447 | | | |
| 574 | 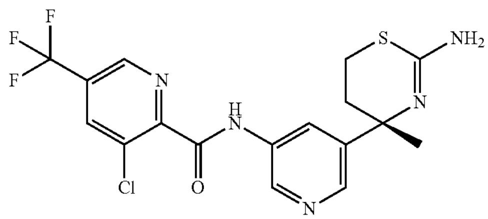 [SMILES: C[C@@]1(c2cncc(NC(=O)c3ncc(C(F)(F)F)cc3Cl)c2)CCSC(N)=N1] | 430 | | | |
| 575 | 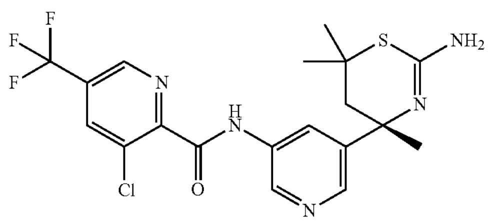 [SMILES: CC1(C)C[C@@](C)(c2cncc(NC(=O)c3ncc(C(F)(F)F)cc3Cl)c2)N=C(N)S1] | 458 | | | |
| 576 | 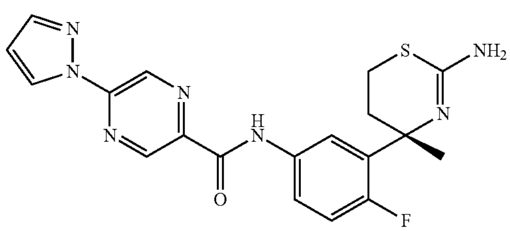 [SMILES: C[C@@]1(c2cc(NC(=O)c3cnc(-n4cccn4)cn3)ccc2F)CCSC(N)=N1] | 412 | | | |
| 577 | 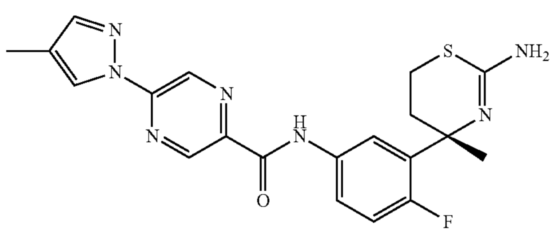 [SMILES: Cc1cnn(-c2cnc(C(=O)Nc3ccc(F)c([C@]4(C)CCSC(N)=N4)c3)cn2)c1] | 426 | | | |
| 578 | 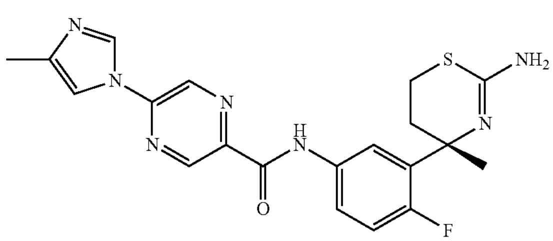 [SMILES: Cc1cn(-c2cnc(C(=O)Nc3ccc(F)c([C@]4(C)CCSC(N)=N4)c3)cn2)cn1] | 426 | | | |

TABLE 119-continued

| Compound No. | Structure | MS (M + 1) | MP | NMR (solvent, shift value: ascending order) | uv |
|---|---|---|---|---|---|
| 579 | 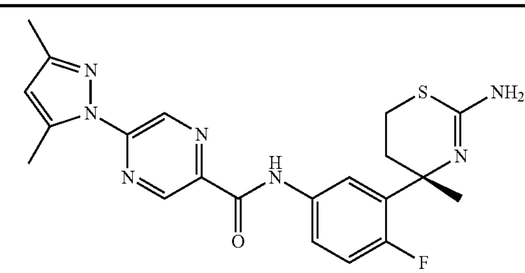 | 440 | | | |

TABLE 120

| Compound No | Structure | MS (M + 1) | MP | NMR (solvent, shift value: ascending order) | uv |
|---|---|---|---|---|---|
| 580 | 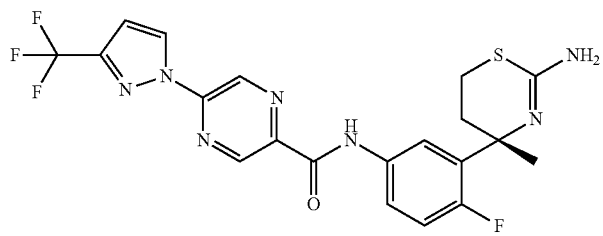 [SMILES: C[C@@]1(c2cc(NC(=O)c3cnc(-n4ccc(C(F)(F)F)n4)cn3)ccc2F)CCSC(N)=N1] | 480 | | | |
| 581 | 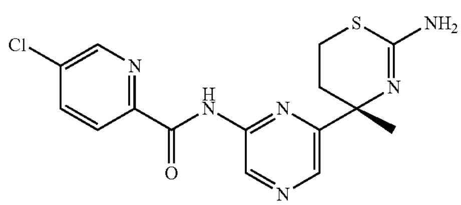 [SMILES: C[C@@]1(c2cncc(NC(=O)c3ccc(Cl)cn3)n2)CCSC(N)=N1] | 363 | | | |
| 582 | 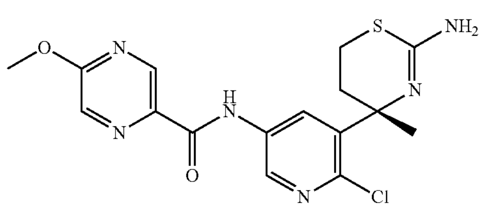 [SMILES: COc1cnc(C(=O)Nc2cnc(Cl)c([C@]3(C)CCSC(N)=N3)c2)cn1] | 393 | | | |
| 583 | 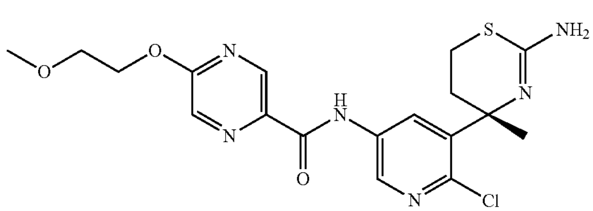 [SMILES: COCCOc1cnc(C(=O)Nc2cnc(Cl)c([C@]3(C)CCSC(N)=N3)c2)cn1] | 437 | | | |
| 584 | 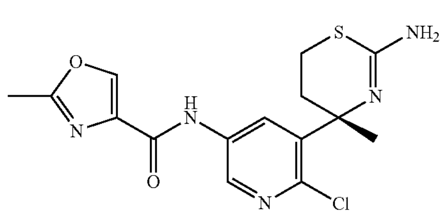 [SMILES: Cc1nc(C(=O)Nc2cnc(Cl)c([C@]3(C)CCSC(N)=N3)c2)co1] | 366 | | | |

TABLE 120-continued

| Compound No | Structure | MS (M + 1) | NMR (solvent, MP shift value: ascending order) | uv |
|---|---|---|---|---|
| 585 | 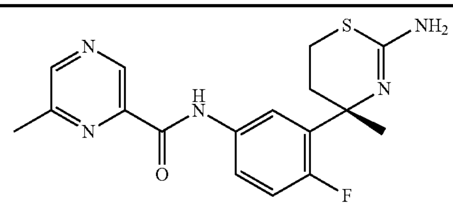 | 360 | | |
| 586 | 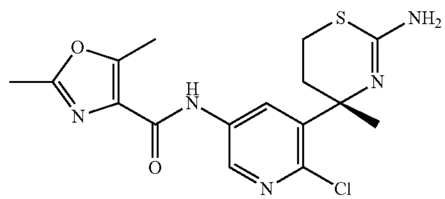 [SMILES: Cc1nc(C(=O)Nc2cnc(Cl)c([C@]3(C)CCSC(N)=N3)c2)c(C)o1] | 380 | | |

TABLE 121

| Compound No | Structure | MS (M + 1) | NMR (solvent, MP shift value: ascending order) | uv |
|---|---|---|---|---|
| 587 | 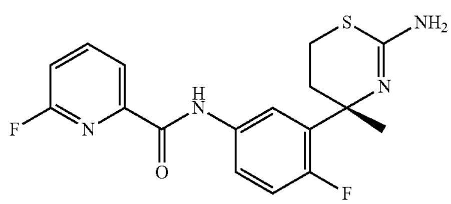 [SMILES: C[C@@]1(c2cc(NC(=O)c3cccc(F)n3)ccc2F)CCSC(N)=N1] | 363 | | |
| 588 | 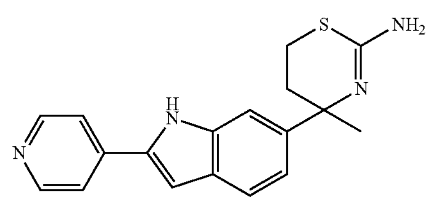 [SMILES: CC1(c2ccc3cc(-c4ccncc4)[nH]c3c2)CCSC(N)=N1] | 323 | | |
| 589 | 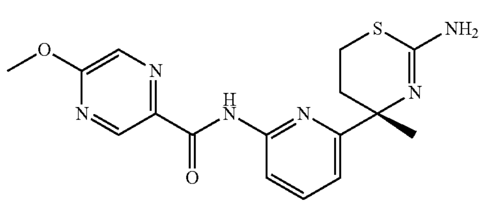 [SMILES: COc1cnc(C(=O)Nc2cccc([C@]3(C)CCSC(N)=N3)n2)cn1] | | | 250.9, 288.7 |
| 590 | 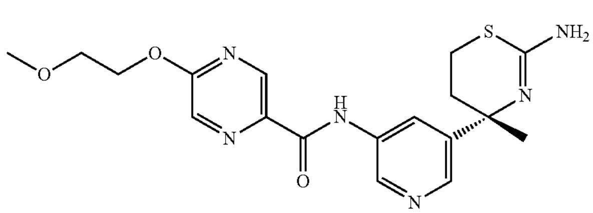 [SMILES: COCCOc1cnc(C(=O)Nc2cncc([C@]3(C)CCSC(N)=N3)c2)cn1] | | | 298.2 |

TABLE 121-continued

| Compound No | Structure | MS (M + 1) | NMR (solvent, MP shift value: ascending order) | uv |
|---|---|---|---|---|
| 591 | 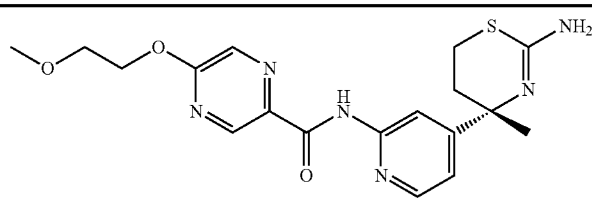 | | | 252.1, 305.3 |
| 592 | 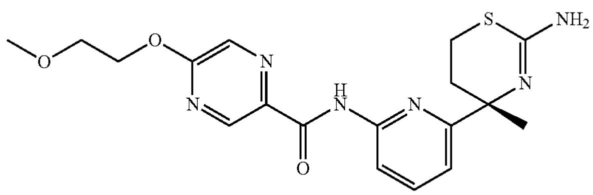 [SMILES: COCCOc1cnc(C(=O)Nc2cccc([C@]3(C)CCSC(N)=N3)n2)cn1] | | | 250.9, 288.7 |
| 593 | 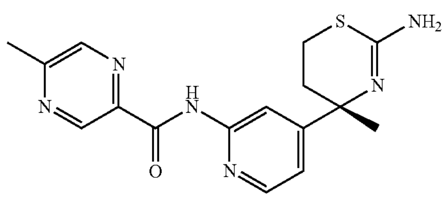 [SMILES: Cc1cnc(C(=O)Nc2cc([C@]3(C)CCSC(N)=N3)ccn2)cn1] | | | 216.9, 292.3 |

TABLE 122

| Compound No | Structure | MS (M + 1) | MP | NMR (solvent, shift value: ascending order) | uv |
|---|---|---|---|---|---|
| 594 | 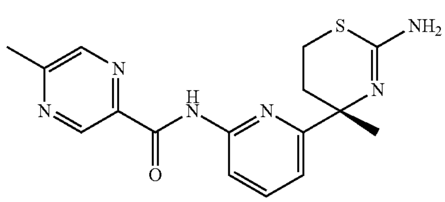 [SMILES: Cc1cnc(C(=O)Nc2cccc([C@]3(C)CCSC(N)=N3)n2)cn1] | | | | 214.5, 289.9 |
| 595 | 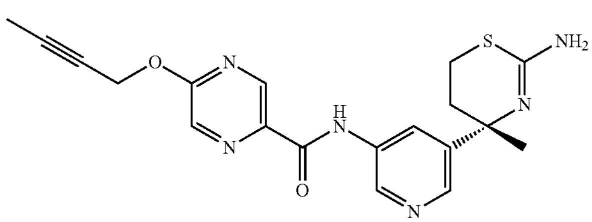 [SMILES: CC#CCOc1cnc(C(=O)Nc2cncc([C@]3(C)CCSC(N)=N3)c2)cn1] | | | | 297 |
| 596 | 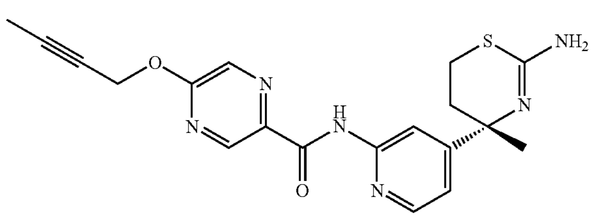 [SMILES: CC#CCOc1cnc(C(=O)Nc2cc([C@]3(C)CCSC(N)=N3)ccn2)cn1] | | | | 250.9, 302.9 |

TABLE 122-continued

| Compound No | Structure | MS (M + 1) | MP | NMR (solvent, shift value: ascending order) | uv |
|---|---|---|---|---|---|
| 597 | 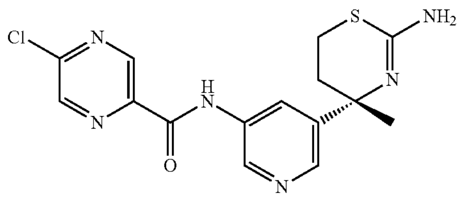 [SMILES: C[C@@]1(c2cncc(NC(=O)c3cnc(Cl)cn3)c2)CCSC(N)=N1] | | | | 289.9 |
| 598 | 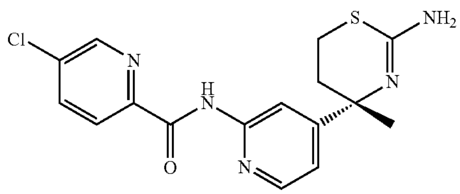 [SMILES: C[C@@]1(c2ccnc(NC(=O)c3ccc(Cl)cn3)c2)CCSC(N)=N1] | | | | 297 |
| 599 | 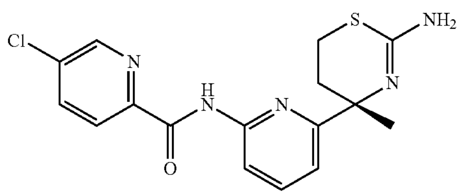 [SMILES: C[C@@]1(c2cccc(NC(=O)c3ccc(Cl)cn3)n2)CCSC(N)=N1] | | | | 214.5, 289.9 |
| 600 | 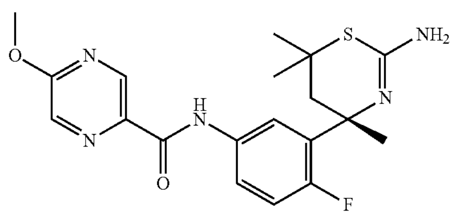 [SMILES: COc1cnc(C(=O)Nc2ccc(F)c([C@]3(C)CC(C)(C)SC(N)=N3)c2)cn1] | 404, 807 (2M + 1) | | | |

TABLE 123

| Compound No. | Structure | MS (M + 1) | MP | NMR (solvent, shift value: ascending order) | uv |
|---|---|---|---|---|---|
| 601 | 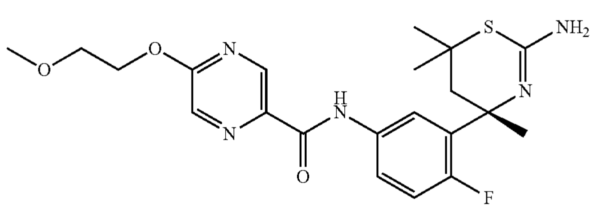 [SMILES: COCCOc1cnc(C(=O)Nc2ccc(F)c([C@]3(C)CC(C)(C)SC(N)=N3)c2)cn1] | 448, 895 (2M + 1) | | | |
| 602 | 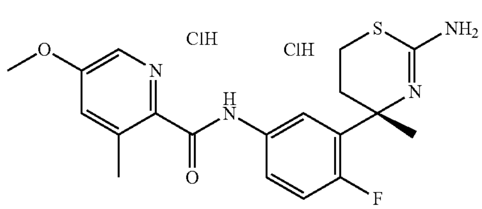 [SMILES: COc1cnc(C(=O)Nc2ccc(F)c([C@]3(C)CCSC(N)=N3)c2)c(C)c1 ; Cl ; Cl] | 389 | | | |

TABLE 123-continued

| Compound No. | Structure | MS (M + 1) | NMR (solvent, MP shift value: ascending order) | uv |
|---|---|---|---|---|
| 603 | 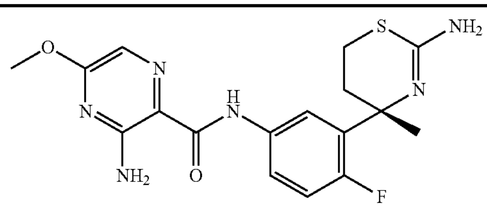 | 391 | | |
| 604 | 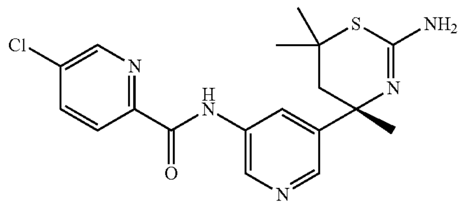 [SMILES: CC1(C)C[C@@](C)(c2cncc(NC(=O)c3ccc(Cl)cn3)c2)N=C(N)S1] | 391 | | |
| 605 | 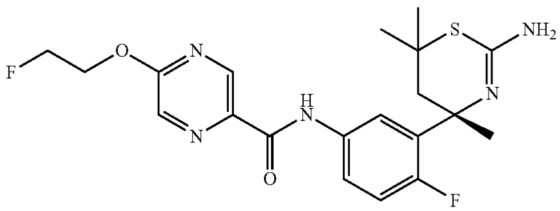 [SMILES: CC1(C)C[C@@](C)(c2cc(NC(=O)c3cnc(OCCF)cn3)ccc2F)N=C(N)S1] | 436 | | |
| 606 | 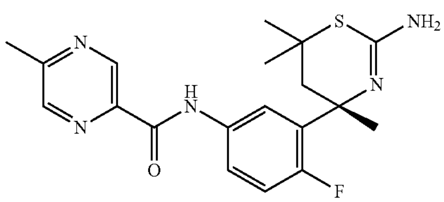 [SMILES: Cc1cnc(C(=O)Nc2ccc(F)c([C@]3(C)CC(C)(C)SC(N)=N3)c2)cn1] | 388 | | |

TABLE 124

| Compound No | Structure | MS (M + 1) | NMR (solvent, MP shift value: ascending order) | uv |
|---|---|---|---|---|
| 607 | 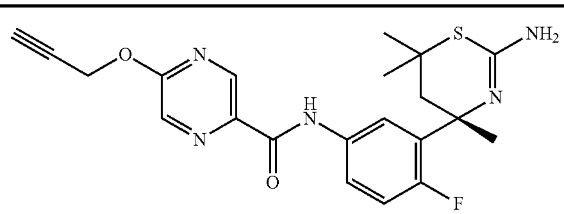 | | | |
| 608 | 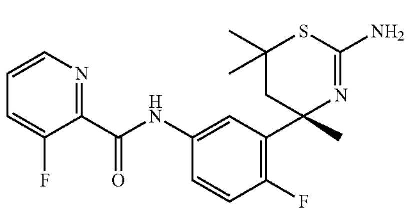 [SMILES: CC1(C)C[C@@](C)(c2cc(NC(=O)c3ncccc3F)ccc2F)N=C(N)S1] | | | |

TABLE 124-continued

| Compound No | Structure | MS (M + 1) | NMR (solvent, MP shift value: ascending order) | uv |
|---|---|---|---|---|
| 609 | 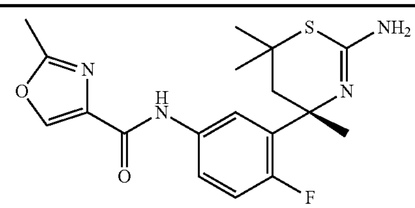 | 377 | | |
| 610 | 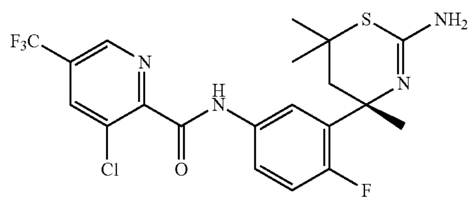 [SMILES: CC1(C)C[C@@](C)(c2cc(NC(=O)c3ncc(C(F)(F)F)cc3Cl)ccc2F)N=C(N)S1] | | | |
| 611 | 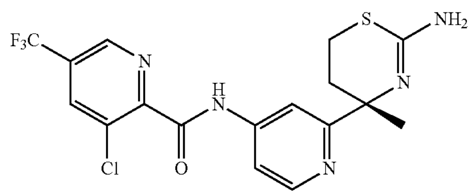 [SMILES: C[C@@]1(c2cc(NC(=O)c3ncc(C(F)(F)F)cc3Cl)ccn2)CCSC(N)=N1] | | | |
| 612 | 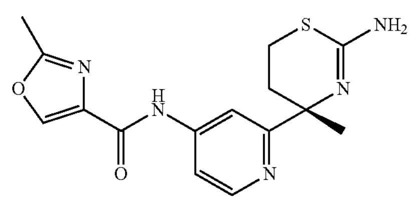 [SMILES: Cc1nc(C(=O)Nc2ccnc([C@]3(C)CCSC(N)=N3)c2)co1] | 332 | | |

TABLE 125

| Compound No | Structure | MS (M + 1) | NMR (solvent, MP shift value: ascending order) | uv |
|---|---|---|---|---|
| 613 | 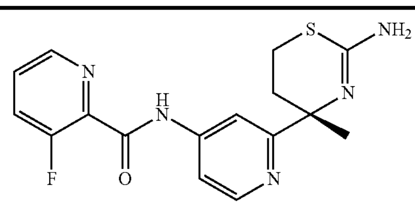 | 346 | | |
| 614 | 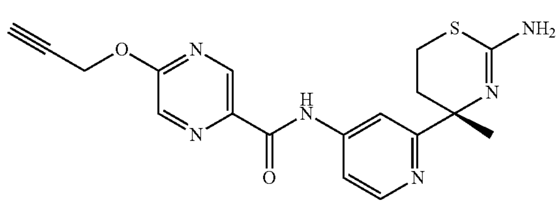 [SMILES: C#CCOc1cnc(C(=O)Nc2ccnc([C@]3(C)CCSC(N)=N3)c2)cn1] | | | |
| 615 | 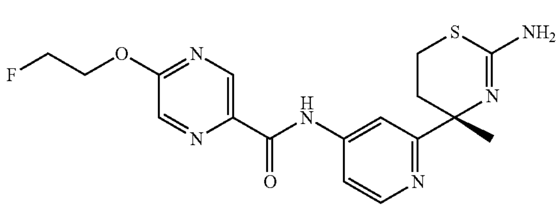 [SMILES: C[C@@]1(c2cc(NC(=O)c3cnc(OCCF)cn3)ccn2)CCSC(N)=N1] | | | |

TABLE 125-continued
| Compound No | Structure | MS (M + 1) | MP | NMR (solvent, shift value: ascending order) | uv |
|---|---|---|---|---|---|
| 616 | 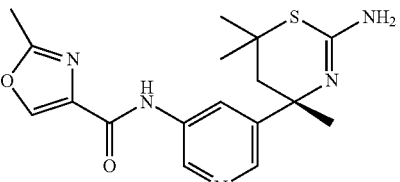 | | | | |
| 617 | 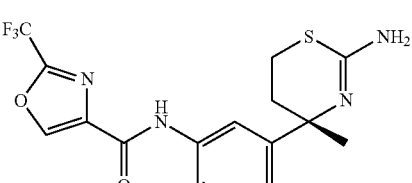 | | | | |
| 618 | 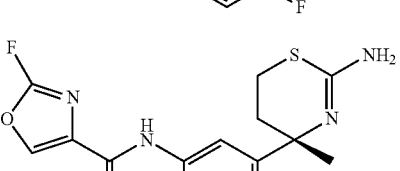 | | | | |
TABLE 126
| Compound No. | Structure | MS (M + 1) | MP | NMR (solvent, shift value: ascending order) | uv |
|---|---|---|---|---|---|
| 619 | 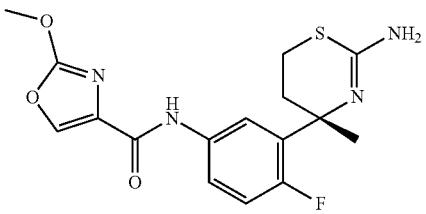 [SMILES: COc1nc(C(=O)Nc2ccc(F)c([C@]3(C)CCSC(N)=N3)c2)co1] | | | | |
| 620 | 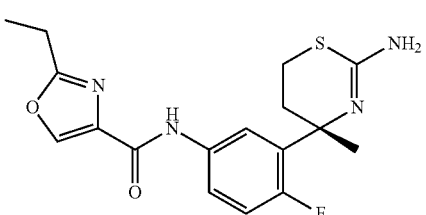 | | | | |
| 621 | 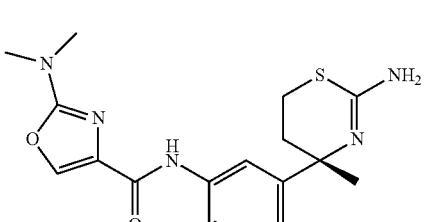 | | | | |

TABLE 126-continued

| Compound No. | Structure | MS (M + 1) | MP | NMR (solvent, shift value: ascending order) | uv |
|---|---|---|---|---|---|
| 622 | 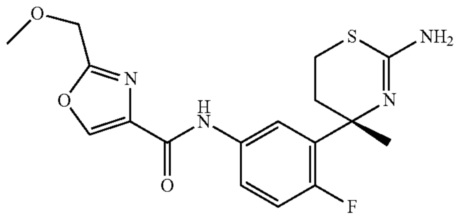 [SMILES: COCc1nc(C(=O)Nc2ccc(F)c([C@]3(C)CCSC(N)=N3)c2)co1] | | | | |
| 623 | 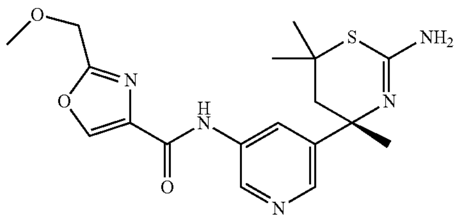 [SMILES: COCc1nc(C(=O)Nc2cncc([C@]3(C)CC(C)(C)SC(N)=N3)c2)co1] | | | | |
| 624 | 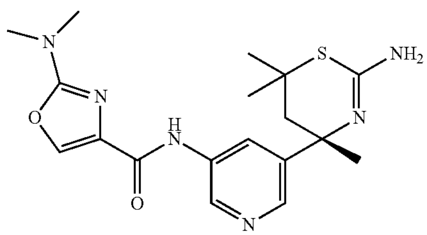 [SMILES: CN(C)c1nc(C(=O)Nc2cncc([C@]3(C)CC(C)(C)SC(N)=N3)c2)co1] | | | | |

TABLE 127

| Compound No | Structure | MS (M + 1) | MP | NMR (solvent, shift value: ascending order) | uv |
|---|---|---|---|---|---|
| 625 | 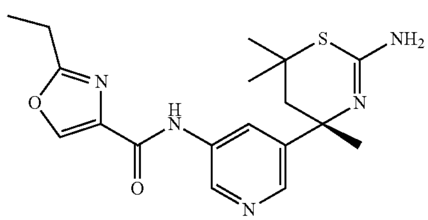 [SMILES: CCc1nc(C(=O)Nc2cncc([C@]3(C)CC(C)(C)SC(N)=N3)c2)co1] | | | | |
| 626 | 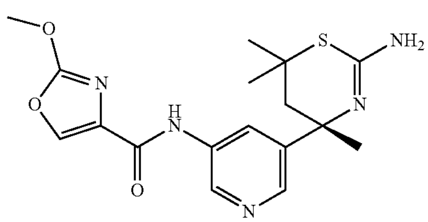 [SMILES: COc1nc(C(=O)Nc2cncc([C@]3(C)CC(C)(C)SC(N)=N3)c2)co1] | | | | |
| 627 | 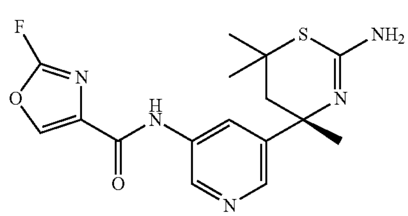 [SMILES: CC1(C)C[C@@](C)(c2cncc(NC(=O)c3coc(F)n3)c2)N=C(N)S1] | | | | |

TABLE 127-continued

| Compound No | Structure | MS (M + 1) | MP | NMR (solvent, shift value: ascending order) | uv |
|---|---|---|---|---|---|
| 628 | 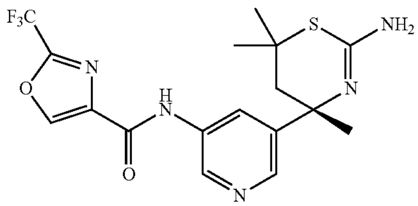 [SMILES: CC1(C)C[C@@](C)(c2cncc(NC(=O)c3coc(C(F)(F)F)n3)c2)N=C(N)S1] | | | | |
| 629 | 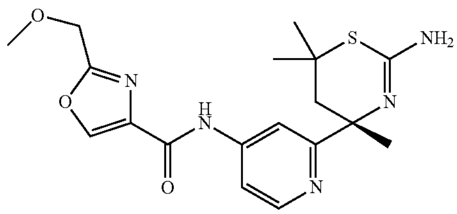 [SMILES: COCc1nc(C(=O)Nc2ccnc([C@]3(C)CC(C)(C)SC(N)=N3)c2)co1] | | | | |
| 630 | 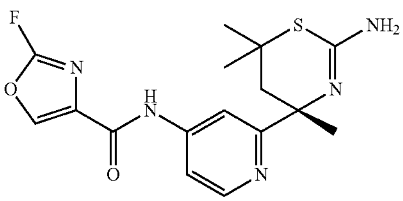 [SMILES: CC1(C)C[C@@](C)(c2cc(NC(=O)c3coc(F)n3)ccn2)N=C(N)S1] | | | | |

TABLE 128

| Compound No. | Structure | MS (M + 1) | MP | NMR (solvent, shift value: ascending order) | uv |
|---|---|---|---|---|---|
| 631 | 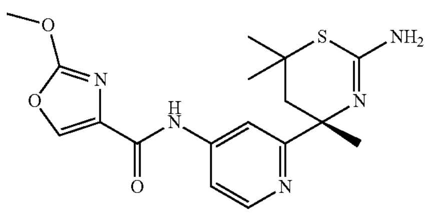 [SMILES: COc1nc(C(=O)Nc2ccnc([C@]3(C)CC(C)(C)SC(N)=N3)c2)co1] | | | | |
| 632 | 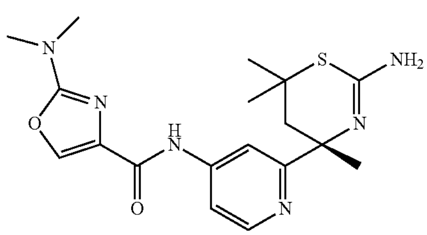 [SMILES: CN(C)c1nc(C(=O)Nc2ccnc([C@]3(C)CC(C)(C)SC(N)=N3)c2)co1] | | | | |
| 633 | 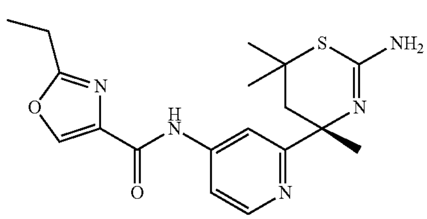 | | | | |

TABLE 128-continued

| Compound No. | Structure | MS (M + 1) | MP | NMR (solvent, shift value: ascending order) | uv |
|---|---|---|---|---|---|
| 634 | 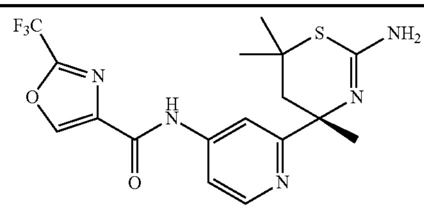 | | | | |
| 635 | 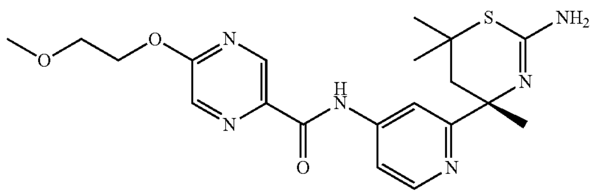 [SMILES: COCCOc1cnc(C(=O)Nc2ccnc([C@]3(C)CC(C)(C)SC(N)=N3)c2)cn1] | | | | |
| 636 | 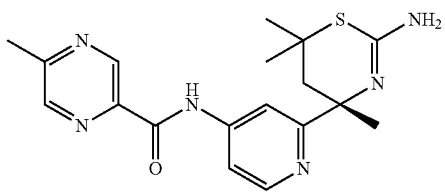 [SMILES: Cc1cnc(C(=O)Nc2ccnc([C@]3(C)CC(C)(C)SC(N)=N3)c2)cn1] | | | | |

TABLE 129

| Compound No | Structure | MS (M + 1) | MP | NMR (solvent, shift value: ascending order) | uv |
|---|---|---|---|---|---|
| 637 | 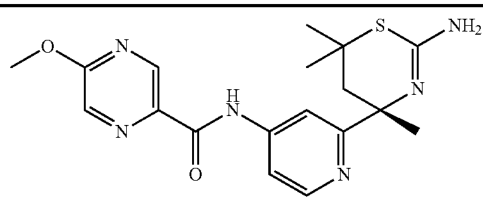 | 387 | | | |
| 638 | 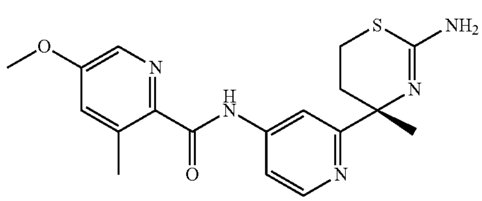 [SMILES: COc1cnc(C(=O)Nc2ccnc([C@]3(C)CCSC(N)=N3)c2)c(C)c1] | | | | |
| 639 | 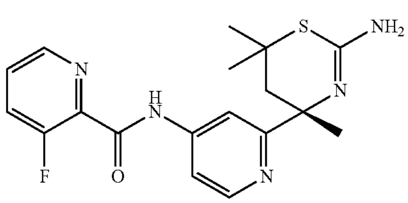 [SMILES: CC1(C)C[C@@](C)(c2cc(NC(=O)c3ncccc3F)ccn2)N=C(N)S1] | | | | |
| 640 | 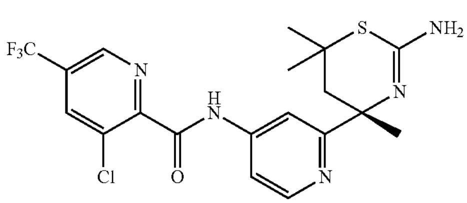 [SMILES: CC1(C)C[C@@](C)(c2cc(NC(=O)c3ncc(C(F)(F)F)cc3Cl)ccn2)N=C(N)S1] | | | | |

TABLE 129-continued

| Compound No | Structure | MS (M + 1) | MP | NMR (solvent, shift value: ascending order) | uv |
|---|---|---|---|---|---|
| 641 | 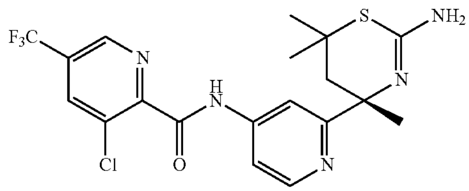 [SMILES: CC1(C)C[C@@](C)(c2cc(NC(=O)c3ncc(C(F)(F)F)cc3Cl)ccn2)N=C(N)S1] | | | | |
| 642 | 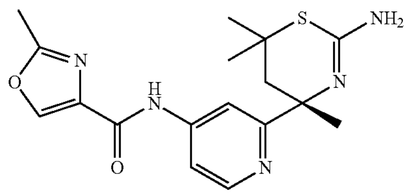 [SMILES: Cc1nc(C(=O)Nc2ccnc([C@]3(C)CC(C)(C)SC(N)=N3)c2)co1] | | | | |

TABLE 130

| Compound No | Structure | MS (M + 1) | MP | NMR (solvent, shift value: ascending order) | uv |
|---|---|---|---|---|---|
| 643 | 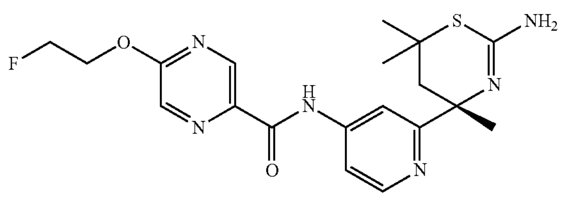 [SMILES: CC1(C)C[C@@](C)(c2cc(NC(=O)c3cnc(OCCF)cn3)ccn2)N=C(N)S1] | | | | |
| 644 | 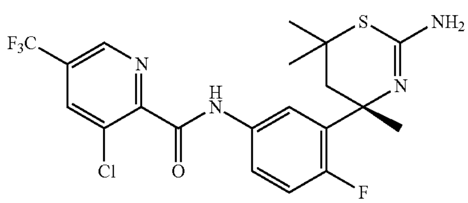 [SMILES: CC1(C)C[C@@](C)(c2cc(NC(=O)c3ncc(C(F)(F)F)cc3Cl)ccc2F)N=C(N)S1] | 475 | | | |
| 645 | 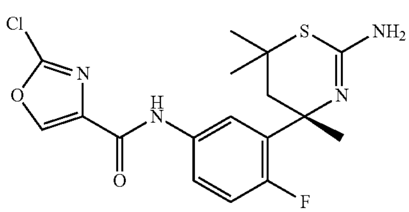 [SMILES: CC1(C)C[C@@](C)(c2cc(NC(=O)c3coc(Cl)n3)ccc2F)N=C(N)S1] | 397 | | | |
| 646 | 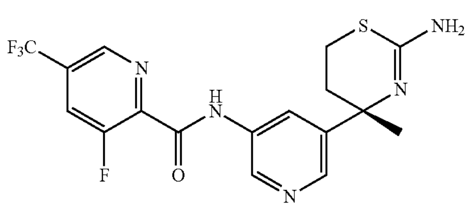 [SMILES: C[C@@]1(c2cncc(NC(=O)c3ncc(C(F)(F)F)cc3F)c2)CCSC(N)=N1] | 414 | | | |

TABLE 131
| Compound No | Structure | MS [M + 1] | NMR (solvent, shift value) |
|---|---|---|---|
| 647 | 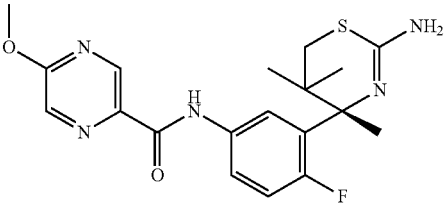 | 404 | |
| 648 | 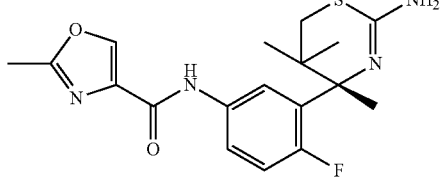 | 377 | |
| 649 | 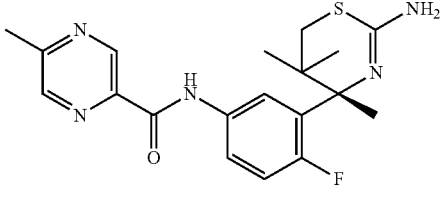 | 388 | |
| 650 | 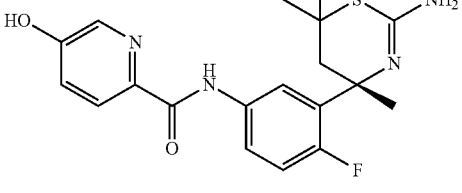 | 389 | |
| 651 | 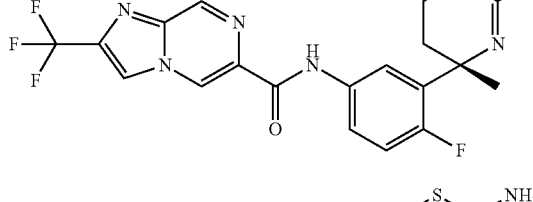 | 453 | |
| 652 | 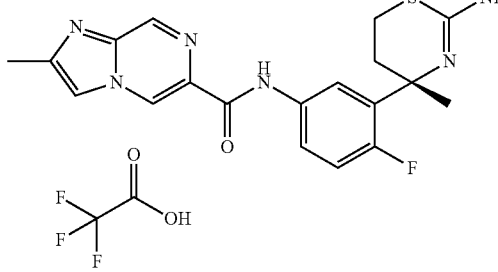 | 399 | |
| 653 | 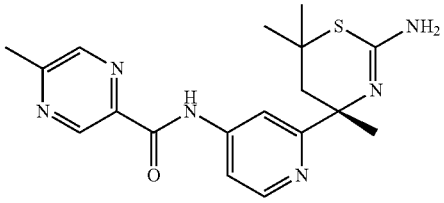 [SMILES: Cc1cnc(C(=O)Nc2ccnc([C@]3(C)CC(C)(C)SC(N)=N3)c2)cn1] | 371 | |

TABLE 132

| Compound No | Structure | MS [M + 1] | NMR (solvent, shift value) |
|---|---|---|---|
| 654 | 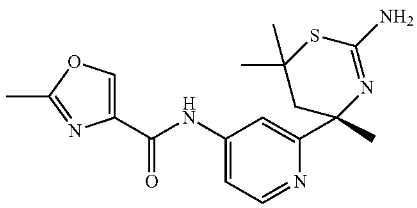 [SMILES: Cc1nc(C(=O)Nc2ccnc([C@]3(C)CC(C)(C)SC(N)=N3)c2)co1] | 360 | |
| 655 | 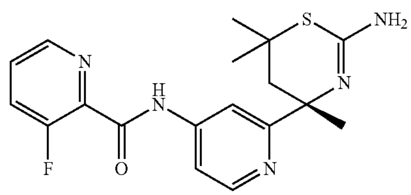 [SMILES: CC1(C)C[C@@](C)(c2cc(NC(=O)c3ncccc3F)ccn2)N=C(N)S1] | 374 | |
| 656 | 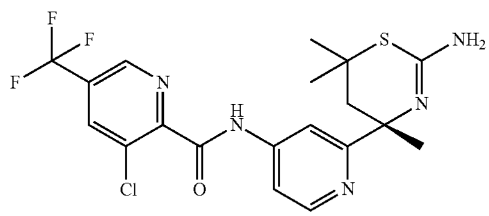 [SMILES: CC1(C)C[C@@](C)(c2cc(NC(=O)c3ncc(C(F)(F)F)cc3Cl)ccn2)N=C(N)S1] | 456 | |
| 657 | 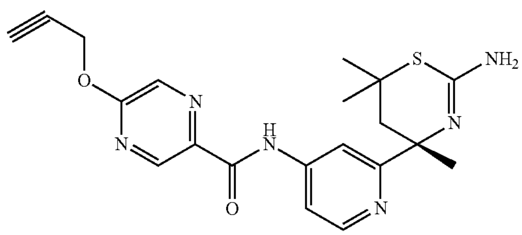 [SMILES: C#CCOc1cnc(C(=O)Nc2ccnc([C@]3(C)CC(C)(C)SC(N)=N3)c2)cn1] | 411 | |
| 658 | 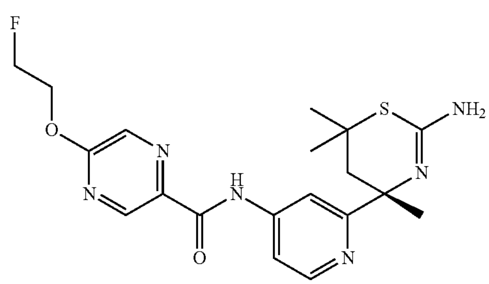 [SMILES: CC1(C)C[C@@](C)(c2cc(NC(=O)c3cnc(OCCF)cn3)ccn2)N=C(N)S1] | 419 | |
| 659 | 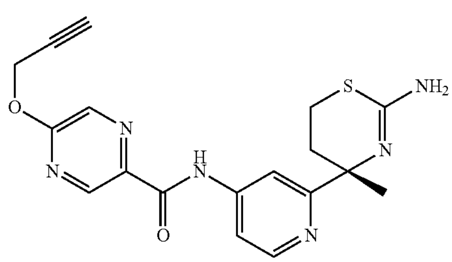 [SMILES: C#CCOc1cnc(C(=O)Nc2ccnc([C@]3(C)CCSC(N)=N3)c2)cn1] | 383 | |

TABLE 132-continued

| Compound No | Structure | MS [M + 1] | NMR (solvent, shift value) |
|---|---|---|---|
| 660 | 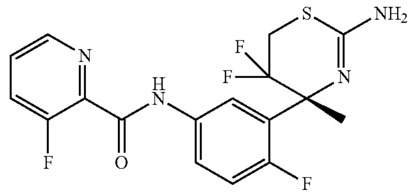 [SMILES: C[C@]1(c2cc(NC(=O)c3ncccc3F)ccc2F)N=C(N)SCC1(F)F] | | 1H-NMR (CDCl3) δ: 1.84 (3H, d-like), 3.16 (1H, ddd, J = 6 9, 12.6, 14.4 Hz), 3.36 (1H, ddd, J = 6.0, 12.6, 18.9 Hz), 4.61 (2H, br), 7.07 (1H, dd, J = 8.7, 11.7 Hz), 7.49-7.63 (2H, m), 7.67 (1H, dd, J = 3.0, 6.9 Hz), 7.95 (1H, ddd, J = 3.0, 6.9, 8.7 Hz), 8.41 (1H, m), 9.85 (1H, brs). |

TABLE 133

| Compound No | Structure | MS [M + 1] | NMR (solvent, shift value) |
|---|---|---|---|
| 661 | 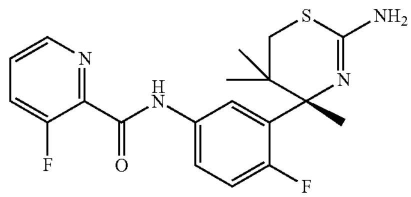 [SMILES: CC1(C)CSC(N)=N[C@]1(C)c1cc(NC(=O)c2ncccc2F)ccc1F] | | 1H-NMR (CDCl3) δ: 0.89 (3H, s), 1.11 (3H, d, J = 3.0 Hz), 1.67 (3H, d, J = 4.2 Hz), 2.63 (1H, d, J = 12.0 Hz), 3.12 (1H, d, J = 12 0 Hz), 4.29 (2H, br), 7.02 (1H, dd, J = 8.7, 12.3 Hz), 7.49-7.64 (3H, m), 7.96 (1H, ddd, J = 3.0, 6.6, 8.7 Hz), 8.45 (1H, m), 9.81 (1H, brs). |
| 662 | 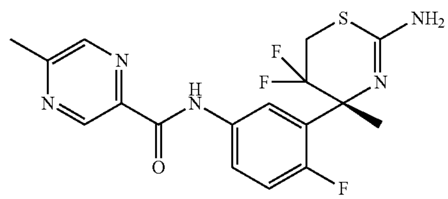 [SMILES: Cc1cnc(C(=O)Nc2ccc(F)c([C@@]3(C)N=C(N)SCC3(F)F)c2)cn1] | | 1H-NMR (CDCl3) δ: 1.85 (3H, d-like), 2.69 (3H, s), 3.17 (1H, ddd, J = 6.9, 12.6, 14.4 Hz), 3.37 (1H, ddd, J = 6.3, 12.9, 18 9 Hz), 4.54 (2H, brs), 7.08 (1H, dd, J = 8.7, 11.7 Hz), 7.69 (1H, dd, J = 2 7, 6.9 Hz), 7 87 (1H, dd, J = 2.4, 8 4 Hz), 7 93 (1H, ddd, J = 2.7, 6.6, 8 7 Hz), 8.24 (1H, dd, J = 0.6, 8.4 Hz), 8.55 (1H, dd, J = 0.6, 2.4 Hz), 9.82 (1H, brs). |
| 663 | 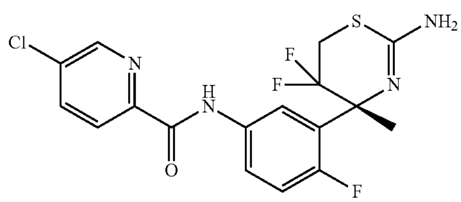 [SMILES: C[C@]1(c2cc(NC(=O)c3ccc(Cl)cn3)ccc2F)N=C(N)SCC1(F)F] | | 1H-NMR (CDCl3) δ: 1.85 (3H, d-like), 3.18 (1H, ddd, J = 7 2, 12.9, 15.0 Hz), 3.37 (1H, ddd, J = 6.0, 12.6, 18.9 Hz), 4.60 (2H, br), 7.08 (1H, dd, J = 8.7, 11.7 Hz), 7.71 (1H, dd, J = 3.0, 6.6 Hz), 7.90 (1H, ddd, J = 3.0, 6.6, 8.7 Hz), 8.41 (1H, d, J = 0.9 Hz), 9.35 (1H, d, J = 0.9 Hz), 9.63 (1H, brs). |
| 664 | 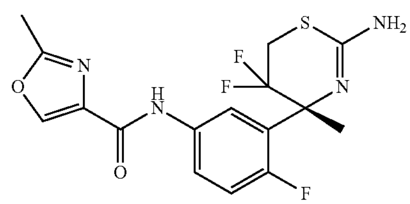 [SMILES: Cc1nc(C(=O)Nc2ccc(F)c([C@@]3(C)N=C(N)SCC3(F)F)c2)co1] | | 1H-NMR (CDCl3) δ: 1.83 (3H, d-like), 2 51 (3H, s), 3.16 (1H, ddd, J = 6.9, 12.9, 15.3 Hz), 3.34 (1H, ddd, J = 6.3, 12.9, 19.2 Hz), 4.53 (2H, brs), 7.05 (1H, dd, J = 8.7, 11.4 Hz), 7.62 (1H, dd, J = 2.7, 6.9 Hz), 7.82 (1H, ddd, J = 2.7, 6.9, 8.7 Hz), 8.16 (1H, s), 8.70 (1H, brs). |
| 665 | 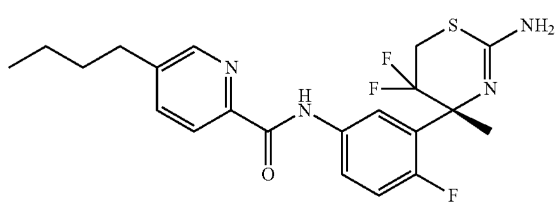 [SMILES: CCCCc1ccc(C(=O)Nc2ccc(F)c([C@@]3(C)N=C(N)SCC3(F)F)c2)nc1] | | 1H-NMR (CDCl3) δ: 0.95 (3H, t, J = 7.5 Hz), 1.32-1.44 (2H, m), 1.59-1.69 (2H, m), 1.85 (3H, d-like), 2.70 (2H, t, J = 7.5 Hz), 3.17 (1H, ddd, J = 6.9, 12.9, 15.3 Hz), 3.34 (1H, ddd, J = 6.3, 12.9, 19.2 Hz), 4.53 (2H, brs), 7.07 (1H, dd, J = 8.7, 11.7 Hz), 7.67-7.70 (2H, m), 7.94 (1H, ddd, J = 2.7, 6.6, 8.7 Hz), 8.18 (1H, dd, J = 0.6, 7.8 Hz), 8.40 (1H, dd, J = 0.6, 1.8 Hz), 9.97 (1H, brs). |
| 666 | 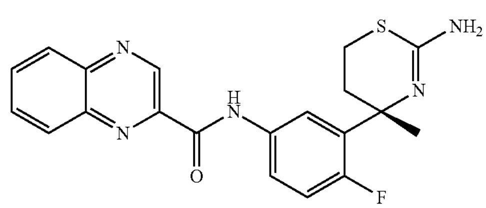 [SMILES: C[C@@]1(c2cc(NC(=O)c3cnc4ccccc4n3)ccc2F)CCSC(N)=N1] | 396 | |

TABLE 133-continued
| Compound No | Structure | MS [M + 1] | NMR (solvent, shift value) |
|---|---|---|---|
| 667 | 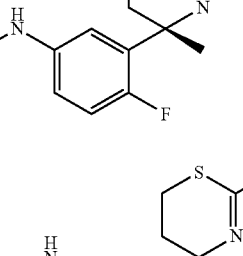 | 365 | |
TABLE 134
| Compound No. | Structure | MS [M + 1] | NMR (solvent, shift value) |
|---|---|---|---|
| 668 | 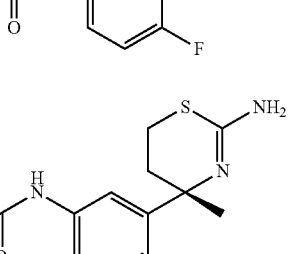 | 356 | |
| 669 | 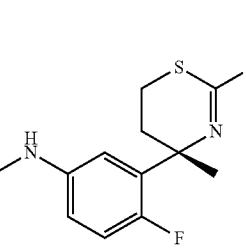 | 403 | |
| 670 | 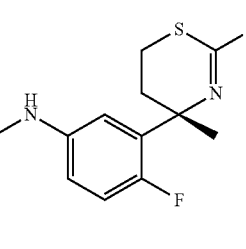 | | 1H-NMR (CDCl3) δ: 1.38 (3H, t, J = 7.6 Hz), 1.63 (3H, s), 1.88-1.97 (1H, m), 2.41-2.50 (1H, m), 2.69-2.78 (1H, m), 2.84 (2H, q, J = 7.6 Hz), 2.93-3.01 (1H, m), 7.02 (1H, dd, J = 11.8, 8 8 Hz), 7.34 (1H, dd, J = 7.1, 2.8 Hz), 7.89 (1H, ddd, J = 8.8, 4.3, 2.8 Hz), 8.16 (1H, s), 8.69 (1H, s) |
| 671 | 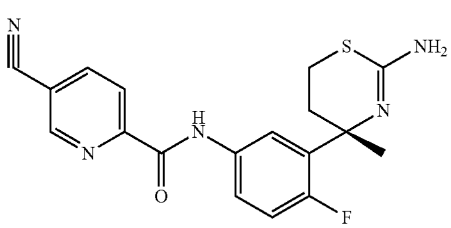 [SMILES: C[C@@]1(c2cc(NC(=O)c3ccc(C#N)cn3)ccc2F)CCSC(N)=N1] | 370 | |
| 672 | 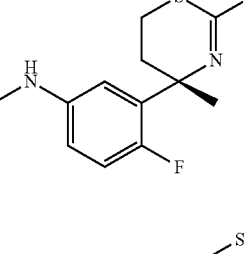 | 432 | |

//TABLE 134-continued

| Compound No. | Structure | MS [M + 1] | NMR (solvent, shift value) |
|---|---|---|---|
| 673 | 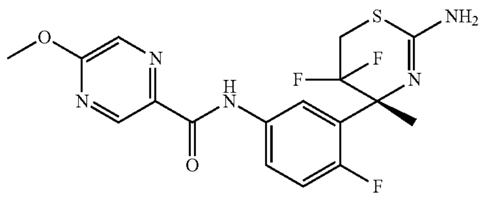 | 412 | |
| 674 | 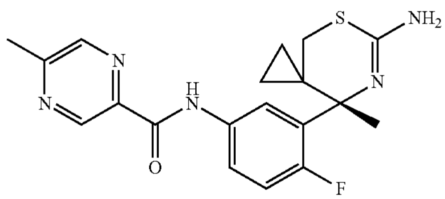 [SMILES: Cc1cnc(C(=O)Nc2ccc(F)c([C@@]3(C)N=C(N)SCC34CC4)c2)cn1] | | 1H-NMR (CDCl₃) δ: 0.53-0.59 (1H, m), 0.65-0.72 (1H, m), 0.85-0.91 (1H, m), 1.14-1.17 (1H, m), 1.47 (3H, d, J = 2.0 Hz), 2.46 (1H, d, J = 12.1 Hz), 2.69 (3H, s), 2.89 (1H, dd, J = 12.1, 1.3 Hz), 7.06 (1H, dd, J = 11.5, 8.8 Hz), 7.45 (1H, dd, J = 6.8, 2.6 Hz), 7.94 (1H, ddd, J = 8.8, 4 0, 2.8 Hz), 8.44 (1H, d, J = 1.3 Hz), 9.36 (1H, d, J = 1.3 Hz), 9.60 (1H, s). |

TABLE 135

| Compound No. | Structure | MS [M + 1] | NMR (solvent, shift value) |
|---|---|---|---|
| 675 | 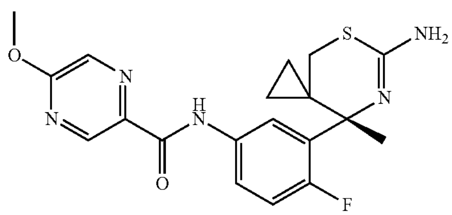 [SMILES: COc1cnc(C(=O)Nc2ccc(F)c([C@@]3(C)N=C(N)SCC34CC4)c2)cn1] | 402 | |
| 676 | 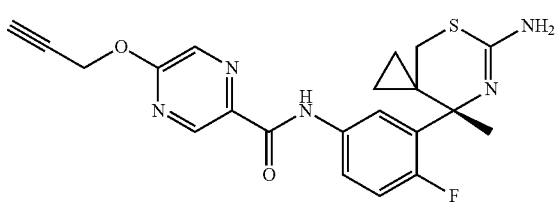 [SMILES: C#CCOc1cnc(C(=O)Nc2ccc(F)c([C@@]3(C)N=C(N)SCC34CC4)c2)cn1] | 426 | |
| 677 | 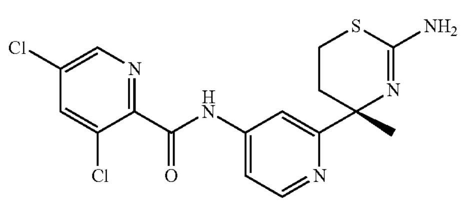 [SMILES: C[C@@]1(c2cc(NC(=O)c3ncc(Cl)cc3Cl)ccn2)CCSC(N)=N1] | 396 | |
| 678 | 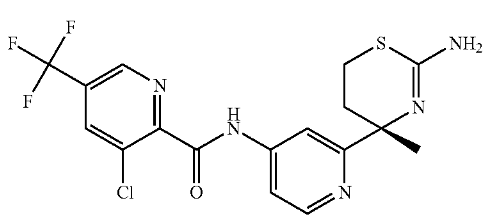 [SMILES: C[C@@]1(c2cc(NC(=O)c3ncc(C(F)(F)F)cc3Cl)ccn2)CCSC(N)=N1] | 430 | |

TABLE 135-continued

| Compound No. | Structure | MS [M + 1] | NMR (solvent, shift value) |
|---|---|---|---|
| 679 | 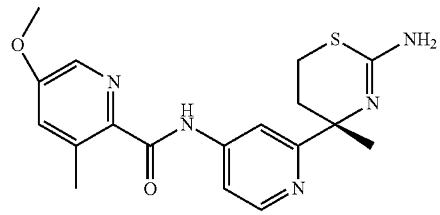 [SMILES: COc1cnc(C(=O)Nc2ccnc([C@]3(C)CCSC(N)=N3)c2)c(C)c1] | 372 | |
| 680 | 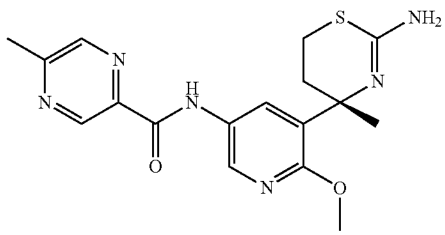 [SMILES: COc1ncc(NC(=O)c2cnc(C)cn2)cc1[C@]1(C)CCSC(N)=N1] | | ¹H-NMR (DMSO-d₆) δ: 1.47 (3H, s), 1.77-1.83 (1H, m), 2.34-2.39 (1H, m), 2.48-2.53 (1H, m), 2.63 (3H, s), 2.89-2.96 (1H, m), 3.90 (3H, s), 5.86 (2H, br s), 8.10 (1H, d, J = 2.3 Hz), 8.47 (1H, d, J = 2.5 Hz), 8.69 (1H, s), 9.14 (1H, s), 10.59 (1H, s). |
| 681 | 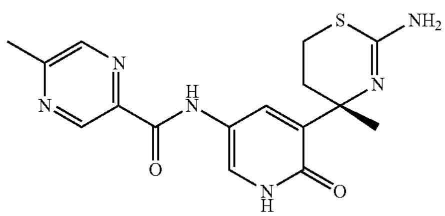 [SMILES: Cc1cnc(C(=O)Nc2c[nH]c(=O)c([C@]3(C)CCSC(N)=N3)c2)cn1] | | ¹H-NMR (DMSO-d₆) δ: 1 52 (3H, s), 1.80-1.85 (1H, m), 2.62 (3H, s), 2.64-2.69 (2H, m), 2.96-3 01 (1H, m), 7.77 (1H, d, J = 2.5 Hz), 7.96 (1H, d, J = 2.3 Hz), 8.67 (1H, s), 9.10 (1H, s), 10.58 (1H, s). |

TABLE 136

| Compound No | Structure | MS [M + 1] | NMR (solvent, shift value) |
|---|---|---|---|
| 682 | 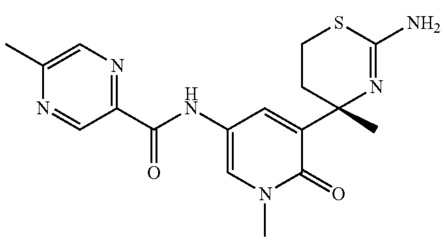 [SMILES: Cc1cnc(C(=O)Nc2cc([C@]3(C)CCSC(N)=N3)c(=O)n(C)c2)cn1] | | ¹H-NMR (DMSO-d₆) δ: 1.46 (3H, s), 1.95-2.01 (1H, m), 2.33-2.39 (1H, m), 2.62 (3H, s), 2.64-2.69 (1H, m), 2.74 (2H, s), 2.92-2.98 (1H, m), 7.90 (1H, d, J = 2.5 Hz), 7.94-7.95 (1H, m), 8.67 (1H, s), 9.09 (1H, s), 10.57 (1H, s). |
| 683 | 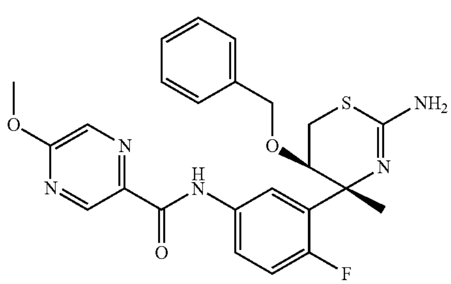 [SMILES: COc1cnc(C(=O)Nc2ccc(F)c([C@@]3(C)N=C(N)SC[C@@H]3OCc3ccccc3)c2)cn1] | 482 | |

TABLE 136-continued
| Compound No | Structure | MS [M + 1] | NMR (solvent, shift value) |
|---|---|---|---|
| 684 | 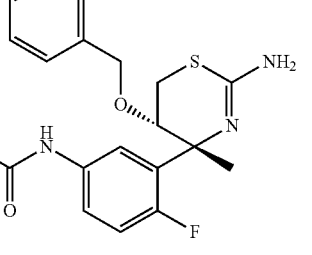 | 482 | |
| 685 | 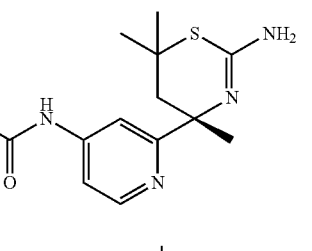 | 400 | |
| 686 | 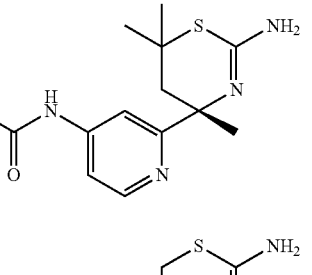 | 424 | |
| 687 | 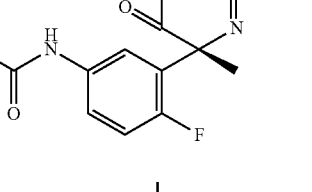 | 427 | |
| 688 | 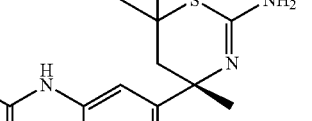 | 402 | |
TABLE 137
| Compound No | Structure | MS [M + 1] | NMR (solvent, shift value) |
|---|---|---|---|
| 689 | 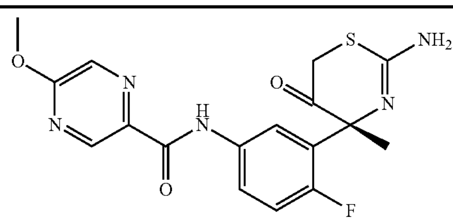 | 390 | |

TABLE 137-continued

| Compound No | Structure | MS [M + 1] | NMR (solvent, shift value) |
|---|---|---|---|
| 690 | 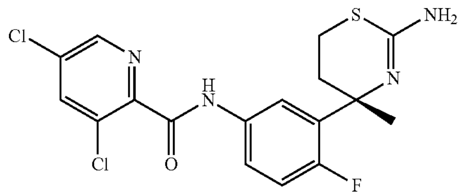 [SMILES: C[C@@]1(c2cc(NC(=O)c3ncc(Cl)cc3Cl)ccc2F)CCSC(N)=N1] | 413 | |
| 691 | 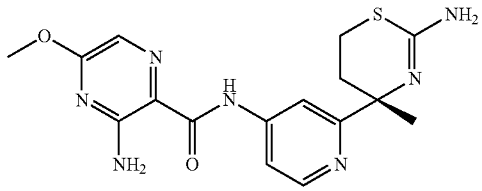 [SMILES: COc1cnc(C(=O)Nc2ccnc([C@]3(C)CCSC(N)=N3)c2)c(N)n1] | 374 | |
| 692 | 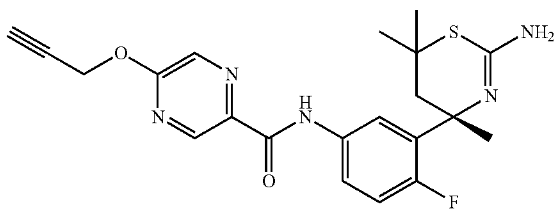 [SMILES: C#CCOc1cnc(C(=O)Nc2ccc(F)c([C@]3(C)CC(C)(C)SC(N)=N3)c2)cn1] | 428 | |
| 693 | 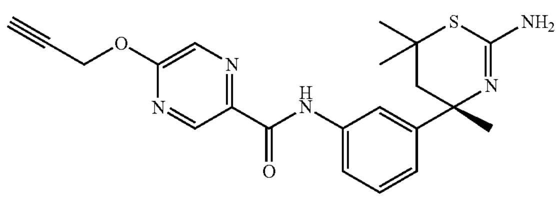 [SMILES: C#CCOc1cnc(C(=O)Nc2cccc([C@]3(C)CC(C)(C)SC(N)=N3)c2)cn1] | | 1H-NMR (DMSO-d6) δ: 0.77 (3H, s), 1.30 (3H, s), 1.43 (3H, s), 1.71 (1H, d, J = 13.8 Hz), 2.33 (1H, d, J = 13.8 Hz), 3.65 (1H, t, J = 2.4 Hz), 5.13 (2H, d, J = 2.4 Hz), 6.05 (2H, br), 7.19 (1H, d-like), 7 25 (1H, t, J = 7 8 Hz), 7.71 (1H, d-like), 7.87 (1H, s-like), 8.47 (1H, d, J = 1.2 Hz), 8.90 (1H, d, J = 1.2 Hz), 10.37 (1H, brs). |
| 694 | 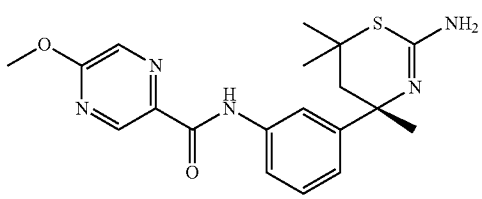 [SMILES: COc1cnc(C(=O)Nc2cccc([C@]3(C)CC(C)(C)SC(N)=N3)c2)cn1] | | 1H-NMR (DMSO-d6) δ: 0.77 (3H, s), 1.28 (3H, s), 1.42 (3H, s), 1.67 (1H, d, J = 14.1 Hz), 2.23 (1H, d, J = 14.1 Hz), 4.02 (3H, s), 5.82 (2H, brs), 7.19 (1H, d-like), 7.24 (1H, t, J = 7.8 Hz), 7.70 (1H, d-like), 7.86 (1H, s-like), 8.40 (1H, d, J = 1.2 Hz), 8.89 (1H, d, J = 1.2 Hz), 10.31 (1H, brs). |
| 695 | 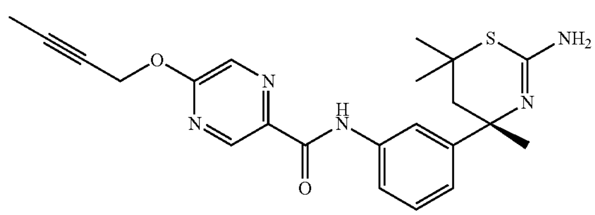 [SMILES: CC#CCOc1cnc(C(=O)Nc2cccc([C@]3(C)CC(C)(C)SC(N)=N3)c2)cn1] | | 1H-NMR (DMSO-d6) δ: 0.79 (3H, s), 1.32 (3H, s), 1.46 (3H, s), 1.78 (1H, d, J = 14.1 Hz), 1.86 (3H, t, J = 2.4 Hz), 2.39 (1H, d, J = 14.1 Hz), 5.90 (1H, q, J = 2.4 Hz), 6.49 (2H, br), 7.16 (1H, (d-like), 7 27 (1H, t, J = 7.8 Hz), 7.73 (1H, d-like), 7.87 (1H, s-like), 8.44 (1H, d, J = 1.2 Hz), 8.89 (1H, d, J = 1.2 Hz), 10.38 (1H, brs). |

TABLE 138

| Compound No | Structure | MS [M + 1] | NMR (solvent, shift value) |
|---|---|---|---|
| 696 | 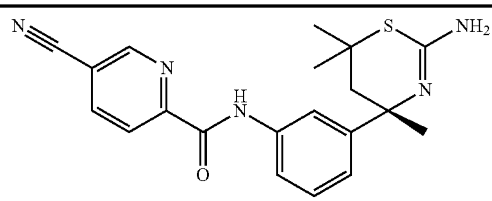 | | 1H-NMR (DMSO-d6) δ: 0.77 (3H, s), 1.30 (3H, s), 1.43 (3H, s), 1.71 (1H, d, J = 14.1 Hz), 2.32 (1H, d, J = 14.1 Hz), 5.95 (2H, br), 7.22 (1H, d-like), 7.27 (1H, t, J = 7.8 Hz), 7.75 (1H, d-like), 7.88 (1H, s-like), 8.29 (1H, dd, J = 0.6, 8.1 Hz), 8.58 (1H, dd, J = 2.1, 8.1 Hz), 8.19 (1H, dd, J = 0.6, 2.1 Hz), 10.65 (1H, brs). |

TABLE 138-continued

| Compound No | Structure | MS [M + 1] | NMR (solvent, shift value) |
|---|---|---|---|
| 697 | 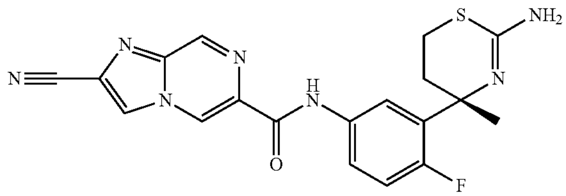 [SMILES: C[C@@]1(c2cc(NC(=O)c3cn4cc(C#N)nc4cn3)ccc2F)CCSC(N)=N1] | 410 | |
| 698 | 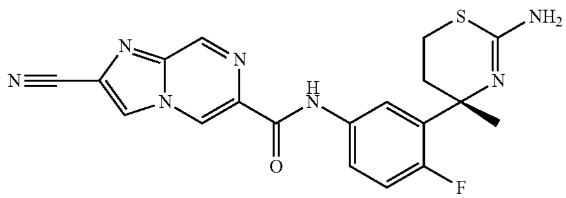 [SMILES: C[C@@]1(c2cc(NC(=O)c3cn4cc(C#N)nc4cn3)ccc2F)CCSC(N)=N1] | | |
| 699 | 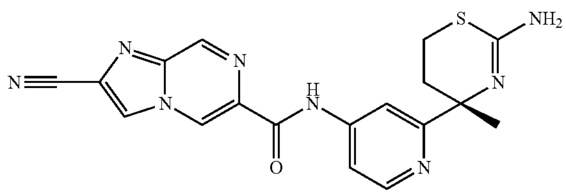 [SMILES: C[C@@]1(c2cc(NC(=O)c3cn4cc(C#N)nc4cn3)ccn2)CCSC(N)=N1] | | |
| 700 | 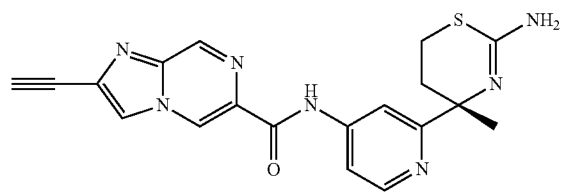 [SMILES: C#Cc1cn2cc(C(=O)Nc3ccnc([C@]4(C)CCSC(N)=N4)c3)ncc2n1] | | |
| 701 | 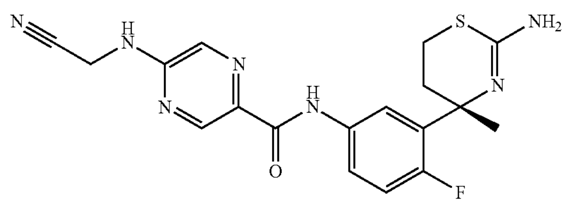 [SMILES: C[C@@]1(c2cc(NC(=O)c3cnc(NCC#N)cn3)ccc2F)CCSC(N)=N1] | 400 | |
| 702 | 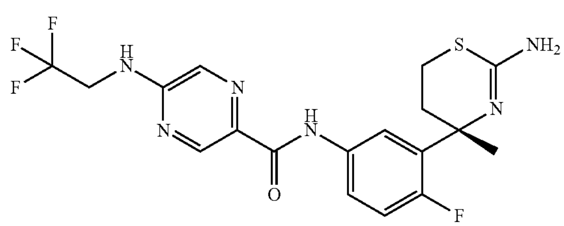 [SMILES: C[C@@]1(c2cc(NC(=O)c3cnc(NCC(F)(F)F)cn3)ccc2F)CCSC(N)=N1] | 443 | |

Test Example Assay of β-Secretase-Inhibiting Activity

Forty eight point five μL of substrate peptide solution (Biotin-XSEVNLDAEFRHDSGC-Eu: X=ε-amino-n-capronic acid, Eu=Europium cryptate) was added to each well of 96-hole half-area plate (a black plate: Corning Incorporated), and after addition of 0.5 μl of the test sample (dissolved in N,N'-dimethylformaldehyde) and 1 μl of Recombinant human BACE-1 (R&D Systems), the reaction mixture was incubated at 30° C. for 3 hours. The substrate peptide was synthesized by reacting Cryptate TBPCOOH mono SMP (CIS bio international) with Biotin-XSEVNLDAE-FRHDSGC (Peptide Institute, Inc.). The final concentrations of the substrate peptide and Recombinant human BACE-1 were adjusted to 18 nM and 7.4 nM respectively, and the reaction was performed in sodium acetate buffer (50 mM sodium acetate, pH 5.0, 0.008% Triton X-10).

After the incubation for reaction, 50 μl of 8.0 μg/ml Streptavidin-XL665 (CIS bio international) dissolved in phosphate buffer (150 mM $K_2 HPO_4$—$KH_2 PO_4$, pH 7.0, 0.008% Triton X-100, 0.8 M KF) was added to each well and left stand at 30° C. for an hour. After then, fluorescence intensity was measured (excitation wavelength: 320 nm, measuring wavelength: 620 nm and 665 nm) using Wallac 1420 multilabel counter (Perkin Elmer life sciences). Enzymatic activity was determined from counting ratio of each wavelength (10,000×Count 665/Count 620) and 50% inhibitory concentration against the enzymatic activity was calculated. $IC_{50}$ values of the test compounds are indicated in Table 139.

TABLE 139

P

| Compound No. | IC50 (uM) |
|---|---|
| 3 | 0.08 |
| 11 | 0.17 |
| 12 | 0.16 |
| 26 | 4.85 |
| 34 | 0.10 |
| 38 | 0.14 |
| 41 | 0.15 |
| 62 | 0.17 |
| 65 | 0.72 |
| 66 | 0.15 |
| 70 | 0.09 |
| 71 | 0.16 |
| 72 | 0.11 |
| 76 | 0.18 |
| 80 | 0.07 |
| 86 | 0.19 |
| 87 | 0.09 |
| 92 | 0.08 |
| 93 | 0.08 |
| 94 | 0.17 |
| 101 | 0.08 |
| 105 | 0.13 |
| 106 | 0.12 |
| 109 | 0.10 |
| 111 | 0.18 |
| 114 | 0.16 |
| 126 | 2.14 |
| 136 | 0.11 |
| 141 | 0.12 |
| 149 | 9.25 |
| 150 | 2.48 |
| 151 | 6.77 |
| 155 | 5.96 |
| 163 | 6.79 |
| 164 | 0.08 |

The following compounds have shown $IC_{50}$ values equal to or under 1 μM in the same assay;

compounds 4, 5, 6, 8, 10, 18, 19, 20, 21, 22, 29, 32, 33, 35, 43, 45, 46, 58, 59, 63, 64, 68, 69, 75, 77, 78, 79, 81, 82, 83, 84, 85, 88, 89, 90, 91, 95, 96, 97, 98, 100, 102, 103, 104, 107, 108, 110, 112, 113, 115, 116, 117, 118, 119, 120, 121, 123, 124, 125, 127, 131, 132, 133, 134, 135, 142, 143, 144, 145, 148, 152, 157, 158, 162 and 165.

Also, compounds 462, 463, 465, 467, 469, 470, 471, 472, 479, 482, 483, 486, 489, 490, 492, 501, 503, 507, 508, 509, 510, 511, 512, 516, 518, 519, 523, 527, 528, 531, 532, 533, 536, 538, 539, 540, 542, 545, 546, 547, 548, 549, 552, 553, 554, 555, 556, 557, 558, 560, 561, 562, 564, 565, 567, 568, 569, 570, 571, 572, 573, 574, 575, 578, 581, 582, 583, 584, 586, 587, 590, 595, 596, 600, 601, 602, 603, 604, 605, 606, 609, 612, 613, 637, 644, 646, 461, 468, 478, 491, 502, 505, 508, 517, 530, 537, 542, 544, 559, 563, 566, 576, 577, 597, 598, 599 and 645 showed $IC_{50}$ values equal to or under 1 μM in the same assay.

| Compound No. | IC50 (μM) |
|---|---|
| 652 | 0.06 |
| 655 | 0.01 |
| 660 | 0.11 |
| 662 | 0.17 |

-continued

| Compound No. | IC50 (μM) |
|---|---|
| 664 | 0.02 |
| 665 | 0.87 |
| 668 | 0.51 |
| 669 | 0.01 |
| 674 | 0.01 |
| 680 | 0.05 |
| 689 | 0.04 |
| 701 | 0.20 |
| 702 | 0.16 |

The following compounds also showed $IC_{50}$ values equal to or under 1 μM in the same assay;

compounds 647, 648, 649, 650, 651, 654, 656, 657, 658, 659, 661, 666, 670, 671, 672, 673, 675, 676, 677, 678, 679, 683, 684, 685, 686, 687, 688, 690, 691, 692, 693, 694, 695, 696 and 697, 652, 655, 660, 662, 664, 665, 667, 669, 674 and 689.

Formulation Example 1

Granular formulation is prepared with the following ingredients;

| Ingredient | compound of the formula (I) | 10 mg |
|---|---|---|
| | lactose | 700 mg |
| | corn starch | 274 mg |
| | HPC-L | 16 mg |
| | | 1000 mg |

Compound of the formula (I) and lactose are put through a sieve of No. 60 mesh. Corn starch is put through a sieve of No. 120 mesh and these are mixed with V-shaped mixer.

An aqueous solution of HPC-L (Hydroxypropyl cellulose of Low viscosity) is added to the mixed powder, kneaded, granulated (extrusion granulation; pore diameter 0.5-1 mm) and put into a drying process. The resulted dried granule is sieved with vibrating screen (12/60 mesh) to give a granular formulation.

Formulation Example 2

Granular formulation for capsule filling is prepared with the following ingredients;

| Ingredient | compound of the formula (I) | 15 mg |
|---|---|---|
| | lactose | 90 mg |
| | corn starch | 42 mg |
| | HPC-L | 3 mg |
| | | 150 mg |

Compound of the formula (I) and lactose are put through a sieve of No. 60 mesh. Corn starch is put through a sieve of No. 120 mesh and these are mixed. An aqueous solution of HPC-L is added to the mixed powder, kneaded, granulated and dried. Particle size of the resulted dried granule is regulated and each of 150 mg is filled in No. 5 hard-gelatin capsule.

Formulation Example 3

Tablet is prepared with the following ingredients;

| Ingredient | compound of the formula (I) | 10 mg |
|---|---|---|
| | lactose | 90 mg |
| | microcrystalline cellulose | 30 mg |
| | CMC-Na | 15 mg |
| | magnesium stearate | 5 mg |
| | | 150 mg |

Compound of the formula (I), lactose, microcrystalline cellulose and CMC-Na (sodium salt of carboxymethylcellulose) are put through sieve of No. 60 mesh and mixed. Magnesium stearate is mixed with the mixed granule above to give a mixed powder for tablet, which is compressed by a tabletting machine to give a tablet of 150 mg.

Formulation Example 4

The following ingredients were warmed, mixed and sterilized to give an injection.

| Ingredient | compound of the formula (I) | 3 mg |
|---|---|---|
| | non-ionic surfactant | 15 mg |
| | purified water for injection | 1 ml |

INDUSTRIAL APPLICABILITY

A compound of the present invention can be a useful drug for treating diseases induced by production, secretion and/or deposition of amyloid β protein.

The invention claimed is:
1. A compound of the formula (I):

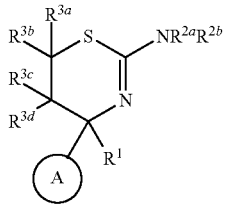

wherein the ring A is an optionally substituted benzofuran, wherein a substituent of the optionally substituted benzofuran is at least one selected from the group consisting of
(A) the substituent group α, the substituent group α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, imino, hydroxyimino, lower alkoxyimino, lower alkylthio, carbamoyl, lower alkylcarbamoyl, hydroxy lower alkylcarbamoyl, sulfamoyl, lower alkylsulfamoyl, lower alkylsulfonyl, cyano, nitro, a carbocyclic group and a heterocyclic group;
(B) lower alkyl optionally substituted with one or more substituent(s) selected from the substituent group α, hydroxyimino and lower alkoxyimino;
(C) amino lower alkyl substituted with one or more substituent(s) selected from the substituent group α;
(D) hydroxyimino lower alkyl;
(E) lower alkoxyimino lower alkyl;
(F) lower alkenyl optionally substituted with one or more substituent(s) selected from the substituent group α;
(G) lower alkynyl optionally substituted with one or more substituent(s) selected from the substituent group α;
(H) lower alkoxy optionally substituted with one or more substituent(s) selected from the substituent group α;
(I) lower alkoxy lower alkoxy optionally substituted with one or more substituent(s) selected from the substituent group α;
(J) lower alkenyloxy optionally substituted with one or more substituent(s) selected from the substituent group α;
(K) lower alkoxy lower alkenyloxy optionally substituted with one or more substituent(s) selected from the substituent group α;
(L) lower alkynyloxy optionally substituted with one or more substituent(s) selected from the substituent group α;
(M) lower alkoxy lower alkynyloxy optionally substituted with one or more substituent(s) selected from the substituent group α;
(N) lower alkylthio optionally substituted with one or more substituent(s) selected from the substituent group α;
(O) lower alkenylthio optionally substituted with one or more substituent(s) selected from the substituent group α;
(P) lower alkynylthio optionally substituted with one or more substituent(s) selected from the substituent group α;
(Q) lower alkylamino substituted with one or more substituent(s) selected from the substituent group α;
(R) lower alkenylamino substituted with one or more substituent(s) selected from the substituent group α;
(S) lower alkynylamino substituted with one or more substituent(s) selected from the substituent group α;
(T) aminooxy optionally substituted with one or more substituent(s) selected from lower alkylidene and the substituent group α;
(U) acyl substituted with one or more substituent(s) selected from the substituent group α;
(V) lower alkylsulfonyl optionally substituted with one or more substituent(s) selected from the substituent group α;
(W) lower alkylsulfinyl optionally substituted with one or more substituent(s) selected from the substituent group α;
(X) sulfamoyl;
(Y) lower alkylsulfamoyl optionally substituted with one or more substituent(s) selected from the substituent group α;
(Z) a carbocyclic group optionally substituted with one or more substituent(s) selected from the substituent group α, azide, lower alkyl and halogeno lower alkyl;
(AA) a heterocyclic group optionally substituted with one or more substituent(s) selected from the substituent group α, azide, lower alkyl and halogeno lower alkyl;
(AB) carbocyclyl lower alkyl optionally substituted with one or more substituent(s) selected from the substituent group α, azide, lower alkyl and halogeno lower alkyl;

(AC) heterocyclyl lower alkyl optionally substituted with one or more substituent(s) selected from the substituent group α, azide, lower alkyl and halogeno lower alkyl;
(AD) carbocyclyloxy optionally substituted with one or more substituent(s) selected from the substituent group α, azide, lower alkyl and halogeno lower alkyl;
(AE) heterocyclyloxy optionally substituted with one or more substituent(s) selected from the substituent group α, azide, lower alkyl and halogeno lower alkyl;
(AF) carbocyclyl lower alkoxy optionally substituted with one or more substituent(s) selected from the substituent group α, azide, lower alkyl and halogeno lower alkyl;
(AG) heterocyclyl lower alkoxy optionally substituted with one or more substituent(s) selected from the substituent group α, azide, lower alkyl and halogeno lower alkyl;
(AH) carbocyclyl lower alkoxycarbonyl optionally substituted with one or more substituent(s) selected from the substituent group α, azide, lower alkyl and halogeno lower alkyl;
(AI) heterocyclyl lower alkoxycarbonyl optionally substituted with one or more substituent(s) selected from the substituent group α, azide, lower alkyl and halogeno lower alkyl;
(AJ) carbocyclylthio optionally substituted with one or more substituent(s) selected from the substituent group α, azide, lower alkyl and halogeno lower alkyl;
(AK) heterocyclylthio optionally substituted with one or more substituent(s) selected from the substituent group α, azide, lower alkyl and halogeno lower alkyl;
(AL) carbocyclyl amino optionally substituted with one or more substituent(s) selected from the substituent group α, azide, lower alkyl and halogeno lower alkyl;
(AM) heterocyclyl amino optionally substituted with one or more substituent(s) selected from the substituent group α, azide, lower alkyl and halogeno lower alkyl;
(AN) carbocyclyl lower alkylamino optionally substituted with one or more substituent(s) selected from the substituent group α, azide, lower alkyl and halogeno lower alkyl;
(AO) heterocyclyl lower alkylamino optionally substituted with one or more substituent(s) selected from the substituent group α, azide, lower alkyl and halogeno lower alkyl;
(AP) lower alkylsulfamoyl optionally substituted with one or more substituent(s) selected from the substituent group α;
(AQ) carbocyclylsulfamoyl optionally substituted with one or more substituent(s) selected from the substituent group α, azide, lower alkyl and halogeno lower alkyl;
(AR) heterocyclylsulfamoyl optionally substituted with one or more substituent(s) selected from the substituent group α, azide, lower alkyl and halogeno lower alkyl;
(AS) carbocyclylsulfonyl optionally substituted with one or more substituent(s) selected from the substituent group α, azide, lower alkyl and halogeno lower alkyl;
(AT) heterocyclylsulfonyl optionally substituted with one or more substituent(s) selected from the substituent group α, azide, lower alkyl and halogeno lower alkyl;
(AU) carbocyclylcarbamoyl optionally substituted with one or more substituent(s) selected from the substituent group α, azide, lower alkyl and halogeno lower alkyl;
(AV) heterocyclyl carbamoyl optionally substituted with one or more substituent(s) selected from the substituent group α, azide, lower alkyl and halogeno lower alkyl;
(AW) carbocyclyl lower alkylcarbamoyl optionally substituted with one or more substituent(s) selected from the substituent group α, azide, lower alkyl and halogeno lower alkyl;
(AX) heterocyclyl lower alkylcarbamoyl optionally substituted with one or more substituent(s) selected from the substituent group α, azide, lower alkyl and halogeno lower alkyl;
(AY) carbocyclyloxycarbonyl optionally substituted with one or more substituent(s) selected from the substituent group α, azide, lower alkyl and halogeno lower alkyl;
(AZ) heterocyclyloxycarbonyl optionally substituted with one or more substituent(s) selected from the substituent group α, azide, lower alkyl and halogeno lower alkyl;
(BA) lower alkylenedioxy optionally substituted with halogen;
(BB) oxo;
(BC) azide; and
(BD) one of the following formulae:

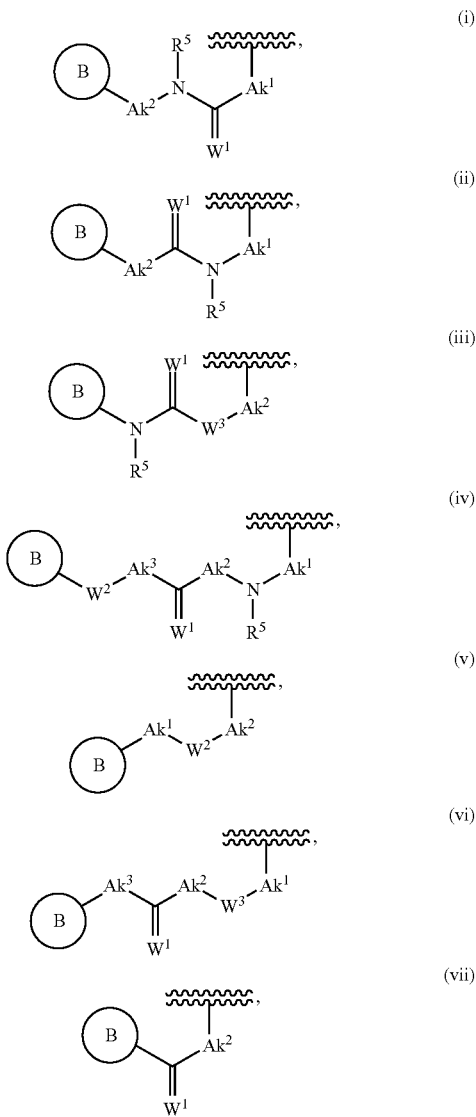

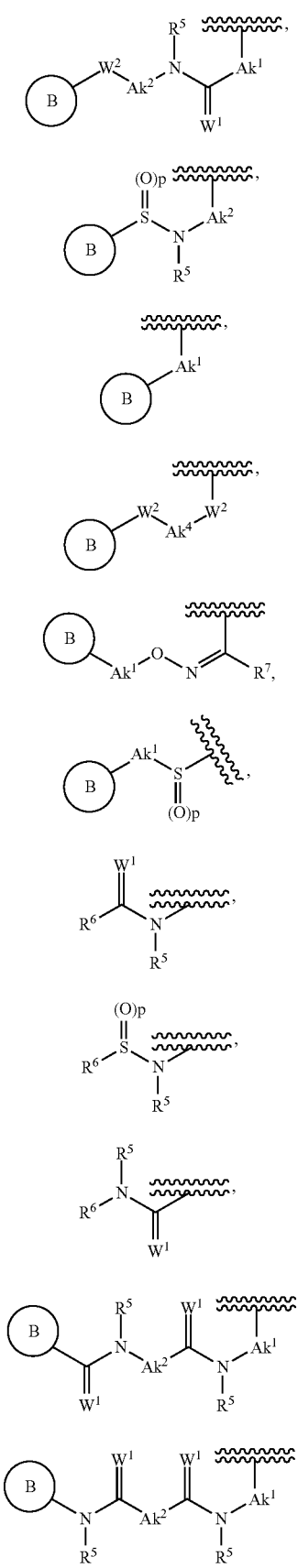
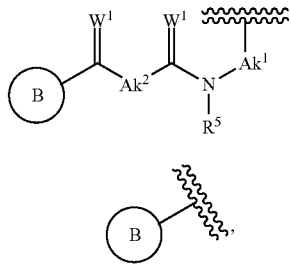

wherein $Ak^1$, $Ak^2$ and $Ak^3$ are each independently a single bond, optionally substituted lower alkylene wherein the substituent(s) is selected from the substituent group α, optionally substituted lower alkenylene wherein the substituent(s) is selected from the substituent group α, or optionally substituted lower alkynylene wherein the substituent(s) is selected from the substituent group α;

$Ak^4$ is optionally substituted lower alkylene wherein the substituent(s) is selected from the substituent group α, optionally substituted lower alkenylene wherein the substituent(s) is selected from the substituent group α, or optionally substituted lower alkynylene wherein the substituent(s) is selected from the substituent group α;

$W^1$ and $W^3$ are each independently O or S, $W^2$ is O, S or $NR^5$, $R^5$ and $R^6$ are each independently hydrogen, lower alkyl, hydroxy lower alkyl, lower alkoxy lower alkyl, lower alkoxycarbonyl lower alkyl, carbocyclyl lower alkyl, lower alkenyl, hydroxyl lower alkenyl, lower alkoxy lower alkenyl, lower alkoxycarbonyl lower alkenyl, carbocyclyl lower alkenyl, lower alkynyl, hydroxyl lower alkynyl, lower alkoxy lower alkynyl, lower alkoxycarbonyl lower alkynyl, carbocyclyl lower alkynyl or acyl;

$R^7$ is hydrogen or lower alkyl;

the ring B is a carbocyclic group or a heterocyclic group, the carbocyclic group and the heterocyclic group being substituted optionally with at least one selected from the above (A) to (BC) and p is 1 or 2; $W^1$, $W^3$ or $W^5$ may be independent when it is pluralized, $R^1$ is optionally substituted lower alkyl wherein the substituent(s) is selected from the substituent group α, optionally substituted lower alkenyl wherein the substituent(s) is selected from the substituent group α, optionally substituted lower alkynyl wherein the substituent is selected from the substituent group α, an optionally substituted carbocyclic group wherein the substituent(s) is selected from a group of lower alkyl and the substituent group α, or an optionally substituted heterocyclic group wherein the substituent(s) is selected from a group of lower alkyl and the substituent group α, $R^{2a}$ and $R^{2b}$ are each independently hydrogen, optionally substituted lower alkyl wherein the substituent(s) is selected from the substituent group a or optionally substituted acyl wherein acyl includes aliphatic acyl, carbocyclyl carbonyl and heterocyclyl carbonyl, and the substituent(s) is selected from the substituent group α, and the substituent(s) for a moiety of the ring in carbocyclyl carbonyl and heterocyclylcarbonyl is selected from a group of lower alkyl, the substituent group α and lower alkyl substituted with one or more substituent(s) selected from the substituent group α, and R³ᵃ, R³ᵇ, R³ᶜ and R³ᵈ are each independently hydrogen, halogen, hydroxy, optionally substituted lower alkyl wherein the substituent(s) is selected from the substituent group α, optionally substituted lower alkenyl wherein the substituent(s) is selected from the substituent group α, optionally substituted acyl wherein acyl includes aliphatic acyl, carbocyclyl carbonyl and heterocyclic carbonyl, and the substituent(s) is selected from the substituent group α, and the substituent(s) for a moiety of the ring in carbocyclyl carbonyl and heterocyclylcarbonyl is selected from a group of lower alkyl, the substituent group α and lower alkyl substituted with one or more substituent(s) selected from the substituent group α, optionally substituted lower alkoxy wherein the substituent(s) is selected from the substituent group α, optionally substituted carbocyclyl lower alkyl wherein the substituent(s) is selected from the substituent group α, optionally substituted heterocyclyl lower alkyl wherein the substituent(s) is selected from a group of lower alkyl and the substituent group α, optionally substituted carbocyclyl lower alkoxy wherein the substituent(s) is selected from a group of lower alkyl and the substituent group α, optionally substituted heterocyclyl lower alkoxy wherein the substituent(s) is selected from a group of lower alkyl and the substituent group α, optionally substituted aralkyl wherein the substituent(s) is selected from a group of lower alkyl and the substituent group α, optionally substituted heteroaralkyl wherein the substituent(s) is selected from a group of lower alkyl and the substituent group α, optionally substituted aralkyloxy wherein the substituent(s) is selected from a group of lower alkyl and the substituent group α, optionally substituted heteroaralkyloxy wherein the substituent(s) is selected from a group of lower alkyl and the substituent group α, optionally substituted lower alkylthio wherein the substituent(s) is selected from the substituent group α, carboxy, optionally substituted lower alkoxycarbonyl wherein the substituent(s) is selected from the substituent group α, optionally substituted amino wherein the substituent(s) is selected from a group of lower alkyl, acyl, hydroxyl, lower alkoxy, lower alkoxycarbonyl, a carbocyclic group and a heterocyclic group, optionally substituted carbamoyl wherein the substituent(s) is selected from a group of lower alkyl, acyl, hydroxyl, lower alkoxy, lower alkoxycarbonyl, a carbocyclic group and a heterocyclic group, an optionally substituted carbocyclic group wherein the substituent(s) is selected from a group of lower alkyl and the substituent group a or an optionally substituted heterocyclic group wherein the substituent(s) is selected from a group of lower alkyl and the substituent group α, or R³ᵃ and R³ᵇ or R³ᶜ and R³ᵈ may form a carbocyclic ring together with a linked carbon atom or may form oxo, or a pharmaceutically acceptable salt.

2. The compound of claim 1, wherein the ring A is

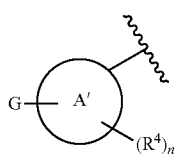

wherein the ring A' is benzofuran and,
G is

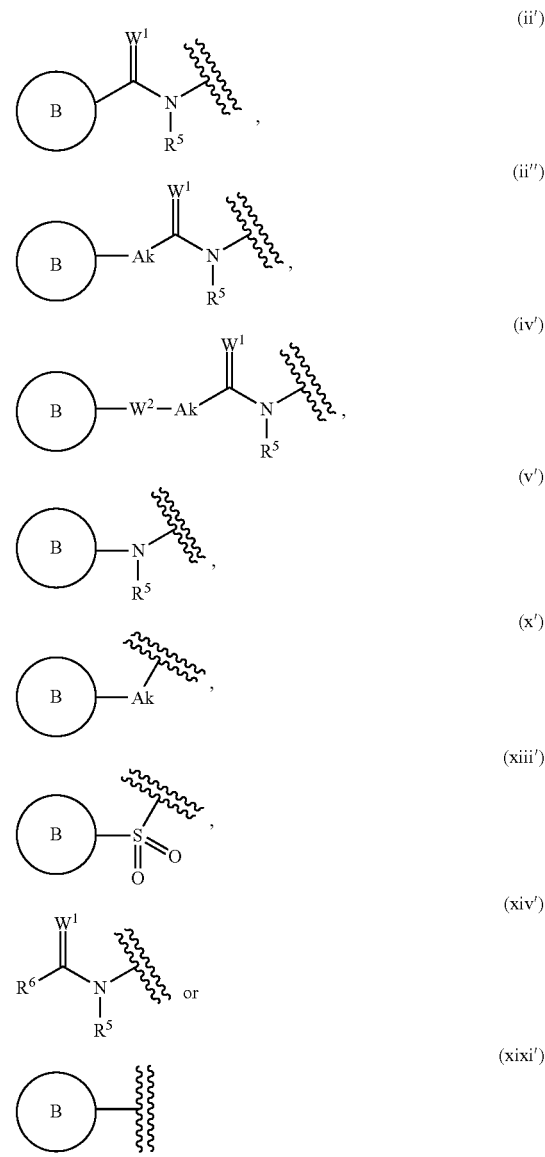

wherein R⁵ is hydrogen, lower alkyl or acyl,

R⁶ is optionally substituted lower alkyl which is substituted with one of more of substituent(s) selected from the substituent group α, optionally substituted lower alkenyl which is substituted with one of more of substituent(s) selected from the substituent group α or optionally substituted lower alkynyl which is substituted with one of more of substituent(s) selected from the substituent group α, W¹ is O or S, W² is O, S or NR⁵, Ak is optionally substituted lower alkylene wherein the substituent(s) is selected from the substituent group α, optionally substituted lower alkenylene wherein the substituent(s) is selected from the substituent group α or optionally substituted lower alkynylene wherein the substituent(s) is selected from the substituent group α, the ring B is a carbocyclic group or a heterocyclic group, the carbocyclic group and the heterocyclic group being substituted optionally with at least one selected from the above (A) to (BC) and each $R^5$ may be independent:

$R^4$ is halogen, hydroxyl, mercapto, halogeno lower alkyl, lower alkoxy, amino, lower alkylamino, acylamino or lower alkylthio, n is an integer of 0 to 2, and each $R^4$ may be independent;

or a pharmaceutically acceptable salt thereof.

3. The compound of claim 1, wherein $R^1$ is C1-C3 alkyl; or a pharmaceutically acceptable salt thereof.

4. The compound of claim 1, wherein both of $R^{2a}$ and $R^{2b}$ are hydrogen; or a pharmaceutically acceptable salt thereof.

5. The compound of claim 1, wherein all of $R^{3a}$, $R^{3b}$, $R^{3c}$ and $R^{3d}$ are hydrogen; or a pharmaceutically acceptable salt thereof.

6. The compound of claim 1, wherein $R^{3a}$ and $R^{3b}$ are the same substituent selected from halogen and optionally substituted lower alkyl wherein the substituent(s) is selected from the substituent group a; or a pharmaceutically acceptable salt thereof.

7. The compound of claim 1, wherein $R^{3c}$ and $R^{3d}$ are the same substituent selected from halogen and optionally substituted lower alkyl wherein the substituent(s) is selected from the substituent group α; or a pharmaceutically acceptable salt thereof.

8. The compound of claim 1, wherein $R^{3a}$ and $R^{3b}$, or $R^{3c}$ and $R^{3d}$ form a carbocyclic ring together with a linked carbon atom; or a pharmaceutically acceptable salt thereof.

9. A pharmaceutical composition comprising a compound of claim 1, or a pharmaceutically acceptable salt thereof as an active ingredient, and a pharmaceutically acceptable carrier.

10. A method for treating a condition selected from the group consisting of Alzheimer's dementia, Down's disease, prion disease, mild cognitive impairment (MCI), Dutch-type hereditary cerebral hemorrhage with amyloidosis, cerebral amyloid angiopathy, vascular degenerated mixed dementia, dementia associated with Parkinson's disease, dementia associated with progressive supranuclear paralysis, dementia associated with corticobasal degeneration, diffuse Lewy Bodies Alzheimer's disease, age-related macular degeneration, Parkinson's disease, or amyloid angiopathy in a subject in need thereof, comprising administering to the subject an effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 8,541,408 B2
APPLICATION NO. : 13/417786
DATED : September 24, 2013
INVENTOR(S) : Tamura et al.

It is certified that error appears in the above-identified patent and that said Letters Patent is hereby corrected as shown below:

On the Title page of the Letters Patent:

Item (75) Inventors: the first listed inventor "Yuusuki Tamura, Osaka (JP)" should be -- Yuusuke Tamura, Osaka (JP) --

Signed and Sealed this
Fourth Day of March, 2014

Michelle K. Lee
*Deputy Director of the United States Patent and Trademark Office*